US009821053B2

(12) United States Patent
Korber et al.

(10) Patent No.: US 9,821,053 B2
(45) Date of Patent: Nov. 21, 2017

(54) HUMAN IMMUNODEFICIENCY VIRUS TYPE 1 GROUP M CONSENSUS AND MOSAIC ENVELOPE GLYCOPROTEINS

(71) Applicants: DUKE UNIVERSITY, Durham, NC (US); LOS ALAMOS NATIONAL SECURITY, LLC, Los Alamos, NM (US); THE UNIVERSITY OF ALABAMA AT BIRMINGHAM RESEARCH FOUNDATION, Birmingham, AL (US); BETH ISRAEL DEACONESS MEDICAL CENTER, Boston, MA (US)

(72) Inventors: Bette T. Korber, Los Alamos, NM (US); William Fischer, Los Alamos, NM (US); Hua-Xin Liao, Durham, NC (US); Barton F. Haynes, Durham, NC (US); Norman Letvin, Boston, MA (US); Beatrice H. Hahn, Birmingham, AL (US)

(73) Assignees: Duke University, Durham, NC (US); Los Alamos National Security, LLC, Los Alamos, NM (US); The UAB Research Foundation, Birmingham, AL (US); Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 14/689,995

(22) Filed: Apr. 17, 2015

(65) Prior Publication Data

US 2016/0067329 A1    Mar. 10, 2016

Related U.S. Application Data

(63) Continuation of application No. 13/094,734, filed on Apr. 26, 2011, now Pat. No. 9,011,873, which is a continuation of application No. 12/192,015, filed on Aug. 14, 2008, now Pat. No. 7,951,377, which is a continuation-in-part of application No. 11/990,222, filed as application No. PCT/US2006/032907 on Aug. 23, 2006, now Pat. No. 8,119,140.

(60) Provisional application No. 60/739,413, filed on Nov. 25, 2005, provisional application No. 60/710,154, filed on Aug. 23, 2005.

(51) Int. Cl.

| | |
|---|---|
| *A61K 39/21* | (2006.01) |
| *C07K 14/005* | (2006.01) |
| *A61K 39/12* | (2006.01) |
| *C12N 7/00* | (2006.01) |
| *A61K 39/00* | (2006.01) |

(52) U.S. Cl.

CPC .............. *A61K 39/21* (2013.01); *A61K 39/12* (2013.01); *C07K 14/005* (2013.01); *C12N 7/00* (2013.01); *A61K 2039/53* (2013.01); *A61K 2039/70* (2013.01); *C12N 2710/24143* (2013.01); *C12N 2740/16022* (2013.01); *C12N 2740/16034* (2013.01); *C12N 2740/16122* (2013.01); *C12N 2740/16134* (2013.01); *C12N 2740/16234* (2013.01); *C12N 2740/16334* (2013.01)

(58) Field of Classification Search

CPC .................. A61K 39/21; C07K 14/005; C12N 2740/16122; C12N 2740/16134

See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,703,055 | A | 12/1997 | Felgner et al. |
| 6,710,173 | B1 | 3/2004 | Binley et al. |
| 7,655,774 | B2 | 2/2010 | Mullins et al. |
| 7,951,377 | B2 | 5/2011 | Korber et al. |
| 8,119,140 | B2 | 2/2012 | Korber et al. |
| 9,011,875 | B2 | 4/2015 | Korber et al. |
| 2002/0198162 | A1 | 12/2002 | Punnonen et al. |
| 2003/0044421 | A1 | 3/2003 | Emini et al. |
| 2003/0104011 | A1 | 6/2003 | Rios |
| 2003/0147888 | A1 | 8/2003 | Haynes et al. |
| 2003/0180314 | A1 | 9/2003 | DeGroot |
| 2003/0194411 | A1 | 10/2003 | Rubinstein et al. |
| 2004/0001851 | A1 | 1/2004 | Haynes et al. |
| 2005/0137387 | A1 | 6/2005 | Mullins et al. |
| 2006/0216305 | A1 | 9/2006 | Lal et al. |
| 2006/0275897 | A1 | 12/2006 | Nabel et al. |
| 2007/0178562 | A1 | 8/2007 | Haynes et al. |
| 2009/0324631 | A1 | 12/2009 | Korber et al. |
| 2011/0150915 | A1 | 6/2011 | Korber et al. |
| 2011/0301328 | A1 | 12/2011 | Korber et al. |
| 2012/0121631 | A1 | 5/2012 | Korber et al. |

FOREIGN PATENT DOCUMENTS

| | | | |
|---|---|---|---|
| WO | 2002/004493 | | 1/2002 |
| WO | 2005/001029 | A2 | 1/2005 |

(Continued)

OTHER PUBLICATIONS

Ferrari, G, et al; Identification of highly conserved and broadly cross-reactive HIV type 1 cytotoxic T lymphocyte epitopes as candidate immunogens for inclusion in *Mycobacterium bovis* BCG-vectored HIV vaccines; AIDS Res Hum Retroviruses; Sep. 20, 2000; 16(14); 1433-43.

(Continued)

*Primary Examiner* — Jeffrey Parkin

(74) *Attorney, Agent, or Firm* — Baker Donelson Bearman Caldwell &

(57) ABSTRACT

The disclosure relates to nucleic acids mosaic clade M HIV-1 Env polypeptides and to compositions and vectors comprising same. The nucleic acids are suitable for use in inducing an immune response to HIV-1 in a human.

18 Claims, 109 Drawing Sheets

(56) References Cited

FOREIGN PATENT DOCUMENTS

| WO | 2005/012502 | 2/2005 |
|---|---|---|
| WO | 2005/028625 | 3/2005 |
| WO | 2005/035555 | 4/2005 |
| WO | 2007/024941 | 3/2007 |
| WO | 2007/047916 | 4/2007 |
| WO | 2010/019262 | 2/2010 |
| WO | 2012/047267 | 4/2012 |

OTHER PUBLICATIONS

Robertson, DL, et al; Recombination in HIV-1; Nature; Mar. 9, 1995; 374(6518); 124-6.
Sbai, H, et al; Use of T cell epitopes for vaccine development; Curr Drug Targets Infect Disord.; Nov. 2001; 1(3); 303-13.
Altfeld et al, "HIV-1 superinfection despite broad CD8+ T-cell responses containing replication of the primary virus", Nature, 420(6914):434-439 (2002).
Barouch et al., "Mosaic HIV-1 Vaccines Expand the Breadth and Depth of Cellular Immune Responses in Rhesus Monkeys", Nat Med., 16(3):319-323 (2010).
Desrosiers, "Prospects for an AIDS Vaccine", Nature Medicine, 10(3):221-223 (2004).
Doria-Rose et al, "Human Immunodeficiency Virus Type 1 Subtype B Ancestral Envelope Protein Is Functional and Elicits Neutralizing Antibodies in Rabbits Similar to Those Elicited by a Circulating Subtype B Envelope", Journal of Virology, 79(17):11214-11224 (2005).
Fischer et al, "Polyvalent vaccines for optimal coverage of potential T-cell epitopes in global HIV-1 variants", Nature Medicine, 13(1): 100-106 (2007).
Gallo, "The end or the beginning of the drive to an HIV-preventive vaccine: a view from over 20 years," The Lancet, 366:1894-1898. (2005).
Gao et al, "Antigenicity and Immunogenicity of a Synthetic Human Immunodeficiency Virus Type 1 Group M Consensus Envelope Glycoprotein", Journal of Virology, 79(2): 1154-1163 (2005).
Gaschen et al, "Diversity Considerations in HIV-1 Vaccine Selection", Science, 296(5577):2354-2360 (2002).
Haynes et al, "Aiming to induce broadly reactive neutralizing antibody responses with HIV-1 vaccine candidates," Expert Rev. Vaccines, 5(3):347-363 (2006).
International Search Report dated Apr. 6, 2010 issued in International Appln. No. PCT/US2009/004664.
International Search Authority Written Opinion dated Apr. 6, 2010 issued in International Appln. No. PCT/US09/004664.
International Search Report dated Jul. 3, 2008 issued in International Appln. No. PCT/US06/32907.
International Search Report dated Aug. 27, 2008 issued in International Appln. No. PCT/US06/32907.
International Search Report dated Apr. 18, 2012 issued in International Appln. No. PCT/US2011/001664.
International Search Authority Written Opinion dated Apr. 18, 2012 issued in International Appln. No. PCT/US2011/001664.
International Search Report dated Aug. 27, 2008 issued in WO 2007/024941.
International Search Report dated Aug. 27, 2008 in WO 2007/024941 (Korber).
Kong et al., "Expanded Breadth of the T-Cell Response to Mosaic Human Immunodeficiency Virus Type 1 Envelope DNA Vaccination", Journal of Virology, 83(5):2201-2215 (2009).
Korber et al., "T-Cell Vaccine Strategies for Human Immunodeficiency Virus, the Virus with a Thousand Faces", Journal of Virology, 83(17).8300-8314 (2009).
Korber et al, "Evolutionary and immunological implications of contemporary HIV-1 variation", British Medical Bulletin, 58:19-42 (2001).
Letvin, N., "Progress and obstacles in the development of an AIDS vaccine" (2006).

McMichael, A. J., "HIV vaccines", Ann. Rev. Immunol., 24:227-255 (2006).
Nabel et al, "HIV vaccine strategies", Vaccine, 20(15):1945-1947 (2002).
Office Action dated Jun. 4, 2010 issued in related U.S. Appl. No. 11/990,222.
Office Actions dated Apr. 2, 2013 and Nov. 21, 2013 in U.S. Appl. No. 13/399,963 (Korber et al.).
Office Actions dated Apr. 27, 2012, Dec. 13, 2012 and Oct. 9, 2013 in U.S. Appl. No. 12/960,287 (Korber et al.).
Office Action dated Sep. 6, 2013 in U.S. Appl. No. 12/737,761 (Korber et al.).
Office Actions dated Feb. 3, 2010, Jun. 4, 2010, Jan. 25, 2011 and May 27, 2011 in U.S. Appl. No. 11/990,222 (Korber et al.).
Office Actions dated Feb. 3, 2010 and Jun. 23, 2010 in U.S. Appl. No. 12/192,015 (Korber et al.).
Peng et al., "Replicating Ad-recombinants encoding non-myristoylated rather than wild-type HIV Nef elicit enhanced cellular immunity", AIDS, 20:2149-2157 (2006).
Santra et al., "Mosaic Vaccines Elicit CD8+ T lymphocyte Responses in Monkeys that Confer Enhanced Immune Coverage of Diverse HIV Strains", Nat Med., 16(3):324-328 (2010).
Santra et al., "A centralized gene-based HIV-1 vaccine elicits broad cross-clade cellular immune responses in rhesus monkeys", PNAS, 105(30):10489-10494 (2008).
Shinoda et al, "Polygene DNA vaccine induces a high level of protective effect against HIV-vaccinia virus challenge in mice", Vaccine, 22:3676-3690 (2004).
Supplementary European Search Report dated Jul. 11, 2012 issued in EP 09 80 698.
Supplementary European Search Report dated Oct. 25, 2012 issued in EP 06 80 2155.
Supplementary European Search Report dated Nov. 9, 2012 issued in EP 06 80 2155.
Walker et al., "Toward an AIDS vaccine", Science, 320:760-765 (2008).
Barugahare et al., "Human Immunodeficiency Virus-Specific Responses in Adult Ugandans: Patterns of Cross-Clade Recognition," J. Virol. Apr. 2005; 79:7 4132-4139.
Oxenius, et al., "HIV-Specific Cellular Immune Response Is Inversely Correlated with Disease Progression as Defined by Decline of CD4+ T Cells in Relation to HIV RNA Load," J Infect Dis. (2004) 189 (7): 1199-1208.
Barouch et al., "Control of Viremia and Prevention of Clinical AIDS in Rhesus Monkeys by Cytokine-Augmented DNA Vaccination", Science Oct. 20, 2000: vol. 290, Issue 5491, pp. 486-492.
Schmitz et al., "Control of Viremia in Simian Immunodeficiency Virus Infection by CD8+ Lymphocytes," Science Feb. 5, 1999: vol. 283, Issue 5403, pp. 857-860.
Barouch et al., "Viral Escape from Dominant Simian Immunodeficiency Virus Epitope-Specific Cytotoxic T Lymphocytes in DNA-Vaccinated Rhesus Monkeys," J. Virol. Jul. 2003; 77:13 7367-7375.
Moore and Burton, "Urgently needed: a filter for the HIV-1 vaccine pipeline," Nat Med. Aug. 2004;10(8):769-71.
Altfeld et al., "Enhanced detection of human immunodeficiency virus type 1-specific T-cell responses to highly variable regions by using peptides based on autologous virus sequences," J Virol. Jul. 2003;77(13):7330-40.
Norris et al., "Fine specificity and cross-clade reactivity of HIV type 1 Gag-specific CD4+ T cells," AIDS Res Hum Retroviruses. Mar. 2004;20(3):315-25.
Jones et al. "Determinants of Human Immunodeficiency Virus Type 1 Escape from the Primary CD8+ Cytotoxic T Lymphocyte Response," J Exp Med. Nov. 15, 2004;200(10):1243-56.
Allen et al. "De Novo Generation of Escape Variant-Specific CD8+ T-Cell Responses following Cytotoxic T-Lymphocyte Escape in Chronic Human Immunodeficiency Virus Type 1 Infection" J. Virol. Oct. 15, 2005; 79:20 12952-12960.
Feeney et al., "HIV-1 viral escape in infancy followed by emergence of a variant-specific CTL response," J Immunol. Jun. 15, 2005;174(12):7524-30.

(56) References Cited

OTHER PUBLICATIONS

Killian et al., "Clonal breadth of the HIV-1-specific T-cell receptor repertoire in vivo as determined by subtractive analysis," AIDS. Jun. 10, 2005;19(9):887-96.

Milicic et al., "CD8+ T Cell Epitope-Flanking Mutations Disrupt Proteasomal Processing of HIV-1 Nef," J Immunol 2005 175:4618-4626.

Kong et al., "Immunogenicity of Multiple Gene and Clade Human Immunodeficiency Virus Type 1 DNA Vaccines," J. Virol. Dec. 2003; 77:23 12764-12772.

Yusmin et al., "Clustering Patterns of Cytotoxic T-Lymphocyte Epitopes in Human Immunodeficiency Virus Type 1 (HIV-1) Proteins Reveal Imprints of Immune Evasion on HIV-1 Global Variation," J. Virol. Sep. 2002; 76:17 8757-8768.

Lee et al., "T Cell Cross-Reactivity and Conformational Changes during TCR Engagement," J Exp Med 2004 200:1455-1466.

Williamson et al., "Characterization and selection of HIV-1 subtype C isolates for use in vaccine development," AIDS Res Hum Retroviruses. Feb. 2003;19(2):133-44.

Frahm et al., "Consistent Cytotoxic-T-Lymphocyte Targeting of Immunodominant Regions in Human Immunodeficiency Virus across Multiple Ethnicities" J. Virol. Mar. 2004; 78:5 2187-2200.

Lichterfeld et al., "HIV-1 Nef is preferentially recognized by CD8 T cells in primary HIV-1 infection despite a relatively high degree of genetic diversity," AIDS. Jul. 2, 2004;18(10):1383-92.

Hel et al., "Improved Vaccine Protection from Simian AIDS by the Addition of Nonstructural Simian Immunodeficiency Virus Genes," J Immunol 2006 176:85-96.

Blagoveshchenskaya et al., "HIV-1 Nef downregulates MHC-I by a PACS-1- and PI3K-regulated ARF6 endocytic pathway," Cell. Dec. 13, 2002;111(6):853-66.

Masemola et al., "Hierarchical Targeting of Subtype C Human Immunodeficiency Virus Type 1 Proteins by CD8+ T Cells: Correlation with Viral Load," J. Virol. Apr. 2004; 78:7 3233-3243.

Bansal et al., "CD8 T-cell responses in early HIV-1 infection are skewed towards high entropy peptides," AIDS. Feb. 18, 2005;19(3):241-50.

Seaman et al., "Multiclade Human Immunodeficiency Virus Type 1 Envelope Immunogens Elicit Broad Cellular and Humoral Immunity in Rhesus Monkeys," J. Virol. Mar. 2005; 79:5 2956-2963.

Singh et al., "The Role of T Cell Antagonism and Original Antigenic Sin in Genetic Immunization," J Immunol 2002 169:6779-6786.

André et al., "Increased Immune Response Elicited by DNA Vaccination with a Synthetic gp120 Sequence with Optimized Codon Usage," J. Virol. Feb. 1998 ; 72:2 1497-1503.

Haas et al., "Codon usage limitation in the expression of HIV-1 envelope glycoprotein," Curr Biol. Mar. 1, 1996;6(3):315-24.

Ammaranond et al., "A new variant cytotoxic T lymphocyte escape mutation in HLA-B27-positive individuals infected with HIV type 1," AIDS Res Hum Retroviruses. May 2005;21(5):395-7.

Kiepiela et al., "Dominant influence of HLA-B in mediating the potential co-evolution of HIV and HLA," Nature. Dec. 9, 2004;432(7018):769-75.

European search report and opinion dated May 11, 2017.

Gag GenBank accession No. AF004885.

Gag GenBank accession No. K03455.

Gag GenBank Accession Nos. U52953, p. 1 of 4.

GenBank accession No. AF530576.

GenBank accession No. AF533131.

GenBank accession No. AY173953.

GenBank accession No. AY856956.

GenBank accession No. AY857186.

Go et al., "Giycosylation Site-Specific Analysis of Clade C HIV-1 Envelope Proteins", Journal ofProteome Research, 8(9):4231-4242 (Author Manuscript). (2009).

Hanke et al, "DNA multi-CTL epitope vaccines for HIV and Plasmodium falciparum: immunogenicity in mice", Vaccine, 16(4):426-435 (1998).

Liao et al., "A Group M Consensus Envelope Glycoprotein Induces Antibodies that Neutralize Subsets of Subtype Band C HIV-1 Primary Viruses", Virology, 353:268-282 (Author Manuscript). (2006).

Net core GenBank accession No. AF069670.

Net core GenBank accession No. K02083.

Tomaras et al., "Initial B-Cell Responses to Transmitted Human Immunodeficiency Virus Type 1: Virion-Binding Immunoglobulin M (IgM) and IgG Antibodies Followed by Plasma Anti-GP41 Antibodies with Ineffective Control of Initial Viremia", Journal of ViroloRJI, 82(24): 14229-14263. (2008).

Weaver et al., "Cross-Subtype T-Cell Immune Responses Induced by a Human Immunodeficiency Virus Type 1 Group M Consensus Env. Immunogen", Journal o/Virology, 80(14):6745-6756. (2006).

NEF core GenBank Accession Nos. U52953, p. 2 of 4.

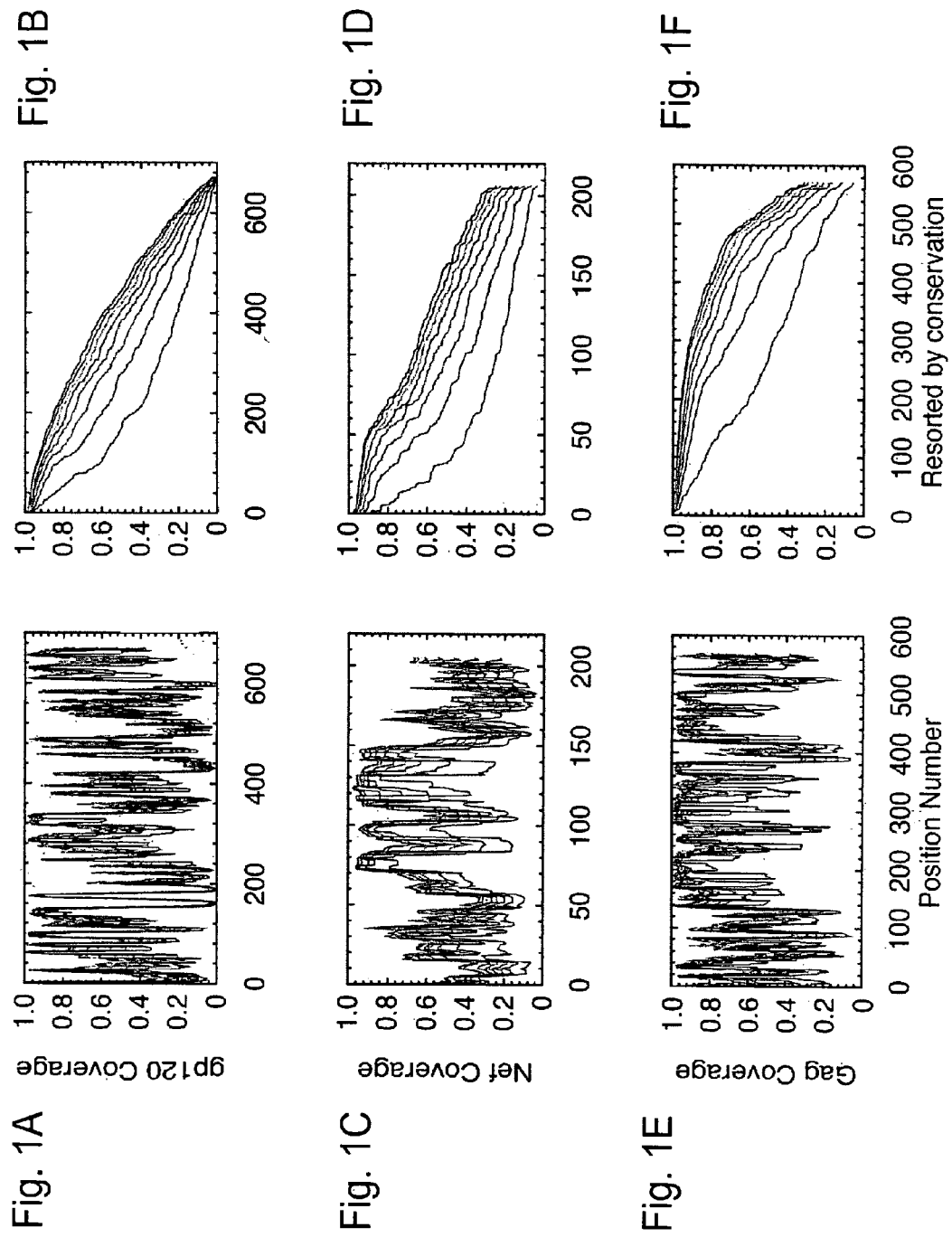

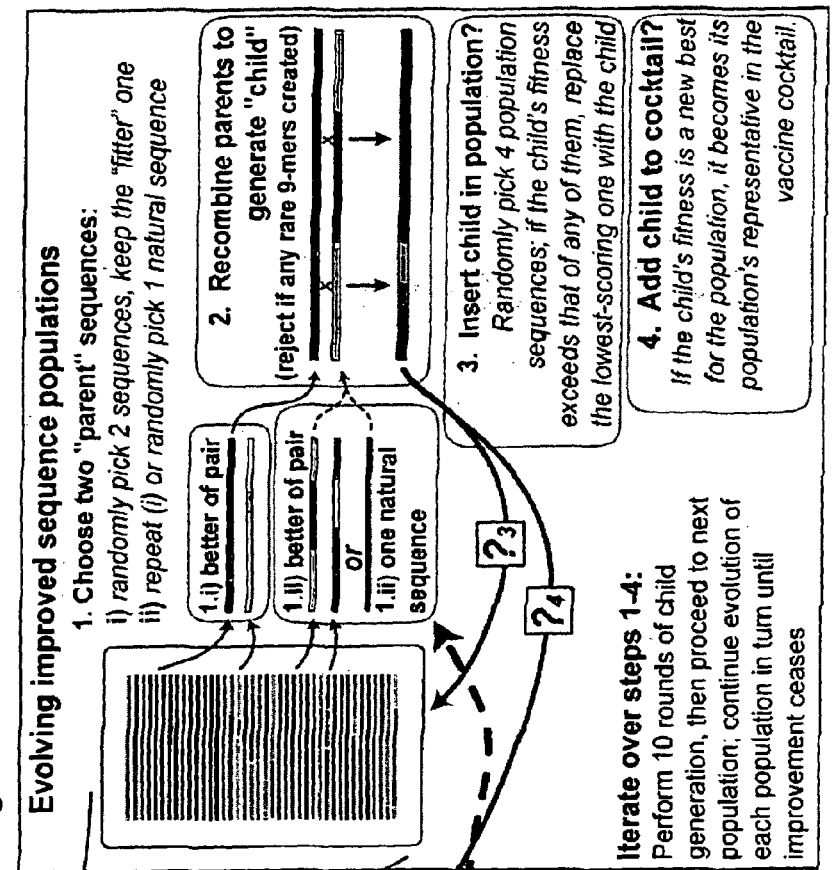
Fig. 2C
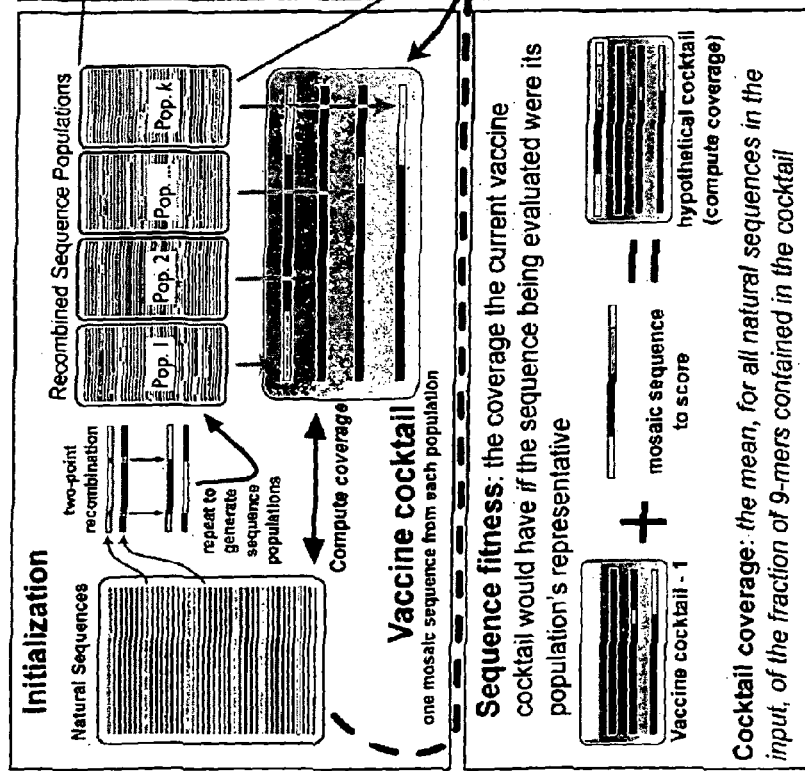
Fig. 2A
Fig. 2B

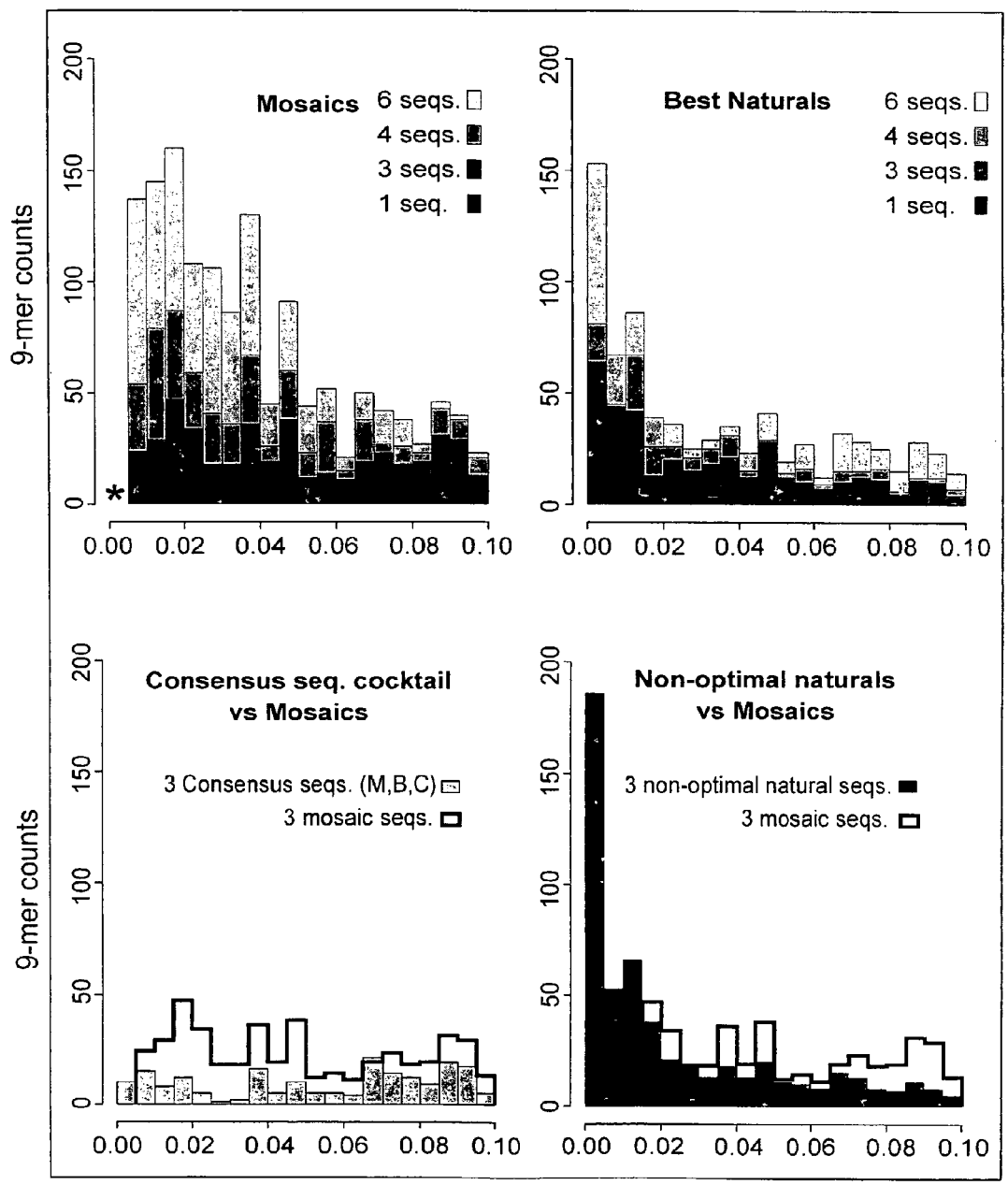

Fig. 9

```
>nef_coreB.syn1.1
EVGFPVRPQVPLRPMTYKGALDLSHFLKEKGGLEGLIYSQKRQDILDLWVYHTQGYFPDW
QNYTPGPGIRYPLTFGWCFKLVPVE >nef_coreB.syn3.1
EVGFPVKPQVPLRPMTYKAAVDLSHFLKEKGGLEGLVYSQKRQDILDLWIYHTQGYFPDW
QNYTPGPGTRFPLTFGWCFKLVPVD
>nef_coreB.syn3.2
EVGFPVTPQVPLRPMTYKGALDLSHFLREKGGLEGLIYSQKRQEILDLWVYHTQGYFPDW
HNYTPGPGVRYPLTFGWCFKLVPVE
>nef_coreB.syn3.3
EVGFPVRPQVPLRPMTYKAALDLSHFLKEKGGLEGLIHSQRRQDILDLWVYHTQGFFPDW
QNYTPGPGIRYPLTFGWCYKLVPVE >nef_coreB.syn4.1
EVGFPVTPQVPLRPMTYKAAVDLSHFLREKGGLEGLIHSQKRQDILDLWIYHTQGYFPDW
QNYTPGPGIRYPLTFGWCYKLVPVE
>nef_coreB.syn4.2
DVGFPVRPQIPLRPMTYKAALDLSHFLREKGGLEGLVYSQKRQDILDLWVYHTQGFFPDW
QNYTPGPGTRFPLTFGWCFKLVPVD
>nef_coreB.syn4.3
EVGFPVRPQVPLRPMTYKGAVDLSHFLKEKGGLEGLIYSQKRQEILDLWVYHTQGYFPDW
GNYTPGPGTRYPLTFGWCLKLVPVE
>nef_coreB.syn4.4
EVGFPVKPQVPLRPMTYKGALDLSHFLKEKGGLDGLIYSQRRQDILDLWVYNTQGYFPDW
HNYTPGPGVRYPLTFGWCFKLVPVE >nef_coreB.syn6.1
EVGFPIRPQVPLRPMTFKGALDLSHFLKEKGGLDGLIYSQKRQEILDLWVYHTQGYFPDW
HNYTPGPGIRYPLCFGWCFKLVPVE
>nef_coreB.syn6.2
EVGFPVTPQVPLRPMTYKGAVDLSHFLKEQGGLEGLIYSQRRQDILDLWIYNTQGYFPDW
QCYTPGPGVRFPLTFGWCFKLEPVD
>nef_coreB.syn6.3
EVGFPVKPQVPLRPMTYKAAVDLSHFLKEKGGLEGLIYSQKRQDILDLWIYHTQGYFPDW
QNYTPGPGIRYPLTFGWCLKLVPVE
>nef_coreB.syn6.4
DVGFPVRPQVPLRPMTYKAALDLSHFLKEEGGLEGLIYSQQRQDILDLWVYHTQGFFPDW
QNYTPGPGTRYPLTFGWCYKLVPVE
>nef_coreB.syn6.5
EVGFPVRPQIPLRPMTYKGALDLSHFLREKGGLEGLVYSQKRQDILDLWVHHTQGYFPDW
GNYTPGPGTRFPLTFGWCFKLVPVD
>nef_coreB.syn6.6
EVGFPVRPQVPLRPMTYKGAFDLSHFLKDKGGLEGLIHSQKRQDILDLWVYNTQGYFPDW
QNYTPGPGVRYPLTFGWCFKLVPLE >nef_coreC.syn1.1
EVGFPVRPQVPLRPMTYKAAFDLSFFLKEKGGLEGLIYSKKRQEILDLWVYHTQGFFPDW
QNYTPGPGVRYPLTFGWCFKLVPVD
```

Fig. 9 cont'd-1

>nef_coreC.syn3.1
EVGFPVTPQVPLRPMTFKGAFDLGFFLKEKGGLDGLIYSKKRQDILDLWVYHTQGYFPDW
QNYTPGPGVRYPLTFGWCYKLVPVD
>nef_coreC.syn3.2
EVGFPVKPQVPLRPMTYKAAFDLSFFLKDKGGLEGLIWSKKRQEILDLWVYHTQGFFPDW
QNYTPGPGIRYPLTFGWPFKLVPVD
>nef_coreC.syn3.3
EVGFPVRPQVPLRPMTYKGAFDLSFFLKEKGGLEGLIYSKKRQEILDLWVYNTQGFFPDW
HNYTPGPGVRFPLTFGWCFKLVPVD >nef_coreC.syn4.1
EVGFPVRPQVPLRPMTYKGAFDLSFFLKEKGGLEGLIWSKKRQEILDLWVYNTQGYFPDW
QCYTPGPGVRFPLTFGWCFKLVPVD
>nef_coreC.syn4.2
DVGFPVRPQVPVRPMTYKAAFDLSFFLKDKGGLEGLIHSKRRQDILDLWVYNTQGFFPDW
HNYTPGPGIRYPLTFGWCFKLVPVD
>nef_coreC.syn4.3
EVGFPVKPQVPLRPMTYKAAVDLSFFLKEKGGLEGLIYSKKRQEILDLWVYHTQGFFPDW
QNYTPGPGTRYPLTFGWPFKLVPVD
>nef_coreC.syn4.4
EVGFPVTPQVPLRPMTFKGAFDLGFFLKEKGGLDGLIYSKKRQDILDLWVYHTQGYFPDW
QNYTPGPGVRYPLTFGWCYKLVPVD >nef_coreC.syn6.1
DVGFPVRPQVPLRPMTYKGAFDLSFFLKEKGGLDGLIYSKKRQEILDLWVYNTQGYFPDW
QCYTPGPGVRYPLTFGWCYKLVPVD
>nef_coreC.syn6.2
EVGFPVKPQVPVRPMTYKAAFDLSFFLKDKGGLEGLIWSKKRQEILDLWVYHTQGFFPDW
QNYTPGPGIRYPLTFGWCFKLVPVD
>nef_coreC.syn6.3
EVGFPVKPQVPLRPMTFKGAFDLGFFLKEKGGLEGLIYSKQRQDILDLWVYHTQGFFPDW
HNYTPGPGVRLPLTFGWCFKLVPVD
>nef_coreC.syn6.4
GVGFPVRPQVPVRPMTYKAAFDLGFFLKDKGGLEGLIYSKKRQDILDLWVYNTQGFFPDW
QNYTPGPGVRFPLTFGWCFKLVPVD
>nef_coreC.syn6.5
EVGFPVTPQVPLRPMTYKAAVDLSWFLKEKGGLDGLIYSRKRQEILDLWVHHTQGFFPDW
QNYTPGPGTRFPLTFGWCFKLVPVD
>nef_coreC.syn6.6
EVGFPVRPQVPVRPMTYKGAVDLSFFLKEKGGLEGLIHSKRRQDILDLWVYHTQGYFPDW
QNYTPGPGTRYPLTFGWPFKLVPVD >nef_coreM.syn1.1
EVGFPVRPQVPLRPMTYKGALDLSHFLKEKGGLEGLIYSKKRQEILDLWVYHTQGYFPDW
QNYTPGPGVRYPLTFGWCFKLVPVD

Fig. 9 cont'd-2

```
>nef_coreM.syn3.1
DVGFPVRPQVPLRPMTYKAAVDLSHFLKEKGGLEGLVYSQKRQDILDLWVYHTQGFFPDW
QNYTPGPGVRYPLTFGWCYKLVPVD
>nef_coreM.syn3.2
EVGFPVRPQVPVRPMTYKGAFDLSFFLKEKGGLEGLIYSKKRQEILDLWVYHTQGYFPDW
HNYTPGPGTRFPLTFGWCFKLVPVD
>nef_coreM.syn3.3
EVGFPVKPQVPLRPMTYKGALDLSHFLKEKGGLDGLIYSKKRQDILDLWVYNTQGYFPDW
QNYTPGPGIRYPLTFGWCFKLVPVE >nef_coreM.syn4.1
EVGFPVTPQVPLRPMTFKGAFDLGFFLKEKGGLEGLIYSKKRQEILDLWVYHTQGFFPDW
QNYTPGPGTRYPLCFGWCFKLVPVE
>nef_coreM.syn4.2
EVGFPVKPQVPLRPMTYKAAVDLSHFLKEKGGLEGLVYSQKRQDILDLWVYHTQGYFPDW
QNYTPGPGIRYPLTFGWCYKLVPVD
>nef_coreM.syn4.3

DVGFPVRPQVPLRPMTYKGALDLSHFLKEEGGLEGLIYSQKRQEILDLWVYNTQGYFPDW
QNYTPGPGVRYPLTFGWCFKLVPVD
>nef_coreM.syn4.4
EVGFPVRPQVPVRPMTYKGAFDLSFFLKEKGGLDGLIYSKKRQDILDLWVYNTQGFFPDW
HNYTPGPGTRFPLTFGWCFELVPVD >nef_coreM.syn6.1
EVGFPVRPQVPTRPMTYKGAVDLSHFLKEKGGLEGLVYSQKRQDILDLWVHHTQGFFPDW
QNYTPGPGTRYPLTFGWPFKLVPVD
>nef_coreM.syn6.2
DVGFPVRPQVPVRPMTYKAAFDLSFFLREKGGLDGLIYSKKRQDILDLWVYNTQGYFPDW
QNYTPGPGVRFPLTFGWCFELVPVD
>nef_coreM.syn6.3
NVGFPVRPQVPLRPMTFKGAFDLGFFLKEKGGLEGLIYSKKRQEILDLWVYHTQGYFPDW
HNYTPGPGTRFPLTFGWCFKLVPVE
>nef_coreM.syn6.4
EVGFPVTPQVPLRPMTYKGAFDLSFFLKEKGGLDGLIYSRKRQEILDLWVYNTQGFFPDW
QNYTPGPGIRYPLTFGWCFKLVPMD
>nef_coreM.syn6.5
EVGFPVKPQVPLRPMTYKAAVDLSHFLREKGGLEGLIHSQRRQDILDLWIYHTQGYFPDW
QCYTPGPGVRYPLTFGWCYKLVPVD
>nef_coreM.syn6.6
GVGFPVRPQIPLRPMTYKGALDLSHFLKEEGGLEGLIYSQKRQDILDLWVYHTQGFFPDW
HNYTPGPGIRYPLCFGWCFKLVPVD
```

Fig. 9 cont'd-3

```
>gagB.syn1.1
MGARASVLSGGELDRWEKIRLRPGGKKKYKLKHIVWASRELERFAVNPGLLETSEGCRQI
LGQLQPSLQTGSEELRSLYNTVATLYCVHQRIEVKDTKEALDKIEEEQNKSKKKAQQAAA
DTGNSSQVSQNYPIVQNLQGQMVHQAISPRTLNAWVKVVEEKAFSPEVIPMFSALSEGAT
PQDLNTMLNTVGGHQAAMQMLKETINEEAAEWDRLHPVHAGPIAPGQMREPRGSDIAGTT
STLQEQIGWMTNNPPIPVGEIYKRWIILGLNKIVRMYSPTSILDIRQGPKEPFRDYVDRF
YKTLRAEQASQEVKNWMTETLLVQNANPDCKTILKALGPAATLEEMMTACQGVGGPGHKA
RVLAEAMSQVTNSATIMMQRGNFRNQRKTVKCFNCGKEGHIAKNCRAPRKKGCWKCGKEG
HQMKDC-TERQANFLGKIWPSHKG-RPGNFLQSRP-----------------EPTAP
PEESFRFGEETTTPSQKQEPIDKELYPLASLRSLFGNDPSSQ >gagB.syn3.1
MGARASILSGGELDRWEKIRLRPGGKKQYRLKHIVWASRELERFAINPGLLETSDGCRQI
LGQLQPALQTGSEELKSLFNTVATLYCVHQRIDVKDTKEALDKIEEEQNKSKKKAQQAAA
DTGNSSQVSQNYPIVQNIQGQMVHQAISPRTLNAWVKVIEEKAFSPEVIPMFSALSEGAT
PQDLNTMLNTVGGHQAAMQMLKETINEEAADWDRLHPVHAGPIAPGQMREPRGSDIAGTT
STLQEQIGWMTNNPPIPVGEIYKRWIIMGLNKIVRMYSPSSILDIKQGPKEPFRDYVDRF
YKVLRAEQASQEVKNWMTETLLVQNSNPDCKTILKALGPGATLEEMMTACQGVGGPGHKA
RVLAEAMSQMTNSATIMMQKGNFRNQRKPVKCFNCGKEGHIAKNCRAPRKKGCWKCGREG
HQMKDC-TERQANFLGKIWPSYKG-RPGNFLQNRP-----------------EPTAP
PAESFRFGEETTTPSQKQETIDKELYPLASLRSLFGSDPSSQ >gagB.syn3.2
MGARASVLSGGQLDRWEKIRLRPGGKKKYRLKHLVWASRELERFAVNPGLLETAEGCRQI
LEQLQPSLQTGSEELRSLFNTVAVLYCVHQRIEVKDTKEALDKVEEEQNKSKKKAQQTAA
DTGNNSQVSQNYPIVQNMQGQMVHQALSPRTLNAWVKVIEEKAFSPEVIPMFTALSEGAT
PQDLNTMLNTVGGHQAAMQMLKDTINEEAAEWDRLHPVQAGPVAPGQIREPRGSDIAGST
STLQEQIGWMTSNPPIPVGEIYKRWIILGLNKIVRMYSPVSILDIRQGPKEPFRDYVDRF
YKTLRAEQATQEVKNWMTETLLVQNANPDCKTILKALGPGATLEEMMTACQGVGGPSHKA
RVLAEAMSQVTNSATIMMQRGNFRNQRKIVKCFNCGKEGHIARNCRAPRKRGCWKCGKEG
HQMKDC-NERQANFLGKIWPSHKG-RPGNFLQSRP-----------------EPSAP
PEESFRFGEEKTTPSQKQEPIDKDLYPLASLKSLFGNDPSLQ >gagB.syn3.3
MGARASVLSGGELDKWEKIRLRPGGKKKYKLKHIVWASRELERFAVNPGLLETSEGCRQI
LGQLQPSLQTGSEELRSLYNTVATLYCVHQKIEVKDTKEALEKIEEEQNKCKKKAQQAAA
GTGNSSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTHNPPIPVGDIYKRWIILGLNKIVRMYSPTSILDIRQGPKESFRDYVDRF
YKTLRAEQASDVKNWMTETLLVQNANPDCRTILKALGPAATLEEMMTACQGVGGPSHKA
RILAEAMSQVTNPATIMMQRGNFRNQRKTVKCFNCGKEGHLARNCRAPRKKGCWKCGKEG
HQMKEC-TERQANFLGKIWPSHKG-RPGNFLQSRP-----------------EPTAP
PEESFRFGEETATPPQKQEPIDKELYPLTSLRSLFGNDPSSQ >gagB.syn4.1
MGARASVLSGGQLDRWEKIRLRPGGKKKYRLKHLVWASRELERFAVNPGLLETAEGCRQI
LEQLQPSLQTGSEELRSLFNTVATLYCVHQRIDVKDTKEALDKIEEEQNKCKKKAQQAAA
DTGNSSQVSQNYPIVQNIQGQMVHQALSPRTLNAWVKVVEEKAFSPEVIPMFTALSEGAT
PQDLNTMLNTVGGHQAAMQMLKETINEEAAEWDRLHPVQAGPVAPGQMREPRGSDIAGST
STLQEQIGWMTNNPPIPVGDIYKRWIILGLNKIVRMYSPVSILDIRQGPKESFRDYVDRF
YKVLRAEQASQEVKNWMTETLLVQNANPDCRTILKALGPAATLEEMMTACQGVGGPGHKA
```

Fig. 9 cont'd-4

```
RVLAEAMSQMTNSATIMMQRGNFRNQRKTVKCFNCGKEGHIAKNCRAPRKKGCWKCGKEG
HQMKEC-TERQANFLGKIWPSYKG-RPGNFLQSRP------------------EPSAP
PAESFRFGEETTTPSQKQETIDKELYPLTSLRSLFGNDPSLQ
>gagB.syn4.2
MGARASVLSGGELDKWEKIRLRPGGKKKYKLKHIVWASRELERFAINPGLLETSEGCRQI
LGQLQPALQTGSEELRSLYNTVATLYCVHQKIEVKDTKEALEKVEEEQNKSKQKAQQAAA
DTGNNSQVSQNYPIVQNLQGQMVHQAISPRTLNAWVKVIEEKAFSPEVIPMFAALSEGAT
PQDLNTMLNTVGGHQAAMQMLKETINEEAADWDRLHPVHAGPIAPGQIREPRGSDIAGTT
SNLQEQIAWMTNNPPIPVGEIYKRWIIMGLNKIVRMYSPTSILDIKQGPKEPFRDYVDRF
YRTLRAEQASQDVKNWMTETLLVQNANPDCRTILKALGPGATLEEMMTACQGVGGPSHKA
RVLAEAMSQVTNPATIMMQRGNFRNQRKPVKCFNCGKEGHLAKNCRAPRKRGCWKCGKEG
HQMKDC-NERQANFLGKIWPSHKG-RPGNFLQNRP------------------EPSAP
PEESFRFGEETATPSQKQEPIDKELYPLASLRSLFGSDPSSQ
>gagB.syn4.3
MGARASILSGGELDRWEKIRLRPGGKKQYRLKHIVWASRELERFAVNPGLLETSEGCKQI
LEQLQPALQTGSEELKSLYNTVAVLYCVHQRIEIKDTKEALEKIEEEQNKSKKKAQQTAA
DTGNNSQVSQNYPIVQNLQGQMVHQPISPRTLNAWVKVIEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTSNPPIPVGEIYKRWIILGLNKIVRMYSPTSILDIRQGPKEPFRDYVDRF
YKTLRAEQATQEVKNWMTETLLVQNANPDCKTILKALGPGATLEEMMTACQGVGGPSHKA
RILAEAMSQVTNSATVMMQRGNFRNQRKTIKCFNCGKEGHLARNCRAPRKKGCWKCGREG
HQMKDC-TERQANFLGKIWPSYKG-RPGNFLQNRP------------------EPTAP
PAESFRFGEETTTPPQKQEPIDKELYPLASLKSLFGNDPSSQ
>gagB.syn4.4
MGARASVLSGGKLDKWEKIRLRPGGKKKYQLKHIVWASRELERFALNPGLLETSDGCRQI
LGQLQPSLQTGSEELKSLFNTVAVLYCVHQRIEVKDTKEALDKVEEEQNKSKKKAQQAAA
GTGNSSQVSQNYPIVQNMQGQMVHQALSPRTLNAWVKVIEEKAFSPEVIPMFSALSEGAT
PQDLNTMLNTVGGHQAAMQMLKDTINEEAAEWDRVHPVHAGPIAPGQMREPRGSDIAGTT
STLQEQIGWMTHNPPIPVGEIYKRWIILGLNKIVRMYSPSSILDIRQGPKEPFRDYVDRF
YKTLRAEQASQEVKNWMTETLLVQNSNPDCKTILKALGPAATLEEMMTACQGVGGPSHKA
RVLAEAMSQVTNSATIMMQKGNFRNQRKIVKCFNCGKEGHIARNCRAPRKKGCWRCGKEG
HQMKDC-TERQVNFLGKIWPSYKG-RPGNFLQSRP------------------EPTAP
PEESFRFGEEKTTPSQKQEPIDKDLYPLASLKSLFGNDPLSQ >gagB.syn6.1
MGARASILSGGELDRWEKIRLRPGGSKKYRLKHIVWASRELERFAVNPGLLETAEGCRQI
LGQLQPSLQTGSEELRSLYNTIATLYCVHQRIEIKDTKEALEKIEEEQNKSKKKAQQTAA
DTGNNSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQIREPRGSDIAGTT
SNLQEQIGWMTSNPPIPVGEIYKRWIILGLNKIVRMYSPISILDIRQGPKEPFRDYVDRF
YRTLRAEQASQDVKNWMTETLLVQNANPDCKTILKALGPGATLEEMMTACQGVGGPGHKA
RVLAEAMSQVTNSATVMMQRGNFRNQRRTVKCFNCGKEGHIARNCRAPRKKGCWKCGQEG
HQMKDC-TERQANFLGKIWPSYKG-RPGNFLQSRP------------------EPTAP
PAESFRFGEETTTPPQKQEPIDKELYPLTSLKSLFGNDPSSQ
>gagB.syn6.2
MGARASVLSGGKLDRWEKIRLRPGGKKKYRLKHVVWASRELERFAVNPGLLESSEGCRQI
LEQLQPSLQTGSEELRSLFNTVATLYCVHQRIDVKDTKEALDKIEEEQNKCKKKAQQAAA
DTGNNSQVSQNYPIVQNLQGQMVHQPISPRTLNAWVKVVEEKAFSPEVIPMFAALSEGAT
PQDLNTMLNTVGGHQAAMQMLKETINEEAAEWDRVHPVHAGPIAPGQMREPRGSDIAGST
STLQEQIGWMTNNPPIPVGDIYKRWIILGLNKIVRMYSPASILDIRQGPKEPFRDYVDRF
YKTLRAEQATQEVKNWMTETLLVQNANPDCRTILKALGPGATLEEMMTACQGVGGPGHKA
RVLAEAMSQMTNSATIMMQKGNFRNQRKTIKCFNCGKEGHIARNCKAPRKKGCWKCGREG
HQMKDC-IERQANFLGKIWPSHKG-RPGNFLQNRP------------------EPTAP
PEESFRFGEETATPPQKQEPIDKELYPLASLKSLFGSDPSSQ
```

Fig. 9 cont'd-5

>gagB.syn6.3
MGARASVLSGGELDRWEKIRLRPGGKKKYRLKHLVWASRELERFAVNPGLLETSDGCRQI
LGQLQPALQTGSEELKSLYNTVATLYCVHQKIDVRDTKEALDKIEEEQNKSKQKAQQAAA
DTGNSSQVSQNYPIVQNIQGQMVHQAISPRTLNAWVKVVEEKAFSPEVIPMFTALSEGAT
PQDLNTMLNTVGGHQAAMQMLKETINEEAAEWDRLHPVQAGPVAPGQMREPRGSDIAGTT
STLQEQIGWMTHNPPIPVGEIYKRWIIMGLNKIVRMYSPSSILDIRQGPKESFRDYVDRF
YKVLRAEQASQEVKNWMTETLLVQNANPDCKTILKALGPGATLEEMMTACQGVGGPSHKA
RVLAEAMSQVTNSATIMMQRGNFRNQRKTVKCFNCGKEGHIAKNCRAPRKRGCWKCGKEG
HQMKEC-TERQANFLGKIWPSHKG-RPGNFLQSRP-------------------EPTAP
PEESFRFGEEKTTPSQKQETIDKELYPLASLRSLFGNDPSSQ
>gagB.syn6.4
MGARASVLSGGELDKWEKIRLRPGGKKKYQLKHIVWASRELERFAVNPGLLETSEGCKQI
LEQLQPALQTGSEELRSLYNTIAVLYCVHQKIEIKDTKEALDKVEEEQNKSKKKAQQAAA
GTGNSSQVSQNYPIVQNLQGQMVHQPLSPRTLNAWVKVVEEKAFSPEVIPMFTALSEGAT
PQDLNTMLNTVGGHQAAMQMLKETINEEAADWDRLHPVHAGPIAPGQMREPRGSDIAGST
STLQEQIGWMTHNPPIPVGDIYKRWIILGLNKIVRMYSPTSILDIKQGPKEPFRDYVDRF
YKTLRAEQATQEVKNWMTETLLVQNANPDCRTILKALGPAATLEEMMTACQGVGGPSHKA
RILAEAMSQVTNPATIMMQRGNFRNQRKPVKCFNCGKEGHIARNCRAPRKRGCWKCGKEG
HQMKDC-TERQVNFLGKIWPSHKG-RPGNFLQNRP-----------------EPSAP
PAESFRFGEETTTPSQKQEPIDKEMYPLASLRSLFGSDPSSQ
>gagB.syn6.5
MGARASVLSGGQLDRWEKIRLRPGGKKQYRLKHIVWASRELERFAINPGLLETSEGCRQI
LGQLQPSLQTGSEELKSLFNTVAVLYCVHQRIEVKDTKEALEKVEEEQNKSKKKAQQAAA
DTGNSSQVSQNYPIVQNLQGQMVHQALSPRTLNAWVKVIEEKAFSPEVIPMFSALSEGAT
PQDLNTMLNTVGGHQAAMQMLKDTINEEAAEWDRLHPVHAGPVAPGQMRDPRGSDIAGTT
STLQEQIAWMTNNPPIPVGEIYKRWIILGLNKIVRMYSPTSILDIRQGPKEPFRDYVDRF
YKVLRAEQASQDVKNWMTETLLVQNANPDCKTILKALGPAATLEEMMTACQGVGGPGHKA
RVLAEAMSQVTNSTTIMMQRGNFRNQRKIVKCFNCGKEGHLAKNCRAPRKKGCWKCGKEG
HQMKEC-TERQANFLGKIWPSHKG-RPGNFLQSRP-------------------EPSAP
PEESFRFGEETATPSQKQEPIDKDLYPLASLKSLFGNDPLSQ
>gagB.syn6.6
MGARASVLSGGKLDKWEKIRLRPGGKKKYKLKHIVWASRELERFALNPGLLETSEGCRQI
LRQLQPSLQTGSEELRSLYNTVATLYCVHQKIEVKDTKEALEKIEEEQNKSKKKAQQTAA
DTGNNSQVSQNYPIVQNMQGQMVHQALSPRTLNAWVKVVEEKAFSPEVIPMFSALSEGAT
PQDLNTMLNTVGGHQAAMQMLKDTINEEAAEWDRLHPAQAGPIAPGQIREPRGSDIAGTT
SNLQEQIAWMTHNPPIPVGDIYKRWIILGLNKIVRMYSPVSILDIRQGPKEPFRDYVDRF
YKTLRAEQASQEVKNWMTETLLVQNSNPDCKTILKALGPGATLEEMMTACQGVGGPGHKA
RVLAEAMSQVTNPATIMMQKGNFKNQRKTVKCFNCGKEGHLARNCRAPRKKGCWRCGKEG
HQMKDC-NERQANFLGKIWPSHKG-RPGNFLQSRP-------------------EPTAP
PEESFRFGEETTTPAQKQEPIDKELYPLTSLRSLFGNDPSLQ
>gagC.syn1.1
MGARASILRGGKLDKWEKIRLRPGGKKHYMLKHLVWASRELERFALNPGLLETSEGCKQI
IKQLQPALQTGTEELRSLYNTVATLYCVHEKIEVRDTKEALDKIEEEQNKSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGDIYKRWIILGLNKIVRMYSPVSILDIKQGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ
>gagC.syn3.1
MGARASVLRGEKLDKWERIRLRPGGKKHYMLKHLVWASRELERFALNPSLLETSEGCKQI
IQQLQPALKTGTEELRSLFNTVATLYCVHAGIEVRDTKEALDKIEEEQNKCQQKTQQAKE
ADG---KVSQNYPIVQNLQGQMVHQALSPRTLNAWVKVIEEKAFSPEVIPMFTALSEGAT

Fig. 9 cont'd-6

```
PSDLNTMLNTVGGHQAAMQMLKDTINEEAAEWDRLHPVQAGPVAPGQMREPRGSDIAGTT
SNLQEQIAWMTGNPPVPVGDIYKRWIILGLNKIVRMYSPVSILDIRQGPKEPFRDYVDRF
FKTLRAEQSTQEVKNWMTETLLVQNANPDCKTILRALGPAASLEEMMTACQGVGGPSHKA
RVLAEAMSQ-ANSTNIMMQRGNFKGPKRIIKCFNCGKEGHLARNCRAPRKKGCWKCGKEG
HQMKDC-IERQANFLGKIWPSNKG-RPGNFLQNRPE------PTAPPVEPTAPPAEPTAP
PAESFKFEE--TTPAPKQEPKDRE--PLTSLRSLFGSDPLSQ
>gagC.syn3.2
MGARASILRGEKLDTWEKIRLRPGGRKHYMLKHIVWASRELEKFALNPGLLETSEGCKQI
MKQLQPALQTGTEELKSLYNTVATLYCVHEKIEVRDTKEAVDKIEEEQNKSQQKTQQAKA
ADE---KVSQNYPIVQNIQGQMVHQPISPRTLNAWVKVIEEKGFNPEVIPMFTALSEGAT
PQDLNTMLNTVGGHQAAMQMLKDTINDEAAEWDRLHPVHAGPIAPGQMREPRGSDIAGST
STLQEQITWMTSNPPVPVGEIYKRWIILGLNKIVRMYSPVSILDIKQGPKEPFRDYVDRF
FKVLRAEQATQDVKNWMTDTLLIQNANPDCKTILKALGPGASLEEMMTACQGVGGPGHKA
RVLAEAMSQ-ANNTNIMMQRSNFKGPKRIVKCFNCGKEGHIAKNCRAPRKKGCWKCGQEG
HQMKDC-TERQANFLGKIWPSQKG-RPGNFLQNRP------------------EPSAP
PAESFRFGE--TTPAPKQELKDRE--PLTSLKSLFGSDPLSQ
>gagC.syn3.3
MGARASILRGGKLDKWEKIRLRPGGKKRYMLKHLIWASRELERFALNPGLLETAEGCKQI
IKQLQPALQTGTEELRSLYNTVATLYCVHKRIDVRDTKEALDKIEEEQNKIQQKTQQAKA
ADG---KVSQNYPIVQNAQGQMVHQAISPRTLNAWVKVVEEKAFSPEIIPMFTALSEGAT
PQDLNSMLNAVGGHQAAMQMLKDTINEEAAEWDRVHPVHAGPVAPGQIREPRGSDIAGTT
STLQEQIAWMTSNPPIPVGDIYKRWIIMGLNKIVRMYSPVSILDIKQGPKESFRDYVDRF
FKTLRAEQATQEVKNWMTDTLLVQNANPDCKTILRALGPGATLEEMMTACQGVGGPSHKA
RVLAEAMSQ-TNSA-ILMQRSNFKGSKRIVKCFNCGKEGHIARNCRAPRKRGCWKCGKEG
HQMKEC-TERQANFLGKIWPSHKG-RPGNFLQSRP------------------EPTAP
PAESFRFEE--TTPAPKQESKDRE--PLISLKSLFGNDPLSQ >gagC.syn4.1
MGARASVLRGEKLDTWERIKLRPGGKKHYMIKHLVWASRELEKFALNPGLLETSEGCKQI
IQQLQPALKTGTEELKSLYNTVATLYCVHERIDVRDTKEALDKIEEEQNKIQQKTQQAKE
ADG---KVSQNYPIVQNAQGQMVHQALSPRTLNAWVKVVEEKAFSPEIIPMFTALSEGAT
PSDLNTMLNTIGGHQAAMQMLKDTINDEAAEWDRLHPVHAGPIAPGQIREPRGSDIAGTT
STLQEQITWMTSNPPVPVGEIYKRWIILGLNKIVRMYSPVSILDIKQGPKESFRDYVDRF
FKTLRAEQSTQEVKNWMTETLLVQNANPDCKTILKALGPGATLEEMMTACQGVGGPGHKA
RVLAEAMSQ-TNSA-ILMQRSNFKGSKRIVKCFNCGREGHIARNCKAPRKKGCWKCGKEG
HQMKDC-IERQANFLGKIWPSHKG-RPGNFLQNRPE------PTAPP--------EPTAP
PAESFRFGE--TTPAPKQEQKDRE--PLISLKSLFGSDPLLQ
>gagC.syn4.2
MGARASILRGEKLDKWERIRLRPGGKKHYMLKHLVWASRELDRFALNPGLLETSDGCKQI
IKQLHPALQTGTEELRSLFNTVATLYCVHAGIEVRDTKEAVDKIEEEQNKSQQKTQQAKA
ADE---KVSQNYPIVQNIQGQMVHQPISPRTLNAWVKVIEEKAFSPEVIPMFTALSDGAT
PQDLNTMLNTVGGHQAAMQMLKDTINEEAAEWDRIHPVHAGPVAPGQMRDPRGSDIAGST
STLQEQIAWMTNNPPVPVGDIYKRWIIMGLNKIVRMYSPVSILDIRQGPKEPFRDYVDRF
FRTLRAEQATQDVKNWMTDTLLIQNANPDCKTILRALGPGASLEEMMTACQGVGGPGHKA
RVLAEAMSQ-ANNTNIMMQKSNFKGPKRTVKCFNCGKEGHIARNCRAPRKRGCWKCGKEG
HQMKEC-TERQANFLGKIWPSQKG-RPGNFLQSRP------------------EPSAP
PAESFRFEE--TTPAPKQESKDRE--PLTSLKSLFGSDPSSQ
>gagC.syn4.3
MGARASILRGGKLDTWEKIRLRPGGKKRYMLKHLIWASRELERFALNPSLLETSEGCKQI
MKQLQPALQTGTEELRSLYNTVATLYCVHKGIKVQDTKEALDKIEEEQKKSQQKTQQAEA
ADK--GKVSQNYPIVQNLQGQMVHQPLSPRTLNAWVKVIERKAFSPEVIPMFSALSEGAT
PQDLNSMLNAVGGHQAAMQMLKDTINEEAAEWDRVHPVHAGPIAPGQMREPRGSDIAGTT
SNLQEQIAWMTSNPPIPVGDIYKRWIVLGLNKIVRMYSPVSILDIKQGPKEPFRDYVDRF
FKTLRAEQATQEVKNWMTDTLLVQNANPDCKTILRALGPAASLEEMMTACQGVGGPGHKA
```

Fig. 9 cont'd-7

```
RVLAEAMSQ-ANS-NIMMQRGNFKGPKRIIKCFNCGKEGHLARNCRAPRKKGCWKCGREG
HQMKDC-TERQANFLGKIWPSNKG-RPGNFLQSRP-------------------EPTAP
PAESFGFGE--TTPAPKQELKDRE--PLTSLKSLFGNDPLSQ
>gagC.syn4.4
MGARASILRGGKLDKWEKIRLRPGGRKHYMLKHIVWASRELERFALNPGLLETAEGCKQI
IKQLQPALQTGTEELKSLFNTVATLYCVHEKIEVRDTKEALDKIEEEQNKCQQKTQQAKA
ADG---KVSQNYPIVQNLQGQMVHQAISPRTLNAWVKVIEEKGFNPEVIPMFTALSEGAA
PQDLNTMLNTIGGHQAAMQMLKDTINEEAAEWDRLHPVQAGPVAPGQMREPRGSDIACTT
SSLQEQIAWMTGNPPVPVGDIYKRWIILGLNKIVRMYSPVSILDIRQGPKEPFRDYVDRF
FKVLRAEQATQDVKNWMTETLLVQNANPDCKTILRALGPGATLEEMMTACQGVGGPSHKA
RVLAEAMSQ-ANNANIMMQRSNFKGPKRIVKCFNCGKEGHIAKNCRAPRKKGCWKCGQEG
HQMKDC-NERQANFLGRIWPSHKG-RPGNFIQSRPEPTAPLEPTAPPA-------EPTAP
PAESFKFEE--TTPAPKQEPKDRE--PLTSLRSLFGSDPLSQ >gagC.syn6.1
MGARASVLRGEKLDTWERIKLRPGGKKHYMIKHLVWASRELEKFALNPGLLETAEGCKQI
IRQLQPALQTGTEELRSLYNTVATLYCVHKRIDVRDTKEALDKIEEEQNKSQQKAQQAKA
ADG---KVSQNYPIVQNLQGQMVHQSLSPRTLNAWVKVIERKAFSPEVIPMFSALSEGAT
PQDLNTMLNTVGGHQAAMQMLKDTINEEAAEWDRIHPVHAGPIAPGQMREPRGSDIAGTT
STLQEQITWMTSNPPVPVGEIYKRWIILGLNKIVRMYSPVSILDIRQGPKEPFRDYVDRF
FKTLRAEQSTQEVKNWMTDTLLAQNANPDCKIILRGLGPGATLEEMMTACQGVGGPGHKA
RVLAEAMSQ-ANS-NILMQRSNFKGPRRTIKCFNCGKEGHLAKNCRAPRKKGCWKCGKEG
HQMKEC-TERQANFLGKIWPSQKG-RPGNFLQSRP-------------------EPSAP
PAESFRFEE--TTPALKQEPKDRE--PLTSLRSLFGSDPLSQ
>gagC.syn6.2
MGASASILRGEKLDRWEKIRLRPGGKKCYMLKHIIWASKELERFALNPGLLETSEGCKQI
MKQLQPALQTGTEELKSLYNTVATLYCVHEKIEVRDTKEALDKIEEEQKKSQQKTQQAEA
ADK--GKVSQNYPIVQNAQGQMVHQALSPRTLNAWVKVVEEKAFSPEIIPMFTALSEGAA
PQDLNTMLNTVGGHQAAMQMLKDTINEEAAEWDRVHPVHAGPIAPGQIREPRGSDIAGTT
STLQEQVAWMTSNPPVPVGDIYKRWIVLGLNKIVRMYSPVSILDIKQGPKEPFRDYVDRF
FKTLRAEQSSQEVKNWMTDTLLVQNANPDCKTILRALGPAASLEEMMTACQGVGGPSHKA
RVLAEAMSQ-ANSTNIMMQRGNFKGPKRIVKCFNCGREGHIARNCRAPRKKGCWKCGQEG
HQMKDC-IERQANFLGKIWPSHKG-RPGNFIQSRPE------PTAPP--------EPTAP
PAESFRFGE--TTPAPKQESKDRE--PLTSLKSLFGNDPLSQ
>gagC.syn6.3
MGARASVLKGEKLDKWERIRLRPGGKKQYRLKHLVWASRELERFALNPSLLETSEGCRQI
IKQLQPALKTGTEELRSLYNTIATLYCVHKGIKVQDTKEALDKVEEEQNKSQQKTQQAKA
ADE---KVSQNYPIVQNLQGQMVHQPLSPRTLNAWVKVIEEKGFNPEVIPMFTALSEGAT
PQDLNSMLNAVGGHQAAMQMLKDTINEEAAEWDRLHPVQAGPVAPGQIREPRGSDIAGTT
SSLQEQIAWMTGNPPVPVGDIYKRWIILGLNKIVRMYSPVSILDIKQGPKESFRDYVDRF
FKTLRAEQATQDVKNWMTETLLVQNANPDCKTILRALGPGATLEEMMTACQGVGGPSHKA
RVLAEAMSQ-ANNANIMMQRSNFKGPKRTVKCFNCGKEGHIAKNCRAPRKKGCWKCGREG
HQMKDC-IERQANFLGKIWPSNKG-RPGNFLQNRTE------PTAPPA-------EPTAP
PAESFRFEE--TTPAPKQELKDRE--PLTSLKSLFGSDPLLQ
>gagC.syn6.4
MGARASILRGEKLDKWEKIRLRPGGRKHYMLKHIVWASRELEGFALNPGLLETSEGCKQI
IKQLQPALQTGTEELRSLFNTVATLYCVHSGIEVRDTKEAVDKIEEEQNKIQQKTQQAKE
ADG---KVSQNYPIVQNSQGQMVHQAISPRTLNAWVKVIEEKAFSPEVIPMFTALSEGAT
PSDLNTMLNTIGGHQAAMQMLKDTINDEAAEWDRLHPVHAGPIAPGQMRDPRGSDIAGST
STLQEQIAWMTNNPPVPVGDIYKRWIIMGLNKIVRMYSPVSILDIKQGPKEPFRDYVDRF
FRTLRAEQATQEVKNWMTETLLVQNANPDCRTILKALGPGATLEEMMTACQGVGGPGHKA
RVLAEAMSQ-ANNINIMMQRNNFKGPKRIIKCFNCGKEGHIARNCKAPRKKGCWKCGKEG
HQMKDC-NERQANFLGKIWPSHKG-RPGNFLQNRP-------------------EPTAP
PAESFRFEE--TTPTPKQEPKDRE--PLTSLKSLFGSDPSSQ
```

Fig. 9 cont'd-8

>gagC.syn6.5
MGARASILRGGKLDKWEKIRLRPGGKKRYMLKHLIWASRELERFALNPGLLETSDGCKQI
IQQLQPALKTGTEELKSLFNTVAVLYCVHKGIEVRDTKEAVDKIEEEQNKIQQKMQQQKV
TDG---KVSQNYPIVQNIQGQMVHQPISPRTLNAWVKVIEEKGFSPEVIPMFTALSEGAT
PSDLNTMLNTVGGHQAAMQMLKDTINEEAAEWDRTHPVHAGPVAPGQMREPRGSDIAGTT
STLQEQIGWMTNNPPIPVGEIYKRWIILGLNKIVRMYSPVSILDIKQGPKEPFRDYVDRF
FKALRAEQATQEVKGWMTDTLLVQNANPDCKTILKALGSGATLEEMMTACQGVGGPGHKA
RVLAEAMSQ-ANNTNIMMQKSNFKGPRRIVKCFNCGREGHIAKNCRAPRKKGCWKCGQEG
HQMKDC-TERQANFLGRIWPSHKG-RPGNFLQSRPE------PTAPL--------QPTAP
PAESFKFEE--TTPAPKQEQKDRE--PLTSLRSLFGNDPLSQ >gagC.syn6.6
MGARASILRGGKLDTWEKIRLRPGGKKHYMLKHLVWASRELDRFALNPGLLETADGCKQI
IKQLHPALQTGTEEIKSLFNTVATLYCVHAGIEVRDTKEALDKIEEEQNKCQQKTQQAKE
ADK---KVSQNYPIVQNLQGQMVHQAISPRTLNAWVKVIEEKAFNPEIIPMFTALSDGAT
PQDLNTMLNTVGGHQAAMQMLKDTINEEAADWDRLHPVHAGPVAPGQLREPRGSDIAGTT
SNLQEQIAWMTSNPPIPVGDIYKRWIILGLNKIVRMYSPVSILDIKQGPKEPFRDYVDRF
FKVLRAEQATQDVKNWMTDTLLIQNANPDCKTILRALGPGASLEEMMTACQGVGGPSHKA
RVLAEAMSQ-TNSA-ILMQRSNFKGSKRIVKCFNCGKEGHLARNCRAPRKRGCWKCGKEG
HQMKDCTTERQANFLGKIWPSHKGGRPGNFLQNRPE------PTAPL--------EPTAP
PAESFGFGE--TTPAPKQEPKDRE--PLISLKSLFGSDPLSQ >gagM.syn1.1
MGARASILRGGKLDKWEKIRLRPGGKKHYMLKHLVWASRELERFALNPGLLETSEGCKQI
IKQLQPALQTGTEELRSLFNTVATLYCVHEKIEVRDTKEALDKIEEEQNSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGEIYKRWIILGLNKIVRMYSPVSILDIRQGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ >gagM.syn3.1
---RASVLSGGKLDAWEKIRLRPGGKKKYKLKHIVWASRELERFAVNPGLLETSEGCRQI
LGQLQPSLQTGSEELRSLYNTVAVLYCVHQRIEVKDTKEALEKIEEEQNKSKKKAQQAAA
DTGNSSQVSQNYPIVQNLQGQMVHQAISPRTLNAWVKVIEEKAFSPEVIPMFTALSEGAT
PSDLNTMLNTIGGHQAAMQILKDTINEEAAEWDRLHPVHAGPIAPGQMREPRGSDIAGTT
STLQEQIGWMTNNPPIPVGEIYKRWIILGLDKIVRMYSPTSILDIRQGPKESFRDYVDRF
YKTLRAEQASQEVKNWMTETLLVQNANPDCKTILKALGPAATLEEMMTACQGVGGPSHKA
RILAEAMSQVTNSATIMMQRGNFRNQRKTVKCFNCGKEGHIAKNCRAPRKKGCWKCGKEG
HQMKDC-NERQANFLGKIWPSHKG-RPGNFLQSRP---------------EPTAP
PEESFRFGEETTTPSQKQEPIDKELYPLASLKSLFGNDPLSQ >gagM.syn3.2
MGARASILRGGKLDKWEKIRLRPGGKKHYMLKHLVWASRELERFALNPGLLETAEGCKQI
IKQLQPALKTGTEELKSLYNTVATLYCVHEKIEVRDTKEALDKLEEEQNKSQQKTQQAAA
GTGSSSKVSQNYPIVQNAQGQMVHQALSPRTLNAWVKVVEEKAFSPEVIPMFSALAEGAT
PQDLNTMLNTVGGHQAAMQMLKDTINEEAADWDRLHPVHAGPVAPGQMREPRGSDIAGST
STLQEQIAWMTSNPPIPVGDIYKRWIILGLNKIVRMYSPVSILDIKQGPKEPFRDYVDRF
FKTLRAEQATQDVKNWMTDTLLVQNANPDCKTILRALGPGASLEEMMTACQGVGGPGHKA
RVLAEAMSQ-ANNANIMMQRGNFKGQKR-IKCFNCGKEGHLARNCRAPRKKGCWKCGREG
HQMKDC-TERQANFLGRIWPSSKG-RPGNFPQSRP---------------EPSAP
PAESFGFGE--TTPAPKQELKDRE--PLTSLKSLFGSDPLSQ >gagM.syn3.3
MGARASVLSGGELDRWEKIRLRPGGKKKYRLKHLVWASRELEKFALNPGLLETSEGCKQI
MKQLQPALQTGTEELRSLFNTVATLYCVHQRIDVKDTKEALDKIEEEQNKIQQKTQQAKA
ADG---KVSQNYPIVQNIQGQMVHQPISPRTLNAWVKVVEEKGFNPEVIPMFSALSEGAT

Fig. 9 cont'd-9

```
PQDLNMMLNIVGGHQAAMQMLKETINEEAAEWDRVHPVHAGPIPPGQMREPRGSDIAGTT
SNLQEQIGWMTSNPPVPVGDIYKRWIVLGLNKIVRMYSPVSILDIRQGPKEPFRDYVDRF
FKVLRAEQATQEVKNWMTDTLLIQNANPDCKSILRALGPGATLEEMMTACQGVGGPSHKA
RVLAEAMSQ-TNSA-ILMQRSNFKGSKRIVKCFNCGKEGHIARNCRAPRKRGCWKCGQEG
HQMKDC-TERQVNFLGKIWPSNKG-RPGNFLQNRPE------PTAPPA-------EPTAP
PAESFRFEE--TTPAPKQEPKDRE--PLTSLRSLFGNDPSSQ

>gagM.syn4.1
MGARASVLSGGELDRWEKIRLRPGGKKKYKLKHIVWASRELERFAVNPGLLETSEGCRQI
LGQLQPSLQTGSEELRSLYNTVAVLYCVHQRIDVKDTKEALEKIEEEQNKSQQKTQQAKA
ADG---KVSQNYPIVQNAQGQMVHQAISPRTLNAWVKVIEEKGFSPEVIPMFSALAEGAT
PQDLNTMLNTIGGHQAAMQMLKDTINDEAAEWDRLHPVQAGPVAPGQIREPRGSDIAGTT
SNLQEQIGWMTSNPPIPVGDIYKRWIIMGLNKIVRMYSPTSILDIRQGPKESFRDYVDRF
FRTLRAEQASQEVKNWMTETLLVQNSNPDCKTILKALGPAATLEEMMTACQGVGGPGHKA
RVLAEAMSQ-VQQPNIMMQRGNFKGQKR-IKCFNCGREGHLARNCRAPRKKGCWKCGREG
HQMKDC-TESKANFLGKIWPSNKG-RPGNFLQSRP-----------------EPSAP
PAESFGFGEE-ITPSQKQEQKDKELYPLASLKSLFGNDPLSQ
>gagM.syn4.2
MGARASVLSGGKLDAWEKIRLRPGGKKKYRLKHLVWASRELDRFALNPSLLETAEGCKQI
MKQLQPALKTGTEELKSLYNTVATLYCVHEKIDVRDTKEALDKIEEEQNKIQQKTQQAKE
ADG---KVSQNYPIVQNIQGQMVHQPISPRTLNAWVKVVEEKAFSPEVIPMFTALSDGAT
PQDLNSMLNAVGGHQAAMQILKDTINEEAADWDRLHPVHAGPVAPGQMREPRGSDIAGTT
STLQEQIGWMTNNPPIPVGEIYKRWIILGLNKIVRMYSPVSILDIKQGPKESFRDYVDRF
FKVLRAEQATQDVKNWMTDTLLIQNANPDCKSILRALGPGATLEEMMTACQGVGGPSHKA
RILAEAMSQVTNSATIMMQRGNFRNQRKTVKCFNCGKEGHLARNCKAPRKRGCWKCGKEG
HQMKEC-TERQANFLGKIWPSSKG-RPGNFPQSRP------------------EPTAP
PEESFRFGEETTTPSQKQEPIDKELYPLASLRSLFGNDPSSQ
>gagM.syn4.3
MGARASILRGGKLDWEKIRLRPGGKKRYMLKHLIWASRELERFALNPGLLETAEGCQQI
IEQLQSTLKTGSEELKSLFNTVATLYCVHQRIEVKDTKEALDKVEEEQNKSKKKAQQAAA
DTGNSSQVSQNYPIVQNLQGQMVHQALSPRTLNAWVKVIEEKAFSPEIIPMFTALSEGAT
PSDLNTMLNTVGGHQAAMQMLKDTINEEAAEWDRVHPVHAGPIPPGQMREPRGSDIAGTT
SSLQEQIAWMTSNPPVPVGEIYKRWIVLGLNKIVRMYSPVSILDIRQGPKEPFRDYVDRF
FKTLRAEQASQDVKNWMTETLLVQNANPDCKTILRALGPGASLEEMMTACQGVGGPSHKA
RVLAEAMSQ-TNSA-ILMQRSNFKGSKRIVKCFNCGKEGHIARNCRAPRKRGCWKCGQEG
HQMKDC-NERQANFLGKIWPSHKG-RPGNFLQNRPE------PTAPP--------EPTAP
PAESFRFEE--TTPAPKQELKDRE--PLTSLKSLFGSDPLSQ
>gagM.syn4.4
MGARASVLRGEKLDKWERIRLRPGGKKHYMLKHLVWASRELEKFALNPGLLETSEGCKQI
IKQLQPALQTGTEELRSLFNTVATLYCVHAGIEVRDTKEALDKIEEIQNKSKQKTQQAAA
GTGSSSKVSQNYPIVQNLQGQMVHQPLSPRTLNAWVKVVEEKGFNPEVIPMFSALSEGAT
PQDLNMMLNIVGGHQAAMQMLKETINEEAAEWDRLHPVHAGPIAPGQMREPRGSDIAGST
STLQEQIAWMTGNPPVPVGDIYKRWIILGLNKIVKMYSPTSILDIKQGPKEPFRDYVDRF
YKTLRAEQATQEVKNWMTDTLLVQNANPDCKSILKALGTGATLEEMMSACQGVGGPAHKA
RVLAEAMSQ-ANNTNIMMQRSNFKGPKRIIKCFNCGKEGHIAKNCRAPRKKGCWKCGKEG
HQMKDC-TERQANFLGRIWPSSKG-RPGNFLQSRPE------PTAPPA-------EPTAP
PAESFKFEE--TTPAPKQEPKDRE--PLTSLRSLFGSDPLLQ >gagM.syn6.1
MGARASILSGGKLDAWEKIRLRPGGRKHYMLKHIVWASRELERFALNPGLLETAEGCQQI
IEQLQSTLKTGSEELKSLFNTVATLWCVHQRIEVKDTKEALDKLEEEQNKSQQKTQQAKA
ADG---KVSQNYPIVQNLQGQMVHQSISPRTLNAWVKAIEEKAFSPEVIPMFSALAEGAT
PQDLNTMLNTIGGHQAAMQILKDTINEEAAEWDRIHPVHAGPVAPGQMRDPRGSDIAGTT
SNLQEQIAWMTSNPPVPVGEIYKRWIILGLDKIVRMYSPVSILDIRQGPKEPFRDYVDRF
FKTLRAEQATQEVKGWMTDTLLVQNANPDCKTILKALGPGATLEEMMSACQGVGGPGHKA
```

Fig. 9 cont'd-10

```
RVLAEAMSQ-ANNTNIMMQKSNFKGPKRIIKCFNCGKEGHLARNCRAPRKKGCWKCGQEG
HQMKDC-TERQANFLGRIWPSHKG-RPGNFPQSRL------------------EPTAP
PAESFGFGEE-IAPSPKQEPKEKELYPLTSLKSLFGNDPLSQ
>gagM.syn6.2
MGARASILRGGKLDKWEKIRLRPGGKKKYKLKHIVWASRELEKFALNPGLLETSEGCRQI
LGQLQPSLQTGSEELKSLYNTVATLYCVHQRIDVKDTKEALEKIEEEQNKSQQKTQQAAA
DKG----VSQNYPIVQNLQGQMVHQAISPRTLNAWVKVIEEKAFSPEIIPMFTALSEGAT
PQDLTTMLNTVGGHQAAMQMLKETINDEAAEWDRLHPVHAGPVAPGQLREPRGSDIAGST
STLQEQIAWMTGNPPVPVGDIYKRWIVLGLNKIVRMYSPTSILDIRQGPKEPFRDYVDRF
YKTLRAEQASQDVKNWMTETLLVQNANPDCRTILKALGPAATLEEMMTACQGVGGPAHKA
RVLAEAMSQVTNPATIMMQRGNFRNQRKTVKCFNCGKEGHLAKNCRAPRKRGCWKCGKEG
HQMKDC-NERQANFLGKIWPSNKG-RPGNFLQNRT------------------EPTAP
PAESFRFGEEKTTPSQKQEPIDKELYPLASLRSLFGNDPSLQ
>gagM.syn6.3
MGARASVLRGEKLDKWERIRLRPGGKKRYMLKHLIWASRELERFALNPSLLETSEGCKQI
IQQLQPALKTGTEELRSLYNTVATLYCVHEKIEVRDTKEAVDKIEEEQNKSKKKAQQAAA
DTGNSSQVSQNYPIVQNIQGQMVHQALSPRTLNAWVKVVEEKGFNPEVIPMFSALSEGAT
PQDLNMMLNIVGGHQAAMQMLKDTINEEAAEWDRLHPVQAGPVAPGQMREPRGSDIAGTT
STLQEQITWMTSNPPIPVGEIYKRWIIMGLNKIVRMYSPVSILDIKQGPKESFRDYVDRF
FRTLRAEQASQEVKNWMTETLLIQNANPDCKTILRALGPAASLEEMMTACQGVGGPGHKA
RVLAEAMSQ-TNSA-ILMQRSNFKGSKRIVKCFNCGKEGHIARNCRAPRKKGCWRCGKEG
HQMKDC-TESKANFLGKIWPSHKG-RPGNFLQNRPEPTAPPEPTAPPAEPTAPPAEPTAP
PAESFKFEE--TTPAPKQELKDRE--PLISLKSLFGSDPLLQ
>gagM.syn6.4
MGARASILRGEKLDTWEKIRLRPGGKKQYRLKHIVWASRELDRFALNPSLLETAEGCKQI
IKQLHPALQTGTEELRSLFNTVATLYCVHAGIEVRDTKEALDKIEEEQNKIQQKTQQAKA
ADE---KVSQNYPIVQNMQGQMVHQPLSPRTLNAWVKVVEEKAFSPEVIPMFAALSEGAT
PSDLNTMLNTVGGHQAAMQMLKDTINDEAAEWDRLHPAQAGPIPPGQIREPRGSDIAGTT
STPQEQIGWMTNNPPIPVGEIYKRWIVLGLNKIVRMYSPISILDIRQGPKEPFRDYVDRF
FKALRAEQATQEVKGWMTETLLVQNSNPDCKTILRALGPGASLEEMMTACQGVGGPSHKA
RILAEAMSQ-ANS-NIMMQRSNFKGPKRIVKCFNCGKEGHIAKNCRAPRKKGCWKCGREG
HQMKDC-IERQANFLGKIWPSQKG-RPGNFLQSRP------------------EPSAP
PAESFRFGE--TTPAPKQEPKDRE--PLTSLRSLFGSDPLSQ
>gagM.syn6.5
MGARASVLSGGELDRWEKIRLRPGGKKKYRLKHLVWASRELERFAINPGLLETSDGCKQI
IKQLQPALQTGSEELRSLYNTIATLYCVHQKIEVKDTKEALDKIEEIQNKSKQKTQQAAA
GTGSSSKVSQNYPIVQNAQGQMVHQSLSPRTLNAWVKVIEEKGFNPEVIPMFTALSEGAT
PHDLNTMLNTVGGHQAAMQMLKETINEEAAEWDRVHPVHAGPIPPGQMREPRGSDIAGST
STLQEQIGWMTSNPPIPVGDIYKRWIILGLNKIVRMYSPSSILDIRQGPKESFRDYVDRF
FKCLRAEQATQEVKNWMTDTLLIQNANPDCKSILRALGPGATLEEMMTACQGVGGPGHKA
RILAEAMSQ-VQQPNIMMQRGNFKGQKR-IKCFNCGREGHIARNCKAPRKKGCWKCGKEG
HQMKDC-TERQVNFLGKIWPSYKG-RPGNFLQSRP------------------EPTAP
PEESFRFGEETTTPSQKQETIDKELYPLASLKSLFGNDPSSQ
>gagM.syn6.6
MGARASVLSGGKLDAWERIRLRPGGKKHYMLKHLVWASRELERFAVNPGLLETSEGCKQI
MKQLQPALQTGTEELKSLYNTVAVLYCVHQRIEIKDTKEALDKIEEEQNKCQQKTQQAKE
ADG---KVSQNYPIVQNLQGQMVHQPISPRTLNAWVKVIEEKGFSPEVIPMFTALSDGAT
PQDLNSMLNAVGGHQAAMQMLKDTINEEAADWDRLHPVHAGPIAPGQMREPRGSDIAGTT
SSLQEQIAWMTNNPPVPVGEIYRRWIILGLNKIVKMYSPTSILDIKQGPKEPFRDYVDRF
FKVLRAEQATQDVKNWMTDTLLVQNANPDCKSILKALGTGATLEEMMTACQGVGGPSHKA
RVLAEAMSQVTNSATIMMQKGNFRNQRKIVKCFNCGREGHLARNCKAPRKRGCWKCGKEG
HQMKEC-TERQANFLGKIWPSSKG-RPGNFPQSRP------------------EPTAP
PAESFRFEE--TTPAPKQESKDRE--PLTSLKSLFGSDPSSQ
```

Fig. 10

>ENV-B.syn1.1
MRVTGIRKNYQHLWRWGTMLLWRWGTMLLGMLMICSATEKLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEIVMHSFNCGGEFFYCNSTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASMTLTVQARQLLSGIVQQQNNLLRAIEA
QQHLLQLTVWGIKQLQARVLAVERYLRDQQLLGIWGCSGKLICTTAVPWNASWSNKSLNE
IWNNMTWMEWEKEIDNYTNLIYNLLEESQNQQEKNEQELLELDKWASLWNWFDISNWLWY
IKIFIMIVGGLVGLRIVFAVLSIVNRVRQGYSPLSFQTRLPAPRGPDRPEGIEEEGGERD
RDRSVRLVDGFLALIWDDLRSLCLFSYHRLRDLLLIVTRIVELLG-------RRGWEALK
YWWNLLQYWSQELKNSAVSLLNATAIAVAEGTDRVIEALQRACRAILHIPRRIRQGLERA
LL-
>ENV-B.syn3.1
MRVKETRKNYQHLWKWGTML--------LGMLMICSATEKLWVTVYYGVPVWRDANATLF
CASDAKAYDTEAHNVWATHACVPTDPNPQEVELKNVTENFNMWKNDMVEQMHEDIINLWD
QSLKPCVELTPLCVTLNCTDYVKNIT-NNATSTNSSW-GKPMEKGEIKFCSFNITTSIRN
KVQKQYALFYKLDIVPI-DNDNTS----------YRLISCNTSTITQACPKVTFEPIPIH
YCAPAGFAILKCNNKTFNGTGPCTNVSTVQCTHGIRPVISTQLLLNGSLAEEEVVIRSEN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR
N-NGTWTRN---DTERSNSTE---EHITLPCRIKQIINMWQEVGKAMYAPPIKGQISCSS
NITGLLLTRDGGNDT-----SGTEIFRPGGGDMRDNWRSELYKYKVVRIEPLGVAPTEAK
RRVVQREKRAVG-IGAVFLGFLGAAGSTMGAASMTLTVQARLLLSGIVQQQSNLLRAIEA
QQHMLQLTVWGIKQLQARLLAVERYLGDQQLLGLWGCSGKLICTTTVPWNTSWSNKSLNE
IWDNMTWMQWEREIDNYTGLIYNLLEKSQNQQEKNEQELLELDKWASLWNWFDITNWLWY
IKIFIMIVGGLVGLRIVFTVLSIVNRVRKGYSPLSFQTRLPTPRGPDRPGGIEEEGGEQD
RDRSGPLVNGFLALIWVDLRSLFLFSYHRLRDLLLIVARIVELLG-------RRGWEILK
YWWNLLLYWSQELKNSAVSLLNATAIAVAEGTDRVIEVVQRAFRAILHIPRRIRQGFERA
LL-
>ENV-B.syn3.2
MRVTGIRKNYQHLWRWGTMLLWRWGTMLLGILMICSAAGKLWVTVYYGVPVWKEANTTLF
CASDAKAYDTEVHNVWATHACVPIDPNPQEVVLGNVTENFNMWKNNMVEQMHEDIISLWD
ESLKPCVKLTPICVTLNCTDDVRNVT-NNATNTNSSW-GEPMEKGEIKNCSFNITTSIRD
KVQKQYALFYKLDVVPI-DNDSNNTN--------YRLISCNTSVITQACPKISFEPIPIH
FCAPAGFAILKCNDKKFNGTGPCKNVSTVQCTHGIKPVVSTQLLLNGSLAEEEIVIRSEN
FTDNAKTIIVQLNESVVINCTRPNNNTRKSIHIGPGRAFYATGEIIGDIRQAHCNLSRAK
WNDTLKQIVIKLREQFG-NKTIVFNQSSGGDPEIVMHSFNCGGEFFYCNTTQLFNSTWTW
N-NSTW--N---NTKRSNDTE---EIITLPCRIKQIVNMWQKVGKAMYAPPIRGQIRCSS
NITGILLTRDGGNNNET---NRTETFRPGGGNMKDNWRSELYKYKVVKIEPLGIAPTKAR
RRVVQREKRAVGTIGAMFLGFLGAAGSTMGAASLTLTVQARQLLPGIVQQQNNLLKAIEA
QQHLLRLTVWGIKQLQARVLAVERYLRDQQLLGIWGCSGKIICTTAVPWNASWSNKSLDK
IWDNMTWMEWEKEIDNYTNLIYNLLEESQNQQEKNELELLELDKWANLWNWFDISNWLWY
IKIFIMIIGGLVGLRIVFAVLSIVNRVRQGYSPLSFQTRLPAPRGPDRPEGIEEEGGERD
RDRSVRLVDGFLALIWDDLRSLCLFLYHRLRDLLLIAARIVELLG-------RRGWEALK
YWWNLLQYWSQELKNSAISLLNATAVAVAEGTDRVIEALQRACRAILHIPRRIRQGLERL
LL-
>ENV-B.syn3.3
MRVKGIRKNCQHLWRWGIML--------LGMLMICSAAEQLWVTVYYGVPVWKEATTTLF
CASDAKAYDKEVHNVWATHASVPTDPNPQEVVLENVTENFNMWKNNMVDQMHEDIISLWD
QSLKPCVKLTPLCVTLNCTD-LRNATNGNDTNTTSSS-REMMGGGEMKNCSFNVTTSIRD
KVQKEYALFYKLDVIPI-DSRNNSNNSTE--YNSYRLINCNTSVITQACPKVSFEPIPIH

Fig. 10 cont'd-1

YCTPAGFAILKCKDKKFNGTGPCTKVSTVQCTHGIRPVVSTQLLLNGSLAEEEVIIRSEN
FTNNAKTIIVQLKEAVEINCTRPSNNTRKSIPIGPGRAFYTTGDIIGDIRKAHCNISRAN
WNNTLRQIVEKLGEQFGNNKTIIFKQSSGGDPEIVTHSFNCGGEFFYCNSTQLFNSTWNF
--NGTWNKN---FNNTWNNTEGTNDTITLPCRIKQIINRWQEVGKAMYAPPISGQIRCSS
NITGLILTRDGGNNGNET--NGTEIFRPGGGNMRDNWRSELYRYKVVKIEPLGVAPTKAK
RRVVQREKRAVG-IGALFLGFLGAAGSTMGAASITLTVQARQLLSGIVQQQNNLLRAIEA
QQHLLQLTVWGIKQLQARILAVERYLKDQQLLGIWGCSGKLICTTAVPWNTSWSNRSLNE
IWNNMTWMEWEREIDNYTSLIYTLIEESQNQQEKNEQELLALDKWASLWNWFSITNWLWY
IRIFIMIVGGLIGLRIVFAVLSVVNRVRQGYSPLSFQTHLPAQRGPDRPEGTEEEGGERD
RDRSGRLVDGFLAIIWVDLRSLCLFSYHRLRDLLLIVTRIVELLG-------RRGWEVLK
YWWNLLQYWIQELKNSAVSLFNAIAIAVAEGTDRIIEVVQRAYRAILHIPTRIRQGLERA
LL-

>ENV-B.syn4.1
MRVTGIRKNYQHLWRWGTMLLWRWGTMLLGILMICSAAGKLWVTVYYGVPVWKDATTTLF
CASDAKAYDTEVHNVWATHASVPTDPNPQEVVLENVTEDFNMWKNNMVDQMHEDIISLWD
QSLKPCVELTPLCVTLNCTDDVRNVT-NNATNTNSSW-GEPMEKGEIKFCSFNITTSIRN
KVQKQYALFYKLDVVPI-DNDSNNTN--------YRLISCNTSVITQACPKVTFEPIPIH
YCAPAGFAILKCNNKTFNGTGPCTKVSTVQCTHGIRPVVSTHLLLNGSLAEEEVIIRSEN
FTDNTKTIIVQLKEAVEINCTRPNNNTRKGIHIGPGRAFYTTGEIIGDIRQAHCNLSRAK
WNDTLKQIVIKLREQFG-NKTIIFNQSSGGDPEIVMHTFNCGGEFFYCNTTQLFNSTW--
-------QN---ETSGSINITDIGENITLPCRIKQIVNMWQKVGKAMYAPPIKGQISCSS
NITGLLLTRDGGNNGNET--NGTEIFRPGGGNMKDNWRSELYRYKVVKIEPLGVAPTRAK
RRVVQREKRAVT-LGAMFLGFLGAAGSTMGAASMTLTVQARLLLSGIVQQQSNLLRAIEA
QQHLLRLTVWGIKQLQARILAVERYLQDQQLLGIWGCSGKLICTTAVPWNASWSNKSQDE
IWNNMTWMQWEKEIDNYTGLIYTLLEESQIQQEKNEQELLELDKWASLWNWFDITNWLWY
IKIFIMIVGGLIGLRIVFTVLSIVNRVRKGYSPLSFQTHLPAPRGPDRPGGIEEEGGEQD
RDRSGPLVNGFLALIWVDLRSLFLFSYHRLRDLLLIVARIVELLG-------RRGWEVLK
YWWNLLQYWSQELKNSAISLLNATAVAVAEGTDRVIEALQRACRAILHIPRRIRQGLERL
LL- >ENV-B.syn4.2
MRVKGIRKNCQHLWRWGILL--------LGMLMICSAAEQLWVTVYYGVPVWRDANATLF
CASDAKAYDTEAHNVWATHACVPTDPNPQEVELKNVTENFNMWKNNMVEQMQEDIISLWD
QSLKPCVKLTPICVTLNCTDYVKNIT-NNATSTNSSW-GKPMEKGEIKNCSFNVTTSIRD
KVQKEYALFYRLDVVPI-DNDSNNNDSTNTNYTNYRLISCNTSTITQACPKVSFQPIPIH
YCAPAGFALLKCNDKKFNGTGPCKNVSTVQCTHGIKPVVSTQLLLNGSLAEEEIVIRSEN
FTNNAKTIIVQLNESVVINCTRPNNNTRKSIHIGPGRAFYATGDIIGDIRKAHCNISRAN
WNNTLRQIVEKLGEQFG-NKTIVFNQSSGGDVEIVMHSFNCGGEFFYCNSTQLFNSTWNF
--NGTWNKN---FNNTWNNTEGTNDTITLPCRIKQIINMWQGVGKAMYAPPISGQIRCSS
NITGLILTRDGGNN-NET--NRTETFRPGGGDMRDNWRSELYKYKVVKIEPLGIAPTKAR
RRVVQREKRAVGTIGAMFLGFLGTAGSTMGAASLTLTVQARLLLSGIVQQQNNLLKAIEA
QQHLLQLTVWGIKQLQARLLAVERYLGDQQLLGLWGCSGKLICTTTVPWNASWSNKSLDK
IWDNMTWMEWEREIDNYTGLIYNLLEKSQNQQEKNELELLELDKWANLWNWFDITKWLWY
IKIFIMIIGGLIGLRIVFAVLSVVNRVRQGYSPLSLQTRLPTQRGPDRPEGIAEEGGERD
RDRSGPLVDGFLAIIWVDLRSLCLFSYHHLRDLLLIVTRIVELLG-------RRGWEALK
YWWNLLLYWSQELKNSAVNLLNTTAIAVAEGTDRIIEVLQRIYRAFLHIPRRIRQGFERA
LL- >ENV-B.syn4.3
MRVKEIRKNYQHLWKWGTML--------LGMLMICSAAGNLWVTVYYGVPVWKEANTTLF
CASDAKAYETEVHNVWATHACVPIDPNPQEVVLGNVTENFNMGKNNMVEQMHEDIISLWD
ESLKPCVKLTPLCVTLNCTDELKNATFRSNTTTNSSW--EKMEKGEIKNCSFNITTNMRD
KMQKEYALFYKLDVIPI-DSRNNSNNSTE--YNSYRLINCNTSVITQACPKISFEPIPIH
YCTPAGFAILKCKDKKFNGKGPCTNVSTVQCTHGIRPVVSTQLLLNGSLAEKEVVIRSDN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR

Fig. 10 cont'd-2

N-NGTWTRN---DTERSNSTE---EHITLPCRIKQIINMWQEVGKAMYAPPIRGQIRCSS
NITGILLTRDGGNDT-----SGTEIFRPGGGDMKDNWRSELYKYKVVRIEPLGVAPTEAK
RRVVQREKRAVG-IGAVFLGFLGAAGSTMGAAAVTLTVQARLLLSGIVQQQNNLLRAIEA
QQRLLQLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IKIFIIIVGGLVGLRIVFAVLSIVNRVRQGYSPLSFQTRLPAPRGPDRPEGIEEEGGERD
RDRSVRLVDGFLALIWDDLRSLCLFSYHRLRDLLLI----VELLG-------RRGWEILK
YWWNLLQYWGQELKNSAVSLLNATAIAVAEGTDRVIEVVQRAYRAILHIPTRIRQGLERA
LL-
>ENV-B.syn4.4
MRVKETRKNYQHLWRWGIML--------LGMLMICSATEKLWVTVYYGVPVWKEATTTLF
CASDAKAYDKEVHNVWATHACVPTDPSPQEVVLENVTENFNMWKNDMVEQMHEDIINLWD
QSLKPCVRLTPLCVTLNCTN-VNVTNLKNETNTKSSSGGEKMEEGEMKNCSFNITTSIRD
KVQKQYALFYKLDVVPI-DNDNTS----------YRLISCNTSVIKQACPKVSFEPIPIH
FCAPAGFAILKCNDKKFNGTGPCTNVSTVQCTHGIRPVISTQLLLNGSLAEEEVVIRSEN
FTDNAKTIIVQLNETVEINCTRPSNNTRKSIPIGPGRAFYTTGDIIGDIRQAYCNISRAK
WNNTLKQIVTKLREQFGNNKTIIFKQSSGGDPEIVTHSFNCGGEFFYCNSTKLFNSTWTW
N-NSTW--N---NTKRSNDTE---EIITLPCRIKQIINRWQEVGKAMYAPPIEGQIRCLS
NITGLLLTRDGGTNNT----NTNETFRPGGGNMRDNWRSELYKYKVVQIEPLGVAPTKAK
RRVVQREKRAVG-IGALFLGFLGAAGSTMGAASITLTVQARQLLSGIVQQQRNLLRAIEA
QQHMLQLTVWGIKQLRARVLAVERYLKDQQLLGIWGCSGRLICTTNVPWNTSWSNKSLNE
IWDNMTWMQWEREIDNYTSLIYTLIEESQNQQEKNEQDLLALDKWASLWNWFSITNWLWY
IRIFIMIVGGLVGLRIVFTVISIVTRVRQGYSPLSFQTRLPTPRGPDRPEGTEEEGGERD
RDRSGRLVDGFLALFWDDLRSLCLFLYHRLRDLLLIAARIVELLG-------RRGWELLK
YWWNLLQYWIQELKNSAVSLFNAIAIAVAEGTDWVIEISQRAFRAVLHIPVRIRQGLERA
LQ-
>ENV-B.syn6.1

MRVTGIRKNYQHLWRWGTMLLWRWGTMLLGILMICSAAGKLWVTVYYGVPVWKDATTTLF
CASDAKAYDTEAHNVWATHACVPIDPNPQEVVLENVTENFNAWKNNMVEQMHEDMISLWD
QSLQPCVRLTPLCVTLNCTDDVRN-----ATSTNSSW-GKPMEKGEIKNCSFNITTSIRD
KVQKQYALFYKLDVVPI-DNDSNNTN--------YRLISCNTSIITQACPKITFEPIPIH
YCTPAGFALLKCNDKKFNGTGPCTKVSTVQCTHGIRPVVSTHLLLNGSLAEEEVIIRSEN
FTNNAKTIMVQLNVSVEINCTRPSNNTRKSIHIGPGRAFYTTGDIIGDIRKAHCNISRAN
WNNTLRQIVEKLGEQFGNNKTIVFNHSSGGDLEIVTHSFICGGEFFYCNSTKLFNSTWTW
N-NSTW--N---NTKRSNDTE---EIITLPCRIKQIINMWQEVGKAMYAPPIRGKIRCSS
NITGLLLTRDGGTNNT----NTNETFRPGGGDMRDNWRNELYKYKVVRIEPLGIAPTEAK
RRVVQREKRAVG-IGAMFLGFLGTAGSTMGAASVALTVQARQLLPGIVQQQNNLLRAIDA
QQHLLQLTVWGIKQLQARILAVERYLKDQQLLGFWGCSGKLICTTNVPWNTSWSNKSYSQ
IWENMTWMEWEREINNYTGLIYNLLEKSQNQQEKNEQELLELDKWASLWSWFDISNWLWY
IKIFIIIVGGLVGLRIVFAVLSIINRVRQGYSPLSFQTHLPAPRGPDRPEGIAEEGGERD
RDRSGRLVNGFLALIWVDLRSLCLFSYHHLRDLLLI----VELLG-------RRGWEVLK
YWWNLLLYWSQELKNSAISLLNATAVAVAEGTDRVIEALQRACRAILHIPRRIRQGLERL
LL-

>ENV-B.syn6.2

MRVKETRKNYQHLWKWGTML--------LGILMICSATENLWVTVYYGVPVWKEATTTLF
CASDAKAYDKEVHNVWATHACVPTDPNPQEVELKNVTENFNMWKNNMVEQMQEDIISLWD
QSLKPCVRLTPLCVTLNCTD-LRNATNGNDTNTTSSS-REMMGGGEMKNCSFNITTNIRD
KVQKEYALFYKLDIVPI-DNDNTN----------YRLISCNTSVVTQACPKVSFEPIPIH
FCAPAGFAILKCNDKKFNGKGPCTNVSTVQCTHGIRPVISTQLLLNGSLAEEEVVIRSEN

Fig. 10 cont'd-3

```
FTNNVKTIIVQLNETVEINCTRPNNNTRRSIPIGPGRVFYTTEDIIGDIRQAHCNLSRTQ
WNNTLKQIVTKLREQFG-NKTIIFNQSSGGDPEIVMHTFNCGGEFFYCNTTKLFNSTW--
--NDTTINR----TEGSNNTR----NITLPCRIKQIINLWQEVGKAMYAPPIQGQISCSS
NITGLLLTRDGGNN-NET--NRTETFRPGGGNMRDNWRSELYKYKVVKIEPLGVAPTKAK
RRVVQREKRAVG-IGALFLGFLGAAGSTMGAASVTLTVQARQLLSGIVQQRNNLLRAIEA
QQRMLQLTVWGIKQLRARVLAVERYLKDQQLMGIWGCSGKLICTTTVPWNASWSNKSLNE
IWDNMTWMEWEREIDNYTSLIYTLIEESQNQQEKNELELLELDKWASLWNWFSITNWLWY
IRLFIMIVGGLVGLRIVFTVISIVTRVRQGYSPLSFQTRLPTPRGPDRPGGIEEEGGEQD
RDRSIRLVDGFLALIWDDLRSLCLFSYHRLRDLLWI----VELLG-------RRGWEALK
YLWNLLQYWSQELKKSAVSLFNATAIAVAEGTDWVIEVIQRAFRAFIHIPTRVRQGLERA
LQ-
>ENV-B.syn6.3
MRVKGIRKNCQHLWRWGILL--------LGMLMICSATEKLWVTVYYGVPVWKETTTTLF
CASDAKAYVAEKHNVWATHACVPTDPNPREVVMGNVTEEFNIWNNSMVEQMHEDIISLWE
QSLKPCVKLTPLCVSLKCTDL------KNDTNTNSSSGRMIMEKGEIKNCSFNITTGIRG
KVQ-EYSLFYKLDVVQM-DEDNTS---------YRLINCNTSVITQACPKVSFQPIPIH
YCAPAGFAILKCKDKKFNGTGSCKNVSTVQCTHGIRPVISTQLLLNGSLAEGEVVIRSEN
FTDNAKTIIVQLKDPVKINCTRPNNNTRKSIPIGPGRAFYATGDIIGDIRQAHCNISTTK
WNKTLGQVVKKLREQFK-NKTIVFKQSSGGDPEVVMHSFNCGGEFFYCNTSQLFNSTW--
--------N---STSLFNSTN---GTITLQCRIKQIINRWQEVGKAMYAPPIEGQIRCLS
NITGLLLVRDGGINVTNN--TGTEVFRPGGGDMRDNWRSELYKYKVIKIEPLGVAPTRAK
RRVVQREKRAVG-LGAMFLGFLGAAGSTMGAASITLTVQARQLLSGIVQQQRNLLRAIEA
QQHMLQLTVWGIKQLQARVLAVERYLQDQQLLGIWGCSGKLICTTTVPWNTSWSNKSLNQ
IWDNMTWMQWEKEIDNYTGLIYTLLEESQNQQEKNEHELLELDKWASLWNWFNITNWLWY
IKIFIMIIGGLIGLRIVFAVLSIVNRVRQGYSPISFQTRLPAPRGPDRPDGIEEEGGDRD
RDRSGRLVDGFLTLIWVDLRSLCLFSYRRLRDLLLIAARIVELLG------HRGWEALK
YWWNLLQYWIQELKNSAVNLLNTTAIAVAEGTDRVIEVVQRAYRAILNIPTRIRQGFERA
LL-
>ENV-B.syn6.4
MRVKEIRKNCQRLWRWGTML--------LGMLMICSAAEQLWVTVYYGVPVWRDANATLF
CASDAKAYDTEVHNVWATHASVPTDPNPQEVVLGNVTENFNMWKNDMVEQMHEDVISLWD
QSLKPCVKLTPICVTLNCTDYVKNIT-NNATSTNSSW-GEPMEKGEIKNCSFNITTSMKD
KVQKTYALFYKLDVVPI-DNDSNNNDSTNTNYTNYRLISCNTSVIKQACPKVSFDPIPIH
YCTPAGFAILKCRDKKFNGTGPCKNVSTVQCTHGIRPVVPTQLLLNGSLAEEEIVIRSEN
FSDNAKTIIVHLNESVEINCTRLNNNTRKSIHMGPGRAFYATGEIIGDIRQAHCNISRAK
WNNTLKQIAIKLREQFGNNKTIIFKQSSGGDPEIVTHSFNCGGEFFYCNSTQLFNSTWNF
--NGTWNKN---FNNTWNNTEGTNDTITLPCRIKQIINMWQKVGKAMYAPPISGQIRCTS
NITGLLLTRDGGN---DT--SGTEIFRPGGGNMKDNWRSELYKYKVVQIEPLGVAPTEAK
RRVVQREKRAVG-IGAVFLGFLGAAGSTMGAAAVTLTVQARLLLSGIVQQQNNLLKAIEA
QQHLLRLTVWGIKQLQARLLAVERYLGDQQLLGLWGCSGKLICTTAVPWNTSWSNRSLNE
IWNNMTWMEWEKEIDNYTNLIYNLLEESQNQQEKNEKELLELDKWANLWNWFDISNWLWY
IRIFIMIVGGLIGLRIVFIVLSVVNRVRQGYSPLSLQTRLPTQRGPDRPEGTEEEGGERD
RDTSGRLVDGFLAIIWVDLRSLFLFSYHRLRDLLLIVTRIVELLG------RRGWEILK
YWWNLLQYWGQELKNSAVSLLNATAITVAEGTDRVIEVLQRAGRAILHIPTRIRQGLERI
LL-
>ENV-B.syn6.5
MRVKGIRRNYQHLWRWGIML--------LGMLMICSATEQLWVTVYYGVPVWKEANTTLF
CASDAKAYKTEAHNVWATHASVPTDPNPQEIVLENVTENFNMWKNNMAEQMHEDIINLWD
QSLKPCVELTPLCVTLNCTDELKNATFRSNTTTNSSW--EKMEKGEIKNCSFNVTTSIRD
KMQKEYALFYRLDVVPI-DNDNTS---------YRLISCNTSVITQACPKISFEPIPIH
YCVPAGFAILKCNNKTFNGTGPCTNVSTVQCTHGIKPVVSTQLLLNGSLAEEDVVIRSEN
FTDNTKTIIVQLKEAVEINCTRPNNNTRKGIHIGPGRAFYTTGEIIGNIRQAHCNLSRAK
WNDTLKQIVIKLREQFG-NKTIVFNQSSGGDVEIVMHSFNCGGEFFYCNTTQLFNSTW--
---NANDIRN---VTRGSNRTTGGNDTLILPCRIKQIVNMWQEVGKAMYAPPIKGQIKCSS
```

Fig. 10 cont'd-4

```
NITGLLLTRDGGNNGNET--NGTEIFRPGGGDMRNNWRSELYKYKVVRIEPLGVAPTKAR
RRVVQREKRAVT-LGAMFLGFLGAAGSTMGAASMTLTVQARLLLSGIVQQQSNLLRAIEA
QQRLLQLTVWGIKQLQARILAIERYLKDQQLLGIWCSGKIICTTAVPWNASWSNKSQDE
IWNNMTWMQWEREIDNYTGLIYNLIEESQNQQEKNEQELLALDKWANLWNWFDITKWLWY
IKIFIMIVGGLIGLRIVFTVLSIVNRVRKGYSPLSFQTRLPAQRGPDRPEGIEEEGGERD
RDRSGPLVDGFLAIFWVDLRSLFLFSYRHLRDLLLIVARIVELLG------RRGWELLK
YWWNLLQYWSQELKSSAVSLLNATAIAVAEGTDRILEVLQRAYRAILHIPVRIRQGLERA
LL-
>ENV-B.syn6.6
MRVKGIRKNYQHLWRWGMML--------FGMLMICSAAGNLWVTVYYGVPVWREATTTLF
CASDAKAYETEVHNVWATHACVPTDPSPQEVVLENVTEDFNMWKNNMVDQMHEDIISLWD
ESLKPCVKLTPLCVTLNCTDDVRNVT-NNATNTNSSW-GEPMEKGEIKFCSFNITTSIRN
KVQKQYALFYKLDVIPI-DSRNNSNNSTE--YNSYRLINCNSSTITQACPKVTFEPIPIH
YCAPAGFAILKCNNKKFNGTGPCNNVSTVQCTHGIRPVVSTQLLLNGSLAEKEVVIRSDN
FTNNAKTIIVQLNESVVINCTRPNNNTRKRISMGPGRVYYTTGEIIGDIRRAHCNISRAQ
WNNTLKHIVEKLGKQFGNNKTI-FNHSSGGDPEIVMHSFNCRGEFFYCKSTKLFNSTWTR
N-NGTWTRN---DTERSNSTE---EHITLPCRIKQIINMWQGVGKAMYAPPIRGQIRCSS
NITGLILTRDGGNNDT----RGTEIFRPGGGDMKDNWRSELYRYKVVKIEPLGIAPTKAK
RRVVQREKRAVGTIGAMFLGFLGTAGSTMGAASLTLTVQARLLLSGIVQQQNNLLRAIEA
QQHLLQLTVWGIKQLQAKVLAVERYLRDQQLLGIWCSGRLICTTNVPWNASWSNKSLDK
IWNNMTWMEWDREINNYTSLIYSLIEESQNQQEKNEQDLLALDKWASLWNWFDITNWLWY
IKIFIMVVGGLVGLRIIFAVLSIVNKVRQGYSPLSLQTHLPARRGPDRPEGIEGEGGERD
RDRSVRLVDGFLALFWDDLRSLCLFLYHRLRDLLLIVTRTVELLG-------RRGWEALK
YCWNLLQYWSQELKNSAVSLFNAIAIAVAEGTDRIIEVVQRICRAIRHIPRRIRQGFERA
LL- >ENV-C.syn1.1
MRVRGIQRNWPQWWIWGILG--------FWMLMICNVVGNLWVTVYYGVPVWKEAKTTLF
CASDAKAYEKEVHNVWATHACVPTDPNPQEIVLENVTENFNMWKNDMVDQMHEDIISLWD
QSLKPCVKLTPLCVTLNCTDVKVNATSNGTTTYNNSI-DS--MNGEIKNCSFNTTTEIRD
KKQKVYALFYRLDIVPL-DNNSSE---------YRLINCNTSTITQACPKVSFDPIPIH
YCAPAGYAILKCNNKTFNGTGPCNNVSTVQCTHGIKPVVSTQLLLNGSLAEEEIIIRSEN
LTNNAKTIIVHLNESVEIVCTRPNNNTRKSIRIGPGQTFYATGDIIGDIRQAHCNISEKQ
WDQTLYRVSEKLKEHFP-NKTIKFAPSSGGDLEITTHSFNCRGEFFYCNTSKLFNSTY--
--NSTQMHN---DTGS--NST-----ITLPCRIKQIINMWQEVGRAMYAPPIAGNITCKS
NITGLLLTRDGGTNN-----NNTETFRPGGGDMRDNWRSELYKYKVVEIKPLGIAPTKAK
RRVVEREKRAVG-IGAVFLGFLGAAGSTMGAASITLTVQARQLLSGIVQQQSNLLRAIEA
QQHMLQLTVWGIKQLQTRVLAIERYLKDQQLLGIWCSGKLICTTAVPWNSSWSNKSQTD
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRLGRIEEEGGEQD
RDRSIRLVSGFLALAWDDLRSLCLFSYHRLRDFILVTARAVELLGRSSLRGLQRGWEALK
YLGSLVQYWGLELKKSAISLLDTIAIAVAEGTDRIIELIQRICRAIRNIPRRIRQGFEAA
LL- >ENV-C.syn3.1
MRVMGIQRNCQQWWIWGSLG--------FWMLMIYNVMGNLWVTVYYGVPVWKEAKTTLF
CASDAKAYDTEVHNVWATYACVPTDPNPQEMVLENVTENFNMWKNNMVDQMHEDIISLWD
QSLKPCVKMTPLCVTLNCSNAKKD---------NTTI-DNE-MKGEIKNCSFNITTELRD
KKKQVYALFYKLDIVPL-NSNSSE---------YRLINCNTSAITQACPKVSFDPIPIH
YCAPAGYAILKCNNETFNGTGPCNNVSTVQCTHGIRPVVSTQLLLNGSLAEKEIIIRSEN
LTDNVKTIIVHLNESVEINCTRPNNNTRRSIRIGPGQAFYATGEIIGDIRQAYCNISGEK
WNETLQRVGKKLKEHFP-NKTIKFAPSSGGDLEITTHSFNCRREFFYCNTSGLFNGTY--
--NGNGTYN---GTGTDTNST-----ITIPCRIKQIINMWQEVGRAMYAPPIEGNITCKS
NITGLLLVRDGGTENNTET-NNTETFRPGGGDMRDNWRSELYRYRVVEIKPLGIAPTKAK
RRVVERGKRAVG-IGAVFLGFLGVAGSTMGAASITLTVQARQVLSGIVQQQSNLLRAIEA
QQHLLQLTVWGIKQLQTRVLAIERYLKDQQLGIWGYSGKLICTTAVPWNSSWSNRSQED
```

Fig. 10 cont'd-5

```
IWNNMTWMQWDREINNYTNTIYRLLEDSQNQQEKNEQDLLALDSWKNLWNWFDITNWLWY
IRIFIMIVGGLIGLRIIFAVLSIVNRVRQGYSPLSLQTLTPNPRELDRLGRIEEGGGEQD
RDRSIRLVSGFLALAWDDLRSLCLFSYHRLRDFILIAARAAELLGRSSLKGLQRGWEILK
YLGSLIQYWGLELKKSAINLLDTIAIVVAEGTDRIIELIQRICRAICNIPRRIRQGFEAA
LQ-
>ENV-C.syn3.2
MRVRGILRNWQQWWIWGILG--------FWMLMICNVVGNLWVTVYYGVPVWREAKTTLF
CASDAKAYEREVHNVWATHACVPTDPNPQELVLENVTENFNMWKNDMVDQMHQDIISLWD
ESLKPCVKLTPLCVTLKCVNVTKNS--NATVNSNATV-NNNTMGEEIKNCSFNATTEIRD
KKQNVYALFYRLDIVPL-NENNDNSS--------YRLINCNTSTITQACPKVTFDPIPIH
YCTPAGYAILKCNDKTFNGTGPCHNVSTVQCTHGIKPVISTQLLLNGSLAEEEIIIRSEN
LTNNVKTIIVHLNKSVEIVCTRPGNNTRKSVRIGPGQTFYATGDIIGDIRQAHCNISRTA
WNKTLQEVGKKLAEHFP-NKTIEFKPSSGGDLEVTTHSFNCRGEFFYCNTSKLFNSTYNS
TYNSTYNSN---STNSNSNST-----ITLQCRIKQIINMWQKVGRAIYAPPIAGNITCRS
NITGLLLTRDGGNNNDTGNNNDTEIFRPGGGDMKDNWRNELYKYKVVEVKPLGIAPTGAK
RRVVEREKRAVG-LGAVFLGFLGAAGSTMGAASMTLTVQARQLLSGIVQQQNNLLRAIEA
QQHMWQVTVWGIKQLQARVLALERYLKDQQLLGLWGCSGKLICTTNVPWNSSWSNKSLTD
IWENMTWMQWDKEISNYTDTIYRLLEVSQNQQEKNEKDLLALDSWNNLWNWFSITKWLWY
IKIFIMIVGGLIGLRIIFGVLSIVKRVRQGYSPLSFQTLTPNPRGPDRLGRIEEEGGEQD
KDRSIRLVNGFLALAWDDLRNLCLFSYHQLRDFILIVARAVELLGHSSLRGLQRGWEALK
YLGSLVQYWGLELKRSAISLLDTTAIAVAEGTDRIIEVIQRICRAIRNIPTRIRQGFEAA
LLQ
>ENV-C.syn3.3
MRVRGIQRNWPQWWIWGILG--------FWMIIICRVVGNLWVTVYYGVPVWTEAKATLF
CASDAKAYEKEVHNVWATHSCVPTDPNPQEIVLGNVTENFNMWENDMVDQMHEDVISLWD
QSLKPCVKLTPLCVTLNCT--------NANVTVNATSDGS--IKEEIKNCSFNTTTEIRD
KKQKVYALFYRPDIVPLSGSNSSE---------YILINCNTSTVTQACPKVSFEPIPIH
YCAPASYAILKCNNKTFNGTGPCQNVSTVQCTHGIKPVVSTQLLLNGSLAEGEIIIRSEN
LTNNAKTIIVHLNESIEIVCTRPNNNTRKSIRIGPGQTFFATGDIIGNIRQAHCNISEEK
WNKTLQEVSRKLREHFP-NKTIIFNSSSGGDLEITTHSFNCGGEFFYCNTTKLFNDS---
------------ALSAFNKTS--NETITLPCRIKQIINMWQGVGRAMYAPPIAGNITCNS
SITGLLLTRDGGT-------NNTEIFRPGGGNMKDNWRSELYKYKVVEIKPLGVAPTEAK
RRVVEREKRAVG-IGAVLLGFLGAAGSTMGAASITLTAQARQLLSGIVQQQSNLLKAIEA
QQHMLQLTVWGIKQLQARVLAIERYLQDQQLLGIWGCSGKLICTTTVPWNSSWSNKSQTD
IWDNMTWMQWDREISNYTNTIYRLLEESQNQQEQNEKDLLALDKWQNLWSWFSITNWLWY
IKIFIIIVGGLIGLRIILGVLSIVRRVRQGYSPLSFQTLIPNPRGPDRLGGIEEEGGEQD
RDRSVRLVSGFLSLAWDDLRSLCLFCYHRLRDFILVTARAVELLGRSSLRGLQKGWEALK
YLGNLVQYWGLELKKSAISLLDTIAIAVAEGTDRIIEFIQRICRAIRNIPRRIRQGLEAA
LQ-
>ENV-C.syn4.1
MRVRGILRNYQQWWIWGSLG--------FWMLMIYNVGGNLWVTVYYGVPVWKEAKTTLF
CASDAKAYDTEVHNVWATHACVPTDPDPQEIVLENVTENFNMWENDMVDQMHEDIISLWD
ESLKPCVKLTPLCVTLKCTNVTST---GNTTRGNNTS-EN---REEMKNCSFNTTTEIRD
KKQKVYALFYKPDVVPL-KENSSE---------YILINCNTSTVTQACPKVSFDPIPIH
YCAPAGFAILKCNNKTFNGTGPCNNVSTVQCTHGIKPVVSTQLLLNGSLAEEEIIIRSEN
LTDNAKTIIVHLNESIEIVCTRPGNNTRKSIRIGPGQAFYATGDIIGDIRQAYCNISKAT
WNKTLQEVGKELAKHFP-NKTINFNSSSGGDLEITTHSFNCGGEFFYCNTTKLFNNSL--
------------LNNTADNST---STITLQCRIKQIINMWQGVGQAMYAPPIAGNITCKS
NITGLLLLRDGGDTST----NGTEIFRPGGGNMKDNWRSELYKYKVVEVKPLGIAPTGAK
RRVVEREKRAVG-IGAVLLGFLGAAGSTMGAASITLTAQARQVLSGTVQQQSNLLRAVEA
QQHMLQLTVWGIKQLQTRVLAIERYLKDQQLLGIWGCSGKLICTTNVPWNSSWSNKSQEE
IWENMTWMQWDREISNYTGTIYRLLEESQNQQEKNEQDLLALDSWKNLWNWFDISNWLWY
IKIFIIIVGGLIGLRIIFGVLSIVKRVRQGYSPLSFQTLIPNPRGPDRLERIEEEGGEQD
RGRSIRLVSGFLAIAWDDLRSLCLFSYHQLRDFILIAVRAVELLGHSSLRGLQRGWEALK
YLGSLVQYWGLELKRSAISLLDTIAIVVAEGTDRIIEFIQRICRAIRNIPTRIRQGFEAA
LQ-
```

Fig. 10 cont'd-6

```
>ENV-C.syn4.2
MRVMGIQRNCQQWWIWGILG--------FWILMICNVMGNLWVTVYYGVPVWKEAKATLF
CASDAKAYEKEVHNIWATHACVPTDPNPQELVLENVTENFNMWDNDMVDQMHQDIISLWD
QSLKPCVKLAPLCVTLNCTNATVTATRNGSDIMNTTS-ND----GEMKNCSFNVTTELRD
KKKKEYALFYRLDIVPL-NEGSGNANQNNSNYSDYRLINCNTSAITQACPKVTFDPIPIH
YCTPAGYAILKCNDKTFNGTGPCHNVSTVQCTHGIRPVVSTQLLLNGSLAEGEIMIRSEN
LTNNAKTIIVHLNKSVEIVCTRPNNNTRKSVRIGPGQTFYATNDIIGDIRQAHCNISEEK
WNKTLQQVGKKLAEHFP-NKTIEFKPSSGGDLEVTTHSFNCRGEFFYCNTSGLFNGTF--
--DGT-------ESNSTSNAT-----ITIPCRIKQIINMWQKVGRAIYAPPIAGNITCRS
NITGLLLVRDGGNDNKT---NDTETFRPGGGDMRDNWRSELYKYKVVEVKPLGVAPTKAK
RRVVQREKRAVG-IGAVFLGFLGVAGSTMGAASMTLTVQARQVLSGIVQQQSNLLRAIEA
QQHLLQLTVWGIKQLQARVLALERYLRDQQLLGMWGCSGKLICTTAVPWNSSWSNKSQED
IWGNMTWMQWDKEISNYTNTIYRLLEDSQNQQERNEKDLLALDSWKNLWSWFDITNWLWY
IKIFIMIIGGLIGLRIIFAVLSIVNRVRQGYSPLSLQTLTPNPRGPDRLGRIEEEGGEQD
KDRSIRLVNGFLALAWDDLRNLCLFSYHRLRDFILIVARAVELLGRNSLRGLQRGWETLK
YLGSLIQYWGLELKKSAISLLDTTAIAVAEGTDRIIELIQRICRAICNIPRRIRQGLEAA
LQ-
>ENV-C.syn4.3
MRVRGIQRNWPQWWIWGILG--------FWMIIICRVVGNLWVTVYYGVPVWREAKTTLF
CASNAKAYEKEVHNVWATHACVPTDPNPQEIVLGNVTENFNMWKNDMVDQMHEDVISLWD
QSLKPCVKMTPLCVTLNCTDVKVNATSNGTTTYNNSI-DS--MNGEIKNCSFNTTTELRD
KKKQKAYALFYRPDIVPLPGKDNSKDNSSEYEE--YILINCNSSTITQACPKVSFEPIPIH
YCAPASYAILKCNNETFNGTGPCKNVSTVQCTHGIKPVISTQLLLNGSLAEKEIIIRSEN
LTNNVKTIIVHLKESVEINCTRPNNNTRKSIRIGPGQTFYATGDIIGNIRQAHCNISREK
WNTTLKRVKEKLKEHFP-NKTIKFAPSSGGDLEITTHTFNCRGEFFYCNTSKLFNSTYV-
--NRTDMND---D--TGNNST-----ITLPCRIKQIINMWQEVGRAMYAPPIAGNITCNS
SITGLLLTRDGGNNT-----ENTETFRPGGGNMKDNWRNELYKYKVVEIKPLGVAPTEAK
RRVVEREKRAVG-LGAVFLGFLGAAGSTMGAASITLTVQARQLLSGIVQQQNNLLRAIEA
QQHMLQLAVWGIKQLQARVLAIERYLQDQQLLGIWGCSGKLICTTSVPWNSSWSNRSQED
IWNNMTWMQWDREISNYTDTIYRLLEVSQNQQEQNEKDLLALDKWQNLWSWFSITNWLWY
IRIFIMIVGGLIGLRIVFAVLSLVNRVRQGYSPLSFQTLTPSPRGPDRLGGIEEEGGEQD
RDRSIRLVSGFLSLAWDDLRSLCLFSYHRLRDFILIAARAAELLGRSSLRGLQRGWEILK
YLGSLAQYWGLELKKSAINLLDTIAIAVAEGTDRIIEVIQRICRAIYNIPRRIRQGFEAS
LL-
>ENV-C.syn4.4
MRVRGIPRNWQQWWIWGILG--------FWMLMICNVVGNLWVTVYYGVPVWTEAKTTLF
CASDAKAYEREVHNVWATYACVPTDPNPQEMVLENVTENFNMWKNDMVEQMHEDIISLWD
QGLKPCVKLTPLCVTLNCSNAKKD---------NTTI-DNE-MKGEIKNCSFNITTELRD
KKQQVYALFYKLDIVPL-NSNSSE----------YRLINCNTSTITQACPKVNFDPIPIH
YCAPAGYAILKCNNKTFNGTGPCQNVSTVQCTHRIKPVVSTQLLINGSLAEGEIIIRSEN
LTDNVKTIIVHLNESVEIVCTRPNNNTRKSMRIGPGQTFYATGEIIGDIRQAHCNISKEK
WNNTLQEVREKLREHFP-NKTIKFAPHSGGDPEITTHSFNCRGEFFYCNTSQLFNSTY--
--NSTQMHN---DTGS--NST-----ITLPCKIKQIINMWQGVGRAMYAPPIEGNITCTS
NITGLLLTRDGGT-------NNTEIFRPGGGDMRNNWRSELYKYKVVEIKPLGIAPTKAK
RRVVERGKRAVG-IGAVFLGFLGAAGSTMGAASIALTAQARQLLSGIVQQQSNLLKAIEA
QQHMWQVTVWGIKQLQARVLAMERYLKDQQLLGLWGCSGKLICTTTVPWNSSWSNKSQTD
IWDNMTWMQWDREINNYTNTIYKLLEDSQNQQEKNEKDLLALDSWNNLWNWFSITKWLWY
IKIFIMIVGGLIGLRIILGVLSIVRRVRQGYSPLSFQTLTPNPRELDRLGRIEEGGGEQD
RDRSVRLVSGFLALAWDDLRSLCLFCYHRLRDFILVTARAVELLGRSSLKGLQRGWEALK
YLGNLVQYWGLELKKSAISLFDTIAITVAEGTDRIIELVQRICRAIRNIPRRIRQGFEAA
LL-
>ENV-C.syn6.1
MRVRGIQRNWPQWWIWGILG--------FWIIIMCRVMGNMWVTVYYGVPVWREAKTTLF
CASDAKGYEKEVHNAWATHACVPTGPNPQEMVLENVTENFNMWKNNMVDQMHEDIINLWD
QSLKPCVRLTPLCVTLKCVNVTKNS--NATVNSNATV-NNNTMGEEIKNCSFNATTEIRD
KKQKAYALFYRPDIVPL-NENSSSENNSSE----YILINCNTSTITQACPKVSFDPIPIH
YCAPASYAILKCNNETFNGTGPCQNVSTVQCTHGIKPVISTQLLLNGSLAEEDIIIRSEN
```

Fig. 10 cont'd-7

```
LTNNAKTIIVHLNQSVEIVCTRPGNNTRKSMRIGPGQTFYATNDIIGNIRQAHCNISEGK
WNETLLRVKKKLEEHFP-NKTIKFEPSSGGDLEITTHTFNCRGEFFYCDTSTLFNHTY--
---VSAYMNNTDVSADRKNDTQ-SNSTITLPCRIRQIINMWQEVGRAIYAPPIAGNITCRS
NITGLLLVRDGGNTT-----NSTETFRPEGGNMKDNWRSELYKYKVVEIRPLGIAPTGAK
RRVVEREKRAVG-IGAVFLGFLGVAGSTMGAASMTLTVQARQVLSGVVQQQSNLLQAIEA
QQHLLQLTVWGIKQLQTRVLALERYLRDQQLLGIWCSGKIICTTAVPWNTSWSNKSQED
IWNNMTWMQWDREINNYTNTIYKLLEESQNQQEKNEQDLLALDSWNSLWNWFSITKWLWY
IRIFIIIVGSLIGLRIIFGVLSIVKRVRQGYSPLLSQTLTPNPREPDRLGRIEEGGGEQD
RDRSVRLVNGFLALVWDDLRSLCLFCYHRLRDFILVTARVVELLGRSSLRGLQKGWEALK
YLGSLVQYWGLELKKSAINLLDTIAIAVGEGTDRIIEVIQRICRAIYNIPRRIRQGFEAS
LL-
>ENV-C.syn6.2
MRVRGILRNYQQWWIWGSLG--------FWMLMIYNVGGNLWVTVYYGVPVWTDAKTTLF
CASDAKAYDKEVHNVWATHACVPTDPNPQELVLENVTENFNMWKNDMVNQMHEDIISLWD
ESLKPCVKLTPLCVTLNCTNATVTATRNGSDIMNTTS-ND----GEMKNCSFNITTELRD
KKRKEYALFYRLDIVPL-DENNSSEKSSENSSEYYRLINCNTSAITQACPKVTFDPIPLH
YCAPAGYAILKCKDKTFNGTGPCSNVSTVQCTHGIKPVVSTRLLLNGSLAEGEIIIRSEN
LTNNVKTIIVHLKEPVEINCTRPNNNTRESIRIGPGQTFYATGDIIGDIRQAHCNISREK
WNKTLQEVGKKLAEHFP-NKTIKFAPHSGGDLEITMHSFNCRGEFFYCNTSGLFNGTY--
---MPTYMPN---GTESNSNST-----ITIPCRIKQIINMWQEVGRAMYAPPIEGNITCNS
NITGLLLVRDGGINKT----NNTETFRPGGGDMRNNWRSELYKYKVVEIKPLGVAPTEAK
RRVVEREKRA-A-LGAMFLGFLGAAGSNMGAASITLTAQARQLLSGIVQQRSNLLRAIEA
QQHLLQLTVWGVKQLQARVLAMERYLKDQQLLGLWCSGKLICTTSVPWNSSWSNRSQEE
IWNNMTWMEWDREISNYTNTIYRLLEDSQNQQEKNEKDLLALDSWKNLWSWFDITNWLWY
IKIFIMIIGGLIGLRIVFAVLSIVNRVRQGYSPLSFQTLTPSPRGPDRLGRIEEEGGEQD
KDRSVRLVSGFLSLAWDDLRSLCLFSYHRLRDLILIAARAVELLGHSSLRGLQRGWEILK
YLGSLAQYWGLELKRSAISLLDTIAITVAEGTDRIIEIIQRICRAICNIPRRIRQGFETA
LL-
>ENV-C.syn6.3
MRVMGILRNCQQWWIWGVLG--------FWMLMICNVVGNLWVTVYYGVPVWKEAKTTLF
CASNAKAYEREVHNIWATHACVPTDPNPQEMVLKNVTENFNMWKNDMVDQMHEDVISLWD
QSLKPCVKLAPLCVTLNCTNVTVNDTLHQNFT--------------DMKNCSFNVTTELRD
KKQKVYALFYRLDVVPL-GDNNSS---------YRLINCNTSTIAQACPKVNFDPIPIH
YCTPAGYAILKCNDKTFNGTGPCKNVSTVQCTHEIKPVVSTQLLLNGSLAEEGIIIRSEN
LTDNAKTIIVHLNESVEINCTRPGNNTRQSIRIGPGQAFYATGAIIGDIRQAHCNISKDE
WEKTLKRVSEKLKEHFP-NKTIEFKPSSGGDLEVTTHSFNCRREFFYCNTSKLFNSTY--
---NSTQMHN---DTGS--NST-----ITLPCKIKQIINMWQGVGQAMYAPPIKGNITCKS
NITGILLTRDGGNLT-----NGTETFRPGGGDMKDNWRSELYRYRVVEIKPLGIAPTKAK
RRVVQREKRAVG-IGALFLGFLGTAGSTMGAASLTLTVQARQLLSSIVQQQSNLLRAIEA
QQHMLQLTIWGIKQLQTRVLAVERYLKDQQLLGMWCSGKLICTTAVPWNASWSNKSQEE
IWGNMTWMQWDREISNYTDIIYRLLEESQNQQERNEKDLLALDSWNNLWNWFNITNWLWY
IKIFIMIVGGVIGLRIIFAVLSLVNRVRQGYSPLSFQTLTPNPRELDRLGRIEEEGGEQG
RDRSIRLVNGFLAIAWDDLRSLCLFSYRRLRDFILIAARAAELLGRSSLRGLQRGWETLK
YLGSLIQYWGLELKKSAISLFDTIAIAVAEGTDRIIELIQRICRAIRNIPRRIRQGLEAA
LQ-
>ENV-C.syn6.4
MRVMGIQRNCQQWWIWGILG--------FWMLMIYNVVGNLWVTIYYGVPVWKEAKATLF
CASDAKAYDTEVHNVWATHACVPTDPDPQEMVLGNVTENFNMWKNDMADQMHEDIISLWD
QGLKPCVKLTPLCVTLHCTN-------TNITNENRTI-GDKLNE-EMKNCSFNTTTELRD
KKQQVYALFYKPDVVPL-NGGEHNETGE------YILINCNSSTITQACPKVSFEPIPIH
YCAPAGFAILKCNNKTFNGTGPCHNVSTVQCTHGIRPVVSTQLLLNGSLAEEEIIIRSEN
LTDNVKTIIVHLNKSVEIVCTRPNNNTRKSIRIGPGQTFFATNDIIGDIRQAYCNISAEK
WNKTLERVEEKLKEHFP-NKTIKFNSSSGGDLEITTHSFNCRGEFFYCNTSNLFNGTY--
---HGTQSTN---ST----NST-----ITLQCRIKQIINMWQKVGRAMYAPPIAGNITCKS
NITGLLLLRDGGTEN-----NDTETFRPGGGNMRDNWRSELYKYVVEVKPLGIAPTTAK
RRVVERDKRAVG-IGAVLLGFLGAAGSTMGAASMALTVQARQLLSGIVQQQSNLLRAVEA
```

Fig. 10 cont'd-8

```
QQHMLQLTVWGIKQLQARVLALERYLKDQQLLGIWGCSGRLICTTAVPWNSSWSNKTQGE
IWENMTWMQWDKEINNYTNTIYRLLEESQTQQEQNEKDLLALDSWKNLWNWFDITKWLWY
IKIFIMVVGGLIGLRIIFAVLSIVNSVRQGYSPLSLQTLTPNPRGPDRLERIEEEGGEQD
RNRSIRLVNGFLALAWDDLRSLCLFSYHHLRDFILVTARAVELLGRSSLKGLQRGWEALK
YLGNLVQYWGLELKKSAISLLDTTAIAVAEGTDRIIELVQRICRAILNIPTRIRQGFEAA
LQ-
>ENV-C.syn6.5
MRVRGIPRNWPQWWTWGILG--------FWMIIICRVVGNLWVTVYYGVPVWTEAKTTLF
CASDAKAYEREVHNVWATHSCVPTDPNPQEIVLGNVTENFNMWENDMVDQMHQDIISLWD
QSLKPCVKMTPLCVTLNCSNAKKD---------NTTI-DNE-MKGEIKNCSFNITTEIRD
KKQKVHALFYRLDIVPL--NEGSGNANQNNSNYSDYRLINCNTSTVTQACPKVTFDPIPIH
YCAPARYAILKCNNNTFNGTGPCNNVSTVQCTHGIKPVVSTQLLLSGSLAEEEIVIRSEN
LTNNAKIIIVHLNESVEIVCTRPNNNTRRSIRIGPGQTFYATGEIIGDIRQAHCNISAKQ
WNTTLERVKEKLREHFP-NKTIKFEPHSGGDPEITTHSFNCGGEFFYCNTSQLFNSTY--
--NSTYMSN---NTGENSNET------ITLPCRIKQIINMWQQVGRAMYAPPIAGNITCNS
SITGLLLTRDGGNNNDTGNNNDTEIFRPGGGDMRDNWRSELYKYKVVELKPLGIAPTEAK
RRVVKREKRAVG-IGAVLFGFLGAAGSTMGAASIALTAQARQVLSGIVQQQNNLLRAIEA
QQHVLQLTVWGIKQLQTRVLAIERYLKDQQLLSLWGCSGKLICTTTVPWNSSWSNKSLTD
IWDNMTWMQWDREISNYTGTIYRLLEDSQSQQEKNEKDLLELDKWNNLWNWFDISNWLWY
IKIFIIIVGGLIGLRIIFAVLSIINRVRQGYSPLLFQTLTPNPRGLDRLGRIEEEGGEQD
KDRSIRLVNGFLALAWEDLRSLCLFSYHQLRDFILIVARAVELLG-------RRGWEALK
YLGNLVLYWGLELKKSAVSLLDTIAIAVAGGTDRIIEVVQRICRAIRNIPTRIRQGLEAA
LL-
>ENV-C.syn6.6
MRVRGILRNWQQWWIWGILG--------FWMVMICNVMGNLWVTVYYGVPVWQEAKTTLF
CASDAKAYEKEVHNVWATHACVPTDPSPQEIVLENVTENFNMWKNDMVEQMHEDIISIWD
QSLKPCVTLTPLCVTLNCTDVKVNATSNGTTTYNNSI-DS--MNGEIKNCSFNTTTEIRD
KKKQVYALFYKLDIVPL-NSNSSE----------YRLINCNTSAVTQACPKVSWDPIPIH
YCAPAGYAILKCNNKTFNGTGPCTNVSTVQCTHRIKPVVTTQLLLNGSLAEKEIIIRSEN
LTNNIKTIIVHLNESIEIVCTRPNNNTRKSVRIGPGQTFFATGDIIGDIRKAHCNISEDK
WNETLQRVGKKLVEHFP-NKTIKFAPSSGGDLEVTTHSFNCKGEFFYCNTTKLFD-----
---------------DSERINTTT---TTIILPCRIKQFINMWQGVGRAMYAPPIAGNITCTS
NITGLLLLTRDGGT-------NNTEIFRPGGGNMKDNWRNELYKYKVVEVKPLGVAPTKAK
RRVVEREKRAVG-LGAVFLGFLGAAGSTMGAASITLTVQARQLLFGIVQQQSNLLKAIEA
QQHMWQVTVWGIKQLQARVLAIERYLQDQQLLGIWGCSGKLICTTNVPWNSSWSNKSQTD
IWDNMTWMQWDKEISNYTDTIYRLLEVSQNQQEENEKDLLALDKWQNLWNWFSITNWLWY
IRIFIMIVGGLIGLRIILGVLSIVRRVRQGYSPLSFQTLIPNPRGPDRLGGIEEEGGEQD
RDRSIRLVSGFLALAWDDLRNLCLFSYHRLRDFILIVVRAVELLGRNSLRGLQRGWEALK
YLGSLGQYWGLEIKKSAISLLDTIAIVVAEGTDRIIEFIQRFCRAIRNLPRRIRQGFEAA
LL- >ENV-M.syn1.1
MRVTGIRKNYQHLWRWGTMLLWRWGTMLLGMLMICSAAGNLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIKPVVSTQLLLNGSLAEEEVVIRSEN
FTNNAKTIIVQLNESVEINCTRPNNNTRKSIRIGPGQTFYATGDIIGDIRQAHCNISRAQ
WNNTLKHIVEKLGKQFGNNKTIVFNHSSGGDPEIVMHSFNCGGEFFYCNTTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASITLTVQARQLLSGIVQQQNNLLRAIEA
QQHLLQLTVWGIKQLQARVLAVERYLKDQQLLGIWGCSGKLICTTAVPWNSSWSNKSLNE
IWNNMTWMEWEREIDNYTGLIYTLIEESQNQQEKNEQELLELDKWASLWNWFDISNWLWY
IKIFIMIVGGLIGLRIVFAVLSIVNRVRQGYSPLSFQTRLPAPRGPDRPEGIEEEGGERD
RDRSIRLVSGFLALAWDDLRSLCLFSYHRLRDLLLIVTRIVELLG-------RRGWEALK
```

Fig. 10 cont'd-9

```
YWWNLLQYWSQELKNSAVSLLNATAIAVAEGTDRVIEALQRACRAILHIPRRIRQGLERA
LL-
>ENV-M.syn3.1
MRVRGIQRNWPQWWIWGILG--------FWMLMICNVVGNLWVTVYYGVPVWKEAKTTLF
CASDAKAYEKEVHNVWATYACVPTDPNPQEIHLENVTEEFNMWKNDMVDQMHEDIISLWD
QSLKPCVQLTPLCVTLNCTN-VNVTNLKNETNTKSSSGGEKMEEGEMKNCSFNITTSIRD
KVQKEYALFYKLDVVPI-DNDSNNTN--------YRLISCNTSVITQACPKVTFEPIPIH
YCTPAGFAILKCKDKKFNGTGPCKNVSTVQCTHGIKPVISTQLLLNGSLAEEEIIIRSEN
ITNNAKTIIVQLNESVEINCTRPGNNTRKSVRIGPGQTFYATGEIIGDIRQAHCNLSRAK
WNDTLKQIVIKLREQFG-NKTIVFNQSSGGDPEIVMHSFNCGGEFFYCNTTQLFNSTW--
----------N---STSLFNSTN---GTITLQCRIKQIINMWQEVGKAMYAPPIEGNITCKS
NITGLLLVRDGGT---EP--NDTETFRPGGGNMKDNWRSELYKYKVVKIEPLGVAPTKAK
RRVVQREKRAVGTIGAMFLGFLGAAGSTMGAASMTLTVQARLLLSGIVQQQNNLLRAIEA
QQHLLQLTVWGIKQLQARILAVERYLKDQQLLGLWCSGKLICTTAVPWNTSWSNKSQTD
IWDNMTWMEWEREIDNYTGLIYTLIEESQNQQEKNEQELLELDKWASLWNWFDITKWLWY
IKIFIMIVGGLVGLRIVFAVLSIVNRVRKGYSPLSFQTLTPNPRGPDRLGRIEEEGGEQD
RDRSIRLVSGFLALAWDDLRSLCLFSYHQLRDFILIVARAVELLGRSSLRGLQRGWEALK
YLGSLVQYWGLELKKSAISLLDTIAIAVAEGTDRIIEVIQRICRAIRNIPRRIRQGFERA
LL-
>ENV-M.syn3.2
MRVTGIRKNYQHLWRWGTMLLWRWGTMLLGILMICSAAGKLWVTVYYGVPVWRDAETTLF
CASDAKAHETEVHNIWATHACVPTDPNPQEVVLGNVTENFNMWKNNMVEQMHEDIISLWD
ESLKPCVKLTPICVTLNCTDDVRNVT-NNATNTNSSW-GEPMEKGEIKNCSFNMTTELRD
KKQKVHALFYKLDIVPL-NSNSSE----------YRLINCNTSAITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEITTHSFNCGGEFFYCNSTKLFNSTWTR
N-NGTWTRN---DTERSNSTE---EHITLPCRIKQIVNMWQRVGQAMYAPPIRGQIRCSS
NITGLLLTRDGGNDT-----SGTEIFRPGGGDMRNNWRNELYKYKVVRIEPLGVAPTRAK
RRVVEREKRAVG-LGAVFLGFLGAAGSTMGAASLTLTVQARQVLSGIVQQQSNLLKAIEA
QQHLLKLTVWGIKQLQARVLAVERYLRDQQLLGIWCSGKLICTTTVPWNASWSNKSLNE
IWNNMTWMEWEKEIDNYTNLIYNLLEESQNQQEKNEQDLLALDKWANLWNWFDISNWLWY
IKIFIIIVGGLIGLRIVFAVLSIINRVRQGYSPLSLQTLIPNPRGPDRPGGIEEEGGEQG
RDRSIRLVNGFLALAWDDLRNLCLFSYHRLRDLLLIVTRIVELLG------RRGWEALK
YWWNLLQYWSQELKNSAISLLNATAVAVAEGTDRVIEALQRACRAILHIPRRIRQGLERL
LL-
>ENV-M.syn3.3
MRVKETRKNYQHLWKWGTML--------LGMLMICSAAEQLWVTVYYGVPVWKEATTTLF
CASDAKAYDTEVHNVWATHACVPTDPSPQEVVLENVTENFNMWKNDMVEQMHTDIISLWD
QSLKPCVKLTPLCVTLNCTDYVKNIT-NNATSTNSSW-GKPMEKGEIKNCSFNITTSIRN
KVQKQYALFYKLDIVPI-DNDNTS----------YRLINCNTSTITQACPKVSFDPIPIH
YCAPAGYAILKCNNKTFNGTGPCNNVSTVQCTHGIKPVVSTQLLLNGSLAEGEIIIRSEN
LTNNAKTIIVHLNKSVEINCTRPSNNTRKSIRIGPGQAFYATGDIIGDIRKAHCNISGTK
WNHTLEQVMEELKKHFP-NKTIKFNSSSGGDLEITTHSFNCRGEFFYCNTSGLFNSTW--
---NDTTINR----TEGSNNTR----NITLPCRIKQIINMWQGVGRAMYAPPIAGNITCKS
NITGILLTRDGGNNN-----STNETFRPGGGDMRDNWRSELYKYKVVEIKPLGIAPTKAK
RRVVEREKRAVG-IGAVFLGFLGTAGSTMGAASITLTVQARQLLSGIVQQQSNLLRAIEA
QQHMLQLTVWGIKQLQTRVLAIERYLKDQQLLGIWCSGKLICTTNVPWNSSWSNKSQSE
IWDNMTWMQWDREISNYTDTIYRLLEDSQNQQEKNEKDLLALDSWKNLWNWFDITNWLWY
IRIFIMIVGGLIGLRIIFAVLSIVNRVRQGYSPLSFQTRLPAPRGPDRPEGIEEEGGERD
RDRSVRLVDGFLALIWDDLRSLCLFSYHRLRDFILIAARTVELLGHSSLKGLRLGWEGLK
YLWNLLQYWIQELKNSAVSLLNATAIAVAEGTDRVIEVVQRAYRAILHIPTRIRQGLERA
LL-
```

Fig. 10 cont'd-10

>ENV-M.syn4.1
MRVKETRKNYQHLWKWGTML--------LGMLMICSAAEQLWVTVYYGVPVWKEATTTLF
CASDAKAHETEVHNIWATHACVPTDPNPQEVVLGNVTENFNMWKNDMVEQMHTDIISLWD
QSLKPCVELTPLCVTLHCTDL------GNATNT--------MEKGEIKNCSFNMTTELRD
KKQKVYALFYRLDIVPI-DNDNTS----------YRLINCNTSVIKQACPKVTFEPIPIH
YCTPAGFAILKCNDKNFNGTGPCKNVSTVQCTHGIRPVVSTQLLLNGSLAEKEIIRSEN
LTDNAKTIIVHLNKSVEINCTRPSNNTRKSVRIGPGQTFYATGDIIGDIRQAHCNISRAK
WNNTLKQIVTKLREQFK-NKTIVFNQSSGGDLEITTHSFNCRGEFFYCNTTQLFNSTW--
-------KN---DTEVSNNTK-GNDTITLPCRIKQIVNMWQEVGRAMYAPPIEGNITCNS
NITGILLTRDGGNNGNET--NGTEIFRPGGGNMRDNWRNELYKYKVVEIKPLGVAPTEAK
RRVVEREKRAVG-IGAVFLGFLGAAGSTMGAASITLTVQARQLLTGIVQQQSNLLRAIEA
QQHMLQLTVWGIKQLQTRVLAIERYLKDQQLLGLWGCSGKLICTTAVPWNSSWSNKTYND
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRPGGIEEEGGEQG
RDRSIRLVNGFLALAWDDLRNLCLFSYHQLRDFILIVARAVELLGRSSLRGLQRGWEALK
YLGSLVQYWGLELKKSAISLLDTIAIAVAEGTDRVIEVVQRAYRAILHIPTRIRQGLERL
LL-
>ENV-M.syn4.2
MRVRGIQRNWPQWWIWGILG--------FWMLMICNVVGNLWVTVYYGVPVWKEAKTTLF
CASDAKAYEKEVHNVWATHACVPTDPSPQEVVLENVTENFDMWKNNMVEQMQEDVISLWD
QSLKPCVKLAPLCVTLNCTDYVKNIT-NNATSTNSSW-GKPMEKGEIKFCSFNITTSIRN
KVQKQYALFYKLDVVQM-DEDNTS----------YRLISCNTSTITQACPKVTFDPIPIH
YCAPAGFAILKCNNKTFNGTGPCTNVSTVQCTHGIKPVVSTQLLLNGSLAEEEIIIRSEN
LTNNAKTIIVHLNESVEIVCTRPNNNTRKSIHIGPGRAFYATGEIIGDIRQAHCNLSRAK
WNDTLKQIVIKLREQFG-NKTIIFNQSSGGDPEITTHSFNCGGEFFYCNSTQLFNSTWNF
--NGTWNKN---FNNTWNNTEGTNDTITLPCKIKQIINMWQRVGQAMYAPPISGQIRCSS
NITGLILTRDGGN---DT--SGTEIFRPGGGDMRDNWRSELYKYKVVKIEPLGVAPTKAK
RRVVQREKRAVG-IGALFLGFLGAAGSTMGAASMTLTVQARQLLSGIVQQQSNLLKAIEA
QQHLLQLTVWGIKQLQARILAVERYLKDQQLLGIWGCSGKLICTTTVPWNASWSNKSLNE
IWDNMTWMEWEREIDNYTGLIYNLIEESQTQQEKNEQELLELDKWASLWNWFDITKWLWY
IKIFIMIIGGLIGLRIVFTVLSIVNRVRKGYSPLSFQTLTHHQREPDRPERIEEGGGEQD
RDRSGRLVDGFLAIIWVDLRSLCLFSYHRLRDLLLIVTRIVELLG-------RRGWEVLK
YWWNLLQYWSQELKNSAVSLLNATAIAVAEGTDRIIEVIQRICRAIRNIPRRIRQGLERA
LL-
>ENV-M.syn4.3
MRVKETQMNWPNLWKWGTLI--------LGLVIICSASDNLWVTVYYGVPVWKDAETTLF
CASDAKAYDTEVHNVWATYACVPTDPNPQEIHLENVTEEFNMWKNDMVDQMHEDIISLWD
ESLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGYAILKCNDKKFNGTGPCNNVSTVQCTHGIKPVVTTQLLLNGSLAEGEIIIRSEN
ITNNAKTIIVQLNESVVINCTRPNNNTRKSIRIGPGQAFYATGDIIGNIRQAHCNISRAN
WNNTLRQIVEKLGEQFGNNKTIVFNHSSGGDPEIVTHSFNCAGEFFYCNTTKLFNSTWTR
N-NGTWTRN---DTERSNSTE---EHITLPCRIKQIINMWQEVGKAMYAPPIRGQIRCSS
NITGLLLTRDGGNNN-----STNETFRPGGGNMKDNWRSELYKYKVVQIEPLGIAPTKAK
RRVVEREKRAVG-LGAVFLGFLGTAGSTMGAASLTLTVQARQVLSGIVQQQRNLLRAIEA
QQHLLKLTVWGIKQLQARVLAIERYLQDQQLLGMWGCSGKLICTTNVPWNSSWSNKSQTD
IWDNMTWLQWDKEISNYTSLIYTLIEESQNQQEKNEQDLLALDKWASLWSWFDISNWLWY
IKIFIIIVGGLIGLRIVFAVLSIINRVRQGYSPLSLQTLIPNPRGPDRLGRIEEEGGEQD
RDRSIRLVSGFLALAWDDLRSLCIFSYHRLRDFILIAARTVELLGHSSLKGLRLGWEGLK
YLGNLLLYWGQELKNSAINLLDTIAIAVAGWTDRVIEIGQRAGRAILNIPRRIRQGFERA
LL-
>ENV-M.syn4.4
MRVTGIRKNYQHLWRWGTMLLWRWGTMLLGILMICSAAGKLWVTVYYGVPVWRDADTTLF
CASDAKAYDTEAHNVWATHASVPTDPNPQEIVLENVTENFNMWKNNMVEQMHEDIISLWD
QSLKPCVQLTPLCVTLNCTN-VNVTNLKNETNTKSSSGGEKMEEGEMKNCSFNITTEIRD
KKQKVHALFYKLDIVPL-NSNSSE----------YRLINCNTSAITQACPKVSFDPIPIH

Fig. 10 cont'd-11

YCTPAGYAILKCNNKKFNGTGPCKNVSSVQCTHGIKPVISTQLLLNGSLAEEEVVIRSEN
FTNNAKTIMVQLNVSVEINCTRPNNNTRRSIPIGPGRAFYTTGDIIGDIRKAHCNISRAQ
WNNTLKHIVEKLGKQFGNNKTIIFKPSSGGDPEIVMHSFNCGGEFFYCNTSGLFNSTW--
--------N---STSLFNSTN---GTITLQCRIKQIINMWQGVGRAMYAPPIAGNITCKS
NITGLLLVRDGGT---EP--NDTETFRPGGGDMKDNWRSELYKYKVVRIEPLGVAPTRAK
RRVVEREKRAIG-LGAMFLGFLGAAGSTMGAASVTLTVQARLLLSGIVQQQNNLLRAIEA
QQHLLRLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IRIFIMIVGGLVGLRIVFAVLSIVKRVRQGYSPLSFQTRLPAPRGPDRPEGIEEEGGERD
RDRSVRLVDGFLALIWDDLRSLCLFSYHHLRDLLLIVARIVELLG-------RRGWEALK
YWWNLLQYWIQELKNSAISLLNATAVAVAEGTDRVIEALQRACRAILHIPRRIRQGFEAA
LL-
>ENV-M.syn6.1
MRVMGIQRNCQQWWIWGILG--------FWMLMICNVMGNLWVTVYYGVPVWKEANTTLF
CASDAKAYEREVHNVWATHASVPTDPNPQEVVLENVTEDFNMWKNNMVEQMQEDVISLWD
QSLQPCVKLTPLCVTLNCTD-LRNATNGNDTNTTSSS-REMMGGGEMKNCSFNITTEIRD
KKQKVYALFYKLDVVPI-DNDSNNTN--------YRLISCNTSAVTQACPKVTFDPIPIH
YCTPAGFAILKCRDKKFNGTGPCNNVSTVQCTHGIKPVVTTQLLLNGSLAEEEIVIRSEN
FTDNAKTIIVQLKEAVEINCTRPNNNTRKGIHIGPGRAFYATGEIIGDIRQAHCNVSRSE
WNKTLQQVATQLRKHF--NKTIIFNSSSGGDLEITTHSFNCRGEFFYCNTSGLFNSTW--
--NDTTINR----TEGSNNTR----NITLPCRIKQFINMWQEVGRAMYAPPIAGNITCRS
NITGLLLTRDGGNNGNET--NGTEIFRPGGGDMRNNWRSELYKYKVVEIKPLGIAPTKAR
RRVVQREKRAVG-IGAVFLGFLSAAGSTMGAASITLTVQARQLLTGIVQQQSNLLKAIEA
QQHMLQLTVWGVKQLQARVLAVERYLRDQQLLGIWGCSGRLICTTAVPWNTSWSNKSLNE
IWDNMTWMEWEREIDNYTSLIYTLIEESQNQQEKNEQELLELDKWANLWNWFSITNWLWY
IRIFIMIVGGLIGLRIIFGVLSIVKRVRQGYSPLSFQTRLPAPRGPDRPEGIEEEGGERD
RDRSGRLVDGFLALIWDDLRSLCLFSYHRLRDLILIAARIVELLGHSSLKGLRLGWEALK
YLWNLLLYWGQELKNSAISLLNTTAIVVAEGTDRVIEVLQRAGRAILNIPRRIRQGFEAA
LL-
>ENV-M.syn6.2
MRVTGIRKNYQHLWRWGTMLLWRWGTMLLGILMICSAAGKLWVTVYYGVPVWREAKTTLF
CASDAKAYEKEVHNVWATYACVPTDPNPQEMVLENVTENFNMWKNNMVDQMHEDIISLWD
ESLKPCVKLTPLCVTLHCTDL------GNATNT--------MEKGEIKNCSFNTTTEIRD
KKQKVHALFYRLDVVPI-DNDNTS----------YTLINCNTSVITQACPKVTFEPIPIH
YCAPAGFAILKCNNKKFNGTGPCTNVSTVQCTHGIRPVVSTQLLLNGSLAEGEIIIRSEN
LTDNAKTIIVHLNESVEIVCTRPNNNTRKSVRIGPGQTFYATGAIIGDIRQAYCNISRAK
WNNTLKQIVTKLREQFGNNKTIIFKPPSGGDLEITMHHFNCRGEFFYCNTTQLFNSTWNF
--NGTWNKN---FNNTWNNTEGTNDTITLPCKIKQIINMWQGVGRAMYAPPISGQIRCSS
NITGLLLTRDGGT-------NNTEIFRPGGGNMRDNWRSELYKYKVVKIEPLGVAPTKAK
RRVVQREKRAVG-IGALFLGFLGAAGSTMGAASMTLTVQARQVLSGIVQQQRNLLRAIEA
QQHLLQLTVWGIKQLQARILAVERYLKDQKFLGLWGCSGKIICTTAVPWNASWSNKSLDD
IWNNMTWMQWEREIDNYTGLIYSLIEESQTQQEKNEQELLQLDKWASLWNWFDITNWLWY
IRLFIMIVGGLVGLRIVFTVLSIVNRVRKGYSPLSFQTLTHHQREPDRPERIEEGGGEQG
RDRSVRLVSGFLALFWDDLRSLCLFCYHRLRDFILIAARTVELLGHSSLKGLRRGWEGLK
YLWNLLQYWIQELKNSAISLLNATAVAVAEGTDRVIEALQRACRAILHIPRRIRQGLERL
LL-
>ENV-M.syn6.3
MRVRGIQRNWPQWWIWGILG--------FWMIIICRVVGNLWVTVYYGVPVWKDAETTLF
CASDAKSYETEAHNIWATHACVPTDPSPQEVVLGNVTENFNMWKNDMVEQMHEDIISLWD
QSLKPCVELTPLCVTLNCTDDVRNVT-NNATNTNSSW-GEPMEKGEIKNCSFNITTSIRN
KVQKQYALFYKLDVVQI-DDNNSTNTS-------YRLINCNTSAITQACPKVSFDPIPIH
YCAPAGYAILKCNNKTFNGTGPCHNVSTVQCTHGIRPVISTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIIFKPSSGGDPEIVMHSFNCRGEFFYCNTSKLFNSTWTR
N-NGTWTRN---DTERSNSTE---EHITLPCRIKQIINMWQRVGQAMYAPPIAGNITCNS
SITGLLLTRDGGN---DT--SGTEIFRPGGGNIKDNWRSELYKYKVVQIEPLGVAPTRAK

Fig. 10 cont'd-12

```
RRVVEREKRAVG-IGAMIFGFLGAAGSTMGAASMALTVQARQLLSGIVQQQSNLLMAIEA
QQHLLKLTVWGIKQLRARVLAVERYLKDQQLLGIWGCSGKHICTTNVPWNSSWSNKSLDE
IWNNMTWIEWEREINNYTGLIYNLLEKSQNQQEKNEQDLLALDKWASLWSWFDISNWLWY
IKIFIIIVGGLIGLRIVFAVLSLVNRVRQGYSPLSLQTLLPTPRGPDRPEGTEEEGGEQG
RDRSIRLVSGFLALAWDDLRSLCRFSYHRLRDFILIVARTVELLGRSSLKGLRLGWEGLK
YLGNLLLYWGQELKISAISLLDTTAIAVAGWTDRVIEIGQRLCRAIRNIPRRIRQGAERA
LQ-
>ENV-M.syn6.4
MRVKETQMNWPNLWKWGTLI--------LGLVIICSASDNLWVTVYYGVPVWRDADTTLF
CASDAKAHETEVHNVWATHACVPTDPNPQEIHLENVTEEFNMWKNNMVEQMHTDIISLWD
QSLKPCVRLTPLCVTLNCTDELKNATFRSNTTTNSSW--EKMERGEIKNCSFNITTSIRD
KVQKEYALFYKLDIVPL-NSNSSE---------YRLINCNTSVIKQACPKISFDPIPIH
YCAPAGFAILKCKDKKFNGTGPCQNVSTVQCTHRIKPVVSTQFLLNGSLAEEDIIIRSEN
ITNNAKTIIVQLNESVVINCTRPNNNTRRSIPIGPGRVFYTTEDIIGDIRQAHCNLSRAK
WNDTLKQIVIKLREQFG-NKTIVFNQSSGGDLEIVMHSFNCGGEFFYCNSTQLFNSTWF-
--NSTW------STEGSNNTE-GSDTITLPCRIKQIVNMWQGVGKAMYAPPIRGQIRCSS
NITGILLTRDGGTNGT----NETETFRPGGGNMKDNWRSELYRYKVVKIEPLGIAPTKAK
RRVVEREKRAIG-LGAMFLGFLGTAGSTMGAASLTLTVQARQLMSGIVQQQNNLLRAIEA
QQHMLKLTVWGIKQLQARVLALERYLKDQQLLGLWGCSGKLICTTTVPWNSSWSNKSQTD
IWDNMTWMQWDREISNYTNTIYRLLEDSQNQQEKNEKDLLALDSWKNLWNWFDITKWLWY
IKIFIMIVGGLIGLKIVFAVLSIINRVRQGYSPLSFQTLIPNPRGPDRPGGIEEEGGEQD
RDRSIRLVNGFLALIWVDLRSLFLFSYHRLRDLLLIVTRIVELLG------RRGWEALK
YWWNLLQYWSQELKNSAINLLDTIAIAVAEGTDRIIEVIQRICRAIRNIPTRIRQGLERA
LL-
>ENV-M.syn6.5
MRVKGIRKNYQHLWKWGTML--------LGMLMICSATEKLWVTVYYGVPVWKEATTTLF
CASDAKAYDTEVHNVWATYACVPTDPNPQELVLENVTENFDMWKNNMVEQMHEDIINLWD
QSLKPCVKLTPICVTLNCTDYVKNIT-NNATSTNSSW-GKPMEKGEIKNCSFNMTTELRD
KKQKVYSLFYKLDVVQM-DEDNTS---------YRLISCNTSVITQACPKISFEPIPIH
YCTPAGYAILKCNDKNFNGTGPCKNVSSVQCTHGIKPVISTQLLLNGSLAEEEIIIRSEN
LTNNVKTIIVHLNKSVEINCTRPSNNTRTSIRIGPGQAFYATGDIIGDIRKAHCNISRAN
WNNTLRQIVEKLGEQFGNNKTIVFNHSSGGDPEITTHSFNCGGEFFYCNTTKLFNSTWTW
N-NSTW--N---NTKRSNDTE---EIITLPCRIKQIINMWQEVGKAMYAPPIQGVIRCES
NITGLILTRDGGNNN-----STNETFRPGGGDMRDNWRSELYKYKVVRIEPLGVAPTEAK
RRVVQREKRAVGTIGAMFLGFLGAAGSTMGAASVTLTVQARLLLSGIVQQQNNLLKAIEA
QQHLLRLTVWGIKQLQARVLAIERYLQDQQLLGIWGCSGKLICTTNVPWNTSWSNRSLNE
IWNNMTWMEWEKEIDNYTNLIYNLLEESQIQQEKNEQELLALDKWANLWNWFDISNWLWY
IRIFIIIVGGLVGLRIVFAVLSIVNKVRQGYSPLSFQTHLPAQRGPDRPEGIEEGGGEQD
RDRSVRLVDGFLAIIWVDLRSLCLFSYHHLRDLLLIVARIVELLG------RRGWEVLK
YWWNLLKYWSQELKNSAVSLLNATAIAVAEGTDRIIELIQRICRAICNIPRRIRQGFERA
LL-
>ENV-M.syn6.6
MRVKETRKNYQHLWRWGIML--------LGMLMICSAAEQLWVTVYYGVPVWKEAKTTLF
CASNAKAYDTEAHNVWATHACIPTDPNPQEIVLENVTESFNMWKNDMVDQMHEDVISLWD
QSLKPCVQLTPLCVTLNCTN-VNVTNLKNETNTKSSSGGEKMEEGEMKNCSFNVTTELRD
KKKKEYALFYRLDIVPL-NEGNNSNSSY------YRLINCNTSTITQACPKVSFEPIPIH
FCAPAGFAILKCNDKKFNGTGPCKNVSTVQCTHGIKPVVSTQLLLNGSLAEKEIIIRSEN
LTNNAKIIIVQLNESVEINCTRPGNNTRKSIRIGPGQTFYATGDIIGNIRQAHCNISRTQ
WNNTLKQIAIKLREQFG-NKTIIFNQSSGGDPEIVTHSFNCGGEFFYCKSTKLFNSTW--
---------N---STSLFNSTN---GTITLQCRIKQIINRWQEVGKAMYAPPIEGNITCKS
NITGLLLVRDGGINVTNN--TGTEVFRPGGGDMKDNWRNELYKYKVVEIKPLGVAPTRAR
RRVVEREKRAVG-LGAVFLGFLGAAGSTMGAAAVTLTVQARQLLFGIVQQQSNLLRAIEA
QQRMLQLTVWGIKQLQTRVLAIERYLKDQQLLGMWGCSGKLICTTAVPWNSSWSNKTYND
IWDNMTWLQWDKEISNYTDTIYRLLEESQNQQERNEKDLLELDKWASLWNWFNITNWLWY
IKIFIMIIGGLIGLRIIFAVLSIVNRVRQGYSPLSFQTLTPNPRGPDRLGRIEEEGGEQD
KDRSIRLVNGFSALIWDDLRNLCLFSYHQLRDFILVTARAVELLGRSSLRGLQRGWEALK
YLGSLVQYWGLELKKSAISLLDTIAIAVANWTDRVIEVVQRAYRAILHIPTRIRQGFEAA
LQ-
```

Fig. 10 cont'd-13

```
>POL-B.syn1.1
FFRENLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGHKAIGTVLVGPTPVNIIGRNLLTQIGCTLNFPISPIE
TVPVKLKPGMDGPKVKQWPLTEEKIKALVEICTEMEKEGKISKIGPENPYNTPVFAIKKK
DSTKWRKLVDFRELNKRTQDFWEVQLGIPHPAGLKKKKSVTVLDVGDAYFSVPLDKDFRK
YTAFTIPSINNETPGIRYQYNVLPQGWKGSPAIFQSSMTKILEPFRKQNPDIVIYQYMDD
LYVGSDLEIGQHRTKIEELRQHLLRWGFTTPDKKHQKEPPFLWMGYELHPDKWTVQPIVL
PEKDSWTVNDIQKLVGKLNWASQIYAGIKVKQLCKLLRGTKALTEVIPLTEEAELELAEN
REILKEPVHGVYYDPSKDLIAEIQKQGQGQWTYQIYQEPFKNLKTGKYARMRGAHTNDVK
QLTEAVQKIATESIVIWGKTPKFKLPIQKETWETWWTEYWQATWIPEWEFVNTPPLVKLW
YQLEKEPIVGAETFYVDGAANRETKLGKAGYVTDRGRQKVVSLTDTTNQKTELQAIHLAL
QDSGLEVNIVTDSQYALGIIQAQPDKSESELVSQIIEQLIKKEKVYLAWVPAHKGIGGNE
QVDKLVSAGIRKVLFLDGIDKAQEEHEKYHSNWRAMASDFNLPPVVAKEIVASCDKCQLK
GEAMHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIGQVR
DQAEHLKTAVQMAVFIHNFKRKGGIGGYSAGERIVDIIATDIQTKELQKQITKIQNFRVY
YRDSRDPLWKGPAKLLWKGEGAVVIQDNSDIKVVPRRKAKIIRDYGKQMAGDDCVASRQD
ED-
>POL-B.syn3.1
FFRENLAFPQGKAREFPSEQTRANSPTSR--------------ELQVWGGDNNSLSEAGD
DR----QGTVS-FSFPQITLWQRPIVTIKIGGQQKEALLDTGADDTVLEEMNLPGRWKPK
IIGGIGGFIKVKQYDQILIEICGHKAIGTVLVGPTPANIIGRNLLTQIGCTLNFPISPIE
TVPVRLKPGMDGPKVKQWPLTEEKIKALIEICTELENEGKISKIGPENPYNTPVFAIKKK
DGTKWRKLVDFRELNKRTQDFWEVQLGIPHPAGLKKKKSVTVLDVGDAYFSVPLDKEFRK
YTAFTIPSINNETPGIRYQYNVLPQGWKGSPSIFQSSMTKILEPFRKQNPEIVIYQYMDD
LYVGSDLEIEQHRTKIEELRQHLLKWGFYTPDKKHQKEPPFLWMGYELHPDKWTVQPIVL
PEKDSWTVNDIQKLVGKLNWASQIYAGIKVKQLCRLLRGTKALTEVVPLTEEAELELAEN
REILKEPVHGVYYDPSKDLVAEIQKQGLGQWTYQIYQEPYKNLKTGKYAKMRGAHTNDVK
QLTEAVQKIATESIVIWGKTPKFRLPIQKETWEAWWMEYWQATWIPEWEFVNTPPLVKLW
YQLEKEPIVGAETFYVDGAANRDTKLGKAGYVTDRGRQKVVSLTDTTNQKTELQAIHLAL
QDSGLEVNIVTDSQYAIGIIQAQPDRSESELVSQIIEQLIKKEKVYLAWVPAHKGIGGNE
QVDKLVSSGIRKVLFLDGIDKAQEDHEKYHSNWKAMASDFNLPPVVAKEIVACCDKCQLK
GEAMHGQVDCSPGIWQLDCTHLEGKVILVAVHVASGYIEAEVIPAETGQETAYFILKLAG
RWPVTTIHTDNGSNFTSTAVKAACWWAGIKQEFGIPYNPQSQGVVESINKELKKIIKQVR
DQAEHLKTAVQMAVFVHNFKRKGGIGGYSAGERMIDIIATDIQTTELQKQITKLQNFRVY
FRDSRDPLWKGPAKLLWKGEGAVVIQDNSEIKVVPRRKAKIIRDYGKQMAGDDCVASRQD
ED-
>POL-B.syn3.2
FFREDLAFLQGKAREFSSEQTRANSPTRG--------------ELQVWGRDNNSLSEAGA
DR----QGTVS-LSFPQITLWQRPLVTVKIGGQLKEALLDTGADDTVLEEMSLPGRWKPK
MIGGIGGFIKVRQYDQILVEICGHKAIGTVLIGPTPVNIIGRDLLTQIGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKQKKSVTVLDVGDAYFSVPLDEDFRK
YTAFTIPSTNNETPGIRYQYNVLPQGWKGSPAIFQSSMTRILEPFRKQNPDLVIYQYMDD
LYVGSDLEIGQHRTKIEELREHLLKWGFTTPDKKHQKEPPFLWMGYELHPDKWTVQPIML
PEKDSWTVNDIQKLVGKLNWASQIYPGIKVKQLCKLLRGAKALTEVIPLTKEAELELAEN
REILKEPVHGAYYDPSKDLIAEIQKQGQGQWTYQIYQDPFKNLKTGKYARMRGAHTNDVR
QLTEAVQKITTESIVIWGKIPKFKLPIQKETWETWWTEYWQATWIPEWEFVNTPPLVKLW
YQLEKEPIIGAETFYVDGAANRETKLGKAGYVTNKGRQKVVSITDTTNQKTELQAILLAL
QDSGLEVNIVTDSQYAIGIIQAQPDKSESELVSQIIEELIKKEKVYLTWVPAHKGIGGNE
QIDKLVSAGIRKVLFLDGIDQAQEEHEKYHSNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTVHTDNGSNFTSTTVKAACWWAGVKQEFGIPYNPQSQGVVESMNNELKKIIGQIR
DQAEHLKTAVQMAVFIHNFKRKGGIGGYSAGERIVDIIATDIQTKELQKQITKIQNFRVY
YRDNRDPLWKGPAKLLWKGEGAVVIQENSDIKVVPRRKVKIIRDYGKQMAGDDCVASGQD
ED-
```

Fig. 10 cont'd-14

```
>POL-B.syn3.3
FFREDLAFPQGEAREFSSEQTRANSPTRR--------------ELQVWGRDSNSLSEAGA
DR----QGTVS-FNFPQITLWQRPLVTIKIGGQLKEALLDTGADDTVLEDMNLPGKWKPK
MIGGIGGFIKVRQYDQIPIEICGHKAVGTVLVGPTPVNIIGRNLLTQLGCTLNFPISPIE
TVPVKLKPGMDGPKVKQWPLTEEKIKALVEICTELEKEGKISKIGPENPYNTPVFAIKKK
DSTKWRKVVDFRELNKKTQDFWEVQLGIPHPSGLKKKKSVTVLDVGDAYFSVPLDKDFRK
YTAFTIPSVNNETPGVRYQYNVLPQGWKGSPAIFQCSMTKILEPFRKQNPDIVIYQYMDD
LYVGSDLEIGQHRAKIEELRQHLLRWGFTTPDKKHQNEPPFLWMGYELHPDKWTVQPIEL
PEKDSWTVNDIQKLVGKLNWASQIYPGIKVRQLCKLLRGTKALTEVIPLTEEAELELAEN
REILREPVHGVYYDPTKDLIAEIQKQEQGQWTYQIYQEPFKNLKTGKYARTRGAHTNDVK
QLTEAVQKVATESIVIWGKTPKFKLPIQKETWEAWWTEYWQATWIPEWEFVNTPPLVKLW
YQLEKEPIEGAETFYVDGASNRETKLGKAGYVTNRGRQKVVPLTDTTNQKTELQAIYLAL
QDSGSEVNIVTDSQYALGIIQAQPDKSESELVNQIIEQLIKKEKIYLAWVPAHKGIGGNE
QVDKLVSAGIRKILFLDGIDKAQEEHEKYHNNWRAMASDFNLPPIVAKEIVASCDKCQLK
GEAIHGQVDCSPGIWQLDCTHLEGKVILVAVHVASGYIEAEVIPAETGQETAYFILKLAG
RWPVKTIHTDNGSNFTSATVKAACWWAGIKQEFGIPYNPQSQGVVESMNKELKKIIGQVR
DQAEHLKTAVQMAVFIHNFKRKGGIGEYSAGERIIDIIATDIQTRELQKQITKIQNFRVY
YRDSRDPLWKGPAKLLWKGEGAVVIQDNSDIKVVPRRKAKIIRDYGKQMAGDDCVAGRQD
ED- >POL-B.syn4.1
FFRENLAFPQGEAREFSSEQNRANSPTRR--------------ELQVWGGDNNSLSEAGA
DR----QGTVS-LSFPQITLWQRPLVTIRIGGQLKEALLDTGADDTVLEEMSLPGRWKPK
MIGGIGGFIKVRQYDQILIEICGHKAIGTVLIGPTPVNIIGRNLLTQLGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPSGLKKKKSVTVLDVGDAYFSVPLDKDFRK
YTAFTIPSINNETPGVRYQYNVLPQGWKGSPAIFQSSMTKILEPFRKQNPDMVIYQYMDD
LYVGSDLEIGQHRTKIEELRQHLLRWGLTTPDKKHQKEPPFLWMGYELHPDKWTVQPIKL
PEKDSWTVNDIQKLVGKLNWASQIYAGIKVRQLCKLLRGAKALTEVIPLTAEAELELAEN
REILREPVHGVYYDPSKDLIAEIQKQGQGQWTYQIYQDPFKNLKTGKYAKMRGAHTNDVK
QLTEAVQKVATESIVIWGKTPKFRLPIQKETWEAWWTEYWQATWIPEWEFVNTPPLVKLW
YQLEKEPIEGAETFYVDGAANRDTKLGKAGYVTDRGRQKVVSLTDTTNQKTELQAIHLAL
QDSGLEVNIVTDSQYALGIIQAQPDKSESELVSQIIEELIKKEKVYLAWVPAHKGIGGNE
QIDKLVSAGIRRVLFLDGIDQAQEEHEKYHSNWRAMASDFNLPPIVAKEIVASCDKCQLK
GEAIHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIEQVR
DQAEHLKTAVQMAVFIHNFKRKGGIGEYSAGERIIDIIATDIQTRELQKQITKIQNFRVY
YRDNRDPLWKGPAKLLWKGEGAVVIQDNSDIKVVPRRKAKIIRDYGKQMAGDDCVAGRQD
ED- >POL-B.syn4.2
FFRENLAFPQGKAREFPSEQTRANSPTSR--------------ELQVWGRDNNSLSEAGD
DR----QGTVS-FSFPQITLWQRPLVTVKIGGQLKEALLDTGADDTVLEEMNLPGRWKPK
MIGGIGGFIKVRQYDQIPIEICGHKAVGTVLVGPTPVNIIGRDLLTQIGCTLNFPISPIE
TVPVKLKPGMDGPKVKQWPLTEEKIKALIEICTELENEGKISKIGPENPYNTPVFAIKKK
DGTKWRKLVDFRELNKRTQDFWEVQLGIPHPAGLKQKKSVTVLDVGDAYFSVPLDKEFRK
YTAFTIPSTNNETPGIRYQYNVLPQGWKGSPAIFQCSMTKILEPFRKQNPDLVIYQYMDD
LYVGSDLEIEQHRTKIEELREHLLKWGFTTPDKKHQNEPPFLWMGYELHPDKWTVQPIML
PEKDSWTVNDIQKLVGKLNWASQIYAGIKVRQLCKLLRGTKALTEVVPLTEEAELELAEN
REILKVPVHGVYYDPSKDLVAEIQKQGLGQWTYQIYQEPFKNLKTGKYARTRGAHTNDVR
QLTEAVQKIATESIVIWGKTPKFKLPIQKETWEAWWMEYWQATWIPEWEFVNTPPLVKLW
YQLEKEPIVGAETFYVDGAANRETKLGKAGYVTDKGRQKVVPLTDTTNQKTELQAINLAL
QDSGSEVNIVTDSQYAIGIIQAQPDRSESELVSQIIEQLINKEKVYLAWVPAHKGIGGNE
QVDKLVSSGIRKVLFLDGIDKAQEDHEKYHSNWRAMAGDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFISTTVKAACWWAGVKQEFGIPYNPQSQGVVESMNNELKKIIGQVR
DQAEHLKTAVQMAVFVHNFKRKGGIGGYTAGERIVDIIASDIQTKELQKQITKIQNFRVY
```

Fig. 10 cont'd-15

```
YRDSRDPIWKGPAKLLWKGEGAVVIQDNSEIKVVPRRKAKIIRDYGKQMAGDDCVASRQN
ED-
>POL-B.syn4.3
FFREDLAFLQGKAREFSSEQTRANSPTRR--------------ELQVWGRDNNSPSEAGA
DR----QGTVS-FNFPQITLWQRPIVTIKIGGQLKEALLDTGADDTVLEDMNLPGKWKPK
MIGGIGGFIKVRQYDQILVEICGHKAIGTVLVGPTPANIIGRNLLTQIGCTLNFPISPIE
TVPVKLKSGMDGPKVKQWPLTEEKIKALIEICTEMEKEGKISKIGPENPYNTPVFAIKKK
DSTKWRKLVDFRELNKRTQDFWEVQLGIPHPSGLKKKKSVTVLDVGDAYFSVPLDEDFRK
YTAFTIPSVNNETPGIRYQYNVLPQGWKGSPAIFQSSMTRILEPFRKQNPDIVIYQYMDD
LYVGSDLEIGQHRAKIEELRQHLLRWGFTTPDKKHQKEPPFLWMGYELHPDKWTVQPIEL
PEKDSWTVNDIQKLVGKLNWASQIYPGIKVRQLCKLLRGTKALTEVIPLTEEAELELAEN
REILKEPVHGVYYDPSKELIAEIQKQEQGQWTYQIYQEPFKNLKTGKYARMRGTHTNDVK
QLTEAVQKITTESIVIWGRTPKFKLPIQKETWESWWTEYWQATWIPEWEFVNTPPLVKLW
YQLEREPIAGAETFYVDGASNRETKLGKAGYVTNRGRQKVVSLPDTTNQKTELQAIYLAL
QDSGLEVNIVTDSQYAIGIIQAQPDKSESELVNQIIEQLIKKEKIYLAWVPAHKGIGGNE
QVDKLVSNGIRKILFLDGIDKAQDEHEKYHSNWKAMASDFNLPPVVAKEIVACCDKCQLK
GEAMHGQVDCSPGIWQLDCTHLEGKIILVAVHVASGYIEAEVIPAETGQETAYFLLKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERMIDIIATDIQTTELQKQITKLQNFRVY
FRDSRDPLWKGPAKLLWKGEGAVVIQDNNDIKVVPRRKVKIIRDYGKQMAGDDCVASGQD
ED-
>POL-B.syn4.4
FFREDLAFPQGKARELSSEQTRANSPTRG--------------ELQVWGRDSNSLSEAGA
DR----PGTVS-FSFPQITLWQRPLVTIKIGGQQKEALLDTGADDTVLEEINLPGRWKPK
IIGGIGGFIKVKQYDQIPIEICGHKVIGTVLVGPTPANIIGRNLLTQLGCTLNFPISPIE
TVPVRLKPGMDGPKVKQWPLTEEKIKALVEICTELEKEGKISKIGPENPYNTPVFAIKKK
DSTKWRKVVDFRELNKKTQDFWEVQLGIPHPAGLKKKKSVTVLDVGDAYFSVPLDENFRK
YTAFTIPSINNETPGIRYQYNVLPQGWKGSPSIFQSSMTKILEPFRKQNPEIVIYQYMDD
LYVGSDLELGQHRTKIEELRQHLLKWGFYTPDKKHQKEPPFLWMGYELHPDKWTVQPIVL
PEKDSWTVNDIQKLVGKLNWASQIYPGIKVKQLCRLLRGAKALTEVIPLTKEAELELAEN
REILKEPVHGAYYDPTKDLIAEIQKQGEGQWTYQIYQEPYKNLKTGKYARMRGAHTNDVK
QLTETVQKITTESIVIWGKIPKFKLPIQKETWETWWTEYWQATWIPEWEFVNTPPLVKLW
YQLEKEPIIGAETFYVDGAASRETKLGKAGYVTNKGRQKVVSITDTTNQKTELQAILLAL
QDSGLEVNIVTDSQYAIGIIQAQPDKSESEIVSQIIEQLIKKEKVYLTWVPAHKGIGGNE
QVDKLVSAGIRKVLFLDGIDKAQEEHEKYHNNWRAMASDFNIPPVVAKEIVASCDKCQLK
GEAMHGQVDCSPGIWQLDCTHLEGKVILVAVHVASGYIEAEIIPTETGQETAYFILKLAG
RWPVTTIHTDNGSNFTSATVKAACWWAGVKQEFGIPYNPQSQGVIESMNKELKKIIGQIR
DQAEHLKTAVQMAVFIHNFKRKGGIGGYSAGERIVDIIATDIQTKELQNQITKIQNFRVY
YRDSRDPLWKGPAKLLWKGEGAVVIQENSDIKVVPRRKVKIIRDYGKQMAGDDCVASRQD
ED- >POL-B.syn6.1
FFREDLAFPQGEAREFCSEQTRANSPATR--------------ELQVWGRDNTSLSEAGA
DR----PGTVS-FSFPQITLWQRPIVTVKIEGQLKEALLDTGADDTVLEEMNLPGKWKPK
MIGGIGGFIKVRQYDQVSIEICGHKAIGTVLVGPTPANIIGRNLLTQIGCTLNFPISPIE
TVPVKLKPGMDGPKVKQWPLTEEKIKALVEICTELEKEGKISKIGPENPYNTPVFAIKKK
DSTKWRKVVDFRELNKRTQDFWEVQLGIPHPSGLKKKKSVTVLDVGDAYFSVPLDENFRK
YTAFTIPSINNETPGIRYQYNVLPQGWKGSPAIFQSSMTKILEPFRKQNPDIIIYQYMDD
LYVGSDLEIGQHRAKIEELRQHLLKWGFTTPDKKHQKEPPFLWMGYELHPDKWTVQPIEL
PEKDSWTVNDIQKLVGKLNWASQIYAGIKVKELCKLLRGTKALTEVVPLTEEAELELAEN
REILKEPVHGVYYDPSKDLIAELQKQGQGQWTYQIYQEPYKNLKTGKYARTRGAHTNDVR
QLTEAVQKIATEGIVIWGKTPKFKLPIQKETWEAWWTEYWQATWIPEWEFVNTPPLVKLW
YQLEKEPILGAETFYVDGASNRETKLGKAGYVTDRGRQKVVSLTDTTNQKTELQAINLAL
QDSGLEVNIVTDSQYALGIIQAQPDRSESELVSQIIEQLINKEKVYLAWVPAHKGIGGNE
QVDKLVSTGIRRVLFLDGIDKAQEEHEKYHSNWRAMASDFNLPPIVAKEIVASCDKCQLK
GEAIHGQVDCSPGIWQLDCTHLEGKVILVAVHVASGYIEAEVIPAETGQETAYFILKLAG
```

Fig. 10 cont'd-16

```
RWPVKTIHTDNGSNFTSTTVKAACWWAGIKQEFGIPYNPQSQGVVESMNKELKKIIEQVR
DQAEHLKTAVQMAVFVHNFKRKGGIGEYSAGERIVDIIATDIQTKELQKHITKIQNFRVY
YRDSRDPLWKGPAKLLWKGEGAVVIQDNSEIKVVPRRKAKIIRDYGKQMAGDDCVASRQD
ED-
>POL-B.syn6.2
FFREDLAFPQGKARELSSEQTRANSPTSPTRG-----------ELQVWGRDSNSLSEAGA
DR----QGPVS-FSFPQITLWQRPIVTIKIGGQLKEALLDTGADDTVLEDMNLPGRWKPK
MIGGIGGFIKVKQYDEILVEICGHKAIGTVLIGPTPVNIIGRNLLTQLGCTLNFPISPIE
TVPVKLKSGMDGPKVKQWPLTEEKIKALVEICTELEKEGKISKIGPENPYNTPIFAIKKK
DSTKWRKLVDFRELNKRTQDFWEVQLGIPHPAGLKKKKSVTVLDVGDAYFSVPLDKDFRK
YTAFTIPSVNNETPGIRYQYNVLPQGWKGSPAIFQCSMTKILEPFRKQNPDMVIYQYMDD
LYVGSDLEIGQHRIKIEELREHLLKWGFTTPDKKHQNEPPFLWMGYELHPDKWTVQPIVL
PEKDSWTVNDIQKLVGKLNWASQIYPGIKVRQLCKLLRGTKALTEVIPLTEEAELELAEN
REILREPVHGVYYDPTKDLIAEIQKQGQGQWTYQIYQEPFKNLTGKYARMRGAHTNDVK
QLTEAVQKITTESIVIWGKIPKFRLPIQKETWEAWWIEYWQATWIPEWEFVNTPPLVKLW
YQLEREPIAGAETFYVDGAANRETKLGKAGYVTNRGRQKVVSITDTTNQKTELQAILLAL
QDSGLEVNIVTDSQYALGIIQAQPDKSESELVNQIIEQLIKKEKIYLAWVPAHKGIGGNE
QIDKLVSAGIRKVLFLDGIDKAQDEHEKYHSNWRAMAGDFNLPPVVAKEIVACCDKCQLK
GEAMHGQVDCSPGIWQLDCTHLEGKIILVAVHVASGYIEAEVIPAETGQETAYFLLKLAG
RWPVTTIHTDNGSNFTSATVKAACWWAGVKQEFGIPYNPQSQGVIESMNKELKKIIGQVR
DQAEHLKTAVQMAVFIHNFKRKGGIGEYSAGERIIDIIATDIQTKELQKQITKIQNFRVY
YRDSRDPIWKGPAKLLWKGEGAVVIQDNSEIKVVPRRKAKIIRDYGKQMAGDDCVAGRQD
ED-
>POL-B.syn6.3
FFRENLAFPQGEAREFSSEQTRANSPTRG--------------ELQVWGRDSNSLSEAGD
DR----QGTVS-FSFPQITLWQRPLVTIKIGGQQKEALLDTGADDTVLEEMNLPGRWKPK
IIGGIGGFIKVTQYDQIPIEICGHKAVGTVLVGPTPVNIIGRDLLTQIGCTLNFPISPIE
TVPVKLKSGMDGPKVKQWPLTEEKIKALIEICTEMEKEGKISKIGPENPYNTPVFAIKKK
DGTKWRKLVDFRELNKKTQDFWEVQLGIPHPAGLKQKKSVTVLDVGDAYFSVPLDREFRK
YTAFTIPSLNNETPGIRYQYNVLPQGWKGSPSIFQSSMTKILEPFRKQNPDLVIYQYMDD
LYVGSDLELGQHRTKIEELRQHLLKWGFYTPDKKHQKEPPFLWMGYELHPDKWTVQPIKL
PEKDSWTVNDIQKLVGKLNWASQIYPGIKVKQLCRLLRGAKALTEVVPLTKEAELELAEN
REILKEPVHGAYYDPTKDLIAEVQKQELGQWTYQIYQEPFKNLKTGKYARMKGAHTNDVK
QLTETVQKITTESIVIWGKTPKFRLPIQKETWESWWTEYWQATWIPEWEFVNTPPLVKLW
YQLEKEPITGAETFYVDGAANRETKIGKAGYVTDKGRQKVVSLPDTTNQKTELQAIHLAL
QDSGSEVNIVTDSQYAIGIIQAQPDRSESEVVNQIIEQLIKKEKVYLAWVPAHKGIGGNE
QVDKLVSNGIRKILFLDGIDKAQEEHERYHSNWKAMASDFNLPPVVAKEIVACCDKCQLK
GEAIHGQVDCSPGIWQLDCTHLEGKVILVAVHVASGYIEAEVIPAETGQETAYFILKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERIIDIIASDIQTKELQNQITKIQNFRVY
YRDSRDPVWKGPAKLLWKGEGAVVIQDNSDIKVVPRRKAKIIRDYGKQMAGDDCVASRQN
ED-
>POL-B.syn6.4
FFRENLAFPQRKAREFSSEQTRANSPTRR--------------ELQVWGGDNNSLSEAGA
DR----QGTVS-LSFPQITLWQRPLVTIKVGGQLKEALLDTGADDTVLEEINLPGRWKPK
MIGGIGGFIKVRQYDQILVEICGHKAIGTVLVGPTPVNIIGRNLLTQIGCTLNFPISPIE
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKKKKSVTVLDVGDAYFSVPLDEDFRK
YTAFTIPSINNETPGVRYQYNVLPQGWKGSPAIFQASMTKILEPFRKQNPDIVIYQYMDD
LYVGSDLEIGQHRIKIEELRQHLLRWGLTTPDKKHQKEPPFLWMGYELHPDKWTVQPIML
PEKDSWTVNDIQKLVGKLNWASQIYAGIKVRQLCKLLRGAKALTEVIPLTAEAELELAEN
REILKVPVHGVYYDPSKELIAEIQKQEQGQWTYQIYQDPFKNLKTGKYARMRGTHTNDVR
QLTEAVQKITTESIVIWGKIPKFKLPIQKETWETWWTEYWQATWIPEWEFVNTPPLVKLW
YQLEKEPIIGAETFYVDGAASRETKLGKAGYVTDRGRQKVISLTDTTNQKTELQAIHLAL
QDSGVEVNIVTDSQYALGIIQAQPDKSESEIVSQIIEQLIKKEKVYLTWVPAHKGIGGNE
```

Fig. 10 cont'd-17

```
QVDKLVSTGIRKVLFLDGIDQAQEEHEKYHSNWRTMASDFNLPPIVAKEIVASCDKCQLK
GEAMHGQVDCSPGIWQLDCTHLEGKVILVAVHVASGYIEAEVIPAETGQETAYFLLKLAG
RWPVKTIHTDNGPNFISTTVKAACWWAGIKQEFGIPYNPQSQGVVESMNNELKKIIGQVR
EQAEHLKTAVQMAVFIHNFKRKGGIGGYSAGERMIDIIATDIQTTELQKQITKLQNFRVY
FRDSRDPLWKGPAKLLWKGEGAVVIQENSDIKVVPRRKAKIIRDYGKQMAGDDCVAGRQD
ED-
>POL-B.syn6.5
FFRENLAFPQGKAREFPSEQTRANSPTSR-------------ELQVWGRDNNSLSEAGA
NR----QGTVS-FSFPQITLWQRPLVTVKIGGQLKEALLDTGADDTVLEDMDLPGRWKPK
MIGGIGGFIKVRQYDQIPIEICGHKVIGTVLVGPTPANIIGRNLLTQIGCTLNFPISPIE
TVPVRLKPGMDGPKVKQWPLTEEKIKALVEICTELEKEGKISKIGPENPYNTPVFAIKKK
DSTKWRKLVDFRELNKKTQDFWEVQLGIPHPSGLKKKKSVTVLDVGDAYFSVPLDKEFRK
YTAFTIPSTNNETPGIRYQYNVLPQGWKGSPAIFQASMTKILEPFRKQNPEIVIYQYMDD
LYVGSDLEIEQHRTKIEELRQHLLRWGFTTPDKKHQKEPPFLWMGYELHPDKWTVQPIVL
PDKDSWTVNDIQKLVGKLNWASQIYPGIKIRQLCKLLRGAKALTEVIPLTKEAELELAEN
REILKEPVHGVYYDPSKDLIAEIQKQGEGQWTYQIYQEPFKNLKTGKYAKMRGAHTNDVK
QLTEAVQKVATESIVIWGKTPKFKLPIQKETWEAWWMEYWQATWIPEWEFVNTPPLVKLW
YQLEKEPIEGAETFYVDGAANRDTKLGKAGYVTNKGRQKVVTLTDTTNQKTELQAIHLAL
QDSGLEVNIVTDSQYALGIIQAQPDKSESEIVNQIIEQLIKKEKVYLAWVPAHKGIGGNE
QVDKLVSSGIRKVLFLDGIDKAQEDHEKYHSNWRAMANDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFTSNTVKAACWWAGIKQEFGIPYNPQSQGVVESMNKQLKQIIGQVR
DQAEHLKTAVQMAVFIHNFKRKGGIGGYTAGERIVDIIATDIQTRELQKQITKIQNFRVY
YRDSREPLWKGPAKLLWKGEGAVVIQDNSDIKVVPRRKAKIIRDYGKQMAGDDCVASGQD
ED-
>POL-B.syn6.6
FFREDLAFLQGKAREFSSEQTRAISPTRR-------------ELQVWGRDNNSPSEAGA
DR----QGTVS-FNFPQITLWQRPLVTIRIGGQLKEALLDTGADDTVLEEMSLPGRWKPK
MIGGIGGFIKVRQYDQILIEICGHKAVGTVLIGPTPVNIIGRNLLTQIGCTLNFPISPID
TVPVKLKPGMDGPKVKQWPLTEEKIKALIEICTELENEGKISKIGPENPYNTPIFAIKKK
DSTKWRKLVDFRELNKRTQDFWEVQLGIPHPSGLKKKKSVTVLDVGDAYFSIPLDEDFRK
YTAFTIPSINNETPGTRYQYNVLPQGWKGSPAIFQSSMTRILEPFRKQNPDIVIYQYVDD
LYVGSDLEIGQHRTKIEELREHLLRWGFTTPDKKHQKEPPFLWMGYELHPDKWTVQPITL
PEKDSWTVNDIQKLVGKLNWASQIYAGIKVKQLCKLLRGTKSLTEVVPLTAEAELELAEN
REILKEPVHGAYYDPSKDLVAEIQKQGLGQWTYQIYQEPFKNLKTGKYAKMRGTHTNDVK
QLTEAVQKIATESIVIWGRTPKFKLPIQKETWDAWWTEYWQATWIPEWEFVNTPPLVKLW
YQLEKEPIVGAETFYVDGAANRETRLGKAGYVTDRGRQKVVPLTDTTNQKTELQAIYLAL
QDSGLEVNIVTDSQYALGIIQAQPDKSESELVSQIIEELIKKEKVYLAWVPAHKGIGGNE
QVDKLVSAGIRRVLFLDGIDKAQEEHEKYHNNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTIHTDNGRNFTSNSVKAACWWAGIKQEFGIPYNPQSQGVVESMNRELKKIIGQIR
DQAEHLKTAVQMAVFIHNFKRKGGIGGYSAGERIVDIIASDIQTKELQKQITKIQNFRVY
YRDNRDPLWKGPAKLLWKGEGAVVIQDNNDIKVVPRRKVKIIRDYGKQMAGDDCVASRQD
ED- >POL-C.syn1.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQILIEICGKKAIGTVLVGPTPVNIIGRNMLTQLGCTLNFPISPIE
TVPVKLKPGMDGPKVKQWPLTEEKIKALTAICEEMEKEGKITKIGPENPYNTPVFAIKKK
DSTKWRKLVDFRELNKRTQDFWEVQLGIPHPAGLKKKKSVTVLDVGDAYFSVPLDEGFRK
YTAFTIPSINNETPGIRYQYNVLPQGWKGSPAIFQSSMTKILEPFRAQNPEIVIYQYMDD
LYVGSDLEIGQHRAKIEELREHLLKWGFTTPDKKHQKEPPFLWMGYELHPDKWTVQPIQL
PEKDSWTVNDIQKLVGKLNWASQIYPGIKVRQLCKLLRGAKALTDIVPLTEEAELELAEN
REILKEPVHGVYYDPSKDLIAEIQKQGHDQWTYQIYQEPFKNLKTGKYAKMRTAHTNDVK
```

Fig. 10 cont'd-18

QLTEAVQKIAMESIVIWGKTPKFRLPIQKETWETWWTDYWQATWIPEWEFVNTPPLVKLW
YQLEKEPIAGAETFYVDGAANRETKIGKAGYVTDRGRQKIVSLTETTNQKTELQAIQLAL
QDSGSEVNIVTDSQYALGIIQAQPDKSESELVNQIIEQLIKKERVYLSWVPAHKGIGGNE
QVDKLVSSGIRKVLFLDGIDKAQEEHEKYHSNWRAMASEFNLPPIVAKEIVASCDKCQLK
GEAIHGQVDCSPGIWQLDCTHLEGKIILVAVHVASGYIEAEVIPAETGQETAYYILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQIIKIQNFRVY
YRDSRDPIWKGPAKLLWKGEGAVVIQDNSDIKVVPRRKVKIIKDYGKQMAGADCVAGRQD
EDQ
>POL-C.syn3.1
FFRENLAFPQGEAREFPPEQTRANSPT-RANSPTSR-------KLQV--RGDNPCSEAGA
ER----QGT---FNFPQITLWQRPLVTIKVGGQVKEALLDTGADDTVLEEINLPGKWKPK
MIGGIGGFIKVRQYDQIVIEICGKKAIGTVLIGPTPVNIIGRNMLTQLGCTLNFPISPIE
TVPVKLKPGMDGPKIKQWPLTEEKIKALTAICDEMEKEGKIEKIGPENPYNTPIFAIKKK
DSTKWRKLVDFKELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAKNPEIVIYQYMDD
LYIGSDLEIGQHRAKVEELREHLLRWGFTTPDKKHQKEPPFLWMGYELHPDKWTVQPIQL
PEKDSWTVNDIQRLVGKLNWASQIYPGIKVRQLCKLLRGTKALTDIVPLTEEAELELAEN
REILKEPVHGVYYDPSKDLIAEIQKQGDDQWTYQIYQESFKNLKTGKYAKMRSAHTNDVK
QLTEAVQKIALESIVIWGKAPKFRLPIQKETWEIWWTDYWQATWIPDWEFVNTPPLVKLW
YQLEKEPIAGAETFYVDGAANRETKIGKAGYVTDRGRQKVVTLTETTNQKTELQAIQLAL
QDSGLEVNIVTDSQYALGIIQAQPDKSESELVNQIIEELIKKERVYLSWVPAHKGIGENE
QVDKLVSNGIRKVLFLDGIDKAQEEHEKYHSNWRAMANEFNLPPVVAKEIVASCDKCQLK
GEAIHGQVDCSPGMWQLDCTHLEGKVILVAVHVASGYVEAEVIPAETGQETAYFILKLAG
RWPVKIIHTDNGSNFTSNAVKAACWWAGIQQEFGIPYNPQSQGVVESMNKELKKIIGQVR
EQAEHLKTAVQMAVFIHNFKRRGGIGGYSAGERIIDIIASDIQTKELQKQITKIQNFRVY
YRDSRDPVWKGPAKLLWKGEGAVVIQDNGDIKVVPRRKAKIIKDYGKQMAGDDCVAGRQD
EDQ
>POL-C.syn3.2
FFRENLAFQQGEAREFPSEQTRANSPTSRANSPTSRTNSPTSRELQV--RGDNPRSEAGV
ER----QGT---LNFPQITLWQRPLVSIKVGGQIKEALLDTGADDTVLEDINLPGKWKPR
MIGGIGGFIKVRQYDQIPIEICGKKAIGTVLVGPTPVNIIRRNMLTQLRCTLNFPISPIK
TVPVKLKPGMDGPKVKQWPLTEEKIKALTEICEEMEKEGKITKIGPENPYNTPVFAIKKK
DSTKWRKLVDFRELNKRTQDFWEVQLGIPHPSGLKKKKSVTVLDVEDAYFSVPLDEGFRK
YTAFTIPSTNNETPGIRYQYNVLPQGWKGSPAIFQCSMTKILEPFRTQNPDIVIYQYMDD
LYVGSDLEIGQHRAKIEELRAHLLKWGLTTPDKKHQKEPPFLWMGYELHPDKWTVQPIKL
PEKDSWTVNDIQKIVGKLNWASQIYPGIKVQLCKLLRGAKALTDIIPLTEEAELELAEN
REILKEPVHGAYYDPSKDLVAEIQKQGHDQWTYQIYQEPYKNLKTGKYAKMRTAHTNDVR
QLTEAVQKIAQESIVIWGKTPKFRLPIQKETWETWWTDYWQATWIPEWEFINTPPLVKLW
YQLEKEPIVGAETFYVDGAANRETKMGKAGYVTDKGRQKIVSLTETTNQKAELQAIQLAL
QDSGPEVNIVTDSQYALGIIQAQPDRSESELVNQIIEQLINKERIYLSWVPAHKGIGGNE
QVDKLVSSGIRKVLFLDGIDKAQEDHEKYHNNWRAMASDFNLPPIVAREIVASCDKCQLK
GEAMHGQVDCSPGVWQLDCTHLEGKIILVAVHVASGYMEAEVIPAETGQETAYYILKLAG
RWPVKVIHTDNGSNFTSTAVKAACWWAGIKQEFGIPYNPQSQGVVEAMNKELKKIIEQVR
DQAEHLKTAVQMAVLIHNFKRKGGIGGYSAGERIVDIIATDIQTRELQKQIIQIQNFRVY
YRDSRDPIWKGPAKLLWKGEGAVVIQDNSDIKVVPRRKVKIIKDYGKQMAGADCVASRQD
ED-
>POL-C.syn3.3
FFRENLAFPQGKAREFPSEQARANSPTSRANSPTSR-------ELQV--RRDNPRSEAGA
ER----QGT---LNCPQITLWQRPLVSIKIGGQTREALLDTGADDTVLEEISLPGKWKPK
MIGGIGGFIKVRQYDQILIEICGKKAIGSVLVGPTPVNIIGRNLLTQLGCTLNFPISPIE
TIPVKLKPGMDGPRVKQWPLTEEKIKALTAICEEMEKEGKISKIGPENPYNTPIFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAQNPEIVIYQYMDD
LYVGSDLEIEQHRAKIEELREHLLKWGFTTPDKKHQKEPPFLWMGCELHPDKWTVQPIQL

Fig. 10 cont'd-19

PEKESWTVNDIQKLVGKLNWASQIYAGIKVKQLCRLLRGAKALTDIVPLTAEAELELAEN
REILREPVHGVYYDPSKELIAEIQKQGQDQWTYQIYQEPFKNLKTGKYAKRRTAHTNDVK
QLAEAVQKIAMESIVIWGKIPKFRLPIQKETWEAWWTDYWQATWIPEWEFVNTPPLVKLW
YQLEKDPIAGVETFYVDGAANRETKLGKAGYVTDRGRQKIVSLSETTNQKTELHAIQLAL
QDSGSEVNIVTDSQYALRIIQAQPDKSESEIVNQIIEQLIKKERVYLAWVPAHKGIGENE
QVDKLVSKGIRKVLFLDGIEKAQEEHERYHSNWRAMASEFNLPPIVAKEIVASCDKCQLK
GEATHGQVDCSPGIWQLDCTHLEGKVIIVAVHVASGYIEAEVIPAETGQETAYFLLKLAG
RWPVKTIHTDNGSNFTSAAVKAACWWAGIHQEFGIPYNPQSQGVVESMNKELKKIIGQVR
DQAEHLKTAVLMAVFIHNFKRKGGIGDYSAGERIIDIIATDIQTKELQKQIIKIQNFRVY
YRDNRDPIWKGPAKLLWKGEGAVVLQDNSDIKVIPRRKAKIIRDYGKQMAGADCVAGRQD
ENQ

>POL-C.syn4.1
FFRENLAFPQGKAREFPSEQARANSPTSRANSPTSR-------ELQV--RRDNPRSEAGA
ER----QGT---LNLPQITLWQRPLVSIKVGGQIKEALLDTGADDTVLEDINLPGKWKPK
MIGGIGGFIKVRQYDQIPIEICGKKAIGTVLVGPTPVNIIGRNMLTQLGCTLNFPISPIE
TIPVKLKPGMDGPKVKQWPLTEEKIKALTEICKEMEKEGKIEKIGPENPYNTPVFAIKKK
DSTKWRKLVDFRELNKRTQDFWEVQLGIPHPSGLKKKKSVTVLDVEDAYFSVPLDENFRK
YTAFTIPSVNNETPGIRYQYNVLPQGWKGSPAIFQCSMTKILEPFRTQNPEIVIYQYMDD
LYVGSDLEIGQHRAKIEKLREHLLKWGFTTPDKKHQKEPPFLWMGYELHPDKWTVQPIKL
PEKDSWTVNDIQRLVGKLNWASQIYAGIKVRQLCKLLRGAKALTDIVPLTKEAELELAEN
REILKEPVHGVYYDPSKELIAEIQKQGQDQWTYQIYQEPFKNLKTGKYAKRRTAHTNDVK
QLAEAVQKITMESIVIWGRTPKFRLPIQKETWEAWWTDYWQATWIPEWEFVNTPPLVKLW
YQLEKEPIAEAETFYVDGAANRETKMGKAGYVTDKGRQKIVSLTETTNQKTELHAIQLAL
QDSGPEVNIVTDSQYALGIIQAQPDKSESELVSQIIEQLINKERIYLSWVPAHKGIGGNE
QVDKLVSKGIRKVLFLDGIDKAQEEHERYHSNWRAMANEFNLPPIVARETVASCDKCQLK
GEAIHGQVDCSPGVWQLDCTHLEGKIILVAVHVASGYVEAEVIPAETGQETAYFLLKLAG
RWPVKTIHTDNGSNFTSAAVKAACWWAGVQQEFGIPYNPQSQGVVESMNKELKKIIGQIR
DQAEHLKTAVQMAVFIHNFKRKGGIGDYSAGERIIDIIATDIQTRELQKQIIQIQNFRVY
YRDSRDPVWKGPAKLLWKGEGAVVLQDNSDIKVVPRRKVKIIKDYGKQMAGADCVAGRQD
ENQ >POL-C.syn4.2
FFRENLAFPEGEAREFPSEQTRANSPT-RANSPTSR-------KLQV--RGDNPRSEAGV
ER----QGT---LNFPQITLWQRPLVSIKIGGQTREALLDTGADDTVLEEIKLPGNWKPK
MIGGIGGFIKVRQYDQILIEICGKKAIGTVLIGPTPVNIIGRNLLTQLGCTLNFPISPIK
TVPVKLKPGMDGPKVKQWPLSEEKIKALTEICEEMEKEGKISKIGPENPYNTPVFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAKNPEIVIYQYMDD
LYVGSDLEIGQHRAKVEELREHLLKWGLTTPDKKHQKEPPFLWMGYELHPDKWTVQPIQL
PDKDSWTVNDIQKLVGKLNWASQIYPGIKVQLCKLLRGTKALTDIVPLTAEAELELAEN
REILREPVHGVYYDPSKDLVAEIQKQGNDQWTYQIYQEPYKNLKTGKYAKMRSAHTNDVK
QLTEAVQKIALESIVIWGKAPKFRLPIQKETWEIWWTDYWQATWIPDWEFVNTPPLVKLW
YQLEKDPIAGVETFYVDGAANRETKLGKAGYVTDRGRQKIVSLSETTNQKTELQAIQLAL
QDSGLEVNIVTDSQYALGIIQAQPDKSESELVNQIIEELIKKEKVYLSWVPAHKGIGENE
QVDKLVSSGIRKVLFLDGIEKAQEEHEKYHNNWRAMASEFNLPPIVAKEIVASCDKCQLK
GEATHGQVDCSPGMWQLDCTHLEGKIIIVAVHVASGYLEAEVIPAETGQDTAYYILKLAG
RWPVKVIHTDNGTNFTSAAVKAACWWAGIQQEFGIPYNPQSQGVVESMNKELKKIIGQVR
EQAEHLKTAVLMAVFIHNFKRKGGIGEYSAGERIIDMIATDIQTKELQNQITKIQNFRVY
YRDSRDPIWKGPAKLLWKGEGAVVIQDNGDIKVVPRRKVKIIRDYGKQMAGDDCVAGRQD
EDQ >POL-C.syn4.3
FFRENLAFPQGEAREFPPEQTRANSPTSRTNSPTSR-------ELQV--RGDNPHSEAGA
ERQGTLQGT---LNCPQITLWQRPLVSIRVGGQIKEALLDTGADDTVLEEISLPGKWKPK
MIGGIGGFIKVRQYDQIVIEICGKKAIGSVLVGPTPVNIIRRNMLTQLRCTLNFPISSIE
TVPVKLKPGMDGPRVKQWPLTEEKIKALTAICEEMEKEGKITKIGPDNPYNTPVFAIKKK

Fig. 10 cont'd-20

```
DSTKWRKLVDFKELNKRTQDFWEVQLGIPHPAGLKRKKSVTVLDVGDAYFSVPLDEGFRK
YTAFTIPSTNNETPGIRYQYNVLPQGWKGSPAIFQSSMIKILEPFRAQNPDIVIYQYMDD
LYIGSDLEIGQHRAKIEELRAHLLKWGFTTPDKKHQKEPPFLWMGCELHPDKWTVQPIQL
PEKESWTVNDIQRLVGKLNWASQIYSGIKVRQLCKLLRGVKALTDIVPLTEEAELELAEN
REILKETVHGAYYDPSKDLIAEIQKQGHDQWTYQIYQEPFKNLKTGKYAKMRTAHTNDIK
QLTEAVQKIAMESIVIWGKTPKFRLPIQKETWETWWTDYWQATWIPEWEFINTPPLVKLW
YQLEKEPIVGAETFYVDGAANRDTKLGKAGYITDRGRQKVVTLTETTNQKAELQAIQLAL
QDSGSKVNIVTDSQYALGIIQAQPDRSESELVNQIIEQLIKKERVYLSWVPAHKGIGGNE
QIDKLVSSGIRRVLFLDGIDKAQEDHEKYHSNWRAMASDFNLPPIVAKEIIASCDKCQLK
GEAMHGQVDCSPGIWQLDCTHLEGKVIIVAVHVASGYIEAEVIPAETGQETAYYILKLAG
RWPVKIIHTDNGSNFTSNAVKAACWWAGIHQEFGIPYNPQSQGVVEAMNKELKKIIGQVR
DQAEHLKTAVLMAVFIHNFKRRGGIGGYSAGERIIDIIASDIQTKELQKQITKIQNFRVY
YRDSRDPIWKGPAKLLWKGEGAVVIQDNSDIKVIPRRKAKIIKDYGKQMAGADCVAGGQD
EN-
>POL-C.syn4.4
FFRENLAFQQGEAREFPSEQTRAISPTSR--------------ELQV--RGDNPCSEAGA
ER----QGT---FNFPQITLWQRPLVTIKVGGQVKEALLDTGADDTVLEEINLPGKWKPR
MIGGIGGFIKVRQYEQILIEICGKRAIGTVLVGPTPINIIGRNMLTQIGCTLNFPISPIE
TVPVKLKPGMDGPKIKQWPLTEEKIKALTAICDEMEKEGKITKIGPENPYNTPIFAIKKK
DSTKWRKLVDFRELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAQNPEIVIYQYMDD
LYVGSDLEIEQHRAKIEELREHLLRWGFTTPDKKHQKEPPFLWMGYELHPDKWTVQPIQL
PEKDSWTVNDIQKIVGKLNWASQIYPGIKVRQLCRLLRGAKALTDIIPLTEEAELELAEN
REILKEPVHGAYYDPSKDLIAEIQKQGDDQWTYQIYQESFKNLKTGKYAKMRTAHTNDVR
QLTEAVQKIAQESIVIWGKIPKFRLPIQKDTWETWWTDYWQATWIPDWEFVNTPPLVKLW
YQLEKEPIAGAETFYVDGAANRETKIGKAGYVTDRGRQKVITLTETTNQKTELQAIHLAL
QDSGSEVNIVTDSQYALRIIQAQPDKSESEIVNQIIEQLINKERVYLSWVPAHKGIGGNE
QVDKLVSNGIRKVLFLDGIDKAQEEHEKYHSNWRAMASEFNLPPVVAKEIVASCDKCQQK
GEAIHGQVDCSPRIWQLDCTHLEGKVILVAVHVASGYMEAEVIPAETGQETAYFILKLAG
RWPVKVIHTDNGSNFTSTAVKAACWWAGIKQEFGIPYNPQSQGVVESMNKELKKIIEQVR
DQAEHLKTAVQMAVLIHNFKRKGGIGGYSAGERIVDIIATDIQTKELQKQIIKIQNFRVY
YRDNRDPIWKGPAKLLWKGEGAVVIQDNSEIKVVPRRKAKIIRDYGKQMAGADCVASRQD
ED-
>POL-C.syn6.1
FFRENLAFPQGKAREFPSEQTRAISPTSR--------------ELQV--RGNNPRSEAGA
ER----QGT---LNLPQITLWQRPLVSIKIGGQTREALLDTGADDTVLEEIKLPGNWKPK
MIGGIGGFIKVRQYDQILIEICGKRAIGTVLVGPTPVNIIGRNMLTQIGCTLNFPISSIE
TVPVKLKPGMDGPKVKQWPLTEEKIKALTEICEEMEKEGKITKIGPDNPYNTPVFAIKKK
DSTKWRKLVDFKELNKRTQDFWEVQLGIPHPAGLKKNKSVTVLDVGDAYFSVPLDESFRK
YTAFTIPSINNETPGIRYQYNVLPQGWKGSPAIFQSSMTRILEPFRAQNPDIVIYQYMDD
LYVGSDLEIEQHRAKIEELREHLLRWGFTTPDKKHQKEPPFLWMGCELHPDKWTVQPIQL
PEKDSWTVNDIQKLVGKLNWASQIYSGIKVRQLCKLLRGVKALTDIVPLTKEAELELAEN
REILREPVHGVYYDPAKDLIAEIQKQGQDQWTYQIYQEPFKNLKTGKYAKRRTAHTNDVK
QLTEAVQKIATESIVIWGKIPKFRLPIQKDTWETWWTDYWQATWIPDWEFVNTPPLVKLW
YQLEKEPIAEAETFYVDGAASRETKMGKAGYVTDRGRQKVITLTETTNQKTELQAIKLAL
QDSGSEVNVVTDSQYALGIIQAQPDKSESEIVNQIIEQLINKERVYLSWVPAHKGIGGNE
QVDKLVSRGIRKVLFLDGIDKAQDEHEKYHSNWRAMASEFNLPPIVAREIVASCDKCQLK
GEATHGQVDCSPGIWQLDCTHLEGKIILVAVHVASGYIEAEVIPTETGQETAYYILKLAG
RWPVKIIHTDNGSNFTSSAVKAACWWAGIQQEFGIPYNPQSQGVVESMNKELKKIIGQVG
DQAEHLKTAVQMAVFIHNFKRRGGIGGYSAGERIIDIIATDIQTRELQKQIIKIQNFQVY
YRDSRDPIWKGPAKLLWKGEGAVVIQDNSEIKVVPRRKVKIIKDYGKQMAGADCMASRQD
ED-
>POL-C.syn6.2
FFRENLAFPQGEARELPSEQTRANGPTSR--------------ELQV--RGDNPCSEAGA
ER----QGT---FNFPQITLWQRPLVTIKVGGQVKEALLDTGADDTVLEEINLPGKWKPK
```

Fig. 10 cont'd-21

```
MIGGIGGFIKVRQYDQIPIEICGKRAIGTVLVGPTPINIIGRNMLTQLGCTLNFPISPIE
TVPVQLKPGMDGPRVKQWPLTEEKIKALTEICKEMEKEGKISKIGPENPYNTPIFAIKKK
DSTKWRKLVDFRELNKRTQDFWEVQLGIPHPAGLKKKRSVTVLDVGDAYFSVPLDEDFRK
YTAFTIPSINNETPGVRYQYNVLPQGWKGSPSIFQSSMTKILEPFRTQNPEIVIYQYMDD
LYIGSDLEIGQHREKIEELREHLLKWGFTTPDKKHQKEPPFLWMGYELHPDKWTVQPIKL
PEKDSWTVNDIQRLVGKLNWASQIYAGIKVRQLCKLLKGAKALTDIVTLTEEAELELAEN
REILKEPVYGVYYDPSKDLVAEIQKQGNDQWTYQIYQESFKNLKTGKYAKMRTAHTNDIK
QLTEAVQKIAQESIVIWGKTPKFRLPIQKETWEAWWTDYWQATWIPDWEFVNTPPLVKLW
YQLEKEPMAGVETFYVDGAANRETKIGKAGYVTDRGRQKVVTITETTNQKTELQAIYLAL
QDSGSKVNIVTDSQYALGIIQAQPDKSESELVSQIIEQLINKEKIYLSWVPAHKGIGGNE
QVDKLVSSGIRKVLFLDGIDKAQEDHERYHSNWRAMASDFNLPPIVAKEIVASCDQCQLK
GEAMHGQVDCSPGMWQLDCTHLEGKIIIVAVHVASGYIEAEVISAETGQETAYYILKLAG
RWPVKVVHTDNGSNFTSAAVKAACWWAGVQQEFGIPYNPQSQGVVESMNKELKRIIGQVR
DQAEHLKTAVQMAVFIHNFKRKGGIGGYSAGERIIDMIATDIQTKELQKQIIQIQNFRVY
YRDSRDPIWKGPAKLLWKGEGAVVIQDKGDIKVVPRRKAKIIRDYGKQMAGADCMAGRQD
EDQ
>POL-C.syn6.3
FFREDLAFPQGEARKFPPEQTRANSPTSRANSPTSR-------KLQV--RGDNPRSEAGV
ER----QGT---LNFPQITLWQRPLVSIKVGGQIREALLDTGADDTVLEEMSLPGKWKPK
MIGGIGGFIKVKQYEQILIEICGKKAIGSVLVGPTPVNIIGRNLLTQLGCTLNFPISPIE
TVPVKLKPGMDGPKVKQWPLTEEKIKALTAICDEMEKEGKITKIGPENPYNTPVFAIKKK
DSTKWRKLVDFKELNKRTQDFWEVQLGIPHPAGLKKKKSVTVLDVGDAYFSVPLDENFRK
YTAFTIPSRNNETPGIRYQYNVLPQGWKGSPAIFQASMTKILEPFRAKNPEIVIYQYMDD
LYGSDLEIGQHRAKIEELRDHLLKWGFTTPDKKHQKEPPFLWMGYELHPDKWTVQPIEL
PEKDSWTVNDIQKLVGKLNWASQIYPGIQVKQLCKLLRGAKALTDVVPLTEEAELELAEN
REILKEPVHGAYYDPSKDLIAEIQKQGHDQWTYQIYQEPYKNLKTGKYAKRRAAHTNDVK
QLTEAVQKIAMESIVIWGKTPKFRLPIQKETWETWWTEYWQATWIPEWEFVNTPPLVKLW
YQLEKEPIAGAETFYVDGAANRETKMGKAGYITDRGRQKIISLTETTNQKTELHAIQLAL
QDSGSEANIVTDSQYALGIIQAQPDRSESELVNQIIEQLIKKERVYLAWVPAHKGIGENE
QVDKLVSSGIRKILFLDGIDKAQEEHEKYHSNWKAMASEFNLPPVVAREIVASCDKCQLK
GEAMHGQVDCSPRIWQLDCTHLERKVILVAVHVASGYMEAEVIPAETGQETAYFILKLAG
RWPVKVIHTDNGSNFTSNAVKAACWWAGIHQEFGIPYNPQSQGVVESMNKELKKIIEQVR
DQAEHLKTAVQMAVLIHNFKRKGGIGGYTAGERIIDIIATDIQTKELQNQITKIQNFRVY
YRDNRDPIWKGPAKLLWKGEGAVVLQDNSDIKVVPRRKVKIIRDYGKQMAGADCVAGRQD
ED-
>POL-C.syn6.4
FFRKNLAFPQGEAREFPPEQTRANSPTSR--------------ELQV--RGDNPLSEAGA
ERQGTLQGT---LNCPQITLWQRPLVSIKVGGQIKEALLDTGADDTVLEEISLPGKWKPK
MIGGIGGFIKVRQYDQIVIEICGKKAIGAVLVGPTPVNIIRRNMLTQLRCTLNFPISPIK
TVPVKLKPGMDGPKVKQWPLSEEKIKALTAICEDMEKEGKITKIGPENPYNTPIFAIKKK
DSTKWRKLVDFRELNKRTQDFWEVQLGIPHPSGLKKKKSVTVLDVEDAYFSVPLDEGFRK
YTAFTIPSINNATPGIRYQYNVLPQGWKGSPAIFQSSMTKILEPFRTKNPDIVIYQYMDD
LYGSDLEIGQHRAKIEKLREHLLRWGLTTPDKKHQKEPPFLWMGYELHPDKWTVQPIQL
PDKDSWTVNDIQKLVGKLNWASQIYAGIKVKQLCRLLRGAKALTDIIPLTEEAELELAEN
REILKEPVHGAYYDPSKDLIAEIQKQGQGWTYQIYQEPYKNLKTGKYAKMRTAHTNDVK
QLAEAVQKITMESIVIWGRTPKFRLPIQKETWETWWTDYWQATWIPEWEFINTPPLVKLW
YQLEKEPIVGAETFYVDGAANRETKLGKAGYVTDKGRQKIVSLTETTNQKTELQAIHLAL
QDSGSEVNIVTDSQYALRIIQAQPDKSESELVNQIIEQLINKERIYLSWVPAHKGIGGNE
QVDKLVSNGIRKVLFLDGIEKAQEEHERYHSNWRAMANEFNLPPIVAREIVASCDCQIK
GEAMHGQVDCSPGVWQLDCTHLEGKVILVAVHVASGYVEAEVIPAETGQEAAYFILKLAG
RWPVKTIHTDNGSNFTSTAVKAACWWAGIKQEFGIPYNPQSQGVVESMNKELKKIIGQVR
DQAEHLKTAVQMAVLIHNFKRKGGIGDYSAGERIIDIIATDMQTKELQKQIIKVQNFRVY
YRDSRDPIWKGPAKLLWKGEGAVVIQDNGDIKVVPRRKVKIIKDYGRQMAGADCVASRQD
ED-
```

Fig. 10 cont'd-22

>POL-C.syn6.5
FFRENLAFPEGEAREFPSEQARANSPTSR--------------ELQV--RRDNPRSEAGA
EG----QGT---LNFPQITLWQRPLVSIRVGGQIKEALLDTGADDTVLEEINLPGRWKPK
MIGGIGGFIKVRQYDQITIEICGKKAIGTVLVGPTPINIIGRNMLTQIGCTLNFPISPIE
TVPVKLKPGMDGPKIKQWPLTEEKIKALKAICEEMEKEGKIEKIGPENPYNTPVFAIKKK
DSTKWRKLVDFRELNKRTQDFWEIQLGIPHPAGLKRKKSVTVLDVGDAYFSVPLYEDFRK
YTAFTIPSVNNETPGIRYQYNVLPQGWKGSPAIFQCSMTKILEPFRAQNPEIVIYQYMDD
LYVGSDLEIGQHRAKVEELREHLLKWGLTTPDKKHQKEPPFLWMGYELHPDKWTVQPIQL
PEKESWTVNDIQKIVGKLNWASQIYPGIKVRQLCRLLRGAKALTDIVPLTAEAELELAEN
REILKEPVHGVYYDPSKELIAEIQKQGDDQWTYQIYQEPFKNLKTGKYAKMRSAHTNDVK
QLTEAVQKIALESIVIWGKAPKFRLPIQKETWEIWWTDYWQATWIPEWEFINTPPLVKLW
YQLEKEPIAGVETFYVDGAANRDTKIGKAGYVTDRGRQKIVSLSETTNQKTELQAIQLAL
QDSGLEVNIVTDSQYALGIIQAQPDNSESELVNQIIEELIKKERVYLSWVPAHKGIGGNE
QVDKLVSKGIRKVLFLDGIDKAQEEHEKYHNNWRAMASDFNLPPVVAKEIVACCDKCQLK
GEAIHGQVDCSPGIWQLDCTHLEGKVIIVAVHVASGYLEAEVIPAETGQETAYFLLKLAG
RWPVKVIHTDNGPNFTSAAVKAACWWAGINQEFGIPYNPQSQGVVESMNKELKKIIGQVR
EQAEHLKTAVQMAVFIHNFKRKGGIGGYSAGERIVDIIATDIQTKELQNQIIKIQNFRVY
YRDSRDPIWKGPAKLLWKGEGAVVIQENSDIKVVPRRKAKIIKDYGKQMAGDDCVAGRQD
EDQ
>POL-C.syn6.6
FFRENLAFQQGEAREFPSEQTRANSPT-RANSPTSRTNSPTSRELQV--RGDNPHSEAGA
ER----QGS---LNFPQITLWQRPLVTIKIGGQLKEALLDTGADDTVLEDINLPGKWKPR
MIGGIGGFIKVRQYEQIPIEICGKKAIGTVLIGPTPVNIIGRNLLTQLGCTLNFPISPIE
TIPVKLKPGMDGPKVKQWPLTEEKIKALTAICEEMEKEGKITKIGPDNPYNTPVFAIKKK
DSTKWRKLVDFRELNKRTQDFWEVQLGIPHPAGLKKKKSVTVLDVGDAYFSVPLDKDFRK
YTAFTIPSTNNETPGIRYQYNVLPQGWKGSPAIFQSSMIKILEPFRAKNPELVIYQYMDD
LYVGSDLEIMQHRAKIEELRAHLLKWGFTTPDKKHQKEPPFLWMGYELHPDKWTVQPIVL
PEKDSWTVNDIQKLVGKLNWASQIYPGIKVKQLCKLLRGTKALTDIVPLTEEAELELAEN
REILKETVHGAYYDPSKDLIAEIQKQGYDQWTYQIYQEPFKNLKTGKYAKKRTAHTNDVR
QLTEAVQKIAIESIVIWGKTPKFRLPIQKETWETWWADYWQATWIPEWEFVNTPPLVKLW
YQLEKDPIAGAETFYVDGAANRETKKGKAGYVTDKGRQKVVTLTETTNQKAELQAIQLAL
QDSGPEVNIVTDSQYALRIIQAQPDKSESGLVNQIIEQLIKKEKVYLSWVPAHKGIGGNE
QIDKLVSSGIRRVLFLDGIDKAQEDHEKYHSNWRAMAGEFNLPPVVAKEIVASCDKCQQK
GEAIHGQVDCSPGIWQLDCTHLEGKIILVAVHVASGYIEAEVIPAETGQDTAYYILKLAG
RWPVKVIHTDNGTNFTSAAVKAACWWASIQQEFGIPYNPQSQGVVEAMNKELKKIIGQIR
DQAEHLKTAVLMAVFIHNFKRKGGIGEYSAGERIIDIIASDIQTKELQKQITKIQNFRVY
YRDSRDPVWKGPAKLLWKGEGAVVIQDNSDIKVIPRRKAKIIRDYGKQMAGADCVAGGQD
ED- >POL-M.syn1.1
FFRENLAFPQGEAREFPSEQTRANSPTSRANSPTSR-------ELQV--RGDNPRSEAGA
ER----QGT---LNFPQITLWQRPLVTIKIGGQLKEALLDTGADDTVLEDINLPGKWKPK
MIGGIGGFIKVRQYDQILIEICGKKAIGTVLVGPTPVNIIGRNMLTQIGCTLNFPISPIE
TVPVKLKPGMDGPKVKQWPLTEEKIKALTEICTEMEKEGKISKIGPENPYNTPVFAIKKK
DSTKWRKLVDFRELNKRTQDFWEVQLGIPHPAGLKKKKSVTVLDVGDAYFSVPLDESFRK
YTAFTIPSINNETPGIRYQYNVLPQGWKGSPAIFQSSMTKILEPFRKQNPDIVIYQYMDD
LYVGSDLEIGQHRAKIEELREHLLKWGFTTPDKKHQKEPPFLWMGYELHPDKWTVQPIQL
PEKDSWTVNDIQKLVGKLNWASQIYPGIKVKQLCKLLRGAKALTDIVPLTEEAELELAEN
REILKEPVHGVYYDPSKDLIAEIQKQGQDQWTYQIYQEPFKNLKTGKYAKMRTAHTNDVK
QLTEAVQKIATESIVIWGKTPKFRLPIQKETWETWWTDYWQATWIPEWEFVNTPPLVKLW
YQLEKEPIVGAETFYVDGAANRETKLGKAGYVTDRGRQKVVSLTETTNQKTELQAIQLAL
QDSGSEVNIVTDSQYALGIIQAQPDKSESELVNQIIEQLIKKEKVYLSWVPAHKGIGGNE
QVDKLVSSGIRKVLFLDGIDKAQEEHEKYHSNWRAMASDFNLPPIVAKEIVASCDKCQLK
GEAMHGQVDCSPGIWQLDCTHLEGKVILVAVHVASGYIEAEVIPAETGQETAYFILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQITKIQNFRVY

Fig. 10 cont'd-23

```
YRDSRDPIWKGPAKLLWKGEGAVVIQDNSDIKVVPRRKAKIIRDYGKQMAGDDCVAGRQD
EDQ
>POL-M.syn3.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQIPIEICGKRAIGTVLGPTPINIIGRNMLTQLGCTLNFPISPIK
TVPVKLKPGMDGPKVKQWPLTEEKIKALTAICEEMEKEGKITKIGPENPYNTPVFAIKKK
DGTKWRKLVDFRELNKRTQDFWEVQLGIPHPSGLKKKKSVSVLDVGDAYFSVPLDESFRK
YTAFTIPSINNETPGIRYCYNVLPQGWKGSPAIFQCSMTKILEPFRAQNPEIVIYQYMDD
LYIGSDLEIGQHRAKIEELREHLLRWGFTTPDKKHQKEPPFLWMGCELHPDKWTVQPIQL
PEKDSWTVNDIQKIVGKLNWASQIYPGIKVRQLCKLLRGAKALTDIVPLTEEAELELAEN
REILREPVHGVYYDPSKDLVAEIQKQGQDQWTYQIYQEPFKNLKTGKYAKMRTAHTNDVK
QLTEAVQKIALESIVIWGKIPKFRLPIQKETWEAWWMEYWQATWIPEWEFINTPPLVKLW
YQLEKEPIAGAETFYVDGAANRETKIGKAGYVTDRGRQKIVSLTETTNQKAELQAIQLAL
QDSGPEVNIVTDSQYALGIIQAHPDKSESELVNQIIEQLIKKERVYLSWVPAHKGIGENE
QVDKLVSNGIRKILFLDGIDKAQEEHEKYHSNWRAMASEFNLPPIVAKEIVASCNKCQLK
GEALHGQVDCSPGMWQLDCTHLEGKVILVAVHVASGYMEAEVIPAETGQETAYYILKLAG
RWPVKVVHTDNGSNFTSTAVKAACWWAGIQQEFGIPYNPQSQGVIESMNKELKKIIGQIR
DQAEHLKTAVQMAVFIHNFKRKGGIGEYSAGERIIDIIATDIQTRELQKQIIKIQNFRVY
YRDSRDPIWKGPAKLLWKGEGAVVLQDNSDIKVVPRRKVKIIKDYGKQMAGADCVAGRQD
ENQ
>POL-M.syn3.2
FFRENLAFQQGEARKFSSEQTGANSPTSR--------------ELRV-RRGDNPLSEAGA
ER----RGTVPSLSFPQITLWQRPLVTVKIGGQLIEALLDTGADDTVLEDINLPGKWKPR
MIGGIGGFIKVKQYDQILIEICGKKAIGTVLGPTPVNIIGRNMLTQIGCTLNFPISPID
TVPVTLKPGMDGPKIKQWPLTEEKIKALTEICTEMEKEGKISRIGPENPYNTPIFAIKKK
DSTKWRKLVDFRELNKKTQDFWEVQLGIPHPAGLKKKRSVTVLDVGDAYFSVPLDKDFRK
YTAFTIPSTNNETPGIRYQYNVLPQGWKGSPSIFQSSMTRILEPFRAKNPEIVIYQYMDD
LYVGSDLEIEQHRTKIEELRQHLLRWGLTTPDKKHQKEPPFLWMGYELHPDRWTVQPIEL
PEKESWTVNDIQKLVGKLNWASQIYAGIKVQQLCKLLRGTKALTEVVPLTEEAELELEEN
REILKDPVHGAYYDPSKDLIAEIQKQGHDQWTYQIYQEQYKNLKTGKYARKRSAHTNDVR
QLTEAVQKIATESIVIWGKTPKFRLPIQRETWETWWTDYWQATWIPEWEFVNTPPLVKLW
YQLEKDPIAGVETFYVDGASNRETKKGKAGYVTDKGRQKVVSLTETTNQKTELHAIHLAL
QDSGSEVNIVTDSQYALGIIQAQPDRSESELVNQIIEELIKKEKVYLSWVPAHKGIGGNE
QVDKLVSSGIRKVLFLDRIDKAQEEHERYHSNWRTMASDFNLPPIVAKEIVANCDKCQLK
GEAMHGQVDCSPGIWQIDCTHLEGKVIIVAVHVASGYIEAEVIPAETGQETAYFLLKLAG
RWPVKVIHTDNGSNFTSAAVKAACWWANVTQEFGIPYNPQSQGVVESMNKELKKIIGQVR
EQAEHLKTAVQMAVLIHNFKRKGGIGGYSAGERIIDIIASDIQTKELQKQIIKVQNFRVY
YRDSRDPVWKGPAKLLWKGEGAVVIQDNSDIKVVPRRKVKIIRDYGKQMAGDDCVAGRQD
EDQ
>POL-M.syn3.3
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQILIEICGHKAIGTVLIGPTPVNIIGRNLLTQIGCTLNFPISPIE
TVPVKLKPGMDGPRVKQWPLTEEKIKALVEICTEMEKEGKISKIGPENPYNTPVFAIKKK
DSTRWRKLVDFRELNKRTQDFWEIQLGIPHPAGLKKKKSVTVLDVGDAYFSVPLDEGFRK
YTAFTIPSVNNETPGVRYQYNVLPQGWKGSPAIFQSSMTKILEPFRKQNPDIVIYQYMDD
LYVGSDLEIGQHRTKIEELREHLLKWGFTTPDKKHQNEPPFLWMGYELHPDKWTVQPIVL
PEKDSWTVNDLQKLVGKLNWASQIYPGIKVQQLCRLLRGAKALTEVIPLTKEAELELAEN
REILKEPVHGVYYDPSKELIAEIQKQGQGQWTYQIYQEPYKNLKTGKYARMRGAHTNDVK
QLTEVVQKIAMESIVIWGKTPKFKLPIQKETWETWWTEYWQATWIPDWEFVNTPPLVKLW
YQLEKEPIVGAETFYVDGAANRETKLGKAGYVTDRGRQKVVSLTDTTNQKTELQAIHLAL
QDSGLEVNIVTDSQYAIGIIQAQPDKSESELVSQIIEQLIKKEKVYLAWVPAHKGIGGNE
QVDKLVSAGIRKVLFLDGIDKAQEDHEKYHNNWRAMASDFNLPPVVAKEIVASCDKCQLK
```

Fig. 10 cont'd-24

```
GEAIHGQVDCSPGIWQLDCTHLEGKIILVAVHVASGYLEAEVIPAETGQETAYFILKLAG
RWPVKTIHTDNGSNFTSTTVKAACWWAGIKQEFGIPYNPQSQGVVESINKELKKIIGQVR
DQAEHLKTAVLMAVFIHNFKRRGGIGGYSAGERIVDIIATDIQTKELQKQITKIQNFRVY
YRDSRDPLWKGPAKLLWKGEGAVVIQDNSEIKVVPRRKAKIIRDYGKQMAGDDCVASRQD
ED-
>POL-M.syn4.1
FFRENLAFQQGEARKFSSEQTRANSPTRG--------------ELQVWGRDNNPLSEAGA
ER----RGTVPSLSFPQITLWQRPLVTVKIGGQLIEALLDTGADDTVLEDINLPGKWKPK
MIGGIGGFIKVKQYDQILIEICGKKAIGTVLVGPTPVNIIGRNMLTQIGCTLNFPISPID
TVPVTLKPGMDGPRIKQWPLTEEKIKALTEICKEMEEEGKISKIGPENPYNTPIFAIKKK
NSTRWRKLVDFRELNKKTQDFWEVQLGIPHPAGLKRKKSVTVLDVEDAYFSVPLDESFRK
YTAFTIPSINNETPGVRYQYNVLPQGWKGSPAIFQCSMTKILEPFRIKNPEMVIYQYMDD
LYVGSDLEIGQHRIKIEELRAHLLSWGFTTPDKKHQKDPPFLWMGYELHPDRWTVQPIEL
PEKDSWTVNDIQKLVEKLNWASQIYSGIKVRQLCRLLRGAKALTDIVPLTEEAELELAEN
REILKEPVHGAYYDPSKDLVAEIQKQGQDQWTYQIYQEPFKNLKTGKYARKRSAHTNDVK
QLTEVVQKIATESIVIWGKTPKFRLPIQRETWETWWTEYWQATWIPEWEFVNTPPLVKLW
YQLEKDPIAGVETFYVDGAASRETKLGKAGYVTDRGRQKVVSLTETTNQKTELHAIHLAL
QDSGSEVNIVTDSQYVLGIIQAQPDRSESELVNQIIEELIKKEKVYLSWVPAHKGIGGNE
QVDKLVSSGIRKVLFLNGIDKAQEEHERYHSNWRTMASDFNLPPIVAKEIVANCDKCQLK
GEAMHGQVDCSPGVWQLDCTHLEGKVIIVAVHVASGYIEAEVIPAETGQEAAYFILKLAG
RWPVKVVHTDNGSNFTSAAVKAACWWANVRQEFGIPYNPQSQGVVESMNNELKKIIGQIR
DQAEHLKTAVLMAVFIHNFKRKGGIGEYSAGERIIDIIATDIQTRELQKQITKIQNFRVY
FRDSRDPIWKGPAKLLWKGEGAVVIQDNSEIKVVPRRKVKIIRDYGKQMAGDDCVAGRQD
EN-
>POL-M.syn4.2
FFRENLAFPQGEAREFPSEQARANSPTSRANSPTSR-------DLWDGGRDNLP-SEAGA
ER----QGT---LNFPQITLWQRPLVTVRIGGQLREALLDTGADDTVLEDIDLPGKWKPK
IIGGIGGFIKVRQYEQIPIEICGHKAIGTVLVGPTPINIIGRNMLTQLGCTLNFPISPIK
TVPVKLKPGMDGPRVKQWPLTEEKIKALTAICEEMEKEGKITKIGPENPYNTPVFAIKKK
DSTRWRKLVDFRELNRRTQDFWEVQLGIPHPAGLKKKRSVTVLDVGDAYFSVPLDEGFRK
YTAFTIPSVNNETPGIRYQYNVLPQGWKGSPSIFQSSMTRILEPFRAKNPEIVIYQYIDD
LYVRSDLEIGQHRAKIEELREHLLRWGFTTPDKKHQKEPPFLWMGCELHPDKWTVQPIQL
PEKDSWTINDIQKLVGKLNWASQIYPGIKVRQLCKLLRGTKALTDIVTLTEEAELELAEN
REILKDPVHGVYYDPSKELIAEIQKQGDDQWTYQIYQEQYKNLKTGKYAKRRTAHTNDVR
QLTEAVQKIALESIVIWGKIPKFRLPIQKETWEAWWMEYWQATWIPEWEYVNTPPLVKLW
YQLEKEPIIGAETFYVDGAANRETKLGKAGYVTNRGRQKVVSLTDTTNQKTELQAIQLAL
QDSGSEVNVVTDSQYALGIIQAHPDKSESELVNQIIEQLIKKERVYLSWVPAHKGIGGNE
QVDKLVSAGIRKVLFLDGIDKAQEDHERYHSNWRAMASDFNLPPVVAKEIVASCNKCQLK
GEAIHGQVDCSPGIWQLDCTHLEGKIIIVAVHVASGYMEAEVIPAETGQETAYFILKLAG
RWPVKIIHTDNGSNFTSATVKAACWWANVTQEFGIPYNPQSQGVVESINKELKKIIGQVR
DQAEHLRTAVQMAVFIHNFKRRGGIGGYSAGERIVDIIATDIQTKELQKQITKIQKFRVY
YRDSRDPLWKGPAKLLWKGEGAVVIQDNSDIKVIPRRKAKIIKDYGKQMAGADCVAGRQD
EDQ
>POL-M.syn4.3
FFRENLAFPQGKAREFPSEQTRANSPTSRANSPTSR-------ELQV--RGDNPRSEAGA
ER----QGT---FNFPQITLWQRPLVSIKVGGQIKEALLDTGADDTVLEEINLPGKWKPR
MIGGIGGFIKVRQYDQILIEICGKRAIGTVLVGPTPANIIGRNLLTQLGCTLNFPISPIE
TVPVKLKPGMDGPKIKQWPLTEEKIKALTEICTEMEKEGKISKIGPENPYNTPIFAIKKK
DSTKWRKLVDFKELNKRTQDFWEVQLGIPHPSGLKKKKSVTVLDVGDAYFSVPLDEDFRK
YTAFTIPSTNNETPGIRYQYNVLPQGWKGSPAIFQASMTKILEPFRAQNPEIVIYQMDD
LYVGSDLEIEQHRAKVEELREHLLKWGFTTPDKKHQNEPPFLWMGYELHPDKWTVQPIKL
PEKESWTVNDIQKLVGKLNWASQIYPGIKVKQLCRLLRGTKALTEVIPLTKEAELELAEN
REILREPVHGVYYDPTKDLIAEIQKQGHDQWTYQIYQEPHKNLKTGKYAKMRTAHTNDVK
QLAEAVQKIAMESIVIWGKIPKFKLPIQKETWETWWTDYWQATWIPDWEFVNTPPLVKLW
```

Fig. 10 cont'd-25

```
YQLEKEPIAGAETFYVDGAANRETKIGKAGYVTDRGRQKIVSLTETTNQKAELQAIQLAL
QDSGPEVNIVTDSQYALGIIQAPDKSESEIVNQIIEKLIEKDKVYLSWVPAHKGIGGNE
QIDKLVSNGIRKVLFLDGIEKAQEEHEKYHSNWRAMASEFNLPPIVAKEIVASCDKCQLK
GEATHGQVDCSPGMWQLDCTHLEGKIILVAVHVASGYIEAEVIPTETGQETAYYILKLAG
RWPVKVIHTDNGSNFTSTAVKAACWWAGIQQEFGIPYNPQGQGVVESMNKELKKIIGQVR
EQAEHLKTAVQMAVLIHNFKRKGGIGGYSAGERIIDIIASDIQTKELQKQIIKVQNFRVY
YRDSRDPIWKGPAKLLWKGEGAVVLQDNSDIKVVPRRKVKIIKDYGKQMAGADCVASRQD
EN-
>POL-M.syn4.4
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGKKAIGTVLIGPTPVNIIGRNLLTQIGCTLNFPISPIE
TIPVKLKPGMDGPKVKQWPLTEEKIKALVEICTEMEKEGKISRIGPENPYNTPVFAIKKK
DGTKWRKLVDFRELNKRTQDFWEIQLGIPHPAGLKKKKSVSVLDVGDAYFSVPLDKDFRK
YTAFTIPSINNETPGIRYCYNVLPQGWKGSPAIFQSSMTKILEPFRKQNPDIVIYQYMDD
LYIGSDLEIGQHRTKIEELRQHLLRWGLTTPDKKHQNEPPFLWMGYELHPDKWTVQPIVL
PEKDSWTVNDLQKLVGKLNWASQIYAGIKVKQLCKLLRGAKALTEVVPLTEEAELELEEN
REILKEPVHGVYYDPSKDLIAEIQKQGQGQWTYQIYQEPYKNLKTGKYARMRGAHTNDVK
QLTEAVQKIAQECIVIWGKTPKFKLPIQKETWETWWMDYWQATWIPEWEFINTPPLVKLW
YQLEKEPIVGAETFYVDGASNRETKKGKAGYVTDKGRQKVVTLTETTNQKTELQAIHLAL
QDSGLEVNIVTDSQYAIGIIQAPDKSESELVSQIIEQLIKKEKVYLAWVPAHKG1GGNE
QVDKLVSNGIRKILFLDGIDKAQEEHEKYHNNWRAMASDFNIPPVVAKEIVACCDKCQLK
GEALHGQVDCSPRIWQLDCTHLEGKVILVAVHVASGYLEAEVIPAETGQETAYFLLKLAG
RWPVKTIHTDNGSNFTSTTVKAACWWAGIKQEFGIPYNPQSQGVIESMNKELKKIIEQVR
DQAEHLKTAVQMAVFVHNFKRKGGIGDYSAGERIIDIISTDIQTRELQKQIIKIQNFRVY
YRDSRDPVWKGPAKLLWKGEGAVVIQDNNEIKVVPRRKAKIIRDYGKQMAGDDCVASRQD
ED-
>POL-M.syn6.1
FFREDLAFPQGEARKFPSEQTRANSPTRG--------------ELQVWGRDNNSLSEAGD
DR----QGTVS-FNLPQITLWQRPLVTVRIGGQLIEALLDTGADDTVLEDMNLPGKWKPK
MIGGIGGFIKVRQYEQIPIEICGHKAIGTVLIGPTPVNIIGRNLLTQIGCTLNFPISPID
TVPVTLKPGMDGPKIKQWPLTEEKIKALTEICTEMEKEGKISRIGPENPYNTPVFAIKKK
NSTRWRKLVDFRELNKRTQDFCEVQLGIPHPAGLKKKRSVTVLDVGDAYFSVPLDENFRK
YTAFTIPSINNETPGVRYQYNVLPQGWKGSPAIFQASMTKILEPFRTKNPELVIYQYMDD
LYVGSDLEIEQHRTKIEELRAHLLSWGFTTPDKKHQKEPPFLWMGYELHPDKWTVQPIEL
PEKDSWTVNDIQKIVGKLNWASQIYPGIKVRQLCRLLRGTKALTDIVPLTAEAELELAEN
REILREPVHGVYYDPSKELIAEIQKQGHDQWTYQIYQDPFKNLKTGKYARKRSAHTNDVR
QLTEAVQKITTESIVIWGKTPKFRLPIQRETWEAWWMEYWQATWIPEWEFINTPPLVKLW
YQLEKDPIVGAETFYVDGAASRETKLGKAGYVTNKGRQKVVSLNETTNQKTELHAIHLAL
QDSGSEANIVTDSQYALGIIQAPDRSESEVVNQIIEELIKKEKVYLSWVPAHKGIGGNE
QVDKLVSSGIRKVLFLDGIDKAQEDHERYHSNWRTMASDFNLPPIVAREIVASCDKCQQK
GEAMHGQVDCGPGIWQLDCTHLERKVILVAVHVASGYIEAEVIPAETGQETAYFVLKLAG
RWPVKVIHTDNGSNFTSAAVKAACWWANVTQEFGIPYNPQSQGVVESMNNELKKIIGQVR
EQAEHLKTAVLMAVFIHNFKRKRGIGGYSAGERIVDIIASDIQTKELQNQITKIQNFRVY
FRDSRDPIWKGPAKLLWKGEGAVVIQDNNDIKVVPRRKVKIIRDYGKQMAGDDCVAGRQD
EN-
>POL-M.syn6.2
FFREDLAFQQGEARKFSSEQTRANSPTSR--------------ELRVWG-GDNTLSETGA
ER----QGT---LNFPQITLWQRPLVTIKVGGQIKEALLDTGADDTVLEDINLPGKWKPR
MIGGIGGFIKVRQYDQIPIEICGKKAIGSVLVGPTPVNIIGRNMLTQLGCTLNFPISPIK
TVPVKLKPGMDGPKVKQWPLSEEKIKALTAICDEMEKEGKITKIGPDNPYNTPVFAIKKK
DGTKWRKLVDFKELNKRTQDFWEIQLGIPHPAGLKKKKSVSVLDVGDAYFSVPLDESFRK
YTAFTIPSLNNETPGIRYCYNVLPQGWKGSPAIFQSSMTKILEPFRAQNPEIVIYQYIDD
LYVRSDLEIGQHRAKIEELREHLLKWGLTTPDKKHQKEPPFLWMGYELHPDRWTVQPIQL
```

Fig. 10 cont'd-26

```
PDKDSWTVNDLQKLVGKLNWASQIYPGIRVKQLCKLLKGAKALTDIVTLTEEAELELAEN
REILKNPVHGVYYDPAKDLIAEIQKQGNDQWTYQIYQEPHKNLKTGKYAKMRTAHTNDVK
QLTEVVQKIAMESIVIWGKVPKFRLPIQKETWETWWTDYWQATWIPDWEFVNTPPLVKLW
YQLEKEPIAGAETFYVDGAANRETKMGKAGYVTDRGRQKVVSLTETTNQKTELQAIQLAL
QDSGPEVNIVTDSQYAIGIIQAQPDKSESEIVNQIIEQLIKKERVYLSWVPAHKGIGENE
QVDKLVSTGIRRVLFLDGIDKAQEEHERYHSNWRAMASEFNLPPIVAKEIVASCDQCQLK
GEAMHGQVDCSPGVWQLDCTHLEGKIILVAVHVASGYMEAEVIPAETGQETAYFILKLAA
RWPVKVIHTDNGPNFTSATVKAACWWANITQEFGIPYNPQGQGVVESMNKELKKIIKQVR
DQAEHLKTAVQMAVLIHNFKRKGGIGGYSAGERIIDIIASDIQTKELQKQIIKIQNFQVY
YRDSRDPIWKGPAKLLWKGEGAVVLQDNSDIKVVPRRKVKIIKDYGKQMAGADCVAGGQD
ED-
>POL-M.syn6.3
FFRENLAFPQGKAREFPSEQTRAISPTSR--------------ELQVWGGDNNSLSEAGA
ER----QGTVS-FSFPQITLWQRPIVTIKIGGQLREALLDTGADDTVLEEMNLPGRWKPK
MIGGIGGFIKVKQYDNILIEICGHKAVGTVLVGPTPANIIGRNLLTQLGCTLNFPISPIE
TVPVKLKPGIDGPKVKQWPLTEEKIKALVEICTEMEKEGKISKIGPENPYNTPIFAIKKK
DSTRWRKLVDFRELNRRTQDFWEVQLGIPHPAGLKRKKSVTVLDVGDAYFSVPLDKEFRK
YTAFTIPSINNETPGIRYQYNVLPQGWKGSPSIFQSSMTKILEPFRIKNPEMVIYQYMDD
LYIGSDLEIGQHRIKIEELREHLLKWGFTTPDKKHQKEPPFLWMGCELHPDKWTVQPIML
PEKDSWTVNDIQKLVGKLNWASQIYAGIKVRQLCKLLRGTKALTEVVPLTEEAELELAEN
REILKEPVHGAYYDPSKDLIAEVQKQGQDQWTYQIYQEPFKNLKTGKYAKKRSAHTNDVK
QLTEAVQKIALESIVIWGKAPKFRLPIQKETWEAWWTEYWQATWVPEWEFVNTPPLVKLW
YQLETEPIAGAETYYVDGAANRETKLGKAGYVTNRGRQKVVSLTDTTNQKTELQAIHLAL
QDSGLEVNIVTDSQYALGIIHAQPDKSESELVNQIIEQLINKERIYLSWVPAHKGIGENE
QVDKLVSKGIRKVLFLDGIEKAQEEHEKYHSNWKAMASEFNLPPVVAKEIVACCDKCQLK
GEALHGQVDCSPGMWQLDCTHLEGKIIIVAVHVASGYIEAEVIPTETGQETAYFLLKLAG
RWPVKTIHTDNGSNFTSTTVKAACWWAGIKQEFGIPYNPQSQGVVESINKELKKIIGQIR
DQAEHLKTAVLMAVFIHNFKRKGGIGGYTAGERIVDIIATDIQTKELQKQITKVQNFRVY
YRDSREPLWKGPAKLLWKGEGAVVIQDNNEIKVVPRRKAKILRDYGKQMAGADCVASRQD
EN-
>POL-M.syn6.4
FFRENLAFQQGEAREFSSEQTRTNSPTSR--------------ELWDGGRDNLP-SEAGA
ER----RGTVPSLSFPQITLWQRPLVTVKIGGQLKEALLDTGADDTVLEEINLPGKWKPK
LIGGIGGFIKVRQYDQILIEICGKKAIGTVLVGPTPINIIGRNMLTQIGCTLNFPISPIE
TIPVKLKPGMDGPRVKQWPLTEEKIKALIEICTEMEKEGKISRVGPENPYNTPIFAIKKK
NSNRWRKLVDFRELNKRTQDFWEVQLGIPHPGGLKKKKSVTILDVGDAYFSVPLDEDFRK
YTAFTIPSINNATPGIRYQYNVLPQGWKGSPAIFQCSMTKILEPFRKQNPEIIIYQYMDD
LYVRSDLEIGQHRTKIEELRQHLLKWGFYTPDKKHQKEPPFLWMGYELHPDKWTVQPIKL
PEKESWTVNDIQKLVEKLNWASQIYPGIKVKQLCRLLRGAKALTEVIPLTEEAELELEEN
REILKDPVHGVYYDPTKDLIAEIQKQGDDQWTYQIYQEPYKNLKTGKYAKRRTAHTNDVR
QLTEVVQKVATESIVIWGKIPKFKLPIQKETWEIWWTDYWQATWIPEWEFVNTPHLVKLW
YQLEKEPIIGAETFYVDGASNRETKKGKAGYVTDRGRQKIVSLTETTNQKAELQAIQLAL
QDSGSEVNIVTDSQYALGIIQAHPDKSESELVSQIIEQLIKKEKVYLAWVPAHKGIGGNE
QIDKLVSNGIRKILFLDGIDKAQEEHEKYHNNWRAMASDFNLPPVVAKEIVASCNKCQLK
GEAIHGQVDCSPRIWQLDCTHLEGKVIMVAVHVASGYVEAEVIPAETGQDTAYFILKLAG
RWPVKVVHTDNGSNFTSAAFKAACWWANVQQEFGIPYNPQSQGVVEAMNKELKKIIEQVR
DQAEHLKTAVQMAVFVHNFKRKGGIGDYSAGERIIDIIATDIQTRELQKQIIKIQNFRVY
YRDNRDPIWKGPAKLLWKGEGAVVIQDNSDIKVIPRRKAKIIRDYGKQMAGDDCMAGRQD
EDQ
>POL-M.syn6.5
FFREDLAFLQGKAREFSSEQTRANSPTRR--------------ELQVWGRDSNSLSEAGA
DR----QGTVS-FNFPQITLWQRPLVTIKIGGQLKEALLDTGADDTVLEDIDLPGKWKPK
IIGGIGGFIKVKQYDQILIEICGKRAIGTVLVGPTPVNIIGRNILTQIGCTLNFPISPID
TVPVKLKPGMDGPRIKQWPLTEEKIKALTEICKEMEEEGKISKIGPENPYNTPVFAIKKK
```

Fig. 10 cont'd-27

```
DSTKWRKVVDFRELNKGTQDFWEVQLGIPHPAGLKQKKSVTVLDVEDAYFSVPLDKDFRK
YTAFTIPSVNNETPGIRYQYNVLPQGWKGSPAIFQSSMTRILEPFRKQNPDIVIYQYMDD
LYVGSDLEIGQHRTKVEELRQHLLRWGFTTPDKKHQKDPPFLWMGYELHPDKWTVQPIVL
PEKDSWTINDIQKLVGKLNWASQIYSGIKVRQLCKCLRGTKALTEVIPLTKEAELELAEN
KEILKEPVHGVYYDPSKDLVAEIQKQGQGQWTYQIYQEQYKNLKTGKYARMRGAHTNDVK
QLAEAVQKIATESIVIWGKIPKFRLPIQRETWETWWTEYWQATWIPEWEYVNTPPLVKLW
YQLEKEPIVGAETFYVDGAANRDTKLGKAGYVTDRGRQKVVPLTDTTNQKTELQAINLAL
QDSGSKVNIVTDSQYVLGIIQAQPDRSESEIVNQIIEKLIEKDKVYLSWVPAHKGIGGNE
QVDKLVSAGIRKVLFLDGIDKAQDEHEKYHSNWRAMASDFNLPPVIAKEIVASCDKCQLK
GEATHGQVDCSPGIWQLDCTHLEGKVIIVAVHVASGYIEAEVISAETGQETAYYILKLAG
RWPVKIIHTDNGSNFTSTAVKAACWWAGIQQEFGIPYSPQSQGVVESMNKQLKQIIGQVR
DQAEQLKTAVQMAVFIHNFKRKGGIGEYSAGERIIDIISTDIQTRELQKQITKIQNFRVY.
YRDSRDPVWKGPAKLLWKGEGAVVIQDNSEIKVVPRRKAKIIRHYGKQMAGDDCVASRQD
EDQ
>POL-M.syn6.6
FFRENLAFPQGEAREFPSEQARANSPTSRANSPTSR------ELQV--RGDNPRSEAGA
ERQGTLQGT---LNCPQITLWQRPLVSIKVGGQVKEALLDTGADDTVLEEMSLPGKWKPK
MVGGIGGFIKVRQYDQILVEICGHKAIGTVLGPTPVNIIRRNMLTQLRCTLNFPISPIE
TVPVTLKPGMDGPKVRQWPLTEEKIKALTAICEEMEKEGKITKIGPENPYNTPVFAIRKK
DSTKWRKLVDFRELNKKTQDFWEVQLGIPHPSGLKKKKSVTVLDVGDAYFSVPLDEGFRK
YTAFTIPSTNNETPGIRYQYNVLPQGWKGSPAIFQSSMIKILEPFRAKNPEIVIYQYMDD
LYVGSDLEIGQHRAKVEELREHLLRWGFTTPDKKHQNEPPFLWMGYELHPDKWTVQPIQL
PEKDSWTVNDIQRLVGKLNWASQIYAGIKVKQLCKLLRGAKALTDIVPLTEEAELELAEN
REILKTPVHGVYYDPSKDLIAEIQKQGQDQWSYQIYQEPFKNLKTGKYARTRGAHTNDVR
QLTEAVQKIAQECIVIWGKTPKFKLPIQKDTWETWWMDYWQATWIPKWEFVNTPPLVKLW
YQLEKDPIAGVETFYVDGAANRETKIGKAGYVTDKGRQKVVTLTETTNQKTELHAIYLAL
QDSGSEVNVVTDSQYALGIIQAQPDRSESELVNQIIEKLIGKDKVYLSWVPAHKGIGENE
QVDKLVSNGIRKVLFLDGIDKAQEDHEKYHSNWRAMANEFNLPPIVAKEIVANCDKCQLK
GEAMHGQVDCSPGIWQIDCTHLEGKVILVAVHVASGYLEAEVIPAETGQEAAYFILKLAG
RWPVKTVHTDNGSNFTSNAVKAACWWANVRQEFGIPYNPQSQGVIESMNELKKIIGQVR
DQAEHLRTAVQMAVFIHNFKRRGGIGGYSAGERMIDIIATDIQTTELQKQITKIQKFRVY
YRDSRDPLWKGPAKLLWKGEGAVVIQENSDIKVVPRRKAKIIKDYGKQVAGADCVAGRQD
EDQ
```

Fig. 11

This plot is alignment independent, based on splintering all M group proteins, (database and CHAVI, one sequence per person) into all possible 9-mers, attending to their frequencies, and then looking for matches and near matches in each vaccine antigen or cocktail with the database

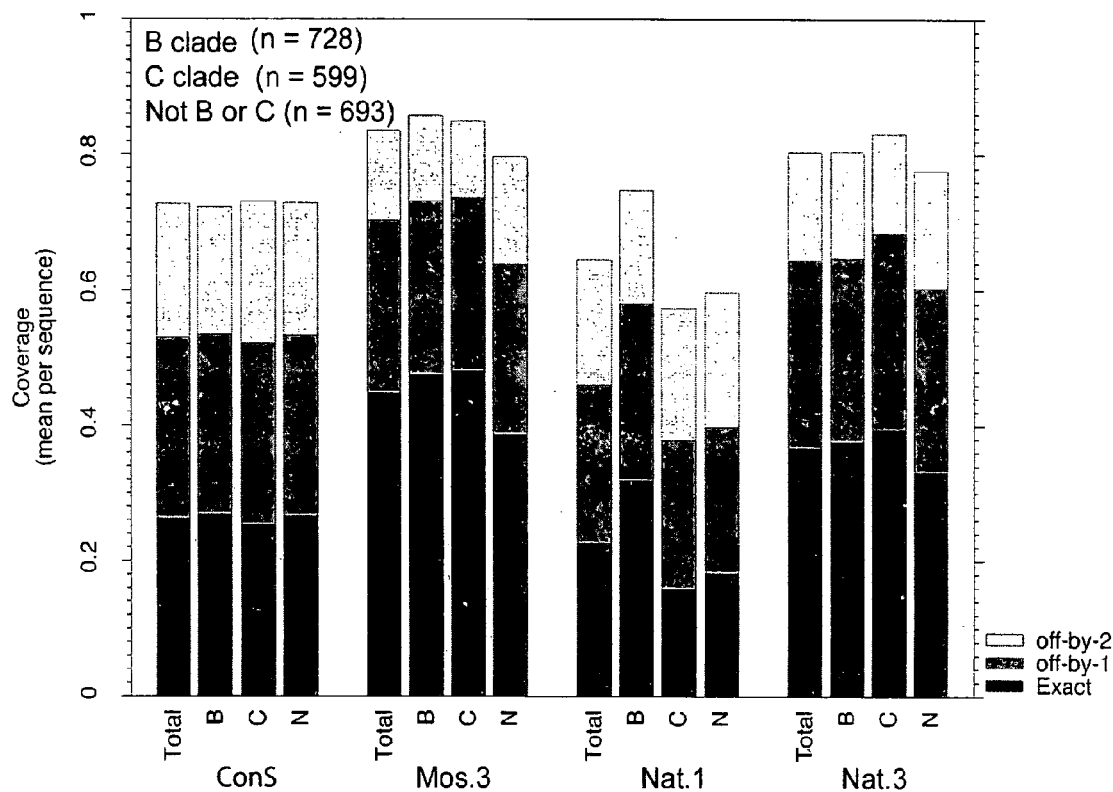

| Vaccine | subset | Off-by0 | Off-by1 | Off-by2 | (<3,>1) | unique | absent | rare < 3 |
|---|---|---|---|---|---|---|---|---|
| ConSgp160 | Total | 0.2628 | 0.5301 | 0.7267 | 9 | 12 | 45 | 66 |
| ConSgp160 | B | 0.2682 | 0.5344 | 0.7223 | 2 | 8 | 45 | |
| ConSgp160 | C | 0.2526 | 0.5214 | 0.7302 | 1 | 0 | 45 | |
| ConSgp160 | N | 0.2662 | 0.5332 | 0.7283 | 7 | 4 | 45 | |
| Mos.3 | Total | 0.4485 | 0.7032 | 0.8358 | 15 | 164 | 8 | 179 |
| Mos.3 | B | 0.4749 | 0.7319 | 0.8576 | 3 | 40 | 8 | |
| Mos.3 | C | 0.4809 | 0.7363 | 0.8498 | 8 | 65 | 8 | |
| Mos.3 | N | 0.3868 | 0.6383 | 0.7970 | 11 | 59 | 8 | |
| Nat.1.acute | Total | 0.2258 | 0.4598 | 0.6458 | 125 | 0 | 0 | 125 |
| Nat.1.acute | B | 0.3190 | 0.5803 | 0.7482 | 125 | 0 | 0 | |
| Nat.1.acute | C | 0.1589 | 0.3781 | 0.5726 | 0 | 0 | 0 | |
| Nat.1.acute | N | 0.1815 | 0.3979 | 0.5968 | 0 | 0 | 0 | |
| Nat.3.acute | Total | 0.3673 | 0.6449 | 0.8036 | 164 | 252 | 0 | 416 |
| Nat.3.acute | B | 0.3765 | 0.6483 | 0.8045 | 130 | 0 | 0 | |
| Nat.3.acute | C | 0.3940 | 0.6840 | 0.8307 | 19 | 102 | 0 | |
| Nat.3.acute | N | 0.3311 | 0.6036 | 0.7766 | 21 | 150 | 0 | |

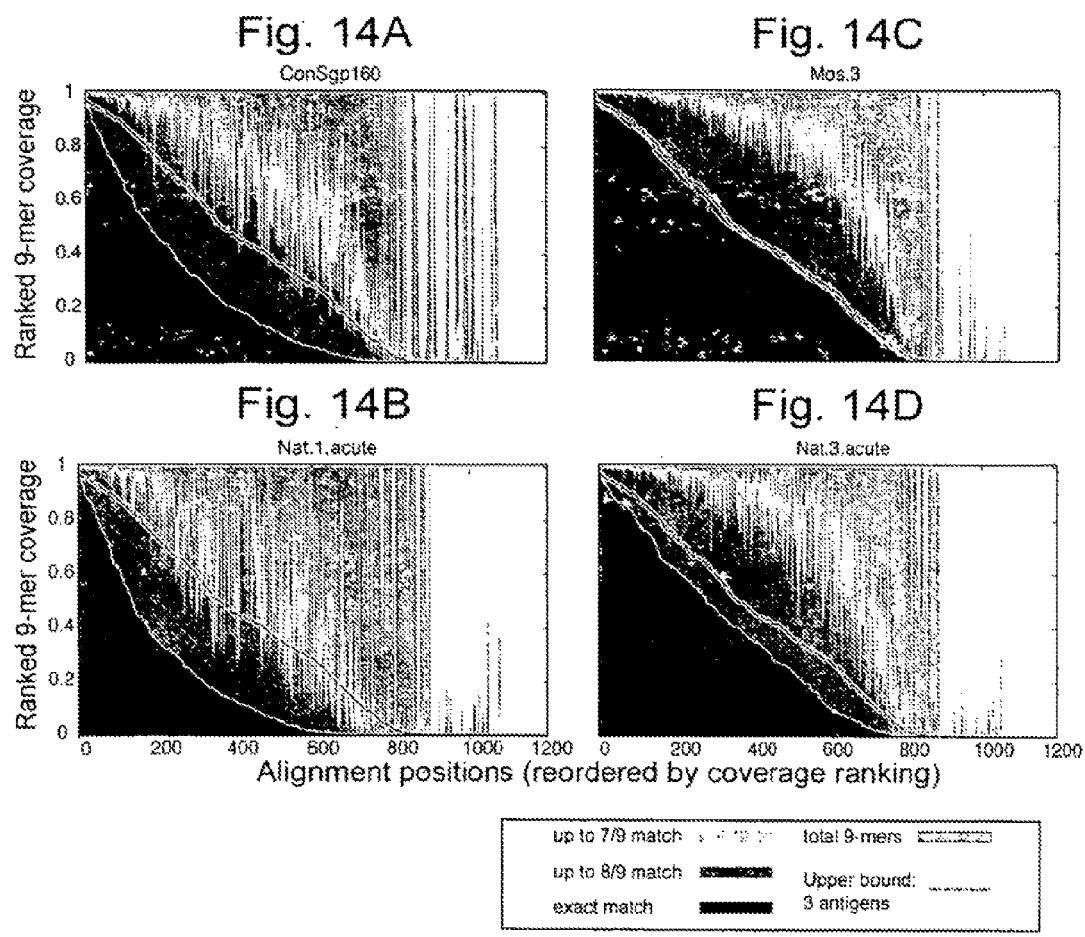
FIGS. 14A-D

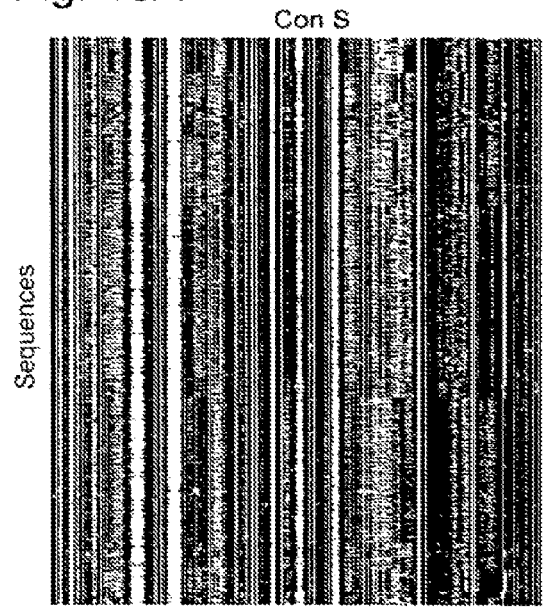
Fig. 15A Con S
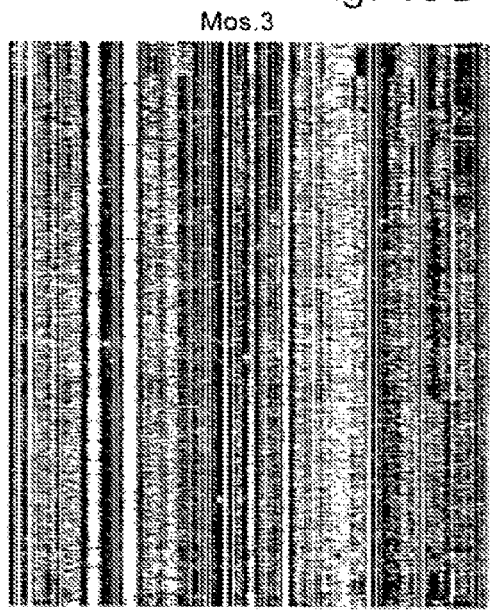
Fig. 15C Mos.3
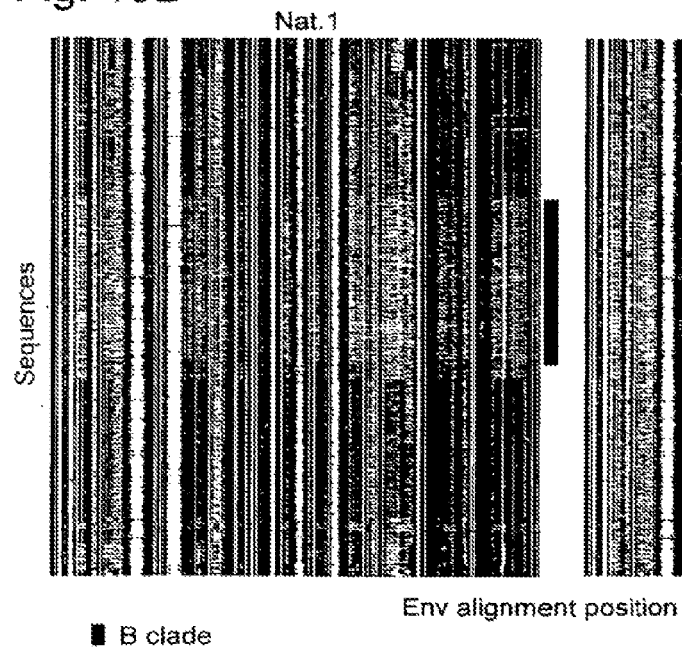
Fig. 15B Nat.1
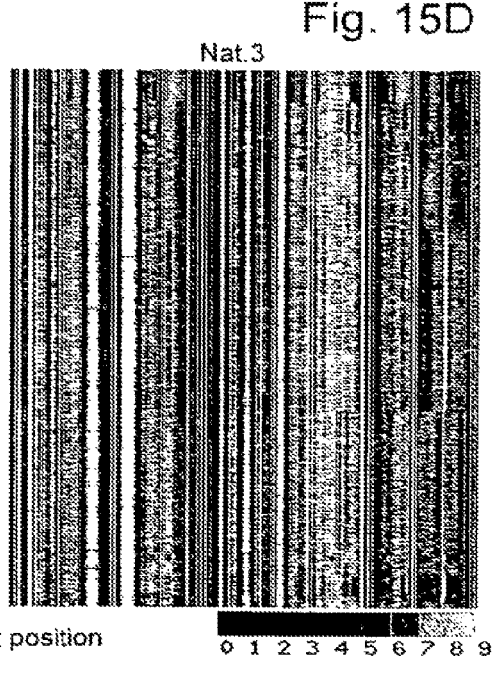
Fig. 15D Nat.3
FIGS. 15A-D

Fig. 17

Coverage of the HIV database plus CHAVI sequences (N = 2020)

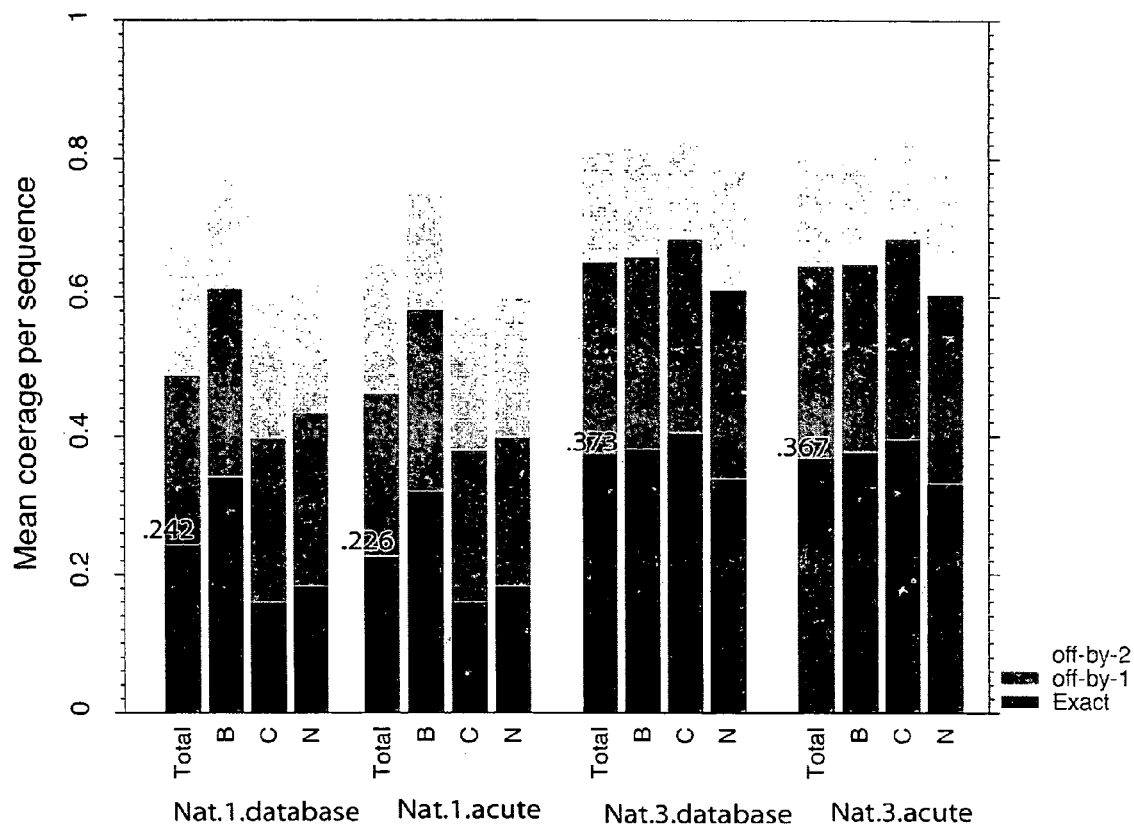

Nat.3.database

Option 1:
B YU2* -- 1986, USA
C DU467, South Africa,
A ML170 -- 1986 Kenya

Optimal for the set
after requiring inclusion
of one each of subtype
A, B and C.

Nat.3.acute

Option 2:
B 1059*
C 0393
A R66201FPB

Optimal for the set
after requiring inclusion
of one each of subtype
A, B and C as well as
restricting antigen selection
to SGA sequences sampled
during acute infection.

>nefM_4.1Dmyr
MAAKWSKSSIVGWPAVRERMRRAEPAADGVGAVSRDLEKHGAITSSNTAATNADCAWLEAQEE
DSEVGFPVRPHVPLRPMTYKAAVDLSHFLKEQGGLEGLIYSQKRQDILDLWVYHTQGYFPDWQN
YTPGPGIRYPLTFGWCFKLVPVDPREVEEANKGENNCLLHPMSQHGMDDPEKEVLMWKFDSRLA
FHHMAREKHPEFYKDC >nefM_4.2Dmyr
MAAKWSKRSIVGWPAIRERMRRTEPAAEGVGAASQDLDKYGALTSSNTAQTNPDCAWLEAQEE
EEVGFPVRPQVPVRPMTYKGALDLSHFLKEKGGLDGLIYSRKRQEILDLWVYNTQGYFPDWQNY
TPGPGVRYPLTFGWCYKLVPVDPEEVEKANEGENNSLLHPMSLHGMEDPEREVLKWKFDSRLAL
KHRARELHPEFYKDC >nefM_4.3Dmyr
MAANWSKSSIVGWPEIRERIRRTDPAAEGVGAASRDLERHGAITSSNTATTNAACAWLEAQEDEE
VGFPVRPQVPLRPMTFKGAFDLGFFLKEKGGLEGLIYSKKRQDILDLWVYNTQGFFPDWQNYTPG
PGTRFPLTFGWCFELVPVDPKEVEEANEGENNCLLHPICQHGMDDEEREVLMWKFDSSLARRHLA
REKHPEYYKDC >nefM_4.4Dmyr
MASKWSKSSIVGWPQVRERIRQTPPAAEGVGAVSQDLDKHGAVTSSNTAANNADCAWLQAQEE
EEEVGFPVKPQVPLRPMTYKGAFDLSFFLKEKGGLDGLIYSKKRQEILDLWVYHTQGFFPDWHNY
TPGPGTRYPLCFGWCFKLVPMDPAEVEEATEGENNSLLHPICQHGMEDEDREVLVWRFDSSLARR
HIARELHPEYYKDC >Gag-M4.1Dmyr
MAARASVLSGGELDRWEKIRLRPGGKKKYKLKHIVWASRELERFAVNPGLLETSEGCRQILGQLQ
PSLQTGSEELRSLYNTVAVLYCVHQRIDVKDTKEALEKIEEEQNKSQQKTQQAKAADGKVSQNYP
IVQNAQGQMVHQAISPRTLNAWVKVIEEKGFSPEVIPMFSALAEGATPQDLNTMLNTIGGHQAAM
QMLKDTINDEAAEWDRLHPVQAGPVAPGQIREPRGSDIAGTTSNLQEQIGWMTSNPPIPVGDIYKR
WIIMGLNKIVRMYSPTSILDIRQGPKESFRDYVDRFFRTLRAEQASQEVKNWMTETLLVQNSNPDC
KTILKALGPAATLEEMMTACQGVGGPGHKARVLAEAMSQVQQPNIMMQRGNFKGQKRIKCFNC
GREGHLARNCRAPRKKGCWKCGREGHQMKDCTESKANFLGKIWPSNKGRPGNFLQSRPEPSAPP
AESFGFGEEITPSQKQEQKDKELYPLASLKSLFGNDPLSQ >Gag_M4.2 Dmyr
MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQNY
PIVQNIQGQMVHQPISPRTLNAWVKVVEEKAFSPEVIPMFTALSDGATPQDLNSMLNAVGGHQAA
MQILKDTINEEAADWDRLHPVHAGPVAPGQMREPRGSDIAGTTSTLQEQIGWMTNNPPIPVGEIYK
RWIILGLNKIVRMYSPVSILDIKQGPKESFRDYVDRFFKVLRAEQATQDVKNWMTDTLLIQNANPD
CKSILRALGPGATLEEMMTACQGVGGPSHKARILAEAMSQVTNSATIMMQRGNFRNQRKTVKCF
NCGKEGHLARNCKAPRKRGCWKCGKEGHQMKECTERQANFLGKIWPSSKGRPGNFPQSRPEPTA
PPEESFRFGEETTTPSQKQEPIDKELYPLASLRSLFGNDPSSQAS

Fig. 21 cont'd-1

>Gag_M4.3 Dmyr
MAARASILRGGKLDKWEKIRLRPGGKKRYMLKHLIWASRELERFALNPGLLETAEGCQQIIEQLQS
TLKTGSEELKSLFNTVATLYCVHQRIEVKDTKEALDKVEEEQNKSKKKAQQAAADTGNSSQVSQ
NYPIVQNLQGQMVHQALSPRTLNAWVKVIEEKAFSPEIIPMFTALSEGATPSDLNTMLNTVGGHQ
AAMQMLKDTINEEAAEWDRVHPVHAGPIPPGQMREPRGSDIAGTTSSLQEQIAWMTSNPPVPVGE
IYKRWIVLGLNKIVRMYSPVSILDIRQGPKEPFRDYVDRFFKTLRAEQASQDVKNWMTETLLVQN
ANPDCKTILRALGPGASLEEMMTACQGVGGPSHKARVLAEAMSQTNSAILMQRSNFKGSKRIVKC
FNCGKEGHIARNCRAPRKRGCWKCGQEGHQMKDCNERQANFLGKIWPSHKGRPGNFLQNRPEPT
APPEPTAPPAESFRFEETTPAPKQELKDREPLTSLKSLFGSDPLSQAS >Gag_M4.4 Dmyr
MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKVSQ
NYPIVQNLQGQMVHQPLSPRTLNAWVKVVEEKGFNPEVIPMFSALSEGATPQDLNMMLNIVGGH
QAAMQMLKETINEEAAEWDRLHPVHAGPIAPGQMREPRGSDIAGSTSTLQEQIAWMTGNPPVPV
GDIYKRWIILGLNKIVKMYSPTSILDIKQGPKEPFRDYVDRFYKTLRAEQATQEVKNWMTDTLLVQ
NANPDCKSILKALGTGATLEEMMSACQGVGGPAHKARVLAEAMSQANNTNIMMQRSNFKGPKRI
IKCFNCGKEGHIAKNCRAPRKKGCWKCGKEGHQMKDCTERQANFLGRIWPSSKGRPGNFLQSRP
EPTAPPAEPTAPPAESFKFEETTPAPKQEPKDREPLTSLRSLFGSDPLLQAS >M_mos_3_1 (M_mos_Env_3_1)
MRVKGIRKNYQHLWRWGTMLLGMLMICSAAEQLWVTVYYGVPVWRDAETTLFCASDAKAYER
EVHNVWATHACVPTDPNPQEIVLENVTEEFNMWKNNMVDQMHEDIISLWDESLKPCVKLTPLCV
TLNCTDVNVTKTNSTSWGMMEKGEIKNCSFNMTTELRDKKQKVVYALFYKLDIVPLEENDTISNST
YRLINCNTSAITQACPKVTFEPIPIHYCTPAGFAILKCNDKKFNGTGPCKNVSTVQCTHGIRPVVTTQ
LLLNGSLAEEEIIIRSENLTNNAKTIIVQLNESVVINCTRPNNNTRKSIRIGPGQTFYATGDIIGNIRQA
HCNISREKWINTTRDVRKKLQEHFNKTIIFNSSSGGDLEITTHSFNCRGEFFYCNTSKLFNSVWGNS
SNVTKVNGTKVKETITLPCKIKQIINMWQEVGRAMYAPPIAGNITCKSNITGLLLVRDGGNVTNNT
EIFRPGGGNMKDNWRSELYKYKVVEIKPLGIAPTKAKRRVVEREKRAVGLGAVFLGFLGAAGST
MGAASMTLTVQARQLLSGIVQQQSNLLRAIEAQQHMLQLTVWGIKQLQARILAVERYLRDQQLL
GIWGCSGKLICTTNVPWNSSWSNKSLDEIWNNMTWMQWEKEIDNYTSLIYTLIEESQNQQEKNEQ
DLLALDKWANLWNWFDISNWLWYIRIFIMIVGGLIGLRIVFAVLSIVNRVRKGYSPLSFQTLTPNPR
GPDRLGRIEEEGGEQDKDRSIRLVNGFLALAWDDLRNLCLFSYHRLRDLLLIVTRIVELLGRRGWE
ALKYLWNLLQYWIQELKNSAVSLLNATAIAVAEGTDRVIEVVQRACRAILHIPRRIRQGLERALL >M_mos_3_2 (M_mos_Env_3_2)
MRVKETQMNWPNLWKWGTLILGLVIICSASDNLWVTVYYGVPVWKEATTTLFCASDAKAYDTE
VHNVWATYACVPTDPNPQEVVLGNVTENFNMWKNNMVEQMHEDIISLWDQSLKPCVRLTPLCV
TLNCSNANTTNTNSTEEIKNCSFNITTSIRDKVQKEYALFYKLDVVPIDNDNTSYRLISCNTSVITQA
CPKVSFEPIPIHYCAPAGFAILKCKDKKFNGTGPCTNVSTVQCTHGIRPVVSTQLLLNGSLAEEEVVI
RSENFTNNAKTIIVHLNKSVEINCTRPNNNTRKSIHIGPGRAFYATGEIIGDIRQAHCNISRAKWNNT
LKQIVKKLKEQFNKTIIFNQSSGGDPEITTHSFNCGGEFFYCNTSGLFNSTWNSTATQESNNTELNG
NITLPCRIKQIVNMWQEVGKAMYAPPIRGQIRCSSNITGLILTRDGGNNNSTNETFRPGGGDMRDN
WRSELYKYKVVKIEPLGVAPTKAKRRVVQREKRAVGTIGAMFLGFLGAAGSTMGAASLTLTVQA
RLLLSGIVQQQNNLLRAIEAQQHLLQLTVWGIKQLQARVLAVERYLKDQQLLGIWGCSGKLICTT
TVPWNTSWSNKSLNEIWDNMTWMEWEREIDNYTGLIYTLLEESQNQQEKNEQELLELDKWASL
WNWFDITKWLWYIKIFIMIVGGLVGLRIVFTVLSIVNRVRQGYSPLSFQTHLPAPRGPDRPEGIEEE
GGERDRDRSGRLVDGFLAIIWVDLRSLCLFSYHQLRDFILIAARTVELLGHSSLKGLRRGWEALKY
WWNLLQYWSQELKNSAISLLNTTAIVVAEGTDRIIEVLQRAGRAILHIPTRIRQGLERLLL

Fig. 21 cont'd-2

>M_mos_3_3 (M_mos_Env_3_3)
MRVRGIQRNWPQWWIWGILGFWMLMICNVVGNLWVTVYYGVPVWKEAKTTLFCASDAKAYEK
EVHNVWATHACVPTDPSPQEVVLENVTENFNMWKNDMVDQMHEDVISLWDQSLKPCVKLTHL
CVTLNCTNATNTNYNNSTNVTSSMIGEMKNCSFNITTEIRDKSRKEYALFYRLDIVPLNEQNSSEY
RLINCNTSTITQACPKVSFDPIPIHYCAPAGYAILKCNNKTFNGTGPCNNVSTVQCTHGIKPVVSTQL
LLNGSLAEGEIIIRSENLTDNAKTIIVHLNESVEIVCTRPNNNTRKSVRIGPGQAFYATGDIIGDIRQA
HCNLSRTQWNNTLKQIVTKLREQFGNKTIVFNQSSGGDPEIVMHSFNCGGEFFYCNTTQLFNSTWE
NSNITQPLTLNRTKGPNDTITLPCRIKQIINMWQGVGRAMYAPPIEGLIKCSSNITGLLLTRDGGNNS
ETKTTETFRPGGGNMRDNWRNELYKYKVVQIEPLGVAPTRAKRRVVEREKRAVGIGAVFLGFLG
TAGSTMGAASITLTVQARQVLSGIVQQQSNLLKAIEAQQHLLKLTVWGIKQLQTRVLAIERYLKD
QQLLGLWGCSGKLICTTAVPWNSSWSNKSQTDIWDNMTWMQWDREISNYTDTIYRLLEDSQNQ
QEKNEKDLLALDSWKNLWNWFDITNWLWYIKIFIIIVGGLIGLRIIFAVLSIVNRCRQGYSPLSLQTL
IPNPRGPDRLGGIEEEGGEQDRDRSIRLVSGFLALAWDDLRSLCLFSYHRLRDFILIVARAVELLGRS
SLRGLQRGWEALKYLGSLVQYWGLELKKSAISLLDTIAIAVAEGTDRIIEVIQRICRAIRNIPRRIRQ
GFEAALL

Fig. 22

| HVI number | Gene name | Nef | Myristylation signal mutated |
|---|---|---|---|
| HV13236 | M.con_Nef01_Dmyr.WLV | Group M (2001) consensus | Yes |
| HV13319 | nefM_4.1Dmyr.wlv | Mosaic No. 1 | Yes |
| HV13231 | nefM_4.2Dmyr.wlv | Mosaic No. 2 | Yes |
| HV13230 | nefM_4.3Dmyr.wlv | Mosaic No. 3 | Yes |
| HV13232 | nefM_4.4Dmyr.wlv | Mosaic No. 4 | Yes |
| HV10001 | No inser | | |

All five constructs were cloned into HV10001 (WLV001AM DNA vaccine plasmid.

M.con_Nef01_Dmyr.WLV (657nt.)(hv13236), 67% GC
XhoI
CTCGAGAAGAAAATGGCGGCCAAGTGGTCGAAGAGCTCCATCGTCGGGTGGCCGGCGGTCCGGGAG
CGCATCCGGCGGACGCACCCCGCGGCCGAGGGGGTCGGCGCGGTCTCGAAGACCTCGACAAGC
ACGGGGCGATCACGTCGAGCAACACCGCCGCGAACAACCCCGACTGCGCGTGGCTGGAGGCCCA
GGAGGAAGAGGAAGAGGTCGGCTTCCCGGTCCGCCCGCAAGTGCCGCTCAGGCCGATGACGTAC
AAGGCGGCCCTCGACCTCTCGCACTTCCTGAAAGAGAAGGGTGGCCTGGAGGGGCTCATCTACT
CGAAGAAGAGGCAGGAGATCCTCGACCTGTGGGTCTACCACACCCAGGGCTACTTCCCGGACTG
GCAGAACTACACGCCAGGCCCGGGAATCCGCTACCCGCTGACCTTCGGGTGGTGCTTCAAGCTC
GTCCCCGTCGACCCGGAGGAGGTCGAGGAAGCCAACGAGGGCGAGAACAACAGCCTCCTGCACC
CGATGTGCCAGCACGGGATGGAGGACGAGGAGCGCGAGGTGCTGATGTGGAAGTTCGACTCGCG
CCTGGCCCTGCGCCACATCGCCCGGGAGCTCCACCCGGAGTACTACAAGGACTGCTGATAAGCTA
GCGGATCCTGATCA
NheI   BamHI  BclI MAAKWSKSSIVGWPAVRERIRRTHPAAEGVGAVSQDLDKHGAITSSNTAANNPDCAWLEAQEEE
EEVGFPVRPQVPLRPMTYKAALDLSHFLKEKGGLEGLIYSKKRQEILDLWVYHTQGYFPDWQNY
TPGPGIRYPLTFGWCFKLVPVDPEEVEEANEGENNSLLHPMCQHGMEDEEREVLMWKFDSRLAL
RHIARELHPEYYKDC_

>HV13236 in hv10001, 3953nt.
AAATGGGGGCGCTGAGGTCTGCCTCGTGAAGAAGGTGTTGCTGACTCATACCAGGCCTGAATCGCCCCATCATCCAG
CCAGAAAGTGAGGGAGCCACGGTTGATGAGAGCTTTGTTGTAGGTGGACCAGTTGGTGATTTTGAACTTTTGCTTTG
CCACGGAACGGTCTGCGTTGTCGGGAAGATGCGTGATCTGATCCTTCAACTCAGCAAAAGTTCGATTTATTCAACAA
AGCCGCCGTCCCGTCAAGTCAGCGTAATGCTCTGCCAGTGTTACAACCAATTAACCAATTCTGCGTTCAAAATGGTA
TGCGTTTTGACACATCCACTATATATCCGTGTCGTTCTGTCCACTCCTGAATCCCATTCCAGAAATTCTCTAGCGAT
TCCAGAAGTTTCTCAGAGTCGGAAAGTTGACCAGACATTACGAACTGGCACAGATGGTCATAACCTGAAGGAAGATC
TGATTGCTTAACTGCTTCAGTTAAGACCGACGCGCTCGTCGTATAACAGATGCGATGATGCAGACCAATCAACATGG
CACCTGCCATTGCTACCTGTACAGTCAAGGATGGTAGAAATGTTGTCGGTCCTTGCACACGAATATTACGCCATTTG
CCTGCATATTCAAACAGCTCTTCTACGATAAGGGCACAAATCGCATCGTGGAACGTTTGGGCTTCTACCGATTTAGC
AGTTTGATACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTTCCACTCA
CCGGTTGTCCATTCATGGCTGAACTCTGCTTCCTCTGTTGACATGACACACATCATCTCAATATCCGAATACGGACC
ATCAGTCTGACGACCAAGAGAGCCATAAACACCAATAGCCTTAACATCATCCCCATATTTATCCAATATTCGTTCCT
TAATTTCATGAACAATCTTCATTCTTTCTTCTCTAGTCATTATTATTGGTCCGTTCATAACACCCCTTGTATTACTG
TTTATGTAAGCAGACAGTTTTATTGTTCATGATGATATATTTTTATCTTGTGCAATGTAACATCAGAGATTTTGAGA
CACAACGTGGCTTTCCCCGGCCCATGACCAAAATCCCTTAACGTGAGTTTTCGTTCCACTGAGCGTCAGACCCCGTA
GAAAAGATCAAAGGATCTTCTTGAGATCCTTTTTTTCTGCGCGTAATCTGCTGCTTGCAAACAAAAAAACCACCGCT

Fig. 22 cont'd-1

```
ACCAGCGGTGGTTTGTTTGCCGGATCAAGAGCTACCAACTCTTTTTCCGAAGGTAACTGGCTTCAGCAGAGCGCAGA
TACCAAATACTGTTCTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACA
CCGAACTGAGATACCTACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGGTATTTCACACCGCATAT
GGTGCACTCTCAGTACAATCTGCTCTGATGCCGCATAGTTAAGCCAGTATCTGCTCCCTGCTTGTGTGTTGGAGGTC
GCTGAGTAGTGCGCGAGCAAAATTTAAGCTACAACAAGGCAAGGCTTGACCGACAATTGCATGAAGAATCTGCTTAG
GGTTAGGCGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTATTGACTA
GTTATTAATAGTAATCACGGGGTCATTAGTTCATAGCCCATATATGGAGTTCCGCGTTACATAACTTACGGTA
AATGGCCCGCCTGGCTGACCGCCCAACGACCCCCGCCCATTGACGTCAATAATGACGTATGTTCCCATAGTAACGCC
AATAGGGACTTTCCATTGACGTCAATGGGTGGAGTATTTACGGTAAACTGCCCACTTGGCAGTACATCAAGTGTATC
ATATGCCAAGTCCGCCCCCTATTGACGTCAATGACGGTAAATGGCCCGCCTGGCATTATGCCCAGTACATGACCTTA
CGGGACTTTCCTACTTGGCAGTACATCTACGTATTAGTCATCGCTATTACCATGGTGATGCGGTTTTGGCAGTACAT
CAATGGGCGTGGATAGCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATGGGCGGTAGGCGTGTA
CGGTGGGAGGTCTATATAAGCAGAGCTCGTTTAGTGAACCGTCAGATCGCCTGGAGACGCCATCCACGCTGTTTTGA
CCTCCATAGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGAGCTCCATCGTCGGGTGGCCGGCGGTCCGGGAGCGCATCCGGCGGAC
GCACCCCGCGGCCGAGGGGGTCGGCGCGGTCTCGCAAGACCTCGACAAGCACGGGCGATCACGTCGAGCAACACCG
CCGCGAACAACCCCGACTGCGCGTGGCTGGAGGCCCAGGAGGAAGAGGAAGAGGTCGGCTTCCCGGTCCGCCCGCAA
GTGCCGCTCAGGCCGATGACGTACAAGGCGGCCCTCGACCTCTCGCACTTCCTGAAAGAGAAGGGTGGCCTGGAGGG
GCTCATCTACTCGAAGAAGAGGCAGGAGATCCTCGACCTGTGGGTCTACCACACCCAGGGCTACTTCCCGGACTGGC
AGAACTACACGCCAGGCCCGGGAATCCGCTACCCGCTGACCTTCGGGTGGTGCTTCAAGCTCGTCCCCGTCGACCCG
GAGGAGGTCGAGGAAGCCAACGAGGGCGAGAACAACAGCCTCCTGCACCCGATGTGCCAGCACGGGATGGAGGACGA
GGAGCGCGAGGTGCTGATGTGGAAGTTCGACTCGCGCCTGGCCCTGCGCCACATCGCCCGGGAGCTCCACCCGGAGT
ACTACAAGGACTGCTGATAAGCTAGCGGATCCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGGGGGAGGATTGGGAAG
ACAATAGCAGGCATGCTGGGGAATTT
```

| | | | | | |
|---|---|---|---|---|---|
| Thursday, August 2, 2007 | | ApaI | GGGCCC | 3485 3541 3678 | |
| | | 1 Site | | 3679 3691 | |
| Sequence 0 Length : 3953 | | 3075 | | BglI | GCCNNNNNGGC |
| | | ApaLI | GTGCAC | 4 Sites | |
| AatII | GACGTC | 2 Sites | | 2475 2597 2668 | |
| 4 Sites | | 1583 2081 | | 3320 | |
| 2510 2563 2646 | | AvaI | CYCGRG | BglII | AGATCT |
| 2832 | | 3 Sites | | 1 Site | |
| AccI | GTMKAC | 3078 3482 3676 | | 458 | |
| 3 Sites | | BamHI | GGATCC | Bsp1286 | GDGCHC |
| 3050 3433 3535 | | 1 Site | | 8 Sites | |
| AflIII | ACRYGT | 3723 | | 652 1587 2085 | |
| 1 Site | | BanI | GGYRCC | 2953 3075 3114 | |
| 1897 | | 3 Sites | | 3391 | |
| AluI | AGCT | 538 2850 3807 | | 3685 | |
| 13 Sites | | BanII | GRGCYC | BspHI | TCATGA |
| 109 633 1340 | | 5 Sites | | 2 Sites | |
| 1597 1643 1733 | | 2953 3075 3114 | | 1007 1105 | |
| 1959 | | 3391 3685 | | BspNI | CCWGG |
| 2184 2951 3112 | | BclI | TGATCA | 13 Sites | |
| 3524 3683 3717 | | 1 Site | | 52 1738 1751 | |
| AlwNI | CAGNNNCTG | 3729 | | 1872 2475 2668 | |
| 2 Sites | | BcnI | CCSGG | 2977 | |
| 1488 2129 | | 12 Sites | | 3270 3381 3444 | |
| AosII | GRCGYC | 1173 1521 3021 | | 3478 3657 3801 | |
| 5 Sites | | 3139 3298 3457 | | BssHII | GCGCGC |
| 2507 2560 2643 | | 3484 | | 1 Site | |
| 2829 2983 | | | | 3045 | |

Mosaic and Group M nef_Dmyr-Patent.doc

Fig. 22 cont'd-2

```
BstNI      CCWGG                         55      771     1175         25 Sites
13 Sites                            1423    1857    1875                   52    1172    1520
       52    1738    1751          1886                                 1738    1751    1872
     1872    2475    2668                2268    2469    2662           2475
     2977                                3073    3096    3128                2668    2977    3020
     3270    3381    3444                3168                                3138    3270    3297
     3478    3657    3801                3267    3323    3342           3381
Cfr10I     RCCGGY                   3379    3481    3660                     3444    3456    3478
2 Sites                             HgiAI      GWGCWC                        3483    3484    3540
      847    3128                   5 Sites                             3657
CfrI       YGGCCR                        1587    2085    2953                3677    3678    3690
4 Sites                             3114    3685                        3801
      769    3094    3126           HhaI       GCGC                     NaeI       GCCGGC
     3166                           19 Sites                            1 Site
ClaI       ATCGAT                         11     496    1273                 3130
1 Site                              1382    1556    1656                NciI       CCSGG
     2287                           1723                                12 Sites
DdeI       CTNAG                         1993    2026    2169                1172    1520    3020
12 Sites                            2249    3045    3047                3138    3297    3456
       12     204     397           3145                                3483
      711     787    1214    1623        3183    3255    3625                3484    3540    3677
     2088    2158    2229           3655    3667                        3678    3690
     3318    3861                   HincII     GTYRAC                   NcoI       CCATGG
DpnI       GATC                     5 Sites                             1 Site
13 Sites                                  413     886    2369                2745
      190     195     460           3051    3536                        NdeI       CATATG
     1239    1247    1258           HinfI      GANTC                    2 Sites
     1333                           15 Sites                                 2076    2619
     2972    3028    3216                  43      59     357           NheI       GCTAGC
     3417    3725    3731                 383     401     725     779   1 Site
DraIII     CACNNNGTG                      807    1527    1923                3717
1 Site                                   1998    2222    2795           NlaIII     CATG
     1161                           3487                                14 Sites
Eco47I     GGWCC                    3648                                      538     762     864
7 Sites                             HinPI      GCGC                          892    1011    1105    1181
      122     586     919           19 Sites                                1901    2219    2349
     1048    3021    3133                   9     494    1271                2367    2689    2749
     3298                                1380    1554    1654           3942
EcoRII     CCWGG                    1721                                NlaIV      GGNNCC
13 Sites                                 1991    2024    2167           9 Sites
       50    1736    1749                2247    3043    3045                  92     540    1830
     1870    2473    2666           3143                                    1869    2852    3023
     2975                                3181    3253    3623           3073
     3268    3379    3442           3653    3665                             3725    3809
     3476    3655    3799           HpaII      CCGG                     NruI       TCGCGA
EcoRV      GATATC                   16 Sites                            1 Site
1 Site                                    848    1172    1329                2257
     2294                                1519    1545    1692           NsiI       ATGCAT
Fnu4HI     GCNGC                    3019                                1 Site
20 Sites                                 3129    3137    3149                 796
      234     769    1283                3297    3456    3483           Nsp7524I   RCATGY
     1489    1492    1557           3540                                2 Sites
     1700                                3677    3690                        1901    3942
     1855    1973    1976           MaeI       CTAG                     NspBII     CMGCKG
     1994    2110    2250           7 Sites                             6 Sites
     2279                                 378     801    1034                1314    1559    2281
     2262    3094    3166           1404    2385    3718                3039    3165    3500
     3235    3315    3340           3751                                RsaI       GTAC
PnuDII     CGCG                     MaeII      ACGT                     11 Sites
17 Sites                            12 Sites                                  559    2093    2263
      494    1273    1854                 669    1160    1196           2330    2604    2684
     2169    2257    2281           2306    2507    2519                2717
     2445                            2560                                    2768    2925    3333
     3039    3045    3047                2643    2724    2829           3696
     3062    3165    3183           3219    3330                        RsrII      CGGWCCG
     3237                           MaeIII     GTNAC                    2 Sites
     3255    3625    3653           8 Sites                                 3134    3299
HaeII      RGCGCY                         270    1134    1361           SacI       GAGCTC
3 Sites                             1477    1540    2446                3 Sites
       12    1657    2027           2533                                    2953    3114    3685
HaeIII     GGCC                     2882                                SacII      CCGCGG
20 Sites                            MvaI       CCNGG                    3 Sites
Mosaic and Group M nef_Dmyr-Patent.doc
```

Fig. 22 cont'd-3

```
        2282     3040    3166         1 Site                            SinI       GGWCC
SalI         GTCGAC                      3696                           7 Sites
2 Sites                                ScrFI       CCNGG                    123       587      920
     3049     3534                     25 Sites                         1049     3022     3134
Sau3A        GATC                          52      1172    1520         3299
13 Sites                               1738     1751    1872            SmaI       CCCGGG
      188      193     458             2475                             2 Sites
    1237     1245    1256                2668     2977    3020             3484     3678
    1331                                3138     3270    3297           SnaBI      TACGTA
    2970     3026    3214               3381                            1 Site
    3415     3723    3729                3444     3456    3478             2725
Sau96A       GGNCC                      3483     3484    3540           SpeI       ACTAGT
17 Sites                               3657                             1 Site
      123      587     920                3677     3678    3690            2384
    1049     1174    2266               3801                            SphI       GCATGC
    2468                                SdnI       GDGCHC               1 Site
    2661     3022    3071               8 Sites                            3942
    3072     3134    3266                 652     1587    2085          SspI       AATATT
    3299                                2953     3075    3114           2 Sites
    3341     3480    3659               3391                                603      991
ScaI         AGTACT                      3685                           StuI       AGGCCT
1 Site
       55
StyI         CCWWGG
1 Site
     2745
TaqI         TCGA
15 Sites
      216     1799    2287
    3050     3079    3105
    3199
    3222     3346    3399
    3421     3535    3550
    3646
    3738
XhoI         CTCGAG
1 Site
     3078
XhoII        RGATCY
5 Sites
      458     1245    1256
    3415     3723
XmaI         CCCGGG
2 Sites
     3482    3676
XmaIII       CGGCCG
1 Site
     3166
XmnI         GAANNNNTTC
1 Site
      811
Following enzymes have no
sites
AccIII    AflII      Asp718
AsuII     AvrII      BalI
BbeI      BspMII     BstEII
BstXI     DraI
Eco47III
EcoO109   EcoRI      EspI
FspI      HindIII    HpaI
KpnI      MluI       MstI
NarI      NotI       OxaNI
PflMI     PpuMI      PssI
PstI      PvuI       PvuII
SfiI      SplI       Tth111I
XbaI      XcaI
```

Fig. 22 cont'd-4 nefM_4.1Dmyr (hv13225 in), (663nt.), GC=67%
CTCGAGAAGAAAATGGCGGCCAAGTGGTCGAAGAGCTCCATCGTCGGGTGGCCGGCGGTCCGGGAGAGGA
TGCGGAGGGCGGAGCCGGCGGCCGACGGGGTCGGGGCGGTCTCGCGGGACCTGGAGAAGCACGGGGCGAT
CACGTCGAGCAACACCGCCGCGACGAACGCGGACTGCGCGTGGCTGGAGGCCCAGGAGGAGGACTCGGAG
GTCGGCTTCCCGGTCCGGCCGCACGTCCCGCTCCGGCCGATGACGTACAAGGCGGCCGTCGACCTCTCCC
ACTTCCTGAAAGAGCAGGGGGGCCTGGAGGGGCTCATCTACTCGCAGAAGAGGCAGGACATCCTCGACCT
GTGGGTCTACCACACCCAGGGCTACTTCCCGGACTGGCAGAACTACACGCCAGGCCCGGGAATCCGCTAC
CCGCTGACCTTCGGGTGGTGCTTCAAGCTCGTCCCCGTGGACCCGCGGGAGGTCGAGGAAGCCAACAAGG
GGGAGAACAACTGCCTCCTGCACCCGATGTCGCAGCACGGGATGGACGACCCGGAGAAGGAGGTGCTGAT
GTGGAAGTTCGACTCGCGGCTGGCGTTCCACCACATGGCCCGCGAGAAGCACCCGGAGTTCTACAAGGAC
TGCTGATAAGCTAGCTGATCAGGATCCACGCGT MAAKWSKSSIVGWPAVRERMRRAEPAADGVGAVSRDLEKHGAITSSNTAATNADCAWLEAQEEDSEVGFP
VRPHVPLRPMTYKAAVDLSHFLKEQGGLEGLIYSQKRQDILDLWVYHTQGYFPDWQNYTPGPGIRYPLTF
GWCFKLVPVDPREVEEANKGENNCLLHPMSQHGMDDPEKEVLMWKFDSRLAFHHMAREKHPEFYKDC_

HV13319 (nefM_4.1Dmyr.wlv), 3918nt.
AAATGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA Mosaic and CON nef_Dmyr_final.doc

Fig. 22 cont'd-5

```
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGAGAAGAAAATGGCGGCCAAGTGGTCGAA
GAGCTCCATCGTCGGGTGGCCGGCGGTCCGGGAGAGGATGCGGAGGGCGGAGCCGGCGGCCGACGGGTC
GGGGCGGTCTCGCGGGACCTGGAGAAGCACGGGCGATCACGTCGAGCAACACCGCCGCGACGAACGCGG
ACTGCGCGTGGCTGGAGGCCCAGGAGGAGGACTCGGAGGTCGGCTTCCCGGTCCGGCCGCACGTCCCGCT
CCGGCCGATGACGTACAAGGCGGCCGTCGACCTCTCCCACTTCCTGAAAGAGCAGGGGGGCCTGGAGGGG
CTCATCTACTCGCAGAAGAGGCAGGACATCCTCGACCTGTGGGTCTACCACACCCAGGGCTACTTCCCGG
ACTGGCAGAACTACACGCCAGGCCCGGGAATCCGCTACCCGCTGACCTTCGGGTGGTGCTTCAAGCTCGT
CCCCGTGGACCCGCGGGAGGTCGAGGAAGCCAACAAGGGGGAGAACAACTGCCTCCTGCACCCGATGTCG
CAGCACGGGATGGACGACCCGGAGAAGGAGGTGCTGATGTGGAAGTTCGACTCGCGGCTGGCGTTCCACC
ACATGGCCCGCGAGAAGCACCCGGAGTTCTACAAGGACTGCTGATAAGCTAGCTGATCAGCCTCGACTGT
GCCTTCTAGTTGCCAGCCATCTGTTGTTTGCCCCTCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGG
GGGGTGGGGTGGGCAGGACAGCAAGGGGGAGGATTGGGAAGACAATAGCAGGCATGCTGGGGAATTT
```

Thursday, August 2, 2007

Sequence 0  Length : 3918

| | | | |
|---|---|---|---|
| AatII | GACGTC | | |
| 4 Sites | | | |
| 2510 | 2563 | 2646 | |
| 2832 | | | |
| AccI | GTMKAC | | |
| 2 Sites | | | |
| 3317 | 3404 | | |
| AflIII | ACRYGT | | |
| 1 Site | | | |
| 1897 | | | |
| AluI | AGCT | | |
| 13 Sites | | | |
| 109 | 633 | 1340 | |
| 1597 | 1643 | 1733 | |
| 1959 | | | |
| 2184 | 2951 | 3083 | |
| 3495 | 3688 | 3692 | |
| AlwNI | CAGNNNCTG | | |
| 2 Sites | | | |
| 1488 | 2129 | | |
| AosII | GRCGYC | | |
| 5 Sites | | | |
| 2507 | 2560 | 2643 | |
| 2829 | 2983 | | |
| ApaLI | GTGCAC | | |
| 2 Sites | | | |
| 1563 | 2081 | | |
| AvaI | CYCGRG | | |
| 1 Site | | | |
| 3453 | | | |
| BanI | GGYRCC | | |
| 3 Sites | | | |
| 538 | 2850 | 3772 | |
| BanII | GRGCYC | | |
| 3 Sites | | | |

| | | | |
|---|---|---|---|
| | 2953 | 3085 | 3362 |
| BclI | TGATCA | | |
| 1 Site | | | |
| 3694 | | | |
| BcnI | CCSGG | | |
| 10 Sites | | | |
| 1173 | 1521 | 3021 | |
| 3110 | 3269 | 3428 | |
| 3455 | | | |
| 3456 | 3590 | 3662 | |
| BglI | GCCNNNNNGGC | | |
| 3 Sites | | | |
| 2475 | 2597 | 2668 | |
| BglII | AGATCT | | |
| 1 Site | | | |
| 458 | | | |
| Bsp1286 | GDGCHC | | |
| 6 Sites | | | |
| 652 | 1587 | 2085 | |
| 2953 | 3085 | 3362 | |
| BspHI | TCATGA | | |
| 2 Sites | | | |
| 1007 | 1105 | | |
| BspNI | CCWGG | | |
| 13 Sites | | | |
| 52 | 1738 | 1751 | |
| 1872 | 2475 | 2668 | |
| 2977 | | | |
| 3169 | 3241 | 3352 | |
| 3415 | 3449 | 3766 | |
| BssHII | GCGCGC | | |
| 1 Site | | | |
| 3045 | | | |
| BstNI | CCWGG | | |
| 13 Sites | | | |
| 52 | 1738 | 1751 | |
| 1872 | 2475 | 2668 | |
| 2977 | | | |

| | | | |
|---|---|---|---|
| 3169 | 3241 | 3352 | |
| 3415 | 3449 | 3766 | |
| Cfr10I | RCCGGY | | |
| 3 Sites | | | |
| 847 | 3099 | 3132 | |
| CfrI | YGGCCR | | |
| 7 Sites | | | |
| 769 | 3065 | 3097 | |
| 3137 | 3274 | 3292 | |
| 3311 | | | |
| ClaI | ATCGAT | | |
| 1 Site | | | |
| 2287 | | | |
| DdeI | CTNAG | | |
| 11 Sites | | | |
| 12 | 204 | 397 | |
| 711 | 787 | 1214 | 1623 |
| 2088 | 2158 | 2229 | |
| 3826 | | | |
| DpnI | GATC | | |
| 11 Sites | | | |
| 190 | 195 | 460 | |
| 1239 | 1247 | 1258 | |
| 1333 | | | |
| 2972 | 3028 | 3187 | |
| 3696 | | | |
| DraIII | CACNNNGTG | | |
| 1 Site | | | |
| 1161 | | | |
| Eco47I | GGWCC | | |
| 9 Sites | | | |
| 122 | 586 | 919 | |
| 1048 | 3021 | 3104 | |
| 3164 | | | |
| 3269 | 3506 | | |
| Eco0109 | RGGNCCY | | |
| 2 Sites | | | |
| 3165 | 3348 | | |
| EcoRII | CCWGG | | |

Mosaic and CON nef_Dmyr_final.doc

Fig. 22 cont'd-6

```
13 Sites                          9     494    1271      NlaIV     GGNNCC
       50   1736    1749   1380    1554    1654         11 Sites
1870    2473    2666       1721                                92     540    1830
2975                       1991    2024    2167         1869    2852    3023
   3167    3239    3350    2247    3043    3045         3131
3413    3447    3764       3224                            3166    3349    3509
EcoRV    GATATC            HpaII    CCGG                3774
1 Site                     17 Sites                     NruI      TCGCGA
   2294                       848    1172    1329       1 Site
Fnu4HI   GCNGC             1519    1545    1692            2257
22 Sites                   3019                         NsiI      ATGCAT
   234     769    1283        3100    3108    3133      1 Site
1489    1492    1557       3268    3273    3291            796
1700                       3427                         Nsp7524I  RCATGY
   1855    1973    1976       3454    3589    3651      2 Sites
1994    2110    2250       MaeI      CTAG                  1901    3907
2279                       7 Sites                      NspBII    CMGCKG
   2282    3065    3137       378     801    1034       6 Sites
3206    3277    3311       1404    2385    3689            1314    1559    2281
3571                       3716                         3039    3471    3513
   3625                    MaeII    ACGT                PflMI     CCANNNNNTGG
FnuDII   CGCG              13 Sites                     1 Site
17 Sites                      669    1160    1196          3642
   494    1273    1854     2306    2507    2519         PpuMI     RGGWCCY
2169    2257    2281       2560                         1 Site
2445                          2643    2724    2829         3165
   3039    3045    3047    3190    3281    3301         PssI      RGGNCCY
3162    3208    3217       MaeIII   GTNAC               2 Sites
3226                       8 Sites                         3168    3351
   3513    3624    3650       270    1134    1361      RsaI      GTAC
HaeII    RGCGCY            1477    1540    2446         10 Sites
3 Sites                    2533                            559    2093    2263
   12    1657    2027         2882                      2330    2604    2684
HaeIII   GGCC              MvaI      CCNGG              2717
20 Sites                   23 Sites                        2768    2925    3304
   55    771    1175          52    1172    1520       RsrII     CGGWCCG
1423    1857    1875       1738    1751    1872         2 Sites
1886                       2475                            3105    3270
   2268    2469    2662       2668    2977    3020      SacI      GAGCTC
3067    3099    3139       3109    3169    3241         2 Sites
3238                       3268                            2953    3085
   3276    3294    3313       3352    3415    3427      SacII     CCGCGG
3350    3452    3646       3449    3454    3455         3 Sites
HgiAI    GWGCWC            3589                            2282    3040    3514
4 Sites                       3661    3766              SalI      GTCGAC
   1587    2085    2953    NaeI      GCCGGC             1 Site
3085                       2 Sites                         3316
HhaI     GCGC                 3101    3134              Sau3A     GATC
14 Sites                   NciI      CCSGG              11 Sites
   11    496    1273       10 Sites                        188     193     458
1382    1556    1656          1172    1520    3020      1237    1245    1256
1723                       3109    3268    3427         1331
   1993    2026    2169    3454                            2970    3026    3185
2249    3045    3047          3455    3589    3661      3694
3226                       NcoI      CCATGG             Sau96A    GGNCC
HincII   GTYRAC            1 Site                       17 Sites
4 Sites                       2745                         123     587     920
   413    886    2369     NdeI      CATATG             1049    1174    2266
3318                       2 Sites                      2468
HinfI    GANTC                2076    2619                 2661    3022    3105
16 Sites                   NheI      GCTAGC             3165    3237    3270
   43    59     357        1 Site                       3348
383     401    725    779     3688                         3451    3507    3645
   807    1527    1923     NlaIII    CATG               ScrFI     CCNGG
1998    2222    2795       15 Sites                     23 Sites
3250                          538     762     864          52    1172    1520
   3458    3619            892    1011    1109    1181 1738    1751    1872
HinPI    GCGC                 1901    2219    2349      2475
14 Sites                   2367    2689    2749            2668    2977    3020
                           3645                         3109    3169    3241
                              3907                      3268
```

Fig. 22 cont'd-7

```
            3352    3415    3427          3907                     3453
    3449    3454    3455          SspI      AATATT        XmaIII     CGGCCG
3589                              2 Sites                 4 Sites
    3661    3766                       603     991            3137    3274    3292
SdnI          GDGCHC              StuI      AGGCCT        3311
6 Sites                           1 Site                  XmnI       GAANNNNTTC
    652     1587    2085                55                1 Site
   2953     3085    3362          StyI      CCWWGG            811
SinI          GGWCC               1 Site
9 Sites                              2745                 Following enzymes have no
    123      587     920          TaqI      TCGA          sites
   1049     3022    3105          11 Sites                AccIII     AflII      ApaI
   3165                               216    1799   2287  Asp718     AsuII      AvrII
    3270    3507                     3050    3076   3193  BalI       BamHI      BbeI
SmaI          CCCGGG                 3317                 BspMII     BstEII     BstXI
1 Site                               3392    3521   3617  DraI       Eco47III   EcoRI
    3455                             3703                 EspI       PspI       HindIII
SnaBI         TACGTA              Tth111I   GACNNNGTC     HpaI       KpnI       MluI
1 Site                            1 Site                  MstI       NarI       NotI
    2725                             3145                 OxaNI      PstI       PvuI
SpeI          ACTAGT              XhoII     RGATCY        PvuII      ScaI       SfiI
1 Site                            3 Sites                 SplI       XbaI       XcaI
    2384                              458    1245   1256  XhoI
SphI          GCATGC              XmaI      CCCGGG
1 Site                            1 Site
``` nefM_4.2Dmyr (654nt.) hv13231, GC=66%
ctcgagAAGAAAATGGCGGCCAAGTGGTCGAAGCGGTCCATCGTCGGGTGGCCGGCGATCCGGGAGAGGA
TGCGGAGGACGGAGCCGGCGGCCGAGGGGGTCGGGGCGGCGTCGCAGGACCTCGACAAATACGGGGCGCT
CACGTCGAGCAACACCGCCCAGACGAACCCGGACTGCGCGTGGCTGGAGGCCCAGGAGGAGGAAGAGGTC
GGCTTCCCGGTCCGGCCGCAAGTCCCAGTCAGGCCGATGACGTACAAGGGCGCCCTGGACCTCTCCCACT
TCCTGAAAGAGAAGGGGGGCCTGGACGGGCTCATCTACTCGCGGAAGAGGCAGGAGATCCTCGACCTGTG
GGTCTACAACACCCAGGGCTACTTCCCCGACTGGCAGAACTACACGCCAGGCCCCGGAGTGCGGTACCCG
CTGACCTTCGGGTGGTGCTACAAGCTCGTCCCCGTGGACCCGGAGGAGGTCGAGAAGGCCAACGAGGGGG
AGAACAACTCCCTCCTGCACCCGATGTCGCTCCACGGGATGGAGGACCCCGAGAGGGAGGTGCTGAAGTG
GAAGTTCGACTCGCGGCTGGCGCTCAAGCACCGGGCCCGGGAGCTCCACCCGGAGTTCTACAAGGACTGC
TGATAAGCTAGCGGATCCTGATCA MAAKWSKRSIVGWPAIRERMRRTEPAAEGVGAASQDLDKYGALTSSNTAQTNPDCAWLEAQEEEEVGFPV
RPQVPVRPMTYKGALDLSHFLKEKGGLDGLIYSRKRQEILDLWVYNTQGYFPDWQNYTPGPGVRYPLTFG
WCYKLVPVDPEEVEKANEGENNSLLHPMSLHGMEDPEREVLKWKFDSRLALKHRARELHPEFYKDC_

>HV13231 in hv10001 (nefM_4.2Dmyr.wlv), 3950nt.
AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT Mosaic and CON nef_Dmyr_final.doc

Fig. 22 cont'd-8

```
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGCGGTCCATCGTCGGGTGGCCGGCGATCCGGGAGAGGATGC
GGAGGACGGAGCCGGCGGCCGAGGGGGTCGGGGCGGCGTCGCAGGACCTCGACAAATACGGGGCGCTCAC
GTCGAGCAACACCGCCCAGACGAACCCGGACTGCGCGTGGCTGGAGGCCCAGGAGGAGGAAGAGGTCGGC
TTCCCGGTCCGGCCGCAAGTCCCAGTCAGGCCGATGACGTACAAGGGCGCCCTGGACCTCTCCCACTTCC
TGAAAGAGAAGGGGGGCCTGGACGGGCTCATCTACTCGCGGAAGAGGCAGGAGATCCTCGACCTGTGGGT
CTACAACACCCAGGGCTACTTCCCCGACTGGCAGAACTACACGCCAGGCCCCGGAGTGCGGTACCCGCTG
ACCTTCGGGTGGTGCTACAAGCTCGTCCCCGTGGACCCGGAGGAGGTCGAGAAGGCCAACGAGGGGAGA
ACAACTCCCTCCTGCACCCGATGTCGCTCCACGGGATGGAGGACCCCGAGAGGGAGGTGCTGAAGTGGAA
GTTCGACTCGCGGCTGGCGCTCAAGCACCGGGCCCGGGAGCTCCACCCGGAGTTCTACAAGGACTGC TGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGCAGGACAGCAAGGGGGAGGATTGG
GAAGACAATAGCAGGCATGCTGGGGAATTT
```

Thursday, August 2, 2007    AflIII   ACRYGT      2 Sites
                                        1 Site                         1488      2129
Sequence 0    Length : 3950         1897                             AosII     GRCGYC
                                        AluI      AGCT                     7 Sites
AatII      GACGTC                      12 Sites                        2507      2560      2643
4 Sites                                     109       633      1340      2829      2983      3186
    2510      2563      2646        1597     1643     1723      3337
2832                                        1959                                 ApaI      GGGCCC
AccI      GTMKAC                     2184      2951      3521      2 Sites
2 Sites                                   3680      3714                     3075      3674
    3050      3430                  AlwNI    CAGNNNCTG               ApaLI    GTGCAC Mosaic and CON nef_Dmyr_final.doc

Fig. 22 cont'd-9

```
2 Sites                    ClaI     ATCGAT          3267     3302     3320
    1583    2081           1 Site                   3376     3478     3555
Asp718   GGTACC                2287                 3672
1 Site                     DdeI     CTNAG           HgiAI    GWGCWC
    3490                   11 Sites                 4 Sites
AvaI     CYCGRG                 12      204    397     1587    2085    2953
3 Sites                       711     787   1214  1623  3682
    3078    3615    3673       2088    2158    2229  HhaI    GCGC
BamHI    GGATCC               3858                  17 Sites
1 Site                     DpnI     GATC                 11    496    1273
    3720                   13 Sites                 1382    1556    1656
BanI     GGYRCC                190     195     460  1723
5 Sites                      1239    1247    1258      1993    2026    2169
     538    2850    3336     1333                       2249    3045    3047
    3490    3804              2972    3028    3135     3215
BanII    GRGCYC              3414    3722    3728      3255    3339    3659
5 Sites                    DraIII   CACNNNGTG      HincII   GTYRAC
    2953    3075    3388   1 Site                  4 Sites
    3674    3682                1161                    413     886    2369
BbeI     GGCGCC             Eco47I   GGWCC         3051
1 Site                     11 Sites                HinfI    GANTC
    3340                        122     586     919  14 Sites
BclI     TGATCA              1048    3021    3111       43      59     357
1 Site                       3193                       383     401     725    779
    3726                      3295    3343    3532      807    1527    1923
BcnI     CCSGG               3610                      1998    2222    2795
12 Sites                   EcoO109  RGGNCCY         3645
    1173    1521    3021   4 Sites                 HinPI    GCGC
    3139    3247    3295       3194    3374    3477  17 Sites
    3482                      3611                         9    494    1271
    3538    3670    3675   EcoRII   CCWGG          1380    1554    1654
    3676    3688            13 Sites                1721
BglI     GCCNNNNNGGC             50    1736    1749    1991    2024    2167
3 Sites                      1870    2473    2666      2247    3043    3045
    2475    2597    2668   2975                        3213
BglII    AGATCT              3268    3340    3376      3253    3337    3657
1 Site                       3439    3473    3796   HpaII    CCGG
     458                   EcoRV    GATATC          18 Sites
Bsp1286  GDGCHC             1 Site                      848    1172    1329
8 Sites                        2294                    1519    1545    1692
     652    1587    2085   Fnu4HI   GCNGC              3019
    2953    3075    3388   20 Sites                    3129    3137    3162
    3674                        234     769    1283    3246    3294    3299
    3682                      1489    1492    1557     3481
BspHI    TCATGA              1700                      3537    3668    3674
2 Sites                      1855    1973    1976      3687
    1007    1105              1994    2110    2250  KpnI     GGTACC
BspNI    CCWGG               2279                   1 Site
13 Sites                     2282    3094    3166      3494
      52    1738    1751     3184    3303    3651  MaeI     CTAG
    1872    2475    2668   FnuDII   CGCG           7 Sites
    2977                   14 Sites                     378     801    1034
    3270    3342    3378        494    1273    1854   1404    2385    3715
    3441    3475    3798     2169    2257    2281     3748
BssHII   GCGCGC              2445                   MaeII    ACGT
1 Site                       3039    3045    3047  12 Sites
    3045                     3062    3255    3398       669    1160    1196
BstNI    CCWGG               3650                      2306    2507    2519
13 Sites                   HaeII    RGCGCY          2560
      52    1738    1751   6 Sites                     2643    2724    2829
    1872    2475    2668        12    1657    2027    3219    3327
    2977                     3216    3340    3660  MaeIII   GTNAC
    3270    3342    3378   HaeIII   GGCC           8 Sites
    3441    3475    3798   21 Sites                     270    1134    1361
Cfr10I   RCCGGY                 55     771    1175    1477    1540    2446
3 Sites                      1423    1857    1875     2533
     847    3128    3161   1886                        2882
CfrI     YGGCCR              2268    2469    2662  MvaI     CCNGG
5 Sites                      3073    3096    3128  25 Sites
     769    3094    3126   3168
    3166    3300
```

Fig. 22 cont'd-10

```
             52    1172    1520      PpuMI      RGGWCCY         11 Sites
   1738    1751    1872              2 Sites                        123      587      920
   2475                                  3194    3611            1049    3022    3112
      2668    2977    3020           PssI       RGGNCCY          3194
   3138    3246    3270              4 Sites                        3296    3344    3533
   3294                                  3197    3377    3480    3611
      3342    3378    3441           3614                        SmaI       CCCGGG
   3475    3481    3537              RsaI       GTAC             1 Site
   3669                              11 Sites                       3675
      3674    3675    3687              559    2093    2263     SnaBI      TACGTA
   3798                              2330    2604    2684        1 Site
NaeI       CCCGGC                    2717                           2725
2 Sites                                 2768    2925    3330    SpeI       ACTAGT
   3130    3163                      3492                        1 Site
NarI       GGCGCC                    RsrII      CGGWCCG             2384
1 Site                               1 Site                     SphI       GCATGC
   3337                                 3296                     1 Site
NciI       CCSGG                     SacI       GAGCTC              3939
12 Sites                             2 Sites                    SspI       AATATT
    1172    1520    3020                2953    3682            2 Sites
   3138    3246    3294              SacII      CCGCGG              603     991
   3481                              2 Sites                    StuI       AGGCCT
      3537    3669    3674              2282    3040            1 Site
   3675    3687                      SalI       GTCGAC              55
NcoI       CCATGG                    1 Site                     StyI       CCWWGG
1 Site                                  3049                     1 Site
   2745                              Sau3A      GATC                2745
NdeI       CATATG                    13 Sites                   TaqI       TCGA
2 Sites                                  188     193    458     12 Sites
   2076    2619                      1237    1245    1256           216    1799    2287
NheI       GCTAGC                    1331                        3050    3079    3105
1 Site                                  2970    3026    3133    3199
   3714                              3412    3720    3726           3222    3418    3547
NlaIII     CATG                      Sau96A     GGNCC            3643    3735
14 Sites                             22 Sites                   XhoI       CTCGAG
    538     762     864                  123     587    920     1 Site
    892    1011    1109    1181      1049    1174    2266           3078
      1901    2219    2349           2468                       XhoII      RGATCY
   2367    2689    2749                 2661    3022    3071    5 Sites
   3939                              3072    3112    3194           458    1245    1256
NlaIV      GGNNCC                    3266                        3412    3720
17 Sites                                 3296    3344    3374   XmaI       CCCGGG
     92     540    1830              3477    3533    3611        1 Site
   1869    2852    3023              3670                           3673
   3073                              3671                       XmaIII     CGGCCG
      3160    3338    3375           ScrFI      CCNGG           2 Sites
   3479    3492    3535              25 Sites                       3166    3300
   3613                                   52    1172    1520    XmnI       GAANNNNTTC
      3672    3722    3806           1738    1751    1872        1 Site
NruI       TCGCGA                    2475                           811
1 Site                                  2668    2977    3020
   2257                              3138    3246    3270       Following enzymes have no
NsiI       ATGCAT                    3294                       sites
1 Site                                  3342    3378    3441    AccIII     AflII     AsuII
   796                               3475    3481    3537       AvrII      BalI      BspMII
Nsp7524I   RCATGY                    3669                       BstEII     BstXI     DraI
2 Sites                                 3674    3675    3687    Eco47III   EcoRI     EspI
   1901    3939                      3798                       FspI       HindIII   HpaI
NspBII     CMGCKG                    SdnI       GDGCHC          MluI       MstI      NotI
5 Sites                              8 Sites                    OxaNI      PstI      PvuI
   1314    1559    2281                  652    1587    2085    PvuII      ScaI      SfiI
   3039    3497                      2953    3075    3388       SplI       Tth111I   XbaI
PflMI      CCANNNNNTGG               3674                       XcaI
1 Site                                  3682
   3605                              SinI       GGWCC
```

>nefM_4.3Dmyr(654nt.), hv13230, GC=66%
ctcgagAAGAAAATGGCGGCCAACTGGTCGAAGAGCTCCATCGTCGGGTGGCCGGAGATCCGGGAGCGCA
TCCGGAGGACGGACCCGGCGGCCGAGGGGGTCGGGGCGGCCTCGCGGGACCTGGAGCGCCACGGGGCGAT

Fig. 22 cont'd-11

```
CACGTCGAGCAACACCGCCACCACGAACGCGGCCTGCGCGTGGCTGGAGGCCCAGGAGGACGAGGAAGTC
GGCTTCCCGGTCCGGCCGCAAGTCCCGCTCAGGCCGATGACGTTCAAGGGGGCCTTCGACCTCGGCTTCT
TCCTGAAAGAGAAGGGGGGCCTGGAGGGGCTCATCTACTCGAAGAAGAGGCAGGACATCCTCGACCTGTG
GGTCTACAACACCCAGGGGTTCTTCCCGGACTGGCAGAACTACACGCCAGGCCCGGGAACCCGGTTCCCG
CTGACCTTCGGGTGGTGCTTCGAGCTCGTCCCCGTGGACCCGAAGGAGGTCGAGGAAGCCAACGAGGGGG
AGAACAACTGCCTCCTGCACCCGATCTGCCAGCACGGGATGGACGACGAGGAGCGCGAGGTGCTGATGTG
GAAGTTCGACTCGTCCCTGGCCCGGCGCCACCTCGCCCGGGAGAAGCACCCGGAGTACTACAAGGACTGC
TGATAAGCTAGCGGATCCTGATCA

MAANWSKSSIVGWPEIRERIRRTDPAAEGVGAASRDLERHGAITSSNTATTNAACAWLEAQEDEEVGFPV
RPQVPLRPMTFKGAFDLGFFLKEKGGLEGLIYSKKRQDILDLWVYNTQGFFPDWQNYTPGPGTRFPLTFG
WCFELVPVDPKEVEEANEGENNCLLHPICQHGMDDEEREVLMWKFDSSLARRHLAREKHPEYYKDC_

>hv13230 in hv10001 (nefM_4.3Dmyr.wlv) (3950nt.)
AAATGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
```

Fig. 22 cont'd-12

```
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGTCGACGGGCGACGCGAAACTTGGGCCCACTC
GAGAAGAAAATGGCGGCCAACTGGTCGAAGAGCTCCATCGTCGGGTGGCCGGAGATCCGGGAGCGCATCC
GGAGGACGGACCCGGCGGCCGAGGGGGTCGGGGCGGCCTCGCGGGACCTGGAGCGCCACGGGCGATCAC
GTCGAGCAACACCGCCACCACGAACGCGGCCTGCGCGTGGCTGGAGGCCCAGGAGGACGAGGAAGTCGGC
TTCCCGGTCCGGCCGCAAGTCCCGCTCAGGCCGATGACGTTCAAGGGGGCCTTCGACCTCGGCTTCTTCC
TGAAAGAGAAGGGGGGCCTGGAGGGGCTCATCTACTCGAAGAAGAGGCAGGACATCCTCGACCTGTGGGT
CTACAACACCCAGGGGTTCTTCCCGGACTGGCAGAACTACACGCCAGGCCCGGGAACCCGGTTCCCGCTG
ACCTTCGGGTGGTGCTTCGAGCTCGTCCCCGTGGACCCGAAGGAGGTCGAGGAAGCCAACGAGGGGGAGA
ACAACTGCCTCCTGCACCCGATCTGCCAGCACGGGATGGACGACGAGGAGCGCGAGGTGCTGATGTGGAA
GTTCGACTCGTCCCTGGCCCGGCGCCACCTCGCCCGGGAGAAGCACCCGGAGTACTACAAGGACTGCTGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGGGGGAGGATTGG
GAAGACAATAGCAGGCATGCTGGGGAATTT
```

Thursday, August 2, 2007

Sequence 0   Length : 3950

| Enzyme | Site | | | |
|---|---|---|---|---|
| AatII | GACGTC | | | |
| 4 Sites | 2510 | 2563 | 2646 | 2832 |
| AccI | GTMKAC | | | |
| 2 Sites | 3050 | 3430 | | |
| AccIII | TCCGGA | | | |
| 1 Site | 3148 | | | |
| AflIII | ACRYGT | | | |
| 1 Site | 1897 | | | |
| AluI | AGCT | | | |
| 12 Sites | 109 | 633 | 1340 | |
| | 1597 | 1643 | 1733 | |
| | 1959 | | | |
| | 2184 | 2951 | 3112 | |
| | 3521 | 3714 | | |
| AlwNI | CAGNNNCTG | | | |
| 2 Sites | 1488 | 2129 | | |
| AosII | GRCGYC | | | |
| 6 Sites | 2507 | 2560 | 2643 | |
| | 2829 | 2983 | 3662 | |
| ApaI | GGGCCC | | | |
| 1 Site | 3075 | | | |
| ApaLI | GTGCAC | | | |
| 2 Sites | 1563 | 2081 | | |
| AvaI | CYCGRG | | | |
| 3 Sites | 3078 | 3479 | 3673 | |
| BamHI | GGATCC | | | |
| 1 Site | 3720 | | | |
| BanI | GGYRCC | | | |
| 4 Sites | 538 | 2850 | 3661 | |
| | 3804 | | | |
| BanII | GRGCYC | | | |
| 5 Sites | 2953 | 3075 | 3114 | |
| | 3388 | 3523 | | |
| BbeI | GGCGCC | | | |
| 1 Site | 3665 | | | |
| BclI | TGATCA | | | |
| 1 Site | 3726 | | | |
| BcnI | CCSGG | | | |
| 14 Sites | 1173 | 1521 | 3021 | |
| | 3139 | 3163 | 3295 | |
| | 3454 | | | |
| | 3481 | 3482 | 3489 | |
| | 3660 | 3675 | 3676 | |
| | 3688 | | | |
| BglI | GCCNNNNNGGC | | | |
| 3 Sites | 2475 | 2597 | 2668 | |
| BglII | AGATCT | | | |
| 1 Site | 458 | | | |
| Bsp1286 | GDGCHC | | | |
| 8 Sites | 652 | 1587 | 2085 | |
| | 2953 | 3075 | 3114 | |
| | 3388 | | | |
| | 3523 | | | |
| BspHI | TCATGA | | | |
| 2 Sites | 1007 | 1105 | | |
| BspMII | TCCGGA | | | |
| 1 Site | 3148 | | | |
| BspNI | CCWGG | | | |
| 14 Sites | 52 | 1738 | 1751 | |
| | 1872 | 2475 | 2668 | |
| | 2977 | | | |
| | 3198 | 3270 | 3378 | |
| | 3441 | 3475 | 3654 | |
| | 3798 | | | |
| BssHII | GCGCGC | | | |
| 1 Site | 3045 | | | |
| BstNI | CCWGG | | | |
| 14 Sites | 52 | 1738 | 1751 | |
| | 1872 | 2475 | 2668 | |
| | 2977 | | | |
| | 3198 | 3270 | 3378 | |
| | 3441 | 3475 | 3654 | |
| | 3798 | | | |
| Cfr10I | RCCGGY | | | |
| 1 Site | 847 | | | |
| CfrI | YGGCCR | | | |
| 5 Sites | 769 | 3094 | 3126 | |
| | 3166 | 3300 | | |
| ClaI | ATCGAT | | | |
| 1 Site | 2287 | | | |
| DdeI | CTNAG | | | |
| 12 Sites | 12 | 204 | 397 | |
| | 711 | 787 | 1214 | 1623 |
| | 2088 | 2158 | 2229 | |
| | 3315 | 3858 | | |
| DpnI | GATC | | | |
| 14 Sites | 190 | 195 | 460 | |
| | 1239 | 1247 | 1258 | |
| | 1333 | | | |
| | 2972 | 3028 | 3135 | |
| | 3216 | 3591 | 3722 | |
| | 3728 | | | |
| DraIII | CACNNNGTG | | | |
| 1 Site | | | | |

Fig. 22 cont'd-13

```
1161                          4 Sites                           3480    3481    3488
Eco47I   GGWCC                  413      886    2369          3659    3674    3675
9 Sites                       3051                            3687
     122      586     919     HinfI    GANTC                  NcoI    CCATGG
1048    3021     3157         14 Sites                        1 Site
3193                               43      59     357             2745
    3295    3532              383      401     725     779    NdeI    CATATG
EcoO109  RGGNCCY                  807    1527    1923         2 Sites
3 Sites                       1998    2222    2795                2076    2618
    3194    3337    3374      3645                            NheI    GCTAGC
EcoRII   CCWGG                HinPI    GCGC                   1 Site
14 Sites                      18 Sites                            3714
      50    1736    1749            9     494    1271         NlaIII  CATG
1870    2473    2666          1380    1554    1654            14 Sites
2975                          1721                                538     762     864
    3196    3268    3376          1991    2024    2167        892    1011    1109    1181
3439    3473    3652          2247    3043    3045                1901    2219    2349
3796                          3143                            2367    2689    2749
EcoRV    GATATC                   3203    3253    3620        3939
1 Site                        3662                            NlaIV   GGNNCC
    2294                      HpaII    CCGG                   17 Sites
Fnu4HI   GCNGC                19 Sites                              92     540    1830
20 Sites                           848    1172    1329        1869    2852    3023
     234     769    1283      1519    1545    1692            3073
1489    1492    1557          3019                                3160    3195    3338
1700                              3129    3137    3149        3375    3485    3492
    1855    1973    1976      3162    3294    3299            3535
1994    2110    2250          3453                                3663    3722    3806
2279                              3480    3488    3659        NruI    TCGCGA
    2282    3094    3166      3674    3687                    1 Site
3184    3247    3303          MaeI     CTAG                       2257
FnuDII   CGCG                 7 Sites                         NsiI    ATGCAT
15 Sites                           378     801    1034        1 Site
     494    1273    1854      1404    2385    3715                796
2169    2257    2281          3748                            Nsp7524I RCATGY
2445                          MaeII    ACGT                   2 Sites
    3039    3045    3047      12 Sites                            1901    3939
3062    3191    3246               669    1160    1196        NspBII  CMGCKG
3255                          2306    2507    2519            5 Sites
    3622                      2560                                1314    1559    2281
HaeII    RGCGCY                   2643    2724    2829        3039    3497
5 Sites                       3219    3327                    PpuMI   RGGWCCY
      12    1657    2027      MaeIII   GTNAC                  1 Site
3206    3665                  8 Sites                             3194
HaeIII   GGCC                      270    1134    1361        PssI    RGGNCCY
23 Sites                      1477    1540    2446            3 Sites
      55     771    1175      2533                                3197    3340    3377
1423    1857    1875              2882                        RsaI    GTAC
1886                          MvaI     CCNGG                  10 Sites
    2268    2469    2662      28 Sites                             559    2093    2263
3073    3096    3128                52    1172    1520        2330    2604    2684
3168                          1738    1751    1872            2717
    3186    3249    3267      2475                                2768    2925    3693
3302    3320    3339              2668    2977    3020        RsrII   CGGWCCG
3376                          3138    3162    3198            1 Site
    3478    3657              3270                                3296
HgiAI    GWGCWC                   3294    3378    3441        SacI    GAGCTC
5 Sites                       3453    3475    3480            3 Sites
    1587    2085    2953      3481                                2953    3114    3523
3114    3523                      3488    3654    3659        SacII   CCGCGG
BhaI     GCGC                 3674    3675    3687            2 Sites
18 Sites                      3798                                2282    3040
      11     496    1273      NarI     GGCGCC                 SalI    GTCGAC
1382    1556    1656          1 Site                          1 Site
1723                              3662                            3049
    1993    2026    2169      NciI     CCSGG                  Sau3A   GATC
2249    3045    3047          14 Sites                        14 Sites
3145                              1172    1520    3020             188     193     458
    3205    3255    3622      3138    3162    3294            1237    1245    1256
3664                          3453                            1331
HincII   GTYRAC
```

Fig. 22 cont'd-14

```
    2970    3026    3133              3523                        3343    3396    3418
3214    3589    3720             SinI       GGWCC            3517    3547    3643
3726                             9 Sites                     3735
Sau96A    GGNCC                      123     587     920     XhoI       CTCGAG
20 Sites                        1049    3022    3158         1 Site
    123     587     920         3194                             3078
1049    1174    2266                3296    3533             XhoII      RGATCY
2468                             SmaI       CCCGGG           5 Sites
2661    3022    3071             2 Sites                         458    1245    1256
3072    3158    3194                3481    3675             3133    3720
3266                             SnaBI      TACGTA           XmaI       CCCGGG
    3296    3337    3374         1 Site                      2 Sites
3477    3533    3656                2725                         3479    3673
ScaI      AGTACT                 SpeI       ACTAGT           XmaIII     CGGCCG
1 Site                           1 Site                      2 Sites
    3693                            2384                         3166    3300
ScrFI    CCNGG                   SphI       GCATGC           XmnI       GAANNNNTTC
28 Sites                         1 Site                      1 Site
    52    1172    1520              3939                         811
1738    1751    1872             SspI       AATATT
2475                             2 Sites                     Following enzymes have no
2668    2977    3020                603     991              sites
3138    3162    3198             StuI       AGGCCT           AflII      Asp718    AsuII
3270                             1 Site                      AvrII      BalI      BstEII
    3294    3378    3441            55                       BstXI      DraI
3453    3475    3480             StyI       CCWWGG           Eco47III   EcoRI     EspI
3481                             1 Site                      FspI
    3488    3654    3659            2745                     HindIII    HpaI      KpnI
3674    3675    3687             TaqI       TCGA             MluI       MstI      NaeI
3798                             14 Sites                    NotI       OxaNI     PflMI
SdnI     GDGCHC                     216    1799    2287      PstI       PvuI      PvuII
8 Sites                         3050    3079    3105         SfiI       SplI      Tth111I
    652    1587    2085         3222                         XbaI       XcaI
2953    3075    3114
3388
``` nefM_4.4Dmyr (657nt.) hv13232, GC=66%
ctcgagAAGAAA<u>ATG</u>GCCTCCAAGTGGTCGAAGAGCTCCATCGTCGGGTGGCCGCAAGTCCGGGAGCGCA
TCCGGCAGACGCCCCCGCGGCCGAGGGGGTCGGCGCGGTCTCGCAGGACCTCGACAAGCACGGGGCGGT
CACGTCGAGCAACACCGCCGCGAACAACGCGGACTGCGCGTGGCTGCAGGCCCAGGAGGAAGAGGAAGAG
GTCGGCTTCCCGGTCAAGCCGCAAGTGCCGCTCAGGCCGATGACGTACAAGGGGGCCTTCGACCTCTCGT
TCTTCCTGAAAGAGAAGGGTGGCCTGGACGGGCTCATCTACTCGAAGAAGAGGCAGGAGATCCTCGACCT
GTGGGTCTACCACACCCAGGGGTTCTTCCCGGACTGGCACAACTACACGCCAGGCCCGGGAACCCGCTAC
CCGCTGTGCTTCGGGTGGTGCTTCAAGCTCGTCCCCATGGACCCGGCCGAGGTCGAGGAAGCCACCGAGG
GCGAGAACAACTCCCTCCTGCACCCGATCTGCCAGCACGGGATGGAGGACGAGGACCGCGAGGTGCTGGT
CTGGCGGTTCGACTCGTCCCTGGCCCGGCGCCACATCGCCCGGGAGCTCCACCCGGAGTACTACAAGGAC
TGCTGATAAG<u>CTAGC</u>GGATCCTGATCA MASKWSKSSIVGWPQVRERIRQTPPAAEGVGAVSQDLDKHGAVTSSNTAANNADCAWLQAQEEEEVGFP
VKPQVPLRPMTYKGAFDLSFFLKEKGGLDGLIYSKKRQEILDLWVYHTQGFFPDWHNYTPGPGTRYPLCF
GWCFKLVPMDPAEVEEATEGENNSLLHPICQHGMEDEDREVLVWRFDSSLARRHIARELHPEYYKDC_

>HV13232 in hv10001 (nefM_4.4Dmyr.wlv), 3953nt.
AAATGGGGGCGCTGAGGTCTGCCTCGTGAAGAAGGTGTTGCTGACTCATACCAGGCCTGAATCGCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC

Fig. 22 cont'd-15

```
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCGAAGGGAGAAAGG
CGGACAGGTATCCGGTAAGCGGCAGGGTCGGAACAGGAGAGCGCACGAGGGAGCTTCCAGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCCTCCAAGTGGTCGAAGAGCTCCATCGTCGGGTGGCCGCAAGTCCGGGAGCGCATCC
GGCAGACGCCCCCGCGGCCGAGGGGGTCGGCGCGGTCTCGCAGGACCTCGACAAGCACGGGCGGTCAC
GTCGAGCAACACCGCCGCGAACAACGCGGACTGCGCGTGGCTGCAGGCCCAGGAGGAAGAGGAAGAGGTC
GGCTTCCCGGTCAAGCCGCAAGTGCCGCTCAGGCCGATGACGTACAAGGGGGCCTTCGACCTCTCGTTCT
TCCTGAAAGAGAAGGGTGGCCTGGACGGGCTCATCTACTCGAAGAAGAGGCAGGAGATCCTCGACCTGTG
GGTCTACCACACCCAGGGGTTCTTCCCGGACTGGCACAACTACACGCCAGGCCCGGGAACCCGCTACCCG
CTGTGCTTCGGGTGGTGCTTCAAGCTCGTCCCCATGGACCCGGCCGAGGTCGAGGAAGCCACCGAGGGCG
AGAACAACTCCCTCCTGCACCCGATCTGCCAGCACGGGATGGAGGACGAGGACCGCGAGGTGCTGGTCTG
GCGGTTCGACTCGTCCCTGGCCCGGCGCCACATCGCCCGGGAGCTCCACCCGGAGTACTACAACGACTGC
TGATAAGCTAGCGGATCCTGATCAGCCTCGACTGTGCCTTCTAGTTGCCAGCCATCTGTTGTTTGCCCT
CCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGGGGGAGGAT
TGGGAAGACAATAGCAGGCATGCTGGGGAATTT
```

Fig. 22 cont'd-16

```
AATII     GACGTC              3685                        1855    1973    1976
4 SITES                       BSPHI   TCATGA             1994    2110    2250
   2510    2563    2646        2 SITES                    2279
2832                              1007    1105              2282    3129    3166
ACCI      GTMKAC              BSPNI   CCWGG              3235    3261    3306
2 SITES                       13 SITES                    3315
   3050    3433                   52    1738    1751    FNUDII    CGCG
AFLIII    ACRYGT              1872    2475    2668       17 SITES
1 SITE                        2977                          494    1273    1854
   1897                          3270    3381    3444    2169    2257    2281
ALUI      AGCT                3478    3657    3801       2445
13 SITES                      BSSHII  GCGCGC                3039    3045    3047
    109     633    1340       1 SITE                     3062    3165    3183
1597    1643    1733             3045                     3237
1959                          BSTNI   CCWGG                 3246    3255    3625
   2184    2951    3112       13 SITES                   HAEII     RGCGCY
3524    3683    3717              52    1738    1751    4 SITES
ALWNI     CAGNNNCTG           1872    2475    2668          12    1657    2027
2 SITES                       2977                        3668
   1488    2129                  3270    3381    3444    HAEIII    GGCC
AOSII     GRCGYC              3478    3657    3801       21 SITES
7 SITES                       CFR10I  RCCGGY                 55     771    1175
   2507    2560    2643       1 SITE                     1423    1857    1875
2829    2983    3156             847                      1886
3665                          CFRI    YGGCCR                2268    2469    2662
APAI      GGGCCC              4 SITES                    3073    3093    3128
1 SITE                           769    3126    3166    3168
   3075                       3541                           3267    3323    3342
APALI     GTGCAC              CLAI    ATCGAT             3379    3481    3543
2 SITES                       1 SITE                     3660
   1583    2081                  2287                    HGIAI     GWGCWC
AVAI      CYCGRG              DDEI    CTNAG              5 SITES
3 SITES                       12 SITES                      1587    2085    2953
   3078    3482    3676           12     204     397    3114    3685
BAMHI     GGATCC               711     787    1214    1623 HHAI    GCGC
1 SITE                           2086    2158    2229    17 SITES
   3723                       3318    3861                    11     496    1273
BANI      GGYRCC              DPNI    GATC               1382    1556    1656
4 SITES                       13 SITES                   1723
    538    2850    3664           190     195     460        1993    2026    2169
3807                          1239    1247    1258       2249    3045    3047
BANII     GRGCYC              1333                        3145
5 SITES                          2972    3028    3417        3183    3255    3667
   2953    3075    3114       3594    3725    3731       HINCII    GTYRAC
3391    3685                  DRAIII  CACNNNGTG          4 SITES
BBEI      GGCGCC              1 SITE                         413     886    2369
1 SITE                           1161                    3051
   3668                       ECO47I  GGWCC              HINFI     GANTC
BCLI      TCATCA              8 SITES                    14 SITES
1 SITE                           122     586     919         43      59     357
   3729                       1048    3021    3193       383     401     725    779
BCNI      CCSGG               3535                           807    1527    1923
13 SITES                      3619                        1998    2222    2795
   1173    1521    3021       ECO0109  RGGNCCY           3648
3139    3298    3457          2 SITES                    HINPI     GCGC
3484                             3194    3340            17 SITES
   3485    3541    3663       ECORII  CCWGG                   9     494    1271
3678    3679    3691          13 SITES                   1380    1554    1654
BGLI      GCCNNNNNGGC             50    1736    1749     1721
4 SITES                       1870    2473    2666           1991    2024    2167
   2475    2597    2668       2975                       2247    3043    3045
3320                             3268    3379    3442    3143
BGLII     AGATCT              3476    3655    3799           3181    3253    3665
1 SITE                        ECORV   GATATC             HPAII     CCGG
    458                       1 SITE                     16 SITES
BSP1286   GDGCHC                 2294                        848    1172    1329
8 SITES                       FNU4HI  GCNGC              1519    1545    1692
    652    1587    2085       21 SITES                    3019
2953    3075    3114              234     769    1283        3137    3149    3297
3391                          1489    1492    1557       3456    3483    3540
                              1700                        3662
```

Fig. 22 cont'd-17

```
MAEI      CTAG
7 SITES
      378      801     1034
  1404     2385     3718
  3751
MAEII     ACGT
12 SITES
      669     1160     1196
  2306     2507     2529
  2560
  2643     2724     2829
  3219     3330
MAEIII    GTNAC
9 SITES
      270     1134     1361
  1477     1540     2446
  2533
  2882     3215
MVAI      CCNGG
26 SITES
       52     1172     1520
  1738     1751     1872
  2475
  2668     2977     3020
  3138     3270     3297
  3381
  3444     3456     3478
  3483     3484     3540
  3657
  3662     3677     3678
  3690     3801
NARI      GGCGCC
1 SITE
  3665
NCII      CCSGG
13 SITES
  1172     1520     3020
  3138     3297     3456
  3483
  3484     3540     3662
  3677     3678     3690
NCOI      CCATGG
2 SITES
  2745     3532
NDEI      CATATG
2 SITES
  2076     2619
NHEI      GCTAGC
1 SITE
  3717
NLAIII    CATG
15 SITES
      538      762      864
   892     1011     1109     1181
  1901     2219     2349
  2367     2689     2749
  3536
  3942
NLAIV     GGNNCC
13 SITES
       92      540     1830
  1869     2852     3023
  3073
  3341     3488     3538
  3666     3725     3809
NRUI      TCGCGA
1 SITE
  2257
NSII      ATGCAT

1 SITE
   796
NSP7524I  RCATGY
2 SITES
  1901     3942
NSPBII    CMGCKG
6 SITES
  1314     1559     2281
  3039     3165     3500
PPUMI     RGGWCCY
1 SITE
  3194
PSSI      RGGNCCY
2 SITES
  3197     3343
PSTI      CTGCAG
1 SITE
  3265
RSAI      GTAC
11 SITES
      559     2093     2263
  2330     2604     2684
  2717
  2768     2925     3333
  3696
SACI      GAGCTC
3 SITES
  2953     3114     3685
SACII     CCGCGG
3 SITES
  2282     3040     3166
SALI      GTCGAC
1 SITE
  3049
SAU3A     GATC
13 SITES
      188      193      458
  1237     1245     1256
  1331
  2970     3026     3415
  3592     3723     3729
SAU96A    GGNCC
18 SITES
      123      587      920
  1049     1174     2266
  2468
  2661     3022     3071
  3072     3194     3266
  3340
  3480     3536     3620
  3659
SCAI      AGTACT
1 SITE
  3696
SCRFI     CCNGG
26 SITES
       52     1172     1520
  1738     1751     1872
  2475
  2668     2977     3020
  3138     3270     3297
  3381
  3444     3456     3478
  3483     3484     3540
  3657
  3662     3677     3678
  3690     3801
SDNI      GDGCHC
8 SITES 652     1587     2085
  2953     3075     3114
  3391
  3685
SINI      GGWCC
8 SITES
      123      587      920
  1049     3022     3194
  3536
  3620
SMAI      CCCGGG
2 SITES
  3484     3678
SNABI     TACGTA
1 SITE
  2725
SPEI      ACTAGT
1 SITE
  2384
SPHI      GCATGC
1 SITE
  3942
SSPI      AATATT
2 SITES
      603      991
STUI      AGGCCT
1 SITE
       55
STYI      CCWWGG
2 SITES
  2745     3532
TAQI      TCGA
14 SITES
      216     1799     2287
  3050     3079     3105
  3199
  3222     3346     3399
  3421     3550     3646
  3738
XHOI      CTCGAG
1 SITE
  3078
XHOII     RGATCY
5 SITES
      458     1245     1256
  3415     3723
XMAI      CCCGGG
2 SITES
  3482     3676
XMAIII    CGGCCG
2 SITES
  3166     3541
XMNI      GAANNNNTTC
1 SITE
   811

FOLLOWING ENZYMES HAVE NO
SITES
ACCIII    AFLII    ASP718
ASUII     AVRII    BALI
BSPMII    BSTEII   BSTXI
DRAI      ECO47III ECORI
ESPI      FSPI     HINDIII
HPAI      KPNI     MLUI
MSTI      NAEI     NOTI
OXANI     PFLMI    PVUI
PVUII     RSRII    SFII
SPLI      TTH111I  XBAI
XCAI
```

Fig. 22 cont'd-18

Gag gene constructs:

| HVI number | Gene name | Gag | Myristylation signal mutated |
|---|---|---|---|
| HV13234 | M.con_Gag01_Dmyr.wlv | Group M (2001) | Yes |
| HV13309 | Gag-M4.1 Dmyr.wlv | Mosaic No. 1 | Yes |
| HV13316 | Gag_M4.2 Dmyr.wlv | Mosaic No. 2 | Yes |
| HV13317 | Gag_M4.3 Dmyr.wlv | Mosaic No. 3 | Yes |
| HV13318 | Gag_M4.4 Dmyr.wlv | Mosaic No. 4 | Yes |

All five constructs were cloned into HV10001 (WLV001AM DNA vaccine plasmid.

M.con_Gag01_Dmyr
MAARASVLSGGKLDAWEKIRLRPGGKKKYRLKHLVWASRELERFALNPGLLETSEGCQQIIGQLQPALQT
GSEELRSLYNTVATLYCVHQRIEVKDTKEALEKIEEEQNKSQQKTQQAAADKGNSSKVSQNYPIVQNLQG
QMVHQAISPRTLNAWVKVIEEKAFSPEVIPMFSALSEGATPQDLNTMLNTVGGHQAAMQMLKDTINEEAA
EWDRLHPVHAGPIPPGQMREPRGSDIAGTTSTLQEQIAWMTSNPPIPVGEIYKRWIILGLNKIVRMYSPV
SILDIRQGPKEPFRDYVDRFFKTLRAEQATQDVKNWMTDTLLVQNANPDCKTILKALGPGATLEEMMTAC
QGVGGPSHKARVLAEAMSQVTNAAIMMQRGNFKGQRRIIKCFNCGKEGHIARNCRAPRKKGCWKCGKEGH
QMKDCTERQANFLGKIWPSNKGRPGNFLQSRPEPTAPPAESFGFGEEITPSPKQEPKDKEPPLASLKSLF
GNDPLSQ_

HV13234 (M.con_Gag01_Dmyr.wlv) (1527nt)
XhoI
CTCGAGAAGAAAATGGCGGCTCGCGCCTCGGTCCTCAGCGGGGGCAAGTTGGATGCGTGGGAGAA
GATCCGCTTGAGGCCAGGAGGGAAGAAGAAGTACCGGCTCAAGCACCTGGTCTGGGCGAGCAGG
GAGCTGGAGCGCTTCGCGCTGAACCCGGGCCTGCTGGAGACATCCGAGGGCTGTCAGCAGATCA
TCGGGCAGCTTCAGCCAGCGCTCCAGACGGGCAGCGAGGAGCTGCGCTCGCTATACAACACGGT
AGCGACCCTCTACTGCGTGCACCAGCGGATCGAGGTCAAGGACACGAAGGAGGCTCTTGAGAAG
ATCGAGGAGGAGCAGAACAAGTCGCAGCAGAAGACCCAGCAGGCGGCGGCCGACAAGGGCAACT
CCTCAAAAGTATCTCAGAACTACCCGATCGTGCAGAACCTGCAGGGACAGATGGTCCACCAGGC
CATCAGCCCACGGACGCTTAACGCCTGGGTCAAGGTGATCGAGGAGAAGGCCTTCTCGCCGGAG
GTCATCCCCATGTTCTCGGCACTCTCCGAGGGAGCCACCCCGCAGGACCTGAACACGATGTTGA
ACACGGTCGGCGGGCACCAGGCGGCCATGCAGATGCTCAAGGATACCATCAACGAGGAGGCTGC
GGAGTGGGACCGCCTGCACCCAGTGCACGCGGGGCCCATCCCCCCGGGCCAGATGAGAGAGCCG
CGGGGATCGGACATCGCGGGCACGACCAGCACCTTGCAGGAGCAAATCGCCTGGATGACTAGCA
ACCCCCCGATCCCGGTCGGGGAGATCTACAAGCGGTGGATCATCCTCGGGTTGAACAAGATCGT
GCGGATGTACAGCCCTGTCTCAATCCTGGACATCCGGCAGGGGCCCAAGGAGCCCTTCCGCGAC
TACGTCGACCGGTTCTTCAAGACTCTCCGGGCGGAGCAGGCGACGCAGGACGTCAAGAACTGGA
TGACGGACACCTTGTTGGTCCAGAACGCTAACCCGGACTGCAAGACGATCCTGAAGGCTCTCGG
CCCGGGAGCGACCTTGGAGGAGATGATGACCGCGTGCCAGGGGGTCGGGGGACCCAGCCACAAG
GCGCGGGTCTTGGCCGAGGCGATGTCCCAGGTCACGAACGCCGCGATCATGATGCAGCGGGGGA
ACTTCAAGGGCCAGCGCCGGATCATCAAGTGCTTCAACTGCGGCAAGGAGGGCCACATCGCCCG
GAACTGCCGGGCCCCGCGGAAGAAGGGCTGCTGGAAGTGCGGAAAGGAGGGGCACCAGATGAAG
GACTGCACGGAGCGCCAGGCGAATTTCCTCGGGAAGATCTGGCCGTCCAACAAGGGGCGGCCAG
GGAACTTCCTGCAATCGCGGCCAGAGCCGACGGCCCCTCCCGCGGAGAGCTTCGGGTTCGGCGA

Fig. 22 cont'd-19

```
GGAGATCACGCCCAGCCCCAAGCAAGAGCCGAAGGACAAGGAGCCGCCCCTTGCGTCCCTCAAG
TCGCTCTTCGGCAACGACCCGCTCTCCCAA TGATAA GCTAGCGGATCCTGATCA
                                        NheI    BamHI  BclI
Cut with XhoI and NheI site for VSV subcloning.
>HV13234 in hv10001 (4,822bp)
AAATGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCTCGCGCCTCGGTCCTCAGCGGGGGCAAGTTGGATGCGTGGGAGAAGATCCGCT
TGAGGCCAGGAGGGAAGAAGAAGTACCGGCTCAAGCACCTGGTCTGGGCGAGCAGGGAGCTGGAGCGCTT
CGCGCTGAACCCGGGCCTGCTGGAGACATCCGAGGGCTGTCAGCAGATCATCGGGCAGCTTCAGCCAGCG
CTCCAGACGGGCAGCGAGGAGCTGCGCTCGCTATACAACACGGTAGCGACCCTCTACTGCGTGCACCAGC
```

Fig. 22 cont'd-20

```
GGATCGAGGTCAAGGACACGAAGGAGGCTCTTGAGAAGATCGAGGAGGAGCAGAACAAGTCGCAGCAGAA
GACCCAGCAGGCGGCGGCCGACAAGGGCAACTCCTCAAAAGTATCTCAGAACTACCCGATCGTGCAGAAC
CTGCAGGGACAGATGGTCCACCAGGCCATCAGCCCACGGACGCTTAACGCCTGGGTCAAGGTGATCGAGG
AGAAGGCCTTCTCGCCGGAGGTCATCCCCATGTTCTCGGCACTCTCCGAGGGAGCCACCCCGCAGGACCT
GAACACGATGTTGAACACGGTCGGCGGGCACCAGGCGGCCATGCAGATGCTCAAGGATACCATCAACGAG
GAGGCTGCGGAGTGGGACCGCCTGCACCCAGTGCACGCGGGGCCCATCCCCCCGGGCCAGATGAGAGAGC
CGCGGGGATCGGACATCGCGGGCACGACCAGCACCTTGCAGGAGCAAATCGCCTGGATGACTAGCAACCC
CCCGATCCCGGTCGGGGAGATCTACAAGCGGTGGATCATCCTCGGGTTGAACAAGATCGTGCGGATGTAC
AGCCCTGTCTCAATCCTGGACATCCGGCAGGGGCCCAAGGAGCCCTTCCGCGACTACGTCGACCGGTTCT
TCAAGACTCTCCGGGCGGAGCAGGCGACGCAGGACGTCAAGAACTGGATGACGGACACCTTGTTGGTCCA
GAACGCTAACCCGGACTGCAAGACGATCCTGAAGGCTCTCGGCCCGGGAGCGACCTTGGAGGAGATGATG
ACCGCGTGCCAGGGGGTCGGGGGACCCAGCCACAAGGCGCGGGTCTTGGCCGAGGCGATGTCCCAGGTCA
CGAACGCCGCGATCATGATGCAGCGGGGGAACTTCAAGGGCCAGCGCCGGATCATCAAGTGCTTCAACTG
CGGCAAGGAGGGCCACATCGCCCGGAACTGCCGGGCCCCGCGGAAGAAGGGCTGCTGGAAGTGCGGAAAG
GAGGGGCACCAGATGAAGGACTGCACGGAGCGCCAGGCGAATTTCCTCGGGAAGATCTGGCCGTCCAACA
AGGGGCGGCCAGGGAACTTCCTGCAATCGCGGCCAGAGCCGACGGCCCCTCCCGCGGAGAGCTTCGGGTT
CGGCGAGGAGATCACGCCCAGCCCCAAGCAAGAGCCGAAGGACAAGGAGCCGCCCCTTGCGTCCCTCAAG
TCGCTCTTCGGCAACGACCCGCTCTCCCAATGATAAGCTAGCGGATCCTGATCAGCCTCGACTGTGCCTT
CTAGTTGCCAGCCATCTGTTGTTTGCCCCTCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGAATTT
```

Thursday, August 2, 2007

Sequence 0   Length : 4823

| | | | | | | | | |
|---|---|---|---|---|---|---|---|---|
| AatII | GACGTC | | BanI | GGYRCC | | | 4140 | 4194 | 4374 |
| 5 Sites | | | 5 Sites | | | 4420 | 4671 | |
| 2510 | 2563 | 2646 | 538 | 2850 | 3667 | BssHII | GCGCGC | |
| 2832 | 4027 | | 4345 | 4677 | | 1 Site | | |
| AccI | GTMKAC | | BanII | GRGCYC | | 3045 | | |
| 2 Sites | | | 6 Sites | | | BstNI | CCWGG | |
| 3050 | 3979 | | 2953 | 3075 | 3754 | 19 Sites | | |
| AflIII | ACRYGT | | 3955 | 3964 | 4307 | 52 | 1738 | 1751 |
| 1 Site | | | BclI | TGATCA | | 1872 | 2475 | 2668 |
| 1897 | | | 1 Site | | | 2977 | | |
| AluI | AGCT | | 4599 | | | 3157 | 3189 | 3522 |
| 14 Sites | | | BcnI | CCSGG | | 3551 | 3672 | 3833 |
| 109 | 633 | 1340 | 14 Sites | | | 3936 | | |
| 1597 | 1643 | 1733 | 1173 | 1521 | 3021 | 4140 | 4194 | 4374 |
| 1959 | | | 3232 | 3233 | 3763 | 4420 | 4671 | |
| 2184 | 2951 | 3209 | 3764 | | | Cfr10I | RCCGGY | |
| 3278 | 3311 | 4471 | 3859 | 4003 | 4072 | 3 Sites | | |
| 4587 | | | 4105 | 4106 | 4293 | 847 | 3175 | 3982 |
| AlwNI | CAGNNNCTG | | 4303 | | | CfrI | YGGCCR | |
| 4 Sites | | | BglI | GCCNNNNNGGC | | 7 Sites | | |
| 1488 | 2129 | 3500 | 3 Sites | | | 769 | 3445 | 3676 |
| 3638 | | | 2475 | 2597 | 2668 | 4177 | 4398 | 4416 |
| AosII | GRCGYC | | BglII | AGATCT | | 4440 | | |
| 6 Sites | | | 3 Sites | | | ClaI | ATCGAT | |
| 2507 | 2560 | 2643 | 458 | 3868 | 4393 | 1 Site | | |
| 2829 | 2983 | 4024 | Bsp1286 | GDGCHC | | 2287 | | |
| ApaI | GGGCCC | | 14 Sites | | | DdeI | CTNAG | |
| 4 Sites | | | 652 | 1587 | 2085 | 13 Sites | | |
| 3075 | 3754 | 3955 | 2953 | 3075 | 3355 | 12 | 204 | 397 |
| 4307 | | | 3670 | | | 711 | 787 | 1214 | 1623 |
| ApaLI | GTGCAC | | 3745 | 3754 | 3804 | 2088 | 2158 | 2229 |
| 4 Sites | | | 3955 | 3964 | 4307 | 3111 | 3475 | 4731 |
| 1583 | 2081 | 3351 | 4348 | | | DpnI | GATC | |
| 3741 | | | BspHI | TCATGA | | 27 Sites | | |
| AvaI | CYCGRG | | 3 Sites | | | 190 | 195 | 460 |
| 6 Sites | | | 1007 | 1105 | 4213 | 1239 | 1247 | 1258 |
| 3078 | 3230 | 3761 | BspNI | CCWGG | | 1333 | | |
| 3891 | 4103 | 4386 | 19 Sites | | | 2972 | 3028 | 3144 |
| BamHI | GGATCC | | 52 | 1738 | 1751 | 3267 | 3363 | 3399 |
| 1 Site | | | 1872 | 2475 | 2668 | 3489 | | |
| 4593 | | | 2977 | | | 3564 | 3788 | 3855 |
| | | | 3157 | 3189 | 3522 | 3870 | 3885 | 3906 |
| | | | 3551 | 3672 | 3833 | 4086 | | |
| | | | 3936 | | | 4212 | 4251 | 4395 |
| | | | | | | 4491 | 4595 | 4601 |

Fig. 22 cont'd-21

```
DraIII    CACNNNGTG              4179    4240    4282         52    1172    1520
2 Sites                    4305    4400    4418        1738    1751    1872
    1161    3740           4442                        2475
Eco47I    GGWCC             4455                           2668    2977    3020
11 Sites                   HgiAI    GWGCWC             3157    3189    3231
    122    586    919      5 Sites                    3232
1048    3021    3106           1587    2085    2953        3522    3551    3672
3514                       3355    3745                3762    3763    3833
    3634    3724    4054   HhaI    GCGC                3858
4151                       21 Sites                       3936    4002    4071
Eco47III    AGCGCT              11    496    1273     4104    4105    4140
2 Sites                    1382    1556    1656       4194
    3216    3289           1723                           4292    4302    4374
EcoO109    RGGNCCY              1993    2026    2169  4420    4671
5 Sites                    2249    3045    3047       NciI    CCSGG
    3635    3750    3951   3102                       14 Sites
4152    4304                   3217    3224    3290        1172    1520    3020
EcoRII    CCWGG             3316    4169    4246      3231    3232    3762
19 Sites                   4372                       3763
    50    1736    1749     HincII    GTYRAC               3858    4002    4071
1870    2473    2666       5 Sites                    4104    4105    4292
2975                           413    886    2369     4302
    3155    3187    3520   3051    3980                NcoI    CCATGG
3549    3670    3831       HinfI    GANTC              1 Site
3934                       14 Sites                       2745
    4138    4192    4372        43    59    357       NdeI    CATATG
4418    4669               383    401    725    779   2 Sites
EcoRV    GATATC                807    1527    1923         2076    2619
1 Site                     1998    2222    2795       NheI    GCTAGC
    2294                   3995                       1 Site
Fnu4HI    GCNGC             HinPI    GCGC                 4587
32 Sites                   21 Sites                   NlaIII    CATG
    234    769    1283          9    494    1271     17 Sites
1489    1492    1557       1380    1554    1654           538    762    864
1700                       1721                       892    1011    1109    1181
    1855    1973    1976        1991    2024    2167     1901    2219    2349
1994    2110    2250       2247    3043    3045       2367    2689    2749
2279                       3100                       3602
    2282    3094    3276        3215    3222    3288     3683    4217    4812
3302    3312    3423       3314    4167    4244       NlaIV    GGNNCC
3442                       4370                       24 Sites
    3445    3676    3715   HpaII    CCGG                   92    540    1830
3780    4207    4221       20 Sites                   1869    2852    3023
4271                           848    1172    1329   3073
    4322    4416    4440   1519    1545    1692           3623    3669    3726
4530                       3019                       3751    3752    3952
FnuDII    CGCG                  3176    3231    3585  3953
23 Sites                   3762    3858    3944           3961    4153    4154
    494    1273    1854    3983                       4305    4306    4347
2169    2257    2281           4001    4071    4104  4456
2445                       4247    4292    4301           4528    4595    4679
    3039    3045    3047   MaeI    CTAG                NruI    TCGCGA
3062    3100    3222       8 Sites                    1 Site
3747                           378    801    1034         2257
    3782    3798    3970   1404    2385    3841       NsiI    ATGCAT
4134    4169    4209       4588                       1 Site
4310                       4621                           796
    4439    4464           MaeII    ACGT               Nsp7524I    RCATGY
HaeII    RGCGCY             12 Sites                   2 Sites
7 Sites                        669    1160    1196        1901    4812
    12    1657    2027     2306    2507    2519       NspBII    CMGCKG
3218    3291    4247       2560                       10 Sites
4373                           2643    2724    2829       1314    1559    2281
HaeIII    GGCC              3976    4024               3039    3115    3359
29 Sites                   MaeIII    GTNAC             3782
    55    771    1175      9 Sites                        4223    4310    4464
1423    1857    1875           270    1134    1361    PpuMI    RGGWCCY
1886                       1477    1540    2446       2 Sites
    2268    2469    2662   2533                           3635    4152
3073    3155    3235           2882    4196           PssI    RGGNCCY
3447                       MvaI    CCNGG               5 Sites
    3525    3576    3678   33 Sites                       3638    3753    3954
3752    3766    3953                                  4155    4307
4102                                                  PstI    CTGCAG
```

Fig. 22 cont'd-22

```
1 Site                    2668    2977    3020      3975
   3505                   3157    3189    3231      XhoI      CTCGAG
PvuI     CGATCG           3232                      1 Site
1 Site                       3522    3551    3672      3078
   3490                      3762    3763    3833   XhoII     RGATCY
RsaI     GTAC                3858                   7 Sites
11 Sites                     3936    4002    4071      458     1245    1256
   559     2093    2263      4104    4105    4140   3142    3868    4393
2330    2604    2684         4194                   4593
2717                         4292    4302    4374   XmaI      CCCGGG
   2768    2925    3174      4420    4671           3 Sites
3918                      SdnI     GDGCHC              3230    3761    4103
SacI     GAGCTC           14 Sites                  XmaIII    CGGCCG
1 Site                       652     1587    2085   1 Site
   2953                   2953    3075    3355         3445
SacII    CCGCGG           3670                      XmnI      GAANNNNTTC
5 Sites                      3745    3754    3804   2 Sites
   2282    3040    3783      3955    3964    4307      811     3576
4311    4465              4348
SalI     GTCGAC           SinI     GGWCC            Following enzymes have no
2 Sites                   11 Sites                  sites
   3049    3978              123     587     920   AccIII    AflII    Asp718
Sau3A    GATC             1049    3022    3107     AsuII     AvrII    BalI
27 Sites                  3515                     BbeI      BspMII   BstEII
   188     193     458       3635    3725    4055  BstXI     DraI     EcoRI
1237    1245    1256      4152                     EspI      FspI     HindIII
1331                      SmaI     CCCGGG          HpaI      KpnI     MluI
   2970    3026    3142   3 Sites                  MstI      NaeI     NarI
3265    3361    3397         3232    3763    4105  NotI      OxaNI    PflMI
3487                      SnaBI    TACGTA          PvuII     RsrII    ScaI
   3562    3786    3853   1 Site                   SfiI      SpII     XbaI
3868    3883    3904         2725                  XcaI
4084                      SpeI     ACTAGT
   4210    4249    4393   1 Site                   1 Site
4489    4593    4599         2384                     2953
Sau96A   GGNCC            SphI     GCATGC          SnaBI     TACGTA
29 Sites                  1 Site                   1 Site
   123     587     920       4812                     2725
1049    1174    2266      SspI     AATATT          SpeI      ACTAGT
2468                      2 Sites                  1 Site
   2661    3022    3071      603     991              2384
3072    3107    3233      StuI     AGGCCT          SphI      GCATGC
3515                      2 Sites                  1 Site
   3635    3725    3750      55      3576             4812
3751    3764    3951      StyI     CCWWGG          Tth111I   GACNNNGTC
3952                      3 Sites                  1 Site
   4055    4101    4152      2745    3955    4114     3975
4238    4280    4303      TaqI     TCGA            XhoI      CTCGAG
4304                      10 Sites                 1 Site
   4454                      216     1799    2287     3078
ScrFI    CCNGG            3050    3079    3364     XmaIII    CGGCCG
33 Sites                  3400                     1 Site
   52      1172    1520      3565    3979    4608     3445
1738    1751    1872      Tth111I  GACNNNGTC
2475                      1 Site
```

Gag-M4.1Dmyr
MAARASVLSGGELDRWEKIRLRPGGKKKYKLKHIVWASRELERFAVNPGLLETSEGCRQILGQL
QPSLQTGSEELRSLYNTVAVLYCVHQRIDVKDTKEALEKIEEEQNKSQQKTQQAKAADGKVSQN
YPIVQNAQGQMVHQAISPRTLNAWVKVIEEKGFSPEVIPMFSALAEGATPQDLNTMLNTIGGHQ
AAMQMLKDTINDEAAEWDRLHPVQAGPVAPGQIREPRGSDIAGTTSNLQEQIGWMTSNPPIPVG
DIYKRWIIMGLNKIVRMYSPTSILDIRQGPKESFRDYVDRFFRTLRAEQASQEVKNWMTETLLV
QNSNPDCKTILKALGPAATLEEMMTACQGVGGPGHKARVLAEAMSQVQQPNIMMQRGNFKGQKR
IKCFNCGREGHLARNCRAPRKKGCWKCGREGHQMKDCTESKANFLGKIWPSNKGRPGNFLQSRP
EPSAPPAESFGFGEEITPSQKQEQKDKELYPLASLKSLFGNDPLSQ

Fig. 22 cont'd-23

HV13309 (Gag-M4.1Dmyr.wlv)
CTCGACAAGAAAATGGCGGCGCGCGCCTCGGTCCTTAGCGGGGGCGAGTTGGATCGGTG
GGAAAAGATCCGCTTGAGGCCAGGAGGGAAGAAGAAGTACAAGCTCAAGCACATCGTCT
GGGCGAGCAGAGAGCTCGAGCGGTTCGCGGTCAACCCGGGCCTGCTTGAGACATCGGAG
GGCTGTCGGCAAATCCTGGGGCAGCTTCAACCGTCCTTGCAAACGGGCAGCGAGGAGCT
GCGATCGCTATACAACACGGTAGCGGTCCTCTACTGCGTGCACCAGCGGATCGACGTCA
AGGACACGAAGGAGGCTCTTGAAGATTGAGGAAGAGCAGAACAAGTCGCAGCAGAAG
ACGCAGCAGGCGAAGGCCGCAGACGGCAAAGTATCTCAGAACTACCCGATCGTGCAGAA
CGCGCAGGGACAGATGGTCCACCAGGCCATCTCCCCACGGACGCTTAACGCCTGGGTCA
AGTAATCGAGGAGAAGGGATTCAGCCCGGAAGTGATCCCCATGTTCTCGGCACTTGCG
GAGGGAGCCACCCCGCAGGACCTGAACACGATGTTGAACACCATCGGCGGGCACCAGGC
GGCCATGCAGATGCTTAAGGACACCATCAACGACGAGGCTGCGGAGTGGGACCGGCTTC
ACCCGGTGCAGGCGGGGCCCGTCGCGCCGGGCCAGATCAGAGAGCCGCGGGATCGGAC
ATCGCGGGAACCACCAGCAACTTGCAGGAGCAAATCGGGTGGATGACTTCGAACCCCCC
GATCCCGGTCGGGGACATCTACAAGAGATGGATCATCATGGGGTTGAACAAGATCGTGA
GGATGTACAGCCCGACCAGCATCCTGGACATCCGACAGGGACCGAAGGAGTCGTTCAGA
GACTACGTAGACCGGTTCTTCCGGACTCTCCGGGCGGAGCAGGCGTCGCAGGAGGTCAA
GAACTGGATGACGGAGACCTTGTTGGTCCAGAACTCGAACCCGGACTGCAAGACCATCC
TGAAGGCTCTCGGCCCGGCGGCGACGTTGGAAGAGATGATGACGGCGTGCCAGGGAGTC
GGGGGACCCGGCCACAAGGCGCGGGTCTTGGCCGAGGCGATGAGCCAGGTGCAGCAGCC
GAACATCATGATGCAGCGGGGCAACTTCAAGGGACAGAAGCGGATCAAGTGTTTCAACT
GTGGCAGGGAGGGACACCTCGCCAGGAACTGCCGGGCCCCGCGGAAGAAGGGCTGCTGG
AAGTGCGGAAGGGAGGGGCACCAAATGAAGGACTGCACGGAGTCGAAGGCGAATTTCCT
CGGGAAGATCTGGCCGTCCAACAAGGGGCGGCCAGGGAACTTTCTGCAAAGCCGGCCGG
AGCCGTCGGCCCCGCCGGCGGAGTCCTTTGGGTTCGGGGAGGAGATCACGCCCTCGCAG
AAGCAAGAGCAAAAGGACAAGGAGCTCTACCCTCTTGCGTCCCTCAAGTCGCTCTTCGGC
AACGACCCGCTTTCGCAATGATAAGCTAGCGGATCCTGATCAGGCGCGCC
                       NheI              AscI HV13309 in HV10001, 4836bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG

Fig. 22 cont'd-24

```
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGACAAGAAAATGGCGGCGCGCGCCTCGGTCCTTAGCGGGGGCGAGTTGGAT
CGGTGGGAAAAGATCCGCTTGAGGCCAGGAGGGAAGAAGAAGTACAAGCTCAAGCACAT
CGTCTGGGCGAGCAGAGAGCTCGAGCGGTTCGCGGTCAACCCGGGCCTGCTTGAGACAT
CGGAGGGCTGTCGGCAAATCCTGGGGCAGCTTCAACCGTCCTTGCAAACGGGCAGCGAG
GAGCTGCGATCGCTATACAACACGGTAGCGGTCCTCTACTGCGTGCACCAGCGGATCGA
CGTCAAGGACACGAAGGAGGCTCTTGAAGATTGAGGAAGAGCAGAACAAGTCGCAGC
AGAAGACGCAGCAGGCGAAGGCCGCAGACGGCAAAGTATCTCAGAACTACCCGATCGTG
CAGAACGCGCAGGGACAGATGGTCCACCAGGCCATCTCCCCACGGACGCTTAACGCCTG
GGTCAAAGTAATCGAGGAGAAGGGATTCAGCCCGGAAGTGATCCCCATGTTCTCGGCAC
TTGCGGAGGGAGCCACCCCGCAGGACCTGAACACGATGTTGAACACCATCGGCGGGCAC
CAGGCGGCCATGCAGATGCTTAAGGACACCATCAACGACGAGGCTGCGGAGTGGGACCG
GCTTCACCCGGTGCAGGCGGGGCCCGTCGCGCCGGGCCAGATCAGAGAGCCGCGGGAT
CGGACATCGCGGGAACCACCAGCAACTTGCAGGAGCAAATCGGGTGGATGACTTCGAAC
CCCCCGATCCCGGTCGGGGACATCTACAAGAGATGGATCATCATGGGGTTGAACAAGAT
CGTGAGGATGTACAGCCCGACCAGCATCCTGGACATCCGACAGGGACCGAAGGAGTCGT
TCAGAGACTACGTAGACCGGTTCTTCCGGACTCTCCGGGCGGAGCAGGCGTCGCAGGAG
```

Fig. 22 cont'd-25

GTCAAGAACTGGATGACGGAGACCTTGTTGGTCCAGAACTCGAACCCGGACTGCAAGAC
CATCCTGAAGGCTCTCGGCCCGGCGGCGACGTTGGAAGAGATGATGACGGCGTGCCAGG
GAGTCGGGGGACCCGGCCACAAGGCGCGGGTCTTGGCCGAGGCGATGAGCCAGGTGCAG
CAGCCGAACATCATGATGCAGCGGGGCAACTTCAAGGGACAGAAGCGGATCAAGTGTTT
CAACTGTGGCAGGGAGGGACACCTCGCCAGGAACTGCCGGGCCCCGCGGAAGAAGGGCT
GCTGGAAGTGCGGAAGGGAGGGGCACCAAATGAAGGACTGCACGGAGTCGAAGGCGAAT
TTCCTCGGGAAGATCTGGCCGTCCAACAAGGGGCGGCCAGGGAACTTTCTGCAAAGCCG
GCCGGAGCCGTCGGCCCCGCCGGCGGAGTCCTTTGGGTTCGGGGAGGAGATCACGCCCT
CGCAGAAGCAAGAGCAAAAGGACAAGGAGCTCTACCCTCTTGCGTCCCTCAAGTCGCTC
TTCGGCAACGACCCGCTTTCGCAATGATAAGCTAGCGGATCCTGATCAGGCGCGCCGAGCTCGC
TGATCAGCCTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGGGGAGGAT
TGGGAAGACAATAGCAGGCATGCTGGGGAATTT

| Thursday, August 2, 2007 | | 1 Site | | | 4185 | 4280 | 4408 |
|---|---|---|---|---|---|---|---|
| | | 4584 | | | 4684 | | |
| Sequence 0 Length : 4836 | | BanI | GGYRCC | | BssHII | GCGCGC | |
| | | 5 Sites | | | 4 Sites | | |
| AatII | GACGTC | 538 | 2850 | 3658 | 3045 | 3098 | 3100 |
| 5 Sites | | 4333 | 4690 | | 4599 | | |
| 2510 | 2563 | 2646 | BanII | GRGCYC | | BstNI | CCWGG |
| 2832 | 3370 | | 7 Sites | | | 18 Sites | |
| AccI | GTMKAC | 2953 | 3075 | 3211 | 52 | 1738 | 1751 |
| 2 Sites | | 3745 | 4295 | 4519 | 1872 | 2475 | 2668 |
| 3050 | 3970 | 4608 | | | 2977 | | |
| AccIII | TCCGGA | BclI | TGATCA | | 3157 | 3270 | 3513 |
| 1 Site | | 2 Sites | | | 3542 | 3663 | 3927 |
| 3982 | | 4590 | 4612 | | 4131 | | |
| AflII | CTTAAG | BcnI | CCSGG | | 4185 | 4280 | 4408 |
| 1 Site | | 14 Sites | | | 4684 | | |
| 3681 | | 1173 | 1521 | 3021 | BstXI | CCANNNNNNTGG | |
| AflIII | ACRYGT | 3232 | 3233 | 3577 | 1 Site | | |
| 1 Site | | 3730 | | | 3926 | | |
| 1897 | | 3755 | 3850 | 3994 | Cfr10I | RCCGGY | |
| AluI | AGCT | 4063 | 4096 | 4148 | 5 Sites | | |
| 16 Sites | | 4291 | | | 847 | 3718 | 3973 |
| 109 | 633 | 1340 | BglI | GCCNNNNNGGC | | 4426 | 4448 |
| 1597 | 1643 | 1733 | 4 Sites | | | CfrI | YGGCCR |
| 1959 | | | 2475 | 2597 | 2668 | 7 Sites | |
| 2184 | 2951 | 3179 | 4449 | | | 769 | 3667 | 4148 |
| 3209 | 3278 | 3311 | BglII | AGATCT | | 4168 | 4386 | 4404 |
| 4517 | | | 2 Sites | | | 4428 | | |
| 4578 | 4606 | | 458 | 4381 | | ClaI | ATCGAT |
| AlwNI | CAGNNNCTG | Bsp1286 | GDGCHC | | 1 Site | | |
| 4 Sites | | 13 Sites | | | 2287 | | |
| 1488 | 2129 | 3629 | 652 | 1587 | 2085 | DdeI | CTNAG |
| 4285 | | | 2953 | 3075 | 3211 | 13 Sites | |
| AosII | GRCGYC | 3355 | | | 12 | 204 | 397 |
| 7 Sites | | 3661 | 3745 | 4295 | 711 | 787 | 1214 | 1623 |
| 2507 | 2560 | 2643 | 4336 | 4519 | 4608 | 2088 | 2158 | 2229 |
| 2829 | 2983 | 3367 | BspHI | TCATGA | | 3111 | 3466 | 4744 |
| 4005 | | | 3 Sites | | | DpnI | GATC | |
| ApaI | GGGCCC | 1007 | 1105 | 4204 | 26 Sites | | |
| 3 Sites | | BspMII | TCCGGA | | 190 | 195 | 460 |
| 3075 | 3745 | 4295 | 1 Site | | | 1239 | 1247 | 1258 |
| ApaLI | GTGCAC | 3982 | | | 1333 | | |
| 3 Sites | | BspNI | CCWGG | | 2972 | 3028 | 3130 |
| 1583 | 2081 | 3351 | 18 Sites | | | 3144 | 3317 | 3363 |
| AsuII | TTCGAA | 52 | 1738 | 1751 | 3480 | | |
| 1 Site | | 1872 | 2475 | 2668 | 3585 | 3762 | 3779 |
| 3834 | | 2977 | | | 3846 | 3876 | 3897 |
| AvaI | CYCGRG | 3157 | 3270 | 3513 | 4242 | | |
| 3 Sites | | 3542 | 3663 | 3927 | 4383 | 4479 | 4586 |
| 3210 | 3230 | 4374 | 4131 | | | 4592 | 4614 | |
| BamHI | GGATCC | | | | DraIII | CACNNNGTG | |

Fig. 22 cont'd-26

```
2 Sites                    21 Sites                           3513     3542     3576
    1161    3731               11      496     1273       3663     3729     3754
Eco47I  GGWCC              1382    1556    1656           3849
13 Sites                   1723                               3927     3993     4062
     122     586     919       1993    2026    2169       4095     4131     4147
1048    3021    3106       2249    3045    3047           4185
3337                       3098                               4280     4290     4408
    3505    3625    3715       3100    3102    3494       4684
3941    4045    4142       3752    4160    4599           NaeI    GCCGGC
EcoO109  RGGNCCY           4601                           2 Sites
4 Sites                    HincII  GTYRAC                     4428    4450
    3626    3741    4143   5 Sites                        NciI    CCSGG
4292                            413     886    2369       14 Sites
EcoRII  CCWGG              3051    3227                       1172    1520    3020
18 Sites                   HinfI   GANTC                  3231    3232    3576
      50    1736    1749   19 Sites                       3729
1870    2473    2666             43      59     357   779     3754    3849    3993
2975                           383     401     725        4062    4095    4147
    3155    3268    3511       807    1527    1923        4290
3540    3661    3925       1998    2222    2795           NcoI    CCATGG
4129                       3568                           1 Site
    4183    4278    4406       3951    3986    4135          2745
4682                       4356    4455                   NdeI    CATATG
EcoRV   GATATC             HinPI   GCGC                   2 Sites
1 Site                     21 Sites                           2076    2619
    2294                         9     494    1271        NheI    GCTAGC
Fnu4HI  GCNGC              1380    1554    1654           1 Site
31 Sites                   1721                               4578
     234     769    1283       1991    2024    2167       NlaIII  CATG
1489    1492    1557       2247    3043    3045           18 Sites
1700                       3096                                538     762     864
    1855    1973    1976       3098    3100    3492       892    1011    1109    1181
1994    2110    2250       3750    4158    4597           1901    2219    2349
2279                       4599                           2367    2689    2749
    2282    3094    3276   HpaII   CCGG                   3593
3302    3312    3423       23 Sites                           3674    3884    4208
3435                           848    1172    1329       4825
    3448    3667    3706   1519    1545    1692           NlaIV   GGNNCC
3771    4099    4191       3019                           23 Sites
4194                           3231    3576    3719            92     540    1830
    4212    4310    4404   3729    3753    3849           1869    2852    3023
FnuDII  CGCG               3974                           3073
21 Sites                       3983    3992    4062           3614    3660    3717
     494    1273    1854   4095    4147    4289           3742    3743    3794
2169    2257    2281       4427                           3943
2445                           4431    4449                   4144    4145    4293
    3039    3045    3047   MaeI    CTAG                   4294    4335    4435
3062    3098    3100       7 Sites                        4444
3222                            378     801    1034           4586    4692
    3492    3750    3773   1404    2385    4579           NruI    TCGCGA
3789    4160    4298       4634                           1 Site
4599                       MaeII   ACCT                       2257
HaeII   RGCGCY             13 Sites                       NsiI    ATGCAT
3 Sites                         669    1160    1196       1 Site
      12    1657    2027   2306    2507    2519               796
HaeIII  GGCC               2560                           Nsp7524I RCATGY
26 Sites                       2643    2724    2829       2 Sites
      55     771    1175   3367    3967    4104              1901    4825
1423    1857    1875       MaeIII  GTNAC                  NspBII  CMGCKG
1886                       8 Sites                        8 Sites
    2268    2469    2662        270    1134    1361          1314    1559    2281
3073    3155    3235       1477    1540    2446           3039    3359    3773
3447                       2533                           4214
    3516    3669    3743       2882                           4298
3757    4093    4150       MvaI    CCNGG                  PpuMI   RGGWCCY
4170                       32 Sites                       2 Sites
    4293    4388    4406        52    1172    1520           3626    4143
4430    4443               1738    1751    1872           PssI    RGGNCCY
HgiAI   GWGCWC             2475                           4 Sites
7 Sites                        2668    2977    3020           3629    3744    4146
    1587    2085    2953   3157    3231    3232           4295
3211    3355    4519       3270                           PvuI    CGATCG
4608                                                      2 Sites
HhaI    GCGC                                                  3318    3481
```

Fig. 22 cont'd-27

```
RsaI       GTAC                  ScrFI      CCNGG              603       991
11 Sites                         32 Sites                 StuI       AGGCCT
    559      2093     2263           52     1172     1520  1 Site
   2330      2604     2684         1738     1751     1872      55
   2717                            2475                    StyI       CCWWGG
   2768      2925     3174         2668     2977     3020  1 Site
   3909                            3157     3231     3232      2745
SacI       GAGCTC                  3270                    TaqI       TCGA
4 Sites                            3513     3542     3576  12 Sites
   2953      3211     4519         3663     3729     3754      216     1799     2287
   4608                            3849                       3050     3079     3211
SacII      CCGCGG                  3927     3993     4062     3364
4 Sites                            4095     4131     4147      3556     3834     4056
   2282      3040     3774         4185                       4359     4621
   4299                            4280     4290     4408  XhoI       CTCGAG
SalI       GTCGAC                  4684                    1 Site
1 Site                         SdnI       GDGCHC                3210
   3049                        13 Sites                   XhoII      RGATCY
Sau3A      GATC                     652     1587     2085  6 Sites
26 Sites                           2953     3075     3211      458     1245     1256
    188       193      458         3355                       3142     4381     4584
   1237      1245     1256         3661     3745     4295  XmaI       CCCGGG
   1331                            4336     4519     4608  1 Site
   2970      3026     3128     SinI       GGWCC                3230
   3142      3315     3361     13 Sites                   XmaIII     CGGCCG
   3478                             123      587      920  1 Site
   3583      3760     3777         1049     3022     3107      4428
   3844      3874     3895         3338                    XmnI       GAANNNNTTC
   4240                            3506     3626     3716  2 Sites
   4381      4477     4584         3942     4046     4143      811     3567
   4590      4612                SmaI       CCCGGG
Sau96A     GGNCC                 1 Site                    Following enzymes have no
27 Sites                            3232                   sites
    123       587      920     SnaBI      TACGTA           Asp718    AvrII     BalI
   1049      1174     2266     2 Sites                     BbeI      BstEII    DraI
   2468                            2725     3968          Eco47III  EcoRI     EspI
   2661      3022     3071     SpeI       ACTAGT          FspI      HindIII   HpaI
   3072      3107     3233     1 Site                     KpnI      MluI      MstI
   3338                            2384                   NarI      NotI      OxaNI
   3506      3626     3716     SphI       GCATGC          Pf1MI     PstI      PvuII
   3741      3742     3755     1 Site                     RsrII     ScaI      SfiI
   3942                            4825                   SplI      Tth111I   XbaI
   4046      4092     4143     SspI       AATATT          XcaI
   4291      4292     4442     2 Sites
```

Gag_M4.2 Dmyr
MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQN
YPIVQNIQGQMVHQPISPRTLNAWVKVVEEKAFSPEVIPMFTALSDGATPQDLNSMLNAVGGHQ
AAMQILKDTINEEAADWDRLHPVHAGPVAPGQMREPRGSDIAGTTSTLQEQIGWMTNNPPIPVG
EIYKRWIILGLNKIVRMYSPVSILDIKQGPKESFRDYVDRFFKVLRAEQATQDVKNWMTDTLLI
QNANPDCKSILRALGPGATLEEMMTACQGVGGPSHKARILAEAMSQVTNSATIMMQRGNFRNQR
KTVKCFNCGKEGHLARNCKAPRKRGCWKCGKEGHQMKECTERQANFLGKIWPSSKGRPGNFPQS
RPEPTAPPEESFRFGEETTTPSQKQEPIDKELYPLASLRSLFGNDPSSQAS HV13316 (Gag_M4.2 Dmyr.wlv) cloned in to XhoI
GTCGAGAAGAAAATGGCGGCTCGCGCCTCGGTCCTTAGCGGGGGCAAGTTGGATGCGTGGGAAA
AGATCCGCTTGAGGCCAGGAGGGAAGAAGAAGTACCGGCTCAAGCACCTTGTCTGGGCGAGCAG
AGAGCTCGACCGGTTCGCGCTGAACCCGTCGCTGCTTGAGACAGCCGAGGGCTGCAAGCAAATC
ATGAAGCAGCTTCAACCGGCGTTGAAGACGGGCACGGAGGAGCTGAAGTCGCTATACAACACGG
TAGCGACGCTCTACTGCGTGCACGAGAAGATCGACGTCAGGGACACGAAGGAGGCTCTTGACAA

Fig. 22 cont'd-28

```
GATTGAGGAAGAGCAGAACAAGATCCAGCAGAAGACGCAGCAGGCGAAGGAGGCAGACGGCAAA
GTATCTCAGAACTACCCGATCGTGCAGAACATCCAGGGACAGATGGTCCACCAGCCGATCTCCC
CACGGACGCTTAACGCCTGGGTCAAAGTAGTCGAGGAGAAGGCATTCAGCCCGGAAGTGATCCC
CATGTTCACTGCACTTAGCGACGGAGCCACCCCGCAGGACCTGAACAGCATGTTGAACGCCGTC
GGCGGGCACCAGGCGGCCATGCAGATCCTTAAGGACACCATCAACGAGGAGGCTGCGGACTGGG
ACCGGCTTCACCCGGTGCACGCGGGGCCCGTCGCGCCGGGCCAGATGAGAGAGCCGCGGGGATC
GGACATCGCGGAACCACCAGCACCTTGCAGGAGCAAATCGGGTGGATGACTAACAACCCCCCG
ATCCCGGTCGGGGAGATCTACAAGAGATGGATCATCCTGGGGTTGAACAAGATCGTGAGGATGT
ACAGCCCAGTCAGCATCCTGGACATCAAGCAGGGACCGAAGGAGTCGTTCAGAGACTACGTCGA
CCGGTTCTTCAAAGTCCTCCGGGCGGAGCAGGCGACGCAGGACGTCAAGAACTGGATGACGGAC
ACCTTGTTGATCCAGAACGCGAACCCGGACTGCAAGTCGATCCTGCGGGCTCTCGGCCCGGGAG
CGACGTTGGAAGAGATGATGACGGCGTGCCAGGGAGTCGGGGGACCCTCGCACAAGGCGCGGAT
CTTGGCCGAGGCGATGTCACAAGTGACTAACAGCGCGACCATCATGATGCAGCGGGGCAACTTC
CGGAACCAGCGGAAGACGGTGAAGTGTTTCAACTGTGGCAAGGAGGGACACCTCGCCAGGAACT
GCAAGGCCCCGCGGAAGCGGGGCTGCTGGAAGTGCGGAAAGGAGGGGCACCAAATGAAGGAGTG
CACGGAGCGGCAGGCGAATTTCCTCGGGAAGATCTGGCCGTCCTCGAAGGGGCGGCCAGGGAAC
TTTCCGCAAAGCCGGCCGGAGCCGACGGCCCCGCCGGAGGAGTCCTTTCGGTTCGGGGAGGAGA
CGACCACGCCCTCGCAGAAGCAAGAGCCGATCGACAAGGAGCTCTACCCTCTTGCGTCCCTCCG
GTCGCTCTTCGGCAACGACCCGTCGTCGCAAGCGTCGTGATAAGCTAGCGGATCCGGCGCGCC
                                        NheI        AscI
>HV13316 in HV10001 4816bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTAGTCATTATTATTGGTCCGTTCATAACACCCCTTGTATTACTGTTTATGTAAG
CAGACAGTTTTATTGTTCATGATGATATATTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
```

Fig. 22 cont'd-29

```
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTAGCGGGGCAAGTTGGATGCGTGGGAAAAGATCCGCTTGAGGCCAGGAGGGA
AGAAGAAGTACCGGCTCAAGCACCTTGTCTGGGCGAGCAGAGAGCTCGACCGGTTCGCGCTGAA
CCCGTCGCTGCTTGAGACAGCCGAGGGCTGCAAGCAAATCATGAAGCAGCTTCAACCGGCGTTG
AAGACGGGCACGGAGGAGCTGAAGTCGCTATACAACACGGTAGCGACGCTCTACTGCGTGCACG
AGAAGATCGACGTCAGGGACACGAAGGAGGCTCTTGACAAGATTGAGGAAGAGCAGAACAAGAT
CCAGCAGAAGACGCAGCAGGCGAAGGAGGCAGACGGCAAAGTATCTCAGAACTACCCGATCGTG
CAGAACATCCAGGGACAGATGGTCCACCAGCCGATCTCCCCACGGACGCTTAACGCCTGGGTCA
AAGTAGTCGAGGAGAAGGCATTCAGCCCGGAAGTGATCCCCATGTTCACTGCACTTAGCGACGG
AGCCACCCCGCAGGACCTGAACAGCATGTTGAACGCCGTCGGCGGGCACCAGGCGGCCATGCAG
ATCCTTAAGGACACCATCAACGAGGAGGCTGCGGACTGGGACCGGCTTCACCCGGTGCACGCGG
GGCCCGTCGCGCCGGGCCAGATGAGAGAGCCGCGGGGATCGGACATCGCGGGAACCACCAGCAC
CTTGCAGGAGCAAATCGGGTGGATGACTAACAACCCCCGATCCCGGTCGGGGAGATCTACAAG
AGATGGATCATCCTGGGGTTGAACAAGATCGTGAGGATGTACAGCCCAGTCAGCATCCTGGACA
TCAAGCAGGGACCGAAGGAGTCGTTCAGAGACTACGTCGACCGGTTCTTCAAAGTCCTCCGGGC
GGAGCAGGCGACGCAGGACGTCAAGAACTGGATGACGGACACCTTGTTGATCCAGAACGCGAAC
CCGGACTGCAAGTCGATCCTGCGGGCTCTCGGCCCGGGAGCGACGTTGGAAGAGATGATGACGG
CGTGCCAGGGAGTCGGGGACCCTCGCACAAGGCGCGGATCTTGGCCGAGGCGATGTCACAAGT
GACTAACAGCGCGACCATCATGATGCAGCGGGGCAACTTCCGGAACCAGCGGAAGACGGTGAAG
TGTTTCAACTGTGGCAAGGAGGGACACCTCGCCAGGAACTGCAAGGCCCCGCGGAAGCGGGGCT
GCTGGAAGTGCGGAAAGGAGGGGCACCAAATGAAGGAGTGCACGGAGCGGCAGGCGAATTTCCT
CGGGAAGATCTGGCCGTCCTCGAAGGGGCGGCCAGGGAACTTTCCGCAAAGCCGGCCGGAGCCG
ACGGCCCCGCCGGAGGAGTCCTTTCGGTTCGGGGAGGAGACGACCACGCCCTCGCAGAAGCAAG
AGCCGATCGACAAGGAGCTCTACCCTCTTGCGTCCCTCCGGTCGCTCTTCGGCAACGACCCGTC
GTCGCAAGCGTCGTGATAAGCTAGCGGATCCGGCGCGCCGAGCTCGCTGATCAGCCTCGACTGT
GCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTC
ATTCTATTCTGGGGGGTGGGTGGGGCAGGACAGCAAGGGGGAGGATTGGGAAGACAATAGCAG
GCATGCTGGGGAATTT
```

Fig. 22 cont'd-30

```
         2510    2563    2646          3632    3707    3716          3596    3686    3912
2832     3341    3989          4059    4313    4330          4113
AccI     GTMKAC                4499                          EcoO109  RGGNCCY
1 Site                         4588                          4 Sites
   3941                        BspHI    TCATGA                  3597    3712    4114
AccIII   TCCGGA                4 Sites                       4269
1 Site                            1007    1105    3239       EcoRII   CCWGG
   4199                        4178                          17 Sites
AflII    CTTAAG                BspMII   TCCGGA                     50    1736    1749
1 Site                         1 Site                        1870    2473    2666
   3652                           4199                       2975
AflIII   ACRYGT                BspNI    CCWGG                3126    3464    3511
1 Site                         17 Sites                      3632    3851    3896
   1897                              52    1738    1751      4100
AluI     AGCT                  1872    2475    2668          4255    4383    4662
15 Sites                       2977                          EcoRV    GATATC
     109     633    1340       3128    3466    3513          1 Site
1597    1643    1733           3634    3853    3898             2294
1959                           4102                          Fnu4HI   GCNGC
   2184    2951    3180           4257    4385    4664      27 Sites
3249    3282    4497           BssHII   GCGCGC                  234     769    1283
4564                           2 Sites                       1489    1492    1557
   4586                           3045    4579              1700
AlwNI    CAGNNNCTG             BstNI    CCWGG                1855    1973    1976
4 Sites                        17 Sites                      1994    2110    2250
   1488    2129    3600              52    1738    1751     2279
4262                           1872    2475    2668          2282    3065    3208
AosII    GRCGYC                2977                          3228    3247    3406
7 Sites                           3128    3466    3513       3638
   2507    2560    2643        3634    3853    3898          3677    3742    4186
2829    2983    3338           4102                          4287    4336    4381
3986                              4257    4385    4664      PnuDII   CGCG
ApaI     GGGCCC                Cfr10I   RCCGGY               21 Sites
1 Site                         7 Sites                           494    1273    1854
   3716                            847    3146    3185       2169    2257    2281
ApaLI    GTGCAC                3255    3689    3944          2445
5 Sites                        4403                             3039    3045    3047
   1583    2081    3322        CfrI     YGGCCR               3071    3193    3709
3703    4326                   6 Sites                       3721
AvaI     CYCGRG                    769    3638    4139          3744    3760    4027
2 Sites                        4363    4381    4405          4131    4171    4275
   4065    4351                ClaI     ATCGAT               4579
BamHI    GGATCC                1 Site                        HaeII    RGCGCY
1 Site                            2287                       3 Sites
   4570                        DdeI     CTNAG                     12    1657    2027
BanI     GGYRCC                14 Sites                      HaeIII   GGCC
5 Sites                              12     204     397      21 Sites
     538    2850    3629        711     787    1214    1623       55     771    1175
4310    4670                      2088    2158    2229      1423    1857    1875
BanII    GRGCYC                3082    3437    3574          1886
6 Sites                        4724                             2268    2469    2662
   2953    3182    3716        DpnI     GATC                 3126    3640    3714
4059    4499    4588           28 Sites                      3728
BclI     TGATCA                     190     195     460         4064    4141    4270
1 Site                         1239    1247    1258          4365    4383    4407
   4592                        1333                          4420
BcnI     CCSGG                    2972    3028    3115       HgiAI    GWGCWC
11 Sites                       3334    3391    3451          9 Sites
   1173    1521    3021        3490                             1587    2085    2953
3548    3701    3726              3556    3649    3750       3182    3326    3707
3821                           3817    3832    3847          4330
   3965    4034    4067        3868                             4499    4588
4068                              4018    4048    4135      HhaI     GCGC
BglI     GCCNNNNNGGC           4360    4486    4572          20 Sites
3 Sites                        4594                               11     496    1273
   2475    2597    2668        DraIII   CACNNNGTG            1382    1556    1656
BglII    AGATCT                2 Sites                       1723
3 Sites                           1161    3702                  1993    2026    2169
     458    3830    4358       Eco47I   GGWCC                2249    3045    3047
Bsp1286  GDGCHC                11 Sites                      3073
15 Sites                            122     586     919         3195    3723    4131
     652    1587    2085       1048    3021    3077          4171    4579    4581
2953    3182    3274           3476                          HincII   GTYRAC
3326                                                         4 Sites
```

Fig. 22 cont'd-31

```
         413       886      2369          3964      4033      4066           3940
3942                                   4067                                Sau3A      GATC
HinfI      GANTC                       NcoI       CCATGG                   28 Sites
16 Sites                               1 Site                                   188       193       458
        43        59       357              2745                           1237      1245      1256
   383       401       725       779   NdeI       CATATG                   1331
       807      1527      1923         2 Sites                                  2970      3026      3113
      1998      2222      2795              2076      2619                      3332      3389      3449
      3922                              NheI       GCTAGC                       3488
      4106      4432                   1 Site                                   3554      3647      3748
HinPI      GCGC                             4564                                3815      3830      3845
20 Sites                               NlaIII     CATG                          3866
         9       494      1271         19 Sites                                 4016      4046      4133
      1380      1554      1654              538       762       864             4358      4484      4570
      1721                               892      1011      1109      1181      4592
      1991      2024      2167              1901      2219      2349       Sau96A     GGNCC
      2247      3043      3045              2367      2689      2749       21 Sites
      3071                                   3243                               123       587       920
      3193      3721      4129              3564      3612      3645       1049      1174      2266
      4169      4577      4579              4182      4805                 2468
HpaII      CCGG                        NlaIV      GGNNCC                        2661      3022      3078
25 Sites                               22 Sites                            3477      3597      3687
       848      1172      1329               92       540      1830        3712
      1519      1545      1692              1869      2852      3023            3713      3726      3913
      3019                                   3585                               4063      4114      4269
      3147      3186      3256              3631      3688      3713            4419
      3547      3690      3700              3714      3765      3914       ScrFI      CCNGG
      3724                                   4115                          28 Sites
      3820      3945      3963              4116      4204      4271            52      1172      1520
      4033      4066      4200              4312      4412      4421       1738      1751      1872
      4404                                   4572                          2475
      4408      4426      4518              4672                                2668      2977      3020
      4574                              NruI       TCGCGA                   3128      3466      3513
MaeI       CTAG                        1 Site                              3547
7 Sites                                     2257                                3634      3700      3725
       378       801      1034         NsiI       ATGCAT                   3820      3853      3898
      1404      2385      4565         1 Site                              3964
      4614                                  796                                 4033      4066      4067
MaeII      ACGT                        Nsp7524I   RCATGY                   4102      4257      4385
14 Sites                               3 Sites                             4664
       669      1160      1196              1901      3612      4805       SdnI       GDGCHC
      2306      2507      2519         NspBII     CMGCKG                   15 Sites
      2560                             8 Sites                                   652      1587      2085
      2643      2724      2829              1314      1559      2281       2953      3182      3274
      3338      3938      3986              3039      3744      4188       3326
      4075                                   4209                               3632      3707      3716
MaeIII     GTNAC                            4275                                4059      4313      4330
10 Sites                               PpuMI      RGGWCCY                  4499
       270      1134      1361         2 Sites                                  4588
      1477      1540      2446              3597      4114                 SinI       GGWCC
      2533                             PssI       RGGNCCY                  11 Sites
      2882      4151      4158         4 Sites                                  123       587       920
MvaI       CCNGG                            3600      3715      4117       1049      3022      3078
28 Sites                                    4272                           3477
        52      1172      1520         PvuI       CGATCG                        3597      3687      3913
      1738      1751      1872         2 Sites                             4114
      2475                                   3452      4487                SmaI       CCCGGG
      2668      2977      3020         RsaI       GTAC                     1 Site
      3128      3466      3513         11 Sites                                 4067
      3547                                   559      2093      2263       SnaBI      TACGTA
      3634      3700      3725              2330      2604      2684       1 Site
      3820      3853      3898              2717                                2725
      3964                                   2768      2925      3145       SpeI       ACTAGT
      4033      4066      4067              3880                           1 Site
      4102      4257      4385         SacI       GAGCTC                        2384
      4664                             4 Sites                             SphI       GCATGC
NaeI       GCCGGC                           2953      3182      4499       1 Site
1 Site                                      4588                                4805
      4405                             SacII      CCGCGG                   SspI       AATATT
NciI       CCSGG                       4 Sites                             2 Sites
11 Sites                                    2282      3040      3745            603       991
      1172      1520      3020              4276                           StuI       AGGCCT
      3547      3700      3725         SalI       GTCGAC                   1 Site
      3820                             1 Site                                    55
```

Fig. 22 cont'd-32

```
StyI       CCWWGG              Tth111I    GACNNNGTC            1 Site
1 Site                         1 Site                             4065
   2745                           3937                         XmaIII     CGGCCG
TaqI       TCGA                XhoII      RGATCY              1 Site
12 Sites                       10 Sites                           4405
     216      1799     2287         458      1245     1256    XmnI       GAANNNNTTC
   3050      3182      3335       3113     3389      3647     3 Sites
   3527                            3830                            811      3538     4225
   3941      4045      4372       4133      4358     4570
   4487      4601                 XmaI      CCCGGG
```

Need re-create XhoI site at the 5' end
Primer:
Gag-M2-4-fG/C:
GGGCGCCTCGAGAAGAAA<u>ATG</u>GCGGCTCG Gag_M4.3 Dmyr
MAARASILRGGKLDKWEKIRLRPGGKKRYMLKHLIWASRELERFALNPGLLETAEGCQQIIEQL
QSTLKTGSEELKSLFNTVATLYCVHQRIEVKDTKEALDKVEEEQNKSKKKAQQAAADTGNSSQV
SQNYPIVQNLQGQMVHQALSPRTLNAWVKVIEEKAFSPEIIPMFTALSEGATPSDLNTMLNTVG
GHQAAMQMLKDTINEEAAEWDRVHPVHAGPIPPGQMREPRGSDIAGTTSSLQEQIAWMTSNPPV
PVGEIYKRWIVLGLNKIVRMYSPVSILDIRQGPKEPFRDYVDRFFKTLRAEQASQDVKNWMTET
LLVQNANPDCKTILRALGPGASLEEMMTACQGVGGPSHKARVLAEAMSQTNSAILMQRSNFKGS
KRIVKCFNCGKEGHIARNCRAPRKRGCWKCGQEGHQMKDCNERQANFLGKIWPSHKGRPGNFLQ
NRPEPTAPPEPTAPPAESFRFEETTPAPKQELKDREPLTSLKSLFGSDPLSQAS HV13317 (Gag_M4.3 Dmyr.wlv)
GTCGAGAAGAAA<u>AT</u>GGCGGCTCGCGCCTCGATCCTTCGAGGGGGCAAGTTGGATAAGTGGGAAA
AGATCCGCTTGAGGCCAGGAGGGAAGAAGAGATACATGCTCAAGCACCTGATCTGGGCGAGCAG
AGAGCTGGAGCGGTTCGCGCTGAACCCGGGCCTGCTTGAGACAGCGGAGGGCTGTCAGCAAATC
ATCGAGCAGCTTCAAAGCACGCTGAAGACGGGCAGCGAGGAGCTGAAGTCGCTATTCAACACGG
TAGCGACCCTCTACTGCGTGCACCAGCGGATCGAGGTCAAGGACACGAAGGAGGCTCTTGACAA
GGTGGAGGAAGAGCAGAACAAGTCGAAGAAGAAGGCGCAGCAGGCGGCGGCCGACACCGGCAAC
TCCTCACAAGTATCTCAGAACTACCCGATCGTGCAGAACCTGCAGGGACAGATGGTCCACCAGG
CCCTCTCCCCACGGACGCTTAACGCCTGGGTCAAAGTAATCGAGGAGAAGGCCTTCAGCCCGGA
AATCATCCCCATGTTCACAGCACTTTCCGAGGGAGCCACCCCGAGCGACCTGAACACGATGTTG
AACACCGTCGGCGGGCACCAGGCGGCCATGCAGATGCTTAAGGACACCATCAACGAGGAGGCTG
CGGAGTGGGACCGGGTGCACCCGGTGCACGCGGGGCCCATCCCACCGGGCCAGATGAGAGAGCC
GCGGGGATCGGACATCGCGGGAACCACCAGCAGCTTGCAGGAGCAAATCGCCTGGATGACTTCG
AACCCCCCGGTCCCGGTCGGGGAGATCTACAAGAGATGGATCGTCCTCGGGTTGAACAAGATCG
TGAGGATGTACAGCCCTGTGTCAATCCTGGACATCCGACAGGGACCGAAGGAGCCCTTCAGAGA
CTACGTCGACCGGTTCTTCAAGACTCTCCGGGCGGAGCAGGCGTCGCAGGACGTCAAGAACTGG
ATGACGGAGACCTTGTTGGTCCAGAACGCTAACCCGGACTGCAAGACCATCCTGCGCGCTCTCG
GCCCGGGAGCGTCCTTGGAAGAGATGATGACGGCGTGCCAGGGAGTCGGGGGACCCTCACACAA
GGCGCGGGTCTTGGCCGAGGCGATGAGCCAGACGAACTCCGCCATCCTCATGCAGCGGTCCAAC
TTCAAGGGAAGCAAGCGGATCGTCAAGTGTTTCAACTGTGGCAAGGAGGGACACATCGCCAGGA
ACTGCCGGGCCCCGCGGAAGCGAGGCTGCTGGAAGTGCGGACAGGAGGGGCACCAAATGAAGGA
CTGCAACGAGCGCCAGGCGAATTTCCTCGGGAAGATCTGGCCGTCCCACAAGGGGCGGCCAGGG
AACTTCCTTCAAAACCGGCCAGAGCCGACGGCCCCTCCCGAGCCGACCGCCCCGCCGGCGGAGT
CCTTTCGCTTCGAGGAGACCACGCCCGCCCCAAGCAAGAGCTCAAGGACCGCGAGCCTCTTAC

Fig. 22 cont'd-33

CTCCCTCAAGTCGCTCTTCGGCTCCGACCCGCTTTCGCAAGCGTCG*TGATAA*GCTAGCGGATCC
GGCGCGC
AscI                                                          NheI
Need re-create XhoI site at the 5' end HV13317 in HV10001 4824bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG

Fig. 22 cont'd-34

```
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGATCCTTCGAGGGGGCAAGTTGGATAAGTGGGAAAAGATCCGCTTGAGGCCAGGAGGGA
AGAAGAGATACATGCTCAAGCACCTGATCTGGGCGAGCAGAGAGCTGGAGCGGTTCGCGCTGAA
CCCGGGCCTGCTTGAGACAGCGGAGGGCTGTCAGCAAATCATCGAGCAGCTTCAAAGCACGCTG
AAGACGGGCAGCGAGGAGCTGAAGTCGCTATTCAACACGGTAGCGACCCTCTACTGCGTGCACC
AGCGGATCGAGGTCAAGGACACGAAGGAGGCTCTTGACAAGGTGGAGGAAGAGCAGAACAAGTC
GAAGAAGAAGGCGCAGCAGGCGGCGGCCGACACCGGCAACTCCTCACAAGTATCTCAGAACTAC
CCGATCGTGCAGAACCTGCAGGGACAGATGGTCCACCAGGCCCTCTCCCCACGGACGCTTAACG
CCTGGGTCAAAGTAATCGAGGAGAAGGCCTTCAGCCCGGAAATCATCCCCATGTTCACAGCACT
TTCCGAGGGAGCCACCCCGAGCGACCTGAACACGATGTTGAACACCGTCGGCGGGCACCAGGCG
GCCATGCAGATGCTTAAGGACACCATCAACGAGGAGGCTGCGGAGTGGGACCGGGTGCACCCGG
TGCACGCGGGGCCCATCCCACCGGGCCAGATGAGAGAGCCGCGGGGATCGGACATCGCGGGAAC
CACCAGCAGCTTGCAGGAGCAAATCGCCTGGATGACTTCGAACCCCCCGGTCCCGGTCGGGGAG
ATCTACAAGAGATGGATCGTCCTCGGGTTGAACAAGATCGTGAGGATGTACAGCCCTGTGTCAA
TCCTGGACATCCGACAGGGACCGAAGGAGCCCTTCAGAGACTACGTCGACCGGTTCTTCAAGAC
TCTCCGGGCGGAGCAGGCGTCGCAGGACGTCAACAACTGGATGACGGAGACCTTGTTGGTCCAG
AACGCTAACCCGGACTGCAAGACCATCCTGCGCGCTCTCGGCCCGGGAGCGTCCTTGGAAGAGA
TGATGACGGCGTGCCAGGGAGTCGGGGGACCCTCACACAAGGCGCGGGTCTTGGCCGAGGCGAT
GAGCCAGACGAACTCCGCCATCCTCATGCAGCGGTCCAACTTCAAGGGAAGCAAGCGGATCGTC
AAGTGTTTCAACTGTGGCAAGGAGGGACACATCGCCAGGAACTGCCGGGCCCCGCGGAAGCGAG
GCTGCTGGAAGTGCGGACAGGAGGGGCACCAAATGAAGGACTGCAACGAGCGCCAGGCGAATTT
CCTCGGGAAGATCTGGCCGTCCCACAAGGGGCGGCCAGGGAACTTCCTTCAAAAACCGGCCAGAG
CCGACGGCCCCTCCCGAGCCGACCGCCCCGCGGCGGAGTCCTTTCGCTTCGAGGAGACCACGC
CCGCCCCCAAGCAAGAGCTCAAGGACCGCGAGCCTCTTACCTCCCTCAAGTCGCTCTTCGGCTC
CGACCCGCTTTCGCAAGCGTCGTGATAAGCTAGCGGATCCGGCGCGCGAGCTCGCTGATCAGCC
TCGACTGTGCCTTCTAGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAGAC
AATAGCAGGCATGCTGGGAATTT
```

Thursday, August 2, 2007

Sequence 2    Length : 4824

| | | | | | |
|---|---|---|---|---|---|
| AatII | GACGTC | | 2184 | 2951 | 3180 |
| 5 Sites | | 3249 | 3282 | 3785 | |
| 2510 | 2563 | 2646 | 4497 | | |
| 2832 | 3998 | | 4573 | 4594 | |
| AccI | GTMKAC | | AlwNI | CAGNNNCTG | |
| 1 Site | | 4 Sites | | | |
| 3950 | | | 1488 | 2129 | 3471 |
| AflII | CTTAAG | | 4265 | | |
| 1 Site | | | AosII | GRCGYC | |
| 3661 | | | 7 Sites | | |
| AflIII | ACRYGT | | 2507 | 2560 | 2643 |
| 1 Site | | | 2829 | 2983 | 3985 |
| 1897 | | | 3995 | | |
| AluI | AGCT | | ApaI | GGGCCC | |
| 16 Sites | | 2 Sites | | | |
| 109 | 633 | 1340 | 3725 | 4275 | |
| 1597 | 1643 | 1733 | ApaLI | GTGCAC | |
| 1959 | | | 5 Sites | | |
| | | | 1583 | 2081 | 3322 |
| | | | 3703 | 3712 | |
| | | | AsuII | TTCGAA | |
| | | | 1 Site | | |
| | | | 3814 | | |
| | | | AvaI | CYCGRG | |

| | | | | |
|---|---|---|---|---|
| 6 Sites | | | | |
| 3201 | 3600 | 3862 | | |
| 4074 | 4354 | 4429 | | |
| BamHI | GGATCC | | | |
| 1 Site | | | | |
| 4579 | | | | |
| BanI | GGYRCC | | | |
| 5 Sites | | | | |
| 538 | 2850 | 3638 | | |
| 4313 | 4678 | | | |
| BanII | GRGCYC | | | |
| 6 Sites | | | | |
| 2953 | 3725 | 3935 | | |
| 4275 | 4499 | 4596 | | |
| BclI | TGATCA | | | |
| 1 Site | | | | |
| 4600 | | | | |
| BcnI | CCSGG | | | |
| 16 Sites | | | | |
| 1173 | 1521 | 3021 | | |
| 3203 | 3204 | 3557 | | |
| 3701 | | | | |

Fig. 22 cont'd-35

```
       3710     3735     3824         4602                          1587     2085     2953
3830       3974      4043         DraIII    CACNNNGTG        3326      3707     3716
4076                              2 Sites                    4499
       4077     4271                 1161     3711               4596
BglI       GCCNNNNNGGC             Eco47I    GGWCC           HhaI       GCGC
4 Sites                            13 Sites                  22 Sites
       2475     2597     2668         122      586      919         11      496     1273
4447                              1048     3021     3485     1382      1556     1656
BglII      AGATCT                  3695                      1723
3 Sites                                3824     3921     4025       1993     2026     2169
        458     3839     4361      4122     4192     4502    2249      3045     3047
Bsp1286    GDGCHC                  Eco0109   RGGNCCY         3073
14 Sites                           4 Sites                          3195     3405     4064
        652     1587     2085         3495     3721     4123    4066      4140     4340
2953      3326     3641            4272                      4588
3707                               EcoRII    CCWGG               4590
       3716     3725     3935      18 Sites                  HincII     GTYRAC
4275      4316     4499                 50     1736     1749 4 Sites
4596                               1870     2473     2666            413      886     2369
BspHI      TCATGA                  2975                      3951
2 Sites                                3126     3491     3520 HinfI     GANTC
       1007     1105               3641     3802     3905    16 Sites
BspNI      CCWGG                   4109                             43       59      357
18 Sites                               4258     4340     4386  383      401      725      779
         52     1738     1751      4670                             807     1527     1923
1872      2475     2668            EcoRV     GATATC          1998      2222     2795
2977                               1 Site                    3966
       3128     3493     3522         2294                          4115     4453
3643      3804     3907            Fnu4HI    GCNGC           HinPI      GCGC
4111                               28 Sites                  22 Sites
       4260     4342     4388          234      769     1283          9      494     1271
4672                               1485     1492     1557    1380      1554     1654
BssHII     GCGCGC                  1700                      1721
3 Sites                                1855     1973     1976       1991     2024     2167
       3045     4064     4588      1994     2110     2250    2247      3043     3045
BstNI      CCWGG                   2279                      3071
18 Sites                               2282     3065     3247       3193     3403     4052
         52     1738     1751      3273     3406     3413    4064      4138     4338
1872      2475     2668            3416                      4586
2977                                   3647     3686     3751       4588
       3128     3493     3522      3783     4189     4290    HpaII      CCGG
3643      3804     3907            4384                      23 Sites
4111                               PnuDII    CGCG                   848     1172     1329
       4260     4342     4388      21 Sites                  1519      1545     1692
4672                                    494     1273     1854 3019
Cfr10I     RCCGGY                  2169     2257     2281           3202     3425     3556
5 Sites                            2445                      3699      3709     3733
        847     3424     3953          3039     3045     3047 3823
4406      4446                     3071     3193     3718           3829     3954     3972
CfrI       YGGCCR                  3753                      4042      4075     4269
7 Sites                                3769     4064     4140 4407
        769     3416     3647      4278     4508     4588           4447     4583
4148      4366     4384            4590                      MaeI       CTAG
4408                               HaeII     RGCGCY          7 Sites
ClaI       ATCGAT                  4 Sites                          378      801     1034
1 Site                                  12     1657     2027 1404      2385     4574
       2287                        4341                      4622
DdeI       CTNAG                   HaeIII    GGCC            MaeII      ACGT
12 Sites                           25 Sites                  12 Sites
         12      204      397           55      771     1175        669     1160     1196
 711       787     1214     1623   1423     1857     1875    2306      2507     2519
       2088     2158     2229      1886                      2560
3446      4732                         2268     2469     2662       2643     2724     2829
DpnI       GATC                    3126     3206     3418    3947      3995
22 Sites                           3496                      MaeIII     GTNAC
        190      195      460          3547     3649     3723 8 Sites
1239      1247     1258            3737     4073     4150           270     1134     1361
1333                               4273                      1477      1540     2446
       2972     3028     3079          4368     4386     4410 2533
3115      3163     3334            4423                             2882
3460                               HgiAI     GWGCWC          MvaI       CCNGG
       3759     3841     3856      8 Sites                   34 Sites
3877      4219     4363
4581
```

Fig. 22 cont'd-36

```
          52     1172     1520        1314     1559     2281        3823     3829     3907
1738     1751     1872          3039     3220     3330          3973     4042     4075
2475                            3753                            4076
   2668     2977     3020          4191     4278                    4111     4260     4270
3128     3202     3203          PpuMI    RGGWCCY                4342     4388     4672
3493                            1 Site                          SdaI     GDGCHC
   3522     3556     3643          4123                         14 Sites
3700     3709     3734          PasI     RGGNCCY                   652     1587     2085
3804                            4 Sites                         2953     3326     3641
   3823     3829     3907          3498     3724     4126       3707
3973     4042     4075          4275                               3716     3725     3935
4076                            PstI     CTGCAG                 4275     4316     4499
   4111     4260     4270       1 Site                          4596
4342     4388     4672             3476                         SinI     GGWCC
NaeI     GCCGGC                 PvuI     CGATCG                 13 Sites
1 Site                          1 Site                             123      587      920
   4448                            3461                         1049     3022     3486
NciI     CCSGG                  RsaI     GTAC                   3696
16 Sites                        10 Sites                           3825     3922     4026
   1172     1520     3020          559     2093     2263       4123     4193     4503
3202     3203     3556          2330     2604     2684          SmaI     CCCGGG
3700                            2717                            2 Sites
   3709     3734     3823          2768     2925     3889          3203     4076
3829     3973     4042          SacI     GAGCTC                 SnaBI    TACGTA
4075                            3 Sites                         1 Site
   4076     4270                    2953     4499     4596         2725
NcoI     CCATGG                 SacII    CCGCGG                 SpeI     ACTAGT
1 Site                          4 Sites                         1 Site
   2745                            2282     3040     3754          2384
NdeI     CATATG                 4279                            SphI     GCATGC
2 Sites                         SalI     GTCGAC                 1 Site
   2076     2619                 1 Site                            4813
NheI     GCTAGC                    3949                         SspI     AATATT
1 Site                          Sau3A    GATC                   2 Sites
   4573                         22 Sites                           603      991
NlaIII   CATG                      188      193      458       StuI     AGGCCT
18 Sites                        1237     1245     1256          2 Sites
   538      762      864       1331                                55     3547
892     1011     1109     1181    2970     3026     3077       StyI     CCWWGG
   1901     2219     2349       3113     3161     3332          2 Sites
2367     2689     2749          3458                               2745     4085
3150                               3757     3839     3854      TaqI     TCGA
   3573     3654     4188       3875     4217     4361          14 Sites
4813                            4579                               216     1799     2287
NlaIV    GGNNCC                    4600                         3050     3076     3084
24 Sites                        Sau96A   GGNCC                  3242
    92      540     1830       26 Sites                           3335     3391     3536
1869     2852     3023             123      587      920       3814     3950     4466
3594                            1049     1174     2266          4609
   3640     3697     3722       2468                            Tth111I  GACNNNGTC
3723     3774     3827             2661     3022     3204      1 Site
3923                            3486     3495     3696             3946
   3932     4124     4125       3721                            XhoII    RGATCY
4273     4274     4315             3722     3735     3825      7 Sites
4424                            3922     4026     4072            458     1245     1256
   4542     4581     4680       4123                            3113     3839     4361
NruI     TCGCGA                    4193     4271     4272       4579
1 Site                          4422     4503                   XmaI     CCCGGG
   2257                         ScrFI    CCNGG                  2 Sites
NsiI     ATGCAT                 34 Sites                           3201     4074
1 Site                             52     1172     1520       XmaIII   CGGCCG
    796                         1738     1751     1872         1 Site
Nsp7524I RCATGY                 2475                               3416
3 Sites                            2668     2977     3020       XmnI     GAANNNNTTC
   1901     3150     4813       3128     3202     3203          2 Sites
NspBII   CMGCKG                 3493                               811     3547
9 Sites                            3522     3556     3643
                                3700     3709     3734
                                3804
```

Fig. 22 cont'd-37

Gag_M4.4 Dmyr

MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKV
SQNYPIVQNLQGQMVHQPLSPRTLNAWVKVVEEKGFNPEVIPMFSALSEGATPQDLNMMLNIVG
GHQAAMQMLKETINEEAAEWDRLHPVHAGPIAPGQMREPRGSDIAGSTSTLQEQIAWMTGNPPV
PVGDIYKRWIILGLNKIVKMYSPTSILDIKQGPKEPFRDYVDRFYKTLRAEQATQEVKNWMTDT
LLVQNANPDCKSILKALGTGATLEEMMSACQGVGGPAHKARVLAEAMSQANNTNIMMQRSNFKG
PKRIIKCFNCGKEGHIAKNCRAPRKKGCWKCGKEGHQMKDCTERQANFLGRIWPSSKGRPGNFL
QSRPEPTAPPAEPTAPPAESFKFEETTPAPKQEPKDREPLTSLRSLFGSDPLLQAS

HV13318 (Gag_M4.4 Dmyr.wlv)

GTCGAGAAGAAA<u>ATG</u>GCGGCTCGCGCCTCGGTCCTTCGAGGGGAGAAGTTGGATAAGTGGGAAC
GGATCCGCTTGAGGCCAGGAGGGAAGAAGCACTACATGCTCAAGCACCTGGTCTGGGCGAGCAG
AGAGCTGGAGAAGTTCGCGCTGAACCCGGGCCTGCTTGAGACATCCGAGGGCTGTAAGCAAATC
ATCAAGCAGCTTAACCAGCGCTCCAGACGGGCACCGAGGAGCTGCGCTCGCTATTCAACACGG
TAGCGACCCTCTACTGCGTGCACGCCGGAATCGAAGTTCGTGACACGAAGGAGGCTCTTGACAA
GATCGAGGAAATCCAGAACAAGTCGAAGCAGAAGACCCAGCAGGCGGCGGCCGGGACCGGCTCG
TCCTCAAAAGTATCTCAGAACTACCCGATCGTGCAGAACCTGCAGGGACAGATGGTCCACCAGC
CGCTCTCCCCACGGACGCTTA<u>ACGCCT</u>GGGTCAAAGTAGTCGAGGAGAAGGGGTTCAACCCGGA
AGTCATCCCCATGTTCTCGGCACTTTCCGAGGGAGCCACCCCGCAGGACCTGAACATGATGTTG
AACATCGTCGGCGGGCACCAGGCGGCCATGCAGATGCTTAAGGAGACCATCAACGAGGAGGCTG
CGGAGTGGGACCGCCTGCACCCGGTGCACGCGGGGCCCATCGCACCGGGCCAGATGAGAGAGCC
GCGGGGATCGGACATCGCGGGATCCACCAGCACCTTGCAGGAGCAAATCGCCTGGATGACTGGG
AACCCCCCGGTCCCGGTCGGGGACATCTACAAGAGATGGATCATCCTCGGGTTGAACAAGATCG
TGAAGATGTACAGCCCTACGTCAATCCTGGACATCAAGCAGGGCCCCAAGGAGCCCTTCAGAGA
CTACGTCGACCGGTTCTACAAGACTCTCCGGGCGGAGCAGGCGACGCAGGAGGTCAAGAACTGG
ATGACGGACACCTTGTTGGTCCAGAACGCTAACCCGGACTGCAAGAGCATCCTGAAGGCTCTCG
GCACGGGAGCGACCTTGGAAGAGATGATGTCCGCGTGCCAGGGAGTCGGGGGACCCGCGCACAA
GGCGCGGGTCTTGGCCGAGGCGATGTCCCAGGCCAACAACACGAACATCATGATGCAGCGGTCC
AACTTCAAGGGACCGAAGCGGATCATCAAGTGTTTCAACTGTGGCAAGGAGGGACACATCGCCA
AGAACTGCCGGGCCCCGCGGAAGAAGGGCTGCTGGAAGTGCGGAAAGGAGGGGCACCAAATGAA
GGACTGCACGGAGCGCCAGGCGAATTTCCTCGGGCGGATCTGGCCGTCCTCGAAGGGGCGGCCA
GGGAACTTCCTTCAATCGCGGCCAGAGCCGACGGCCCCTCCCGCGGAGCCGACCGCCCCGCCGG
CGGAGTCCTTTAAGTTCGAGGAGACCACGCCCGCCCCAAGCAAGAGCCGAAGGACCGCGAGCC
TCTTACCTCCCTCCGGTCGCTCTTCGGCTCCGACCCGCTTCTGCAAGCGTCG<u>TGATAA</u>GCTAGC
GGATCCGGCGCGCC                                                NheI
    AscI

HV13318 in in HV10001 4831bp

AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT

Fig. 22 cont'd-38

```
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTCGAGGGGAGAAGTTGGATAAGTGGGAACGGATCCGCTTGAGGCCAGGAGGGA
AGAAGCACTACATGCTCAAGCACCTGGTCTGGGCGAGCAGAGAGCTGGAGAAGTTCGCGCTGAA
CCCGGGCCTGCTTGAGACATCCGAGGGCTGTAAGCAAATCATCAAGCAGCTTCAACCAGCGCTC
CAGACGGGCACCGAGGAGCTGCGCTCGCTATTCAACACGGTAGCGACCCTCTACTGCGTGCACG
CCGGAATCGAAGTTCGTGACACGAAGGAGGCTCTTGACAAGATCGAGGAAATCCAGAACAAGTC
GAAGCAGAAGACCCAGCAGGCGGCGGCCGGGACCGGCTCGTCCTCAAAAGTATCTCAGAACTAC
CCGATCGTGCAGAACCTGCAGGGACAGATGGTCCACCAGCCGCTCTCCCCACGGACGCTTAACG
CCTGGGTCAAAGTAGTCGAGGAGAAGGGGTTCAACCCGGAAGTCATCCCCATGTTCTCGGCACT
TTCCGAGGGAGCCACCCCGCAGGACCTGAACATGATGTTGAACATCGTCGGCGGGCACCAGGCG
GCCATGCAGATGCTTAAGGAGACCATCAACGAGGAGGCTGCGGAGTGGGACCGCCTGCACCCGG
TGCACGCGGGGCCCATCGCACCGGGCCAGATGAGAGAGCCGCGGGGATCGGACATCGCGGGATC
```

```
CACCAGCACCTTGCAGGAGCAAATCGCCTGGATGACTGGGAACCCCCCGGTCCCGGTCGGGGAC
ATCTACAAGAGATGGATCATCCTCGGGTTGAACAAGATCGTGAAGATGTACAGCCCTACGTCAA
TCCTGGACATCAAGCAGGGCCCCAAGGAGCCCTTCAGAGACTACGTCGACCGGTTCTACAAGAC
TCTCCGGGCGGAGCAGGCGACGCAGGAGGTCAAGAACTGGATGACGGACACCTTGTTGGTCCAG
AACGCTAACCCGGACTGCAAGAGCATCCTGAAGGCTCTCGGCACGGGAGCGACCTTGGAAGAGA
TGATGTCCGCGTGCCAGGGAGTCGGGGGACCCGCGCACAAGGCGCGGGTCTTGGCCGAGGCGAT
GTCCCAGGCCAACAACACGAACATCATGATGCAGCGGTCCAACTTCAAGGGACCGAAGCGGATC
ATCAAGTGTTTCAACTGTGGCAAGGAGGGACACATCGCCAAGAACTGCCGGGCCCCGCGGAAGA
AGGGCTGCTGGAAGTGCGGAAAGGAGGGGCACCAAATGAAGGACTGCACGGAGCGCCAGGCGAA
TTTCCTCGGGCGGATCTGGCCGTCCTCGAAGGGGCGGCCAGGGAACTTCCTTCAATCGCGGCCA
GAGCCGACGGCCCCTCCCGCGGAGCCGACCGCCCGCCGGCGGAGTCCTTTAAGTTCGAGGAGA
CCACGCCCGCCCCCAAGCAAGAGCCGAAGGACCGCGAGCCTCTTACCTCCCTCCGGTCGCTCTT
CGGCTCCGACCCGCTTCTGCAAGCGTCGTGATAAGCTAGCGGATCCGGCGCGCCGAGCTCGCTG
ATCAGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATT
GTCTGAGTAGGTGTCATTCTATTCTGGGGGGTGGGGTGGGGCAGGACAGCAAGGGGGAGGATTG
GGAAGACAATAGCAGGCATGCTGGGGAATTT
```

Primers:

HV1001-F2892
CCGCCCCATTGACGCAAATGG

HV1001-R3113
GCTGGCAACTAGAAGGCACAG
(+ strand: CTGTGCCTTCTAGTTGCCAGC

Thursday, August 2, 2007

Sequence 4    Length : 4831

| | | | | |
|---|---|---|---|---|
| AatII | GACGTC | | | |
| 4 Sites | | | | |
| 2510 | 2563 | 2646 | | |
| 2832 | | | | |
| AccI | GTMKAC | | | |
| 1 Site | | | | |
| 3950 | | | | |
| AflI | CTTAAG | | | |
| 1 Site | | | | |
| 3661 | | | | |
| AflIII | ACRYGT | | | |
| 1 Site | | | | |
| 1897 | | | | |
| AluI | AGCT | | | |
| 14 Sites | | | | |
| 109 | 633 | 1340 | | |
| 1597 | 1643 | 1733 | | |
| 1959 | | | | |
| 2184 | 2951 | 3180 | | |
| 3249 | 3282 | 4579 | | |
| 4601 | | | | |
| AlwNI | CAGNNNCTG | | | |
| 4 Sites | | | | |
| 1488 | 2129 | 3471 | | |
| 3609 | | | | |
| AosII | GRCGYC | | | |
| 5 Sites | | | | |
| 2507 | 2560 | 2643 | | |
| 2825 | 2983 | | | |
| ApaI | GGGCCC | | | |
| 3 Sites | | | | |

| | | | |
|---|---|---|---|
| ApaLI | GTGCAC | | |
| 4 Sites | | | |
| 1583 | 2081 | 3322 | |
| 3712 | | | |
| AvaI | CYCGRG | | |
| 3 Sites | | | |
| 3201 | 3862 | 4357 | |
| BamHI | GGATCC | | |
| 3 Sites | | | |
| 3113 | 3772 | 4585 | |
| BanI | GGYRCC | | |
| 6 Sites | | | |
| 538 | 2850 | 3271 | |
| 3638 | 4316 | 4685 | |
| BanII | GRGCYC | | |
| 6 Sites | | | |
| 2953 | 3725 | 3925 | |
| 3935 | 4278 | 4603 | |
| BclI | TGATCA | | |
| 1 Site | | | |
| 4607 | | | |
| BcnI | CCSGG | | |
| 14 Sites | | | |
| 1173 | 1521 | 3021 | |
| 3203 | 3204 | 3421 | |
| 3557 | | | |
| 3710 | 3735 | 3824 | |
| 3830 | 3974 | 4043 | |
| 4274 | | | |
| BglI | GCCNNNNNGGC | | |
| 4 Sites | | | |
| 2475 | 2597 | 2668 | |
| 4453 | | | |

| | | | |
|---|---|---|---|
| BglII | AGATCT | | |
| 1 Site | | | |
| 458 | | | |
| Bsp1286 | GDGCHC | | |
| 14 Sites | | | |
| 652 | 1587 | 2085 | |
| 2953 | 3274 | 3326 | |
| 3641 | | | |
| 3716 | 3725 | 3925 | |
| 3935 | 4278 | 4319 | |
| 4603 | | | |
| BspHI | TCATGA | | |
| 3 Sites | | | |
| 1007 | 1105 | 4184 | |
| BspNI | CCWGG | | |
| 18 Sites | | | |
| 52 | 1738 | 1751 | |
| 1872 | 2475 | 2668 | |
| 2977 | | | |
| 3128 | 3160 | 3522 | |
| 3643 | 3804 | 3907 | |
| 4111 | | | |
| 4165 | 4345 | 4391 | |
| 4679 | | | |
| BssHII | GCGCGC | | |
| 2 Sites | | | |
| 3045 | 4594 | | |
| BstNI | CCWGG | | |
| 18 Sites | | | |
| 52 | 1738 | 1751 | |
| 1872 | 2475 | 2668 | |
| 2977 | | | |

Fig. 22 cont'd-40

```
        3128    3160    3522           2282    3065    3247        HpaII    CCGG
3643    3804    3907            3283    3413    3416               23 Sites
4111                            3496                                   848     1172    1329
        4165    4345    4391           3647    3686    3751.      1519    1545    1692
4679                            4192    4293    4387               3019
CfrlOI    RCCGGY               4411                                    3202    3329    3419
4 Sites                         FnuDII    CGCG                     3425    3556    3709
        847     3424    3953   23 Sites                            3733
4452                                    494     1273    1854           3823    3829    3954
CfrI    YGGCCR                  2169    2257    2281               3972    4042    4272
7 Sites                         2445                               4453
        769     3416    3647           3039    3045    3047           4533    4589
4148    4369    4387            3071    3193    3718               MaeI    CTAG
4411                            3753                               7 Sites
ClaI    ATCGAT                          3769    4105    4129           378     801     1034
1 Site                          4140    4281    4410               1404    2385    4580
        2287                    4435                               4629
DdeI    CTNAG                           4514    4594               MaeII    ACGT
12 Sites                        HaeII    RGCGCY                    12 Sites
        12      204     397    5 Sites                                 669     1160    1196
711     787     1214    1623           12      1657    2027       2306    2507    2519
        2088    2158    2229    3262    4344                       2560
3446    4739                    HaeIII    GGCC                            2643    2724    2829
DpnI    GATC                   24 Sites                            3898    3947
20 Sites                                55      771     1175       MaeIII    GTNAC
        190     195     460    1423    1857    1875                9 Sites
1239    1247    1258            1886                                   270     1134    1361
1333                                    2268    2469    2662      1477    1540    2446
        2972    3028    3115    3126    3206    3418               2533
3370    3460    3759            3649                                      2882    3343
3774                                    3723    3737    3923      MvaI    CCNGG
        3856    3877    4222    4150    4168    4276               32 Sites
4366    4587    4609            4371                                   52      1172    1520
DraIII    CACNNNGTG                    4389    4413    4426       1738    1751    1872
2 Sites                         HgiAI    GWGCWC                    2475
        1161    3711           6 Sites                                    2668    2977    3020
Eco47I    GGWCC                         1587    2085    2953      3128    3160    3202
16 Sites                        3326    3716    4603               3203
        122     586     919    HhaI    GCGC                               3420    3522    3556
1048    3021    3077           22 Sites                            3643    3709    3734
3421                                    11      496     1273      3804
        3485    3605    3695    1382    1556    1656                      3823    3829    3907
3824    4025    4122            1723                               3973    4042    4111
4195                                    1993    2026    2169      4165
        4209    4508            2249    3045    3047                      4273    4345    4391
Eco47III    AGCGCT              3073                               4679
1 Site                                  3195    3261    3287      NaeI    GCCGGC
        3260                    4131    4140    4343               1 Site
EcoO109    RGGNCCY              4594                                   4454
6 Sites                                 4596                      NciI    CCSGG
        3606    3721    3921   HincII    GTYRAC                   14 Sites
3922    4123    4275           4 Sites                                 1172    1520    3020
EcoRII    CCWGG                         413     886     2369      3202    3203    3420
18 Sites                        3951                               3556
        50      1736    1749   HinfI    GANTC                             3709    3734    3823
1870    2473    2666            17 Sites                           3829    3973    4042
2975                                    43      59      357       4273
        3126    3158    3520   383     401     725     779        NcoI    CCATGG
3641    3802    3905            807     1527    1923               1 Site
4109                            1998    2222    2795                   2745
        4163    4343    4389    3332                              NdeI    CATATG
4677                                    3966    4115    4459      2 Sites
EcoRV    GATATC                 HinPI    GCGC                          2076    2619
1 Site                          22 Sites                          NheI    GCTAGC
        2294                            9       494     1271      1 Site
Pnu4HI    CCNGC                 1380    1554    1654                   4579
28 Sites                        1721                              NlaIII    CATG
        234     769     1283           1991    2024    2167       19 Sites
1489    1492    1557            2247    3043    3045                   538     762     864
1700                            3071                              892     1011    1109    1181
        1855    1973    1976           3193    3259    3285              1901    2219    2349
1994    2110    2250            4129    4138    4341              2367    2689    2749
2279                            4592                              3150
                                4594
```

Fig. 22 cont'd-41

```
      3573      3618      3654          1 Site                          4210      4509
4188      4820                              3949                    SmaI          CCCGGG
NlaIV     GGNNCC                        Sau3A     GATC               1 Site
31 Sites                                20 Sites                        3203
      92      540      1830                 188       193      458   SnaBI         TACGTA
1869      2852      3023                1237      1245      1256     1 Site
3115                                    1331                            2725
      3273      3423      3594              2970      3026      3113 SpeI          ACTAGT
3640      3697      3722                3368      3458      3757     1 Site
3723                                    3772                            2384
      3774      3817      3827              3854      3875      4220 SphI          GCATGC
3923      3924      3932                4364      4585      4607     1 Site
4124                                    Sau96A    GGNCC                 4820
      4125      4211      4276          29 Sites                     SspI          AATATT
4277      4318      4427                     123       587      920  2 Sites
4439                                    1049      1174      2266          603       991
      4548      4587      4687          2468                         StuI          AGGCCT
NruI      TCGCGA                             2661      3022      3078 1 Site
1 Site                                  3204      3422      3486           55
   2257                                 3606                         StyI          CCWWGG
NsiI      ATGCAT                             3696      3721      3722 3 Sites
1 Site                                  3735      3825      3921          2745      3926      4085
    796                                 3922                         TaqI          TCGA
Nsp7524I  RCATGY                             4026      4123      4196 13 Sites
3 Sites                                 4210      4274      4275          216      1799      2287
   1901      3150      4820             4425                         3050      3084      3335
NspBII    CMGCKG                        4509                         3371
8 Sites                                 ScrFI     CCNGG                   3391      3536      3950
   1314      1559      2281             32 Sites                     4378      4472      4616
3039      3753      4194                     52      1172      1520  Tth111I       GACNNNGTC
4281                                    1738      1751      1872     1 Site
   4435                                 2475                            3946
PpuMI     RGGWCCY                            2668      2977      3020 XhoII         RGATCY
2 Sites                                 3128      3160      3202     7 Sites
   3606      4123                       3203                              458      1245      1256
PssI      RGGNCCY                            3420      3522      3556 3113      3772      4364
6 Sites                                 3643      3709      3734     4585
   3609      3724      3924             3804                         XmaI          CCCGGG
3925      4126      4278                     3823      3829      3907 1 Site
PstI      CTGCAG                        3973      4042      4111        3201
1 Site                                  4165                         XmaIII        CGGCCG
   3476                                      4273      4345      4391 1 Site
PvuI      CGATCG                        4679                            3416
1 Site                                  SdnI      GDGCHC             XmnI          GAANNNNTTC
   3461                                 14 Sites                     2 Sites
RsaI      GTAC                               652      1587      2085      811      3547
10 Sites                                2953      3274      3326
    559      2093      2263             3641                         Following enzymes have no
2330      2604      2684                     3716      3725      3925 sites
2717                                    3935      4278      4319     AccIII    Asp718    AsuII
   2768      2925      3889             4603                         AvrII     BalI      BbeI
SacI      GAGCTC                        SinI      GGWCC              BspMII    BstEII    BstXI
2 Sites                                 16 Sites                     DraI      EcoRI     EspI
   2953      4603                            123       587      920  FspI      HindIII   HpaI
SacII     CCGCGG                        1049      3022      3078     KpnI      MluI      MstI
5 Sites                                 3422                         NarI      NotI      OxaNI
   2282      3040      3754                  3486      3606      3696 PflMI    PvuII     RsrII
4282      4436                          3825      4026      4123     ScaI      SfiI      SplI
SalI      GTCGAC                        4196                         XbaI      XcaI      XhoI
```

Primer below can be used for Gag-M4.1 through 4.4 to generate XhoI site:

Gag-M2-4-fG/C: GGGCGCCTCGAGAAGAAAATGGCGGCTCG

WLV001AM (vector sequence), hv10001
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA

Fig. 22 cont'd-42

```
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGAGAGGCGCGCCGAGCTCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTT
```

Fig. 22 cont'd-43

CCTAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGAATTT

HUMAN IMMUNODEFICIENCY VIRUS TYPE 1 GROUP M CONSENSUS AND MOSAIC ENVELOPE GLYCOPROTEINS

This application is a continuation of U.S. application Ser. No. 13/094,734, filed Apr. 26, 2011, now U.S. Pat. No. 9,011,873, which is a continuation of U.S. application Ser. No. 12/192,015, filed Aug. 14, 2008, now U.S. Pat. No. 7,951,377, which is a continuation-in-part of U.S. application Ser. No. 11/990,222, filed Apr. 20, 2009, now U.S. Pat. No. 8,119,140, which is the U.S. national phase of International Application No. PCT/US2006/032907, filed Aug. 23, 2006, which designated the U.S. and claims the benefit of priority from U.S. Provisional Application Nos. 60/710,154, filed Aug. 23, 2005, and 60/739,413, filed Nov. 25, 2005, the entire contents of each of which are hereby incorporated by reference.

This invention was made with Government support under Contract No. DE-AC52-06NA25396 awarded by the U.S. Department of Energy. The Government has certain rights in the invention.

TECHNICAL FIELD

The present invention relates, in general, to an immunogenic composition (e.g., a vaccine) and, in particular, to a polyvalent immunogenic composition, such as a polyvalent HIV vaccine, and to methods of using same. The invention further relates to methods that use a genetic algorithm to create sets of polyvalent antigens suitable for use, for example, in vaccination strategies.

BACKGROUND

Designing an effective HIV vaccine is a many-faceted challenge. The vaccine preferably elicits an immune response capable of either preventing infection or, minimally, controlling viral replication if infection occurs, despite the failure of immune responses to natural infection to eliminate the virus (Nabel, Vaccine 20:1945-1947 (2002)) or to protect from superinfection (Altfeld et al, Nature 420:434-439 (2002)). Potent vaccines are needed, with optimized vectors, immunization protocols, and adjuvants (Nabel, Vaccine 20:1945-1947 (2002)), combined with antigens that can stimulate cross-reactive responses against the diverse spectrum of circulating viruses (Gaschen et al, Science 296:2354-2360 (2002), Korber et al, Br. Med. Bull. 58:19-42 (2001)). The problems that influenza vaccinologists have confronted for decades highlight the challenge posed by HIV-1: human influenza strains undergoing antigenic drift diverge from one another by around 1-2% per year, yet vaccine antigens often fail to elicit cross-reactive B-cell responses from one year to the next, requiring that contemporary strains be continuously monitored and vaccines be updated every few years (Korber et al, Br. Med. Bull. 58:19-42 (2001)). In contrast, co-circulating individual HIV-1 strains can differ from one another by 20% or more in relatively conserved proteins, and up to 35% in the Envelope protein (Gaschen et al, Science 296:2354-2360 (2002), Korber et al, Br. Med. Bull. 58:19-42 (2001)).

Different degrees of viral diversity in regional HIV-1 epidemics provide a potentially useful hierarchy for vaccine design strategies. Some geographic regions recapitulate global diversity, with a majority of known HIV-1 subtypes, or clades, co-circulating (e.g., the Democratic Republic of the Congo (Mokili & Korber, J. Neurovirol 11(Suppl. 1):66-75 (2005)); others are dominated by two subtypes and their recombinants (e.g., Uganda (Barugahare et al, J. Virol. 79:4132-4139 (2005)), and others by a single subtype (e.g., South Africa (Williamson et al, AIDS Res. Hum. Retroviruses 19:133-144 (2003)). Even areas with predominantly single-subtype epidemics must address extensive within-clade diversity (Williamson et al, AIDS Res. Hum. Retroviruses 19:133-44 (2003)) but, since international travel can be expected to further blur geographic distinctions, all nations would benefit from a global vaccine.

Presented herein is the design of polyvalent vaccine antigen sets focusing on T lymphocyte responses, optimized for either the common B and C subtypes, or all HIV-1 variants in global circulation [the HIV-1 Main (M) group]. Cytotoxic T-lymphocytes (CTL) directly kill infected, virus-producing host cells, recognizing them via viral protein fragments (epitopes) presented on infected cell surfaces by human leukocyte antigen (HLA) molecules. Helper T-cell responses control varied aspects of the immune response through the release of cytokines. Both are likely to be crucial for an HIV-1 vaccine: CTL responses have been implicated in slowing disease progression (Oxenius et al, J. Infect. Dis. 189:1199-208 (2004)); vaccine-elicited cellular immune responses in nonhuman primates help control pathogenic SIV or SHIV, reducing the likelihood of disease after challenge (Barouch et al, Science 290:486-92 (2000)); and experimental depletion of CD8+ T-cells results in increased viremia in SIV infected rhesus macaques Schmitz et al, Science 283:857-60 (1999)). Furthermore, CTL escape mutations are associated with disease progression (Barouch et al, J. Virol. 77:7367-75 (2003)), thus vaccine-stimulated memory responses that block potential escape routes may be valuable.

The highly variable Env protein is the primary target for neutralizing antibodies against HIV; since immune protection will likely require both B-cell and T-cell responses (Moore and Burton, Nat. Med. 10:769-71 (2004)), Env vaccine antigens will also need to be optimized separately to elicit antibody responses. T-cell-directed vaccine components, in contrast, can target the more conserved proteins, but even the most conserved HIV-1 proteins are diverse enough that variation is an issue. Artificial central-sequence vaccine approaches (e.g., consensus sequences, in which every amino acid is found in a plurality of sequences, or maximum likelihood reconstructions of ancestral sequences (Gaschen et al, Science 296:2354-60 (2002), Gao et al, J. Virol. 79:1154-63 (2005), Doria-Rose et al, J. Virol. 79:11214-24 (2005), Weaver et al, J. Virol., in press)) are promising; nevertheless, even centralized strains provide limited coverage of HIV-1 variants, and consensus-based reagents fail to detect many autologous T-cell responses (Altfeld et al, J. Virol. 77:7330-40 (2003)).

Single amino acid changes can allow an epitope to escape T-cell surveillance; since many T-cell epitopes differ between HIV-1 strains at one or more positions, potential responses to any single vaccine antigen are limited. Whether a particular mutation results in escape depends upon the specific epitope/T-cell combination, although some changes broadly affect between-subtype cross-reactivity (Norris et al, AIDS Res. Hum. Retroviruses 20:315-25 (2004)). Including multiple variants in a polyvalent vaccine could enable responses to a broader range of circulating variants, and could also prime the immune system against common escape mutants (Jones et al, J. Exp. Med. 200:1243-56 (2004)). Escape from one T-cell receptor may create a variant that is susceptible to another (Allen et al, J. Virol. 79:12952-60 (2005), Feeney et al, J. Immunol. 174:7524-30 (2005)), so stimulating polyclonal responses to epitope variants may be beneficial (Killian et al, Aids 19:887-96 (2005)). Escape mutations that inhibit processing (Milicic et al, J. Immunol. 175:4618-26 (2005)) or HLA binding (Ammaranond et al, AIDS Res. Hum. Retroviruses 21:395-7 (2005)) cannot be directly countered by a T-cell with a different specificity, but responses to overlapping epitopes may block even some of these escape routes.

The present invention relates to a polyvalent vaccine comprising several "mosaic" proteins (or genes encoding these proteins). The candidate vaccine antigens can be cocktails of k composite proteins (k being the number of sequence variants in the cocktail), optimized to include the maximum number of potential T-cell epitopes in an input set of viral proteins. The mosaics are generated from natural sequences: they resemble natural proteins and include the most common forms of potential epitopes. Since CD8+ epitopes are contiguous and typically nine amino-acids long, sets of mosaics can be scored by "coverage" of nonamers (9-mers) in the natural sequences (fragments of similar lengths are also well represented). 9-Mers not found at least three times can be excluded. This strategy provides the level of diversity coverage achieved by a massively polyvalent multiple-peptide vaccine but with important advantages: it allows vaccine delivery as intact proteins or genes, excludes low-frequency or unnatural epitopes that are not relevant to circulating strains, and its intact protein antigens are more likely to be processed as in a natural infection.

SUMMARY OF THE INVENTION

In general, the present invention relates to an immunogenic composition. More specifically, the invention relates to a polyvalent immunogenic composition (e.g., an HIV vaccine), and to methods of using same. The invention further relates to methods that involve the use of a genetic algorithm to design sets of polyvalent antigens suitable for use as vaccines.

Objects and advantages of the present invention will be clear from the description that follows.

BRIEF DESCRIPTION OF THE DRAWINGS

FIGS. 1A-1F. The upper bound of potential epitope coverage of the HIV-1 M group. The upper bound for population coverage of 9-mers for increasing numbers of variants is shown, for k=1-8 variants. A sliding window of length nine was applied across aligned sequences, moving down by one position. Different colors denote results for different numbers of sequences. At each window, the coverage given by the k most common 9-mers is plotted for Gag (FIGS. 1A and 1B), Nef (FIGS. 1C and 1D) and Env gp120 (FIGS. 1E and 1F). Gaps inserted to maintain the alignment are treated as characters. The diminishing returns of adding more variants are evident, since, as k increases, increasingly rare forms are added. In FIGS. 1A, 1C and 1E, the scores for each consecutive 9-mer are plotted in their natural order to show how diversity varies in different protein regions; both p24 in the center of Gag and the central region of Nef are particularly highly conserved. In FIGS. 1B, 1D and 1F, the scores for each 9-mer are reordered by coverage (a strategy also used in FIG. 4), to provide a sense of the overall population coverage of a given protein. Coverage of gp120, even with 8 variant 9-mers, is particularly poor (FIGS. 1E and 1F).

FIGS. 2A-2C. Mosaic initialization, scoring, and optimization. FIG. 2A) A set of k populations is generated by random 2-point recombination of natural sequences (1-6 populations of 50-500 sequences each have been tested). One sequence from each population is chosen (initially at random) for the mosaic cocktail, which is subsequently optimized. The cocktail sequences are scored by computing coverage (defined as the mean fraction of natural-sequence 9-mers included in the cocktail, averaged over all natural sequences in the input data set). Any new sequence that covers more epitopes will increase the score of the whole cocktail. FIG. 2B) The fitness score of any individual sequence is the coverage of a cocktail containing that sequence plus the current representatives from other populations. FIG. 2C) Optimization: 1) two "parents" are chosen: the higher-scoring of a randomly chosen pair of recombined sequences, and either (with 50% probability) the higher-scoring sequence of a second random pair, or a randomly chosen natural sequence. 2) Two-point recombination between the two parents is used to generate a "child" sequence. If the child contains unnatural or rare 9-mers, it is immediately rejected, otherwise it is scored (Gaschen et al, Science 296:2354-2360 (2002)). If the score is higher than that of any of four randomly-selected population members, the child is inserted in the population in place of the weakest of the four, thus evolving an improved population; 4) if its score is a new high score, the new child replaces the current cocktail member from its population. Ten cycles of child generation are repeated for each population in turn, and the process iterates until improvement stalls.

FIG. 4A) Non-optimal natural sequences selected from among strains being used in vaccine studies (Kong et al, J. Virol. 77:12764-72 (2003)) including an individual clade A, B, and C viral sequences (Gag: GenBank accession numbers AF004885, K03455, and U52953; Nef core: AF069670, K02083, and U52953). FIG. 4B) Optimum set of natural sequences [isolates US2 (subtype B, USA), 70177 (subtype C, India), and 99TH.R2399 (subtype CRF15_01B, Thailand); accession numbers AY173953, AF533131, and_AF530576] selected by choosing the single sequence with maximum coverage, followed by the sequence that had the best coverage when combined with the first (i.e. the best complement), and so on, selected for M group coverage FIG. 4C) Consensus sequence cocktail (M group, B- and C-subtypes). FIG. 4D) 3 mosaic sequences, FIG. 4E) 4 mosaic sequences, FIG. 4F) 6 mosaic sequences. FIGS. 4D-4F were all optimized for M group coverage.

FIGS. 7A and 7B. The distribution of 9-mers by frequency of occurrence in natural, consensus, and mosaic sequences. Occurrence counts (y-axis) for different 9-mer frequencies (x-axis) for vaccine cocktails produced by several methods. FIG. 7A: frequencies from 0-60% (for 9-mer frequencies >60%, the distributions are equivalent for all methods). FIG. 7B: Details of low-frequency 9-mers. Natural sequences have large numbers of rare or unique-to-isolate 9-mers (bottom right, FIGS. 7A and 7B); these are unlikely to induce useful vaccine responses. Selecting optimal natural sequences does select for more common 9-mers, but rare and unique 9-mers are still included (top right, FIGS. 7A and 7B). Consensus cocktails, in contrast, under-represent uncommon 9-mers, especially below 20% frequency (bottom left, FIGS. 7A and 7B). For mosaic sequences, the number of lower-frequency 9-mers monotonically increases with the number of sequences (top left, each panel), but unique-to-isolate 9-mers are completely excluded (top left of right panel: * marks the absence of 9-mers with frequencies <0.005).

FIGS. 8A and 8B) HLA binding motif counts. FIGS. 8C and 8D) number of unfavorable amino acids. In all graphs: natural sequences are marked with black circles (●); consensus sequences with blue triangles (▲); inferred ancestral sequences with green squares (■); and mosaic sequences with red diamonds (♦). Left panel (FIGS. 8A and 8C) shows HLA-binding-motif counts (FIG. 8A) and counts of unfavorable amino acids (FIG. 8C) calculated for individual sequences; Right panel (FIGS. 8B and 8D) shows HLA binding motifs counts (FIG. 8B) and counts of unfavorable amino acids (FIG. 8D) calculated for sequence cocktails. The top portion of each graph (box-and-whiskers graph) shows the distribution of respective counts (motif counts or counts of unfavorable amino acids) based either on alignment of M group sequences (for individual sequences, FIGS. 8A and 8C) or on 100 randomly composed cocktails of three sequences, one from each A, B and C subtypes (for sequence cocktails, FIGS. 8B and 8D). The alignment was downloaded from the Los Alamos HIV database. The box extends from the 25 percentile to the 75 percentile, with the line at the median. The whiskers extending outside the box show the highest and lowest values. Amino acids that are very rarely found as C-terminal anchor residues are G, S, T, P, N, Q, D, E, and H, and tend to be small, polar, or negatively charged (Yusim et al, J. Virol. 76:8757-8768 (2002)). Results are shown for Gag, but the same qualitative results hold for Nef core and complete Nef. The same procedure was done for supertype motifs with results qualitatively similar to the results for HLA binding motifs (data not shown).

FIG. 9. Mosaic protein sets limited to 4 sequences (k=4), spanning Gag and the central region of Nef, optimized for subtype B, subtype C, and the M group. Figure discloses SEQ ID NOS: 1-84, respectively, in order of appearance.

FIG. 10. Mosaic sets for Env and Pol. Figure discloses SEQ ID NOS: 85-168, respectively, in order of appearance.

FIG. 11. This plot is alignment independent, based on splintering all M group proteins, (database and CHAVI, one sequence per person) into all possible 9-mers, attending to their frequencies, and then looking for matches and near matches in each vaccine antigen or cocktail with the database.

FIGS. 14A-14D. Plots resorted by frequency of 9-mer matches for each vaccine proposed for use.

FIGS. 15A-15D. Plots mapping every amino acid in every sequence in the full database alignment.

FIG. 17. Coverage of the HIV database plus CHAVI sequences (N=2020).

FIG. 19. The compromise and benefit in terms of coverage for Env M group versus subtype-specific design.

FIG. 21. Gag, Nef and Env sequences. Figure discloses SEQ ID NOS: 169-179, respectively, in order of appearance.

FIG. 22. Mosaic gag and nef genes and M consensus gag and nef genes. Figure discloses SEQ ID NOS 180-187, 183, 188, 184, 189-191, 183, 188, 184, 192-194, 183-184, 195-197, 183-184, 198-200, 183-184, 201-204, 183-184, 205-207, 183-184, 208-211, 183-184, 212-217, 183-184, 208 and 218, respectively, in order of appearance.

DETAILED DESCRIPTION OF THE INVENTION

Figure 3:
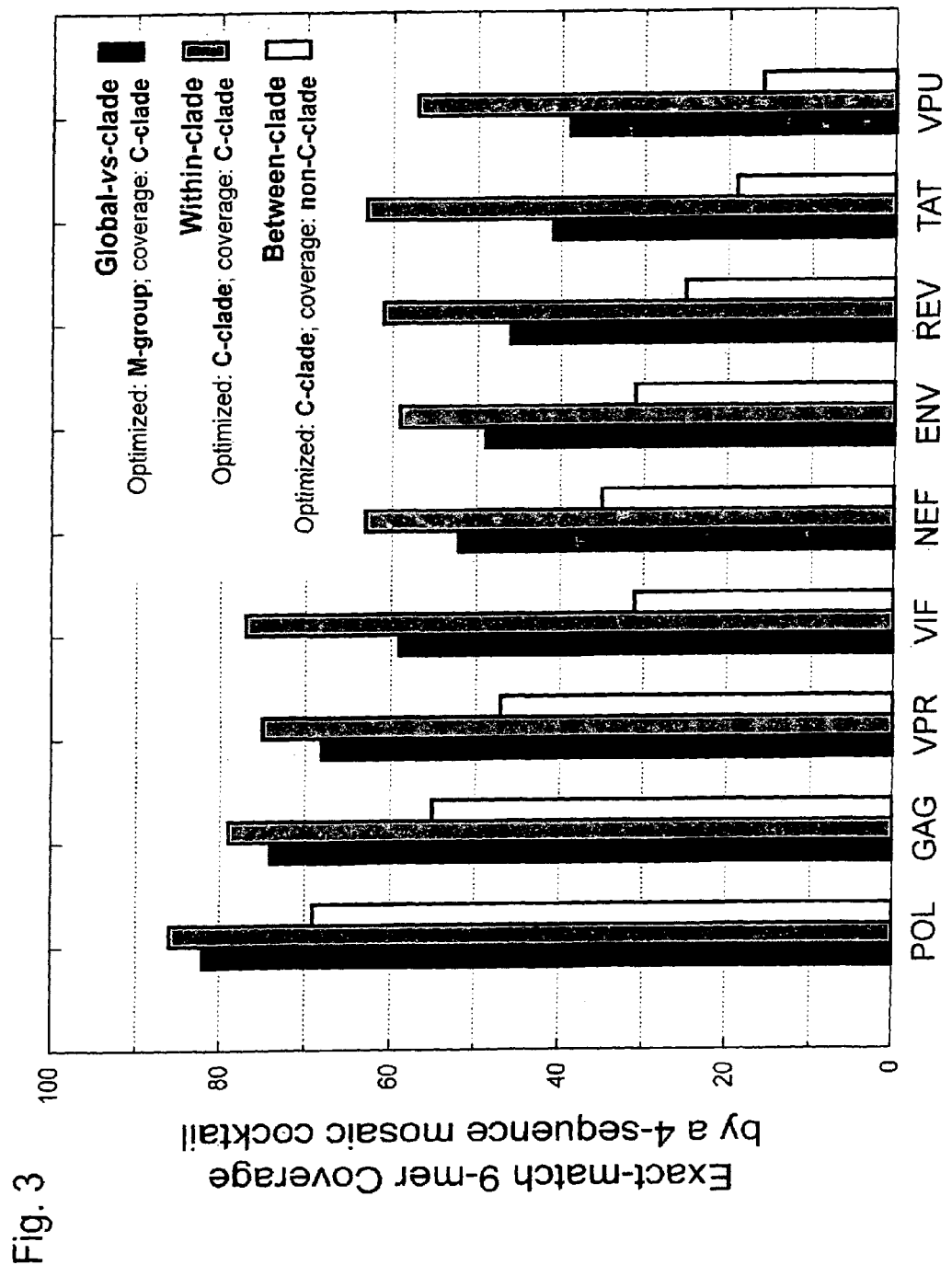
FIG. 3. Mosaic strain coverage for all HIV proteins. The level of 9-mer coverage achieved by sets of four mosaic proteins for each HIV protein is shown, with mosaics optimized using either the M group or the C subtype. The fraction of C subtype sequence 9-mers covered by mosaics optimized on the C subtype (within-clade optimization) is shown in gray. Coverage of 9-mers found in non-C subtype M-group sequences by subtype-C-optimized mosaics (between-clade coverage) is shown in white. Coverage of subtype C sequences by M-group optimized mosaics is shown in black. B clade comparisons gave comparable results (data not shown).
Figure 4A:
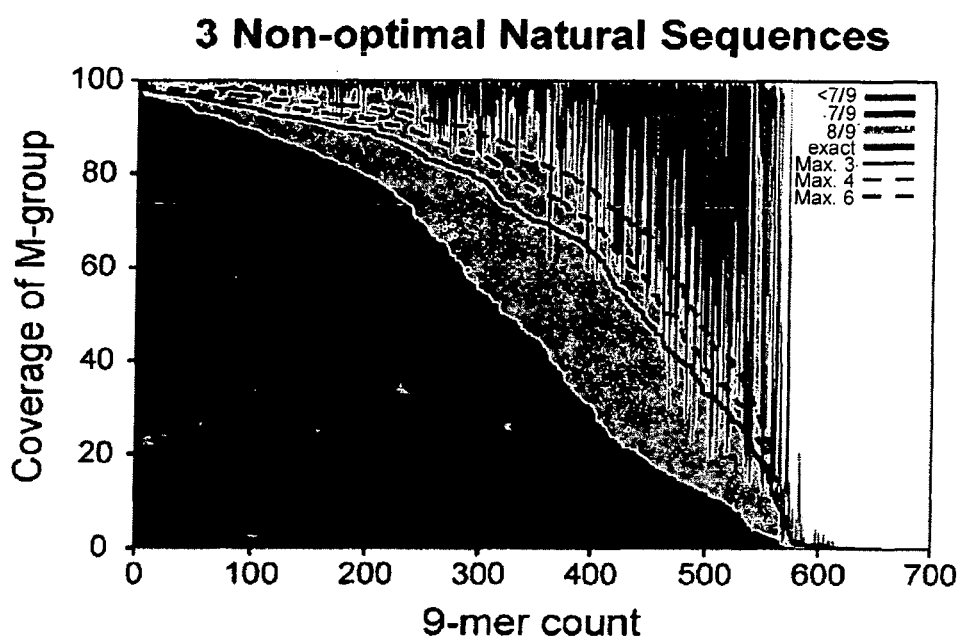
FIGS. 4A-4F. Coverage of M group sequences by different vaccine candidates, nine-mer by nine-mer. Each plot presents site-by-site coverage (i.e., for each nine-mer) of an M-group natural-sequence alignment by a single tri-valent vaccine candidate. Bars along the x-axis represent the proportion of sequences matched by the vaccine candidate for a given alignment position: 9/9 matches (in red), 8/9 (yellow), 7/9 (blue). Aligned 9-mers are sorted along the x-axis by exact-match coverage value. 656 positions include both the complete Gag and the central region of Nef. For each alignment position, the maximum possible matching value (i.e. the proportion of aligned sequences without gaps in that nine-mer) is shown in gray.
Figure 4B:
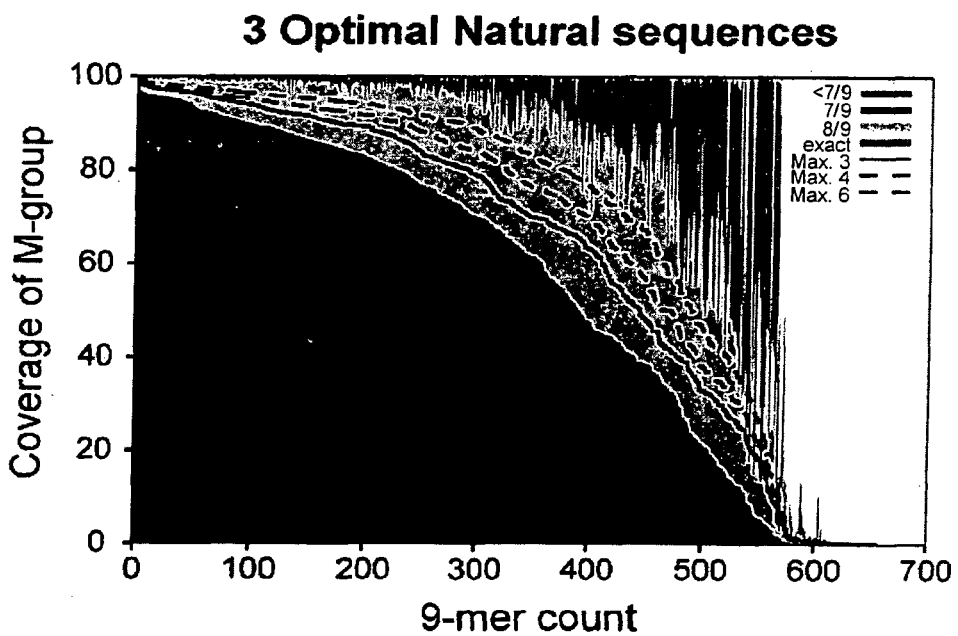
Figure 4C:
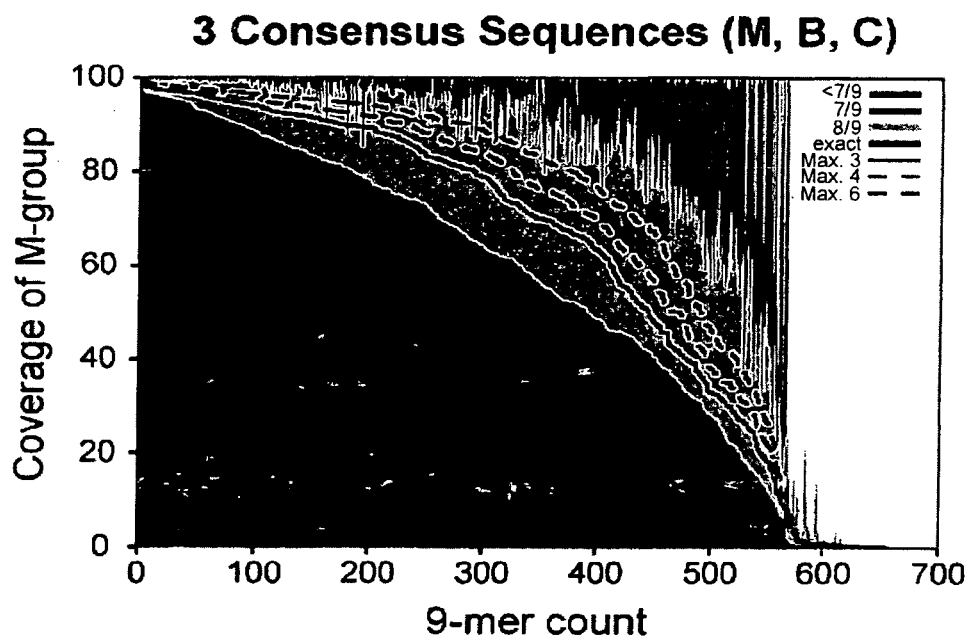
Figure 4D:
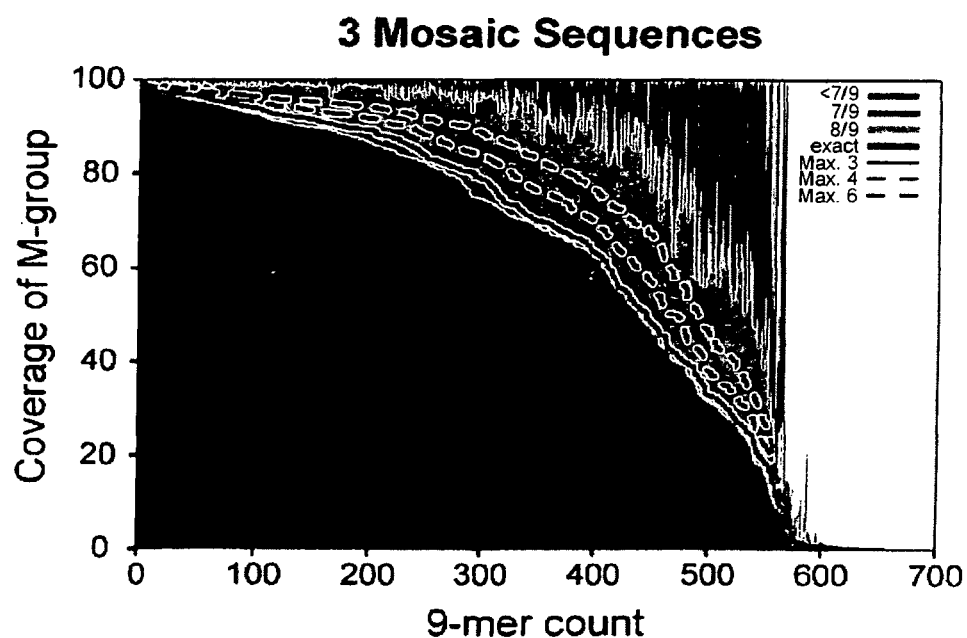
Figure 4E:
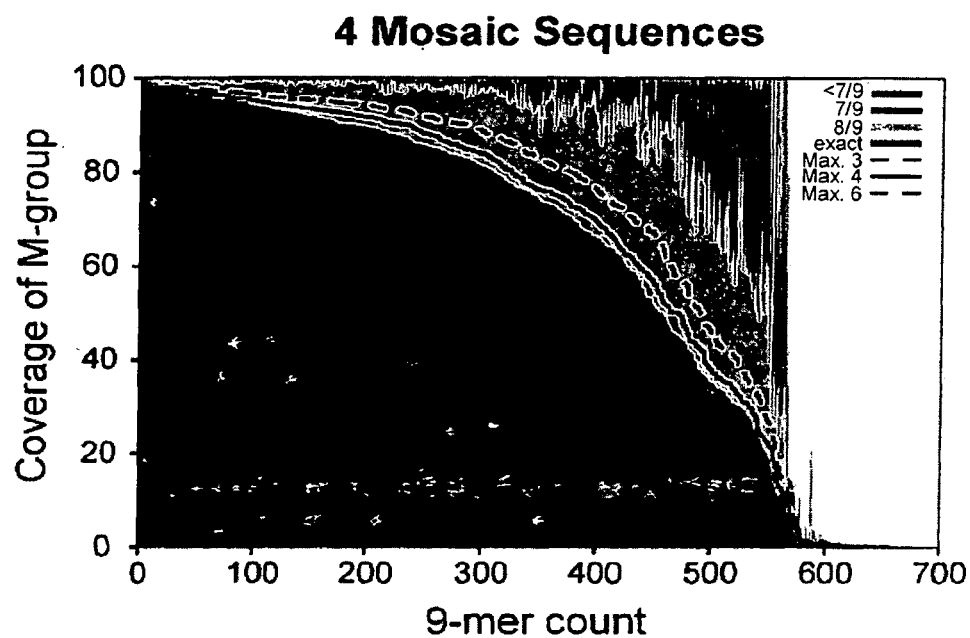
Figure 4F:
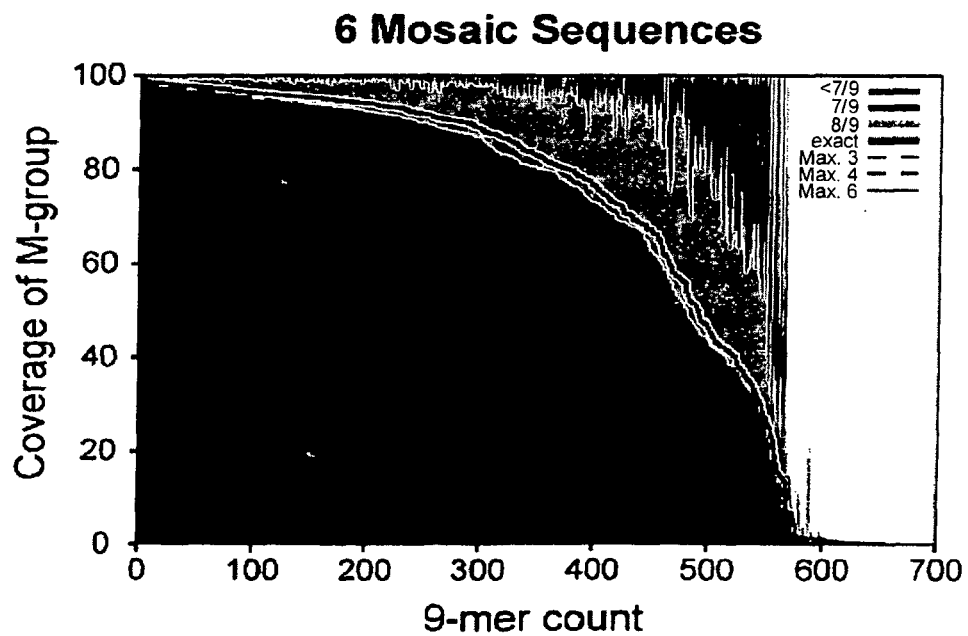

The present invention results from the realization that a polyvalent set of antigens comprising synthetic viral proteins, the sequences of which provide maximum coverage of non-rare short stretches of circulating viral sequences, constitutes a good vaccine candidate. The invention provides a "genetic algorithm" strategy to create such sets of polyvalent antigens as mosaic blends of fragments of an arbitrary set of natural protein sequences provided as inputs. In the context of HIV, the proteins Gag and Nef are ideal candidates for such antigens. To expand coverage, Pol and/or Env can also be used. The invention further provides optimized sets for these proteins.

The genetic algorithm strategy of the invention uses unaligned protein sequences from the general population as an input data set, and thus has the virtue of being "alignment independent". It creates artificial mosaic proteins that resemble proteins found in nature—the success of the consensus antigens in small animals models suggest this works well. 9 Mers are the focus of the studies described herein, however, different length peptides can be selected depending on the intended target. In accordance with the present approach, 9 mers (for example) that do not exist in nature or that are very rare can be excluded—this is an improvement relative to consensus sequences since the latter can contain some 9 mers (for example) that have not been found in nature, and relative to natural strains that almost invariably contain some 9 mers (for example) that are unique to that strain. The definition of fitness used for the genetic algorithm is that the most "fit" polyvalent cocktail is the combination of mosaic strains that gives the best coverage (highest fraction of perfect matches) of all of the 9 mers in the population and is subject to the constraint that no 9 mer is absent or rare in the population.

The mosaics protein sets of the invention can be optimized with respect to different input data sets—this allows use of current data to assess virtues of a subtype or region specific vaccines from a T cell perspective. By way of example, options that have been compared include:

1) Optimal polyvalent mosaic sets based on M group, B clade and C clade. The question presented was how much better is intra-clade coverage than inter-clade or global.
2) Different numbers of antigens: 1, 3, 4, 6
3) Natural strains currently in use for vaccine protocols just to exemplify "typical" strains (Merck, VRC)
4) Natural strains selected to give the best coverage of 9-mers in a population
5) Sets of consensus: A+B+C . . .
6) Optimized cocktails that include one "given" strain in a polyvalent antigen, one ancestral+3 mosaic strains, one consensus+3 mosaic strains.
7) Coverage of 9 mers that were perfectly matched was compared with those that match 8/9, 7/9, and 6/9 or less.

This is a computationally difficult problem, as the best set to cover one 9-mer may not be the best set to cover overlapping 9-mers.

It will be appreciated from a reading of this disclosure that the approach described herein can be used to design peptide reagents to test HIV immune responses, and be applied to other variable pathogens as well. For example, the present approach can be adapted to the highly variable virus Hepatitis C.

The proteins/polypeptides/peptides ("immunogens") of the invention can be formulated into compositions with a pharmaceutically acceptable carrier and/or adjuvant using techniques well known in the art. Suitable routes of administration include systemic (e.g. intramuscular or subcutaneous), oral, intravaginal, intrarectal and intranasal.

The immunogens of the invention can be chemically synthesized and purified using methods which are well known to the ordinarily skilled artisan. The immunogens can also be synthesized by well-known recombinant DNA techniques.

Nucleic acids encoding the immunogens of the invention can be used as components of, for example, a DNA vaccine wherein the encoding sequence is administered as naked DNA or, for example, a minigene encoding the immunogen can be present in a viral vector. The encoding sequences can be expressed, for example, in *mycobacterium*, in a recombinant chimeric adenovirus, or in a recombinant attenuated vesicular stomatitis virus. The encoding sequence can also be present, for example, in a replicating or non-replicating adenoviral vector, an adeno-associated virus vector, an attenuated *mycobacterium tuberculosis* vector, a *Bacillus* Calmette Guerin (BCG) vector, a vaccinia or Modified Vaccinia Ankara (MVA) vector, another pox virus vector, recombinant polio and other enteric virus vector, *Salmonella* species bacterial vector, *Shigella* species bacterial vector, Venezuelean Equine Encephalitis Virus (VEE) vector, a Semliki Forest Virus vector, or a Tobacco Mosaic Virus vector. The encoding sequence, can also be expressed as a DNA plasmid with, for example, an active promoter such as a CMV promoter. Other live vectors can also be used to express the sequences of the invention. Expression of the immunogen of the invention can be induced in a patient's own cells, by introduction into those cells of nucleic acids that encode the immunogen, preferably using codons and promoters that optimize expression in human cells. Examples of methods of making and using DNA vaccines are disclosed in U.S. Pat. Nos. 5,580,859, 5,589,466, and 5,703,055. Examples of methods of codon optimization are described in Haas et al, Current Biology 6:315-324 (1996) and in Andre et al, J. Virol. 72(2):1497-1503 (1998).

It will be appreciated that adjuvants can be included in the compositions of the invention (or otherwise administered to enhance the immunogenic effect). Examples of suitable adjuvants include TRL-9 agonists, TRL-4 agonists, and TRL-7, 8 and 9 agonist combinations (as well as alum). Adjuvants can take the form of oil and water emulsions. Squalene adjuvants can also be used.

The composition of the invention comprises an immunologically effective amount of the immunogen of this invention, or nucleic acid sequence encoding same, in a pharmaceutically acceptable delivery system. The compositions can be used for prevention and/or treatment of virus infection (e.g. HIV infection). As indicated above, the compositions of the invention can be formulated using adjuvants, emulsifiers, pharmaceutically-acceptable carriers or other ingredients routinely provided in vaccine compositions. Optimum formulations can be readily designed by one of ordinary skill in the art and can include formulations for immediate release and/or for sustained release, and for induction of systemic immunity and/or induction of localized mucosal immunity (e.g, the formulation can be designed for intranasal, intravaginal or intrarectal administration). As noted above, the present compositions can be administered by any convenient route including subcutaneous, intranasal, oral, intramuscular, or other parenteral or enteral route. The immunogens can be administered as a single dose or multiple doses. Optimum immunization schedules can be readily determined by the ordinarily skilled artisan and can vary with the patient, the composition and the effect sought.

The invention contemplates the direct use of both the immunogen of the invention and/or nucleic acids encoding same and/or the immunogen expressed as indicated above. For example, a minigene encoding the immunogen can be used as a prime and/or boost.

The invention includes any and all amino acid sequences disclosed herein, as well as nucleic acid sequences encoding same (and nucleic acids complementary to such encoding sequences).

Specifically disclosed herein are vaccine antigen sets optimized for single B or C subtypes, targeting regional epidemics, as well as for all HIV-1 variants in global circulation [the HIV-1 Main (M) group]. In the study described in Example 1 that follows, the focus is on designing polyvalent vaccines specifically for T-cell responses. HIV-1 specific T-cells are likely to be crucial to an HIV-1-specific vaccine response: CTL responses are correlated with slow disease progression in humans (Oxenius et al, J. Infect. Dis. 189:1199-1208 (2004)), and the importance of CTL responses in nonhuman primate vaccination models is well-established. Vaccine elicited cellular immune responses help control pathogenic SIV or SHIV, and reduce the likelihood of disease after challenge with pathogenic virus (Barouch et al, Science 290:486-492 (2000)). Temporary depletion of CD8+ T cells results in increased viremia in SIV-infected rhesus macaques (Schmitz et al, Science 283: 857-860 (1999)). Furthermore, the evolution of escape mutations has been associated with disease progression, indicating that CTL responses help constrain viral replication in vivo (Barouch et al, J. Virol. 77:7367-7375 (2003)), and so vaccine-stimulated memory responses that could block potential escape routes may be of value. While the highly variable Envelope (Env) is the primary target for neutralizing antibodies against HIV, and vaccine antigens will also need to be tailored to elicit these antibody responses (Moore & Burton, Nat. Med. 10:769-771 (2004)), T-cell vaccine components can target more conserved proteins to trigger responses that are more likely to cross-react. But even the most conserved HIV-1 proteins are diverse enough that variation will be an issue. Artificial central-sequence vaccine approaches, consensus and ancestral sequences (Gaschen et al, Science 296:2354-2360 (2002), Gao et al, J. Virol. 79:1154-1163 (2005), Doria-Rose et al, J. Virol. 79:11214-11224 (2005)), which essentially "split the differences" between strains, show promise, stimulating responses with enhanced cross-reactivity compared to natural strain vaccines (Gao et al, J. Virol. 79:1154-1163 (2005)) (Liao et al. and Weaver et al., submitted.) Nevertheless, even central strains cover the spectrum of HIV diversity to a very limited extent, and consensus-based peptide reagents fail to detect many autologous CD8+ T-cell responses (Altfeld et al, J. Virol. 77:7330-7340 (2003)).

A single amino acid substitution can mediate T-cell escape, and as one or more amino acids in many T-cell epitopes differ between HIV-1 strains, the potential effectiveness of responses to any one vaccine antigen is limited. Whether a particular mutation will diminish T-cell cross-reactivity is epitope- and T-cell-specific, although some changes can broadly affect between-clade cross-reactivity (Norris et al, AIDS Res. Hum. Retroviruses 20:315-325 (2004)). Including more variants in a polyvalent vaccine could enable responses to a broader range of circulating variants. It could also prime the immune system against common escape variants (Jones et al, J. Exp. Med. 200: 1243-1256 (2004)); escape from one T-cell receptor might create a variant that is susceptible to another (Lee et al, J. Exp. Med. 200:1455-1466 (2004)), thus stimulating polyclonal responses to epitope variants may be beneficial (Killian et al, AIDS 19:887-896 (2005)) Immune escape involving avenues that inhibit processing (Milicic et al, J. Immunol. 175:4618-4626 (2005)) or HLA binding (Ammaranond et al, AIDS Res. Hum. Retroviruses 21:395-397 (2005)) prevent epitope presentation, and in such cases the escape variant could not be countered by a T-cell with a different specificity. However, it is possible the presence of T-cells that recognize overlapping epitopes may in some cases block these even escape routes.

Certain aspects of the invention can be described in greater detail in the non-limiting Examples that follow.

EXAMPLE 1

Experimental Details

HIV-1 Sequence Data. The reference alignments from the 2005 HIV sequence database (URL: hiv-dot-lanl-dot-gov), which contain one sequence per person, were used, supplemented by additional recently available C subtype Gag and Nef sequences from Durban, South Africa (GenBank accession numbers AY856956-AY857186) (Kiepiela et al, Nature 432:769-75 (2004)). This set contained 551 Gag and 1,131 Nef M group sequences from throughout the globe; recombinant sequences were included as well as pure subtype sequences for exploring M group diversity. The subsets of these alignments that contained 18 A, 102 B, 228 C, and 6 G subtype (Gag), and 62 A, 454 B, 284 C, and 13 G subtype sequences (Nef) sequences were used for within- and between-single-clade optimizations and comparisons.

The Genetic Algorithm. GAs are computational analogues of biological processes (evolution, populations, selection, recombination) used to find solutions to problems that are difficult to solve analytically (Holland, Adaptation in Natural and Artificial Systems: An Introductory Analysis with Applications to Biology, Control, and Artificial Intelligence, (M.I.T. Press, Cambridge, Mass. (1992))). Solutions for a given input are "evolved" though a process of random modification and selection according to a "fitness" (optimality) criterion. GAs come in many flavors; a "steady-state co-evolutionary multi-population" GA was implemented. "Steady-state" refers to generating one new candidate solution at a time, rather than a whole new population at once; and "co-evolutionary" refers to simultaneously evolving several distinct populations that work together to form a complete solution. The input is an unaligned set of natural sequences; a candidate solution is a set of k pseudo-natural "mosaic" sequences, each of which is formed by concatenating sections of natural sequences. The fitness criterion is population coverage, defined as the proportion of all 9-amino-acid sequence fragments (potential epitopes) in the input sequences that are found in the cocktail.

To initialize the GA (FIG. 2), k populations of n initial candidate sequences are generated by 2-point recombination between randomly selected natural sequences. Because the input natural sequences are not aligned, "homologous" crossover is used: crossover points in each sequence are selected by searching for short matching strings in both sequences; strings of c−1=8, were used where a typical epitope length is c=9. This ensures that the recombined sequences resemble natural proteins: the boundaries between sections of sequence derived from different strains are seamless, the local sequences spanning the boundaries are always found in nature, and the mosaics are prevented from acquiring large insertions/deletions or unnatural combinations of amino acids. Mosaic sequence lengths fall within the distribution of natural sequence lengths as a consequence of mosaic construction: recombination is only allowed at identical regions, reinforced by an explicit software prohibition against excessive lengths to prevent reduplication of repeat regions. (Such "in frame" insertion of reduplicated epitopes could provide another way of increasing coverage without generating unnatural 9-mers, but their inclusion would create "unnatural" proteins.) Initially, the cocktail contains one randomly chosen "winner" from each population. The fitness score for any individual sequence in a population is the coverage value for the cocktail consisting of that sequence plus the current winners from the other populations. The individual fitness of any sequence in a population therefore depends dynamically upon the best sequences found in the other populations.

Optimization proceeds one population at a time. For each iteration, two "parent" sequences are chosen. The first parent is chosen using "2-tournament" selection: two sequences are picked at random from the current population, scored, and the better one is chosen. This selects parents with a probability inversely proportional to their fitness rank within the population, without the need to actually compute the fitness of all individuals. The second parent is chosen in the same way (50% of the time), or is selected at random from the set of natural sequences. 2-point homologous crossover between the parents is then used to generate a "child" sequence. Any child containing a 9-mer that was very rare in the natural population (found less than 3 times) is rejected immediately. Otherwise, the new sequence is scored, and its fitness is compared with the fitnesses of four randomly chosen sequences from the same population. If any of the four randomly chosen sequences has a score lower than that of the new sequence, it is replaced in the population by the new sequence. Whenever a sequence is encountered that yields a better score than the current population "winner", that sequence becomes the winner for the current population and so is subsequently used in the cocktail to evaluate sequences in other populations. A few such optimization cycles (typically 10) are applied to each population in turn, and this process continues cycling through the populations until evolution stalls (i.e., no improvement has been made for a defined number of generations). At this point, the entire procedure is restarted using newly generated random starting populations, and the restarts are continued until no further improvement is seen. The GA was run on each data set with n=50 or 500; each run was continued until no further improvement occurred for 12-24 hours on a 2 GHz Pentium processor. Cocktails were generated having k=1, 3, 4, or 6 mosaic sequences.

The GA also enables optional inclusion of one or more fixed sequences of interest (for example, a consensus) in the cocktail and will evolve the other elements of the cocktail in order to optimally complement that fixed strain. As these solutions were suboptimal, they are not included here. An additional program selects from the input file the k best natural strains that in combination provide the best population coverage.

Comparison with Other Polyvalent Vaccine Candidates. Population coverage scores were computed for other potential mono- or polyvalent vaccines to make direct comparisons with the mosaic-sequence vaccines, tracking identities with population 9-mers, as well as similarities of 8/9 and 7/9 amino acids. Potential vaccine candidates based on natural strains include single strains (for example, a single C strain for a vaccine for southern Africa (Williamson et al, AIDS Res. Hum. Retroviruses 19:133-44 (2003))) or combinations of natural strains (for example, one each of subtype A, B, and C (Kong et al, J. Virol. 77:12764-72 (2003)). To date, natural-strain vaccine candidates have not been systematically selected to maximize potential T-cell epitope coverage; vaccine candidates were picked from the literature to be representative of what could be expected from unselected vaccine candidates. An upper bound for coverage was also determined using only intact natural strains: optimal natural-sequence cocktails were generated by selecting the single sequence with the best coverage of the dataset, and then successively adding the most complementary sequences up to a given k. The comparisons included optimal natural-sequence cocktails of various sizes, as well as consensus sequences, alone or in combination (Gaschen et al, Science 296:2354-60 (2002)), to represent the concept of central, synthetic vaccines. Finally, using the fixed-sequence option in the GA, consensus-plus-mosaic combinations in the comparisons; these scores were essentially equivalent to all-mosaic combinations were included for a given k (data not shown). The code used for performing these analyses are available at: ftp://ftp-t10/pub/btk/mosaics.

Results

Protein Variation. In conserved HIV-1 proteins, most positions are essentially invariant, and most variable positions have only two to three amino acids that occur at appreciable frequencies, and variable positions are generally well dispersed between conserved positions. Therefore, within the boundaries of a CD8+ T-cell epitope (8-12 amino acids, typically nine), most of the population diversity can be covered with very few variants. FIG. 1 shows an upper bound for population coverage of 9-mers (stretches of nine contiguous amino acids) comparing Gag, Nef, and Env for increasing numbers of variants, sequentially adding variants that provide the best coverage. In conserved regions, a high degree of population coverage is achieved with 2-4 variants. By contrast, in variable regions like Env, limited population coverage is possible even with eight variants. Since each new addition is rarer, the relative benefits of each addition diminish as the number of variants increases.

Vaccine Design Optimization Strategies. FIG. 1 shows an idealized level of 9-mer coverage. In reality, high-frequency 9-mers often conflict: because of local co-variation, the optimal amino acid for one 9-mer may differ from that for an overlapping 9-mer. To design mosaic protein sets that optimize population coverage, the relative benefits of each amino acid must be evaluated in combination with nearby variants. For example, Alanine (Ala) and Glutamate (Glu) might each frequently occur in adjacent positions, but if the Ala-Glu combination is never observed in nature, it should be excluded from the vaccine. Several optimization strategies were investigated: a greedy algorithm, a semi-automated compatible-9mer assembly strategy, an alignment-based genetic algorithm (GA), and an alignment-independent GA.

The alignment-independent GA generated mosaics with the best population coverage. This GA generates a user-specified number of mosaic sequences from a set of unaligned protein sequences, explicitly excluding rare or unnatural epitope-length fragments (potentially introduced at recombination breakpoints) that could induce non-protective vaccine-antigen-specific responses. These candidate vaccine sequences resemble natural proteins, but are assembled from frequency-weighted fragments of database sequences recombined at homologous breakpoints (FIG. 2); they approach maximal coverage of 9-mers for the input population.

Selecting HIV protein regions for an initial mosaic vaccine. The initial design focused on protein regions meeting specific criteria: i) relatively low variability, ii) high levels of recognition in natural infection, iii) a high density of known epitopes and iv) either early responses upon infection or CD8+ T-cell responses associated with good outcomes in infected patients. First, an assessment was made of the level of 9-mer coverage achieved by mosaics for different HIV proteins (FIG. 3). For each protein, a set of four mosaics was generated using either the M group or the B- and C-subtypes alone; coverage was scored on the C subtype. Several results are notable: i) within-subtype optimization provides the best within-subtype coverage, but substantially poorer between-subtype coverage—nevertheless, B-subtype-optimized mosaics provide better C-subtype coverage than a single natural B subtype protein (Kong et al, J. Virol. 77:12764-72 (2003)); ii) Pol and Gag have the most potential to elicit broadly cross-reactive responses, whereas Rev, Tat, and Vpu have even fewer conserved 9-mers than the highly variable Env protein, iii) within-subtype coverage of M-group-optimized mosaic sets approached coverage of within-subtype optimized sets, particularly for more conserved proteins.

Gag and the central region of Nef meet the four criteria listed above. Nef is the HIV protein most frequently recognized by T-cells (Frahm et al, J. Virol. 78:2187-200 (2004)) and the target for the earliest response in natural infection (Lichterfeld et al, Aids 18:1383-92 (2004)). While overall it is variable (FIG. 3), its central region is as conserved as Gag (FIG. 1). It is not yet clear what optimum proteins for inclusion in a vaccine might be, and mosaics could be designed to maximize the potential coverage of even the most variable proteins (FIG. 3), but the prospects for global coverage are better for conserved proteins Improved vaccine protection in macaques has been demonstrated by adding Rev, Tat, and Nef to a vaccine containing Gag, Pol, and Env (Hel et al, J. Immunol. 176:85-96 (2006)), but this was in the context of homologous challenge, where variability was not an issue. The extreme variability of regulatory proteins in circulating virus populations may preclude cross-reactive responses; in terms of conservation, Pol, Gag (particularly p24) and the central region of Nef (HXB2 positions 65-149) are promising potential immunogens (FIGS. 1,3). Pol, however, is infrequently recognized during natural infection (Frahm et al, J. Virol. 78:2187-200 (2004)), so it was not included in the initial immunogen design. The conserved portion of Nef that were included contains the most highly recognized peptides in HIV-1 (Frahm et al, J. Virol. 78:2187-200 (2004)), but as a protein fragment, would not allow Nef's immune inhibitory functions (e.g. HLA class I down-regulation (Blagoveshchenskaya, Cell 111:853-66 (2002))). Both Gag and Nef are densely packed with overlapping well-characterized CD8+ and CD4+ T-cell epitopes, presented by many different HLA molecules (http://www.hiv.lanl.gov//content/immunology/maps/maps.html), and Gag-specific CD8+ (Masemola et al, J. Virol. 78:3233-43 (2004)) and CD4+ (Oxenius et al, J. Infect. Dis. 189:1199-208 (2004)) T-cell responses have been associated with low viral set points in infected individuals (Masemola et al, J. Virol. 78:3233-43 (2004)).

To examine the potential impact of geographic variation and input sample size, a limited test was done using published subtype C sequences. The subtype C Gag data were divided into three sets of comparable size—two South African sets (Kiepiela et al, Nature 432:769-75 (2004)), and one non-South-African subtype C set. Mosaics were optimized independently on each of the sets, and the resulting mosaics were tested against all three sets. The coverage of 9-mers was slightly better for identical training and test sets (77-79% 9/9 coverage), but essentially equivalent when the training and test sets were the two different South African data sets (73-75%), or either of the South African sets and the non-South African C subtype sequences (74-76%). Thus between- and within-country coverage approximated within-clade coverage, and in this case no advantage to a country-specific C subtype mosaic design was found.

Designing Mosaics for Gag and Nef and Comparing Vaccine Strategies. To evaluate within- and between-subtype cross-reactivity for various vaccine design strategies, a calculation was made of the coverage they provided for natural M-Group sequences. The fraction of all 9-mers in the natural sequences that were perfectly matched by 9-mers in the vaccine antigens were computed, as well as those having 8/9 or 7/9 matching amino acids, since single (and sometimes double) substitutions within epitopes may retain cross-reactivity. FIG. 4 shows M group coverage per 9-mer in Gag and the central region of Nef for cocktails designed by various strategies: a) three non-optimal natural strains from the A, B, and C subtypes that have been used as vaccine antigens (Kong et al, J. Virol. 77:12764-72 (2003)); b) three natural strains that were computationally selected to give the best M group coverage; c) M group, B subtype, and C subtype consensus sequences; and, d, e, f) three, four and six mosaic proteins. For cocktails of multiple strains, sets of k=3, k=4, and k=6, the mosaics clearly perform the best, and coverage approaches the upper bound for k strains. They are followed by optimally selected natural strains, the consensus protein cocktail, and finally, non-optimal natural strains. Allowing more antigens provides greater coverage, but gains for each addition are reduced as k increases (FIGS. 1 and 4).

Figure 5A:
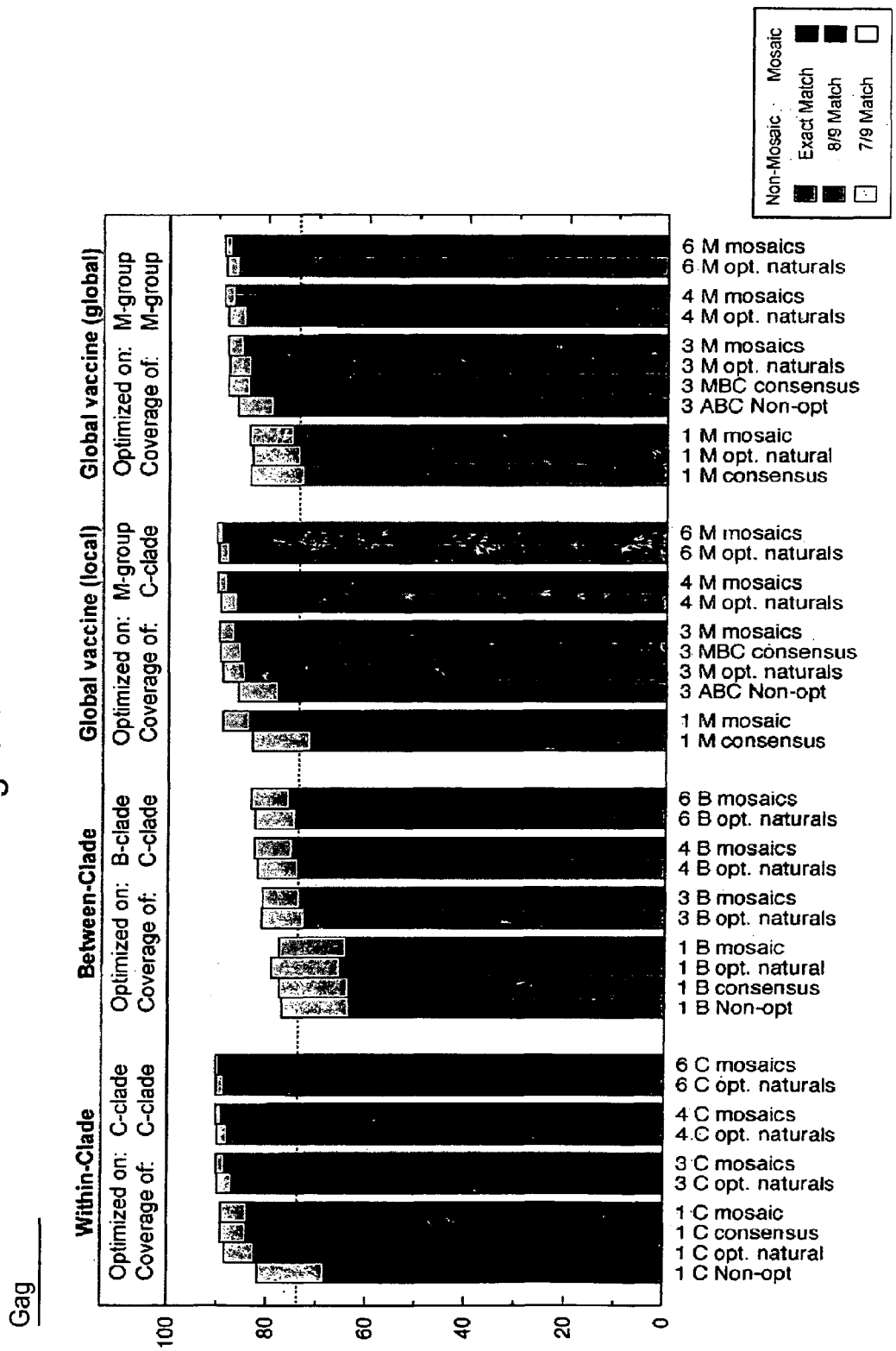
FIGS. 5A and 5B. Overall coverage of vaccine candidates: coverage of 9-mers in C clade sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 5A) and Nef (core) (FIG. 5B) for four test situations: within-clade (C-clade-optimized candidates scored for C-clade coverage), between-clade (B-clade-optimized candidates scored for C-clade coverage), global-against-single-subtype (M-group-optimized candidates scored for C-clade coverage), global-against-global (M-group-optimized candidates scored for global coverage). Within each set of results, vaccine candidates are grouped by number of sequences in the cocktail (1-6); mosaic sequences are plotted with darker colors. "Non-opt" refers to one set of sequences moving into vaccine trials (Kong et al, J. Virol. 77:12764-72 (2003)); "mosaic" denotes sequences generated by the genetic algorithm; "opt. natural" denotes intact natural sequences selected for maximum 9-mer coverage; "MBC consensus" denotes a cocktail of 3 consensus sequences, for M-group, B-subtype, and C-subtype. For ease of comparison, a dashed line marks the coverage of a 4-sequence set of M-group mosaics (73.7-75.6%). Over 150 combinations of mosaic-number, virus subset, protein region, and optimization and test sets were tested. The C clade/B clade/M group comparisons illustrated in this figure are generally representative of within-clade, between-clade, and M group coverage. In particular, levels of mosaic coverage for B and C clade were very similar, despite there being many more C clade sequences in the Gag collection, and many more B clade sequences in the Nef collection (see FIG. 6 for a full B and C clade comparison). There were relatively few A and G clade sequences in the alignments (24 Gag, 75 Nef), and while 9-mer coverage by M-group optimized mosaics was not as high as for subtypes for B and C clades (4-mosaic coverage for A and G subtypes was 63% for Gag, 74% for Nef), it was much better than a non-optimal cocktail (52% Gag, 52% for Nef).
Figure 5B:
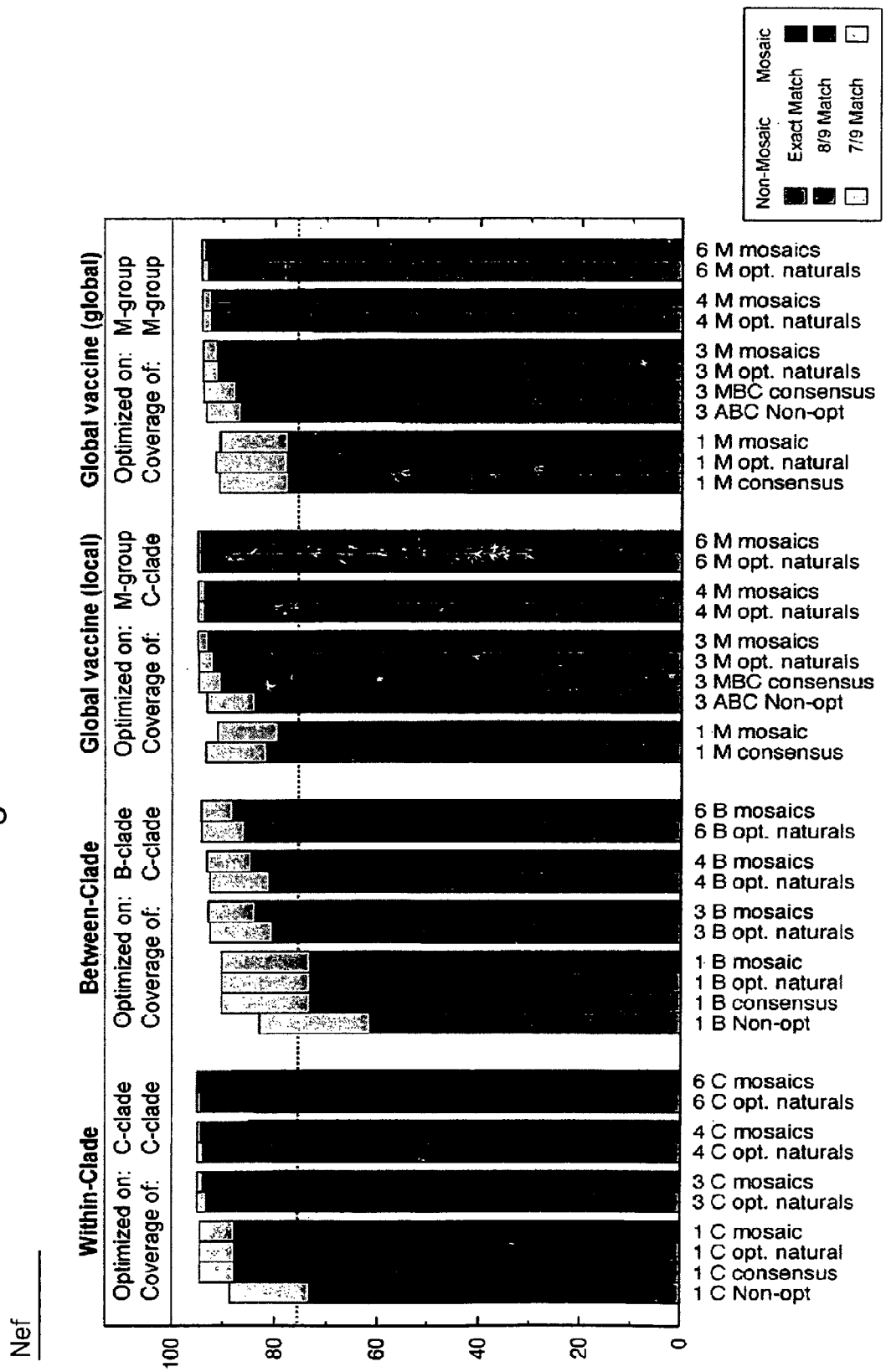
Figure 6A:
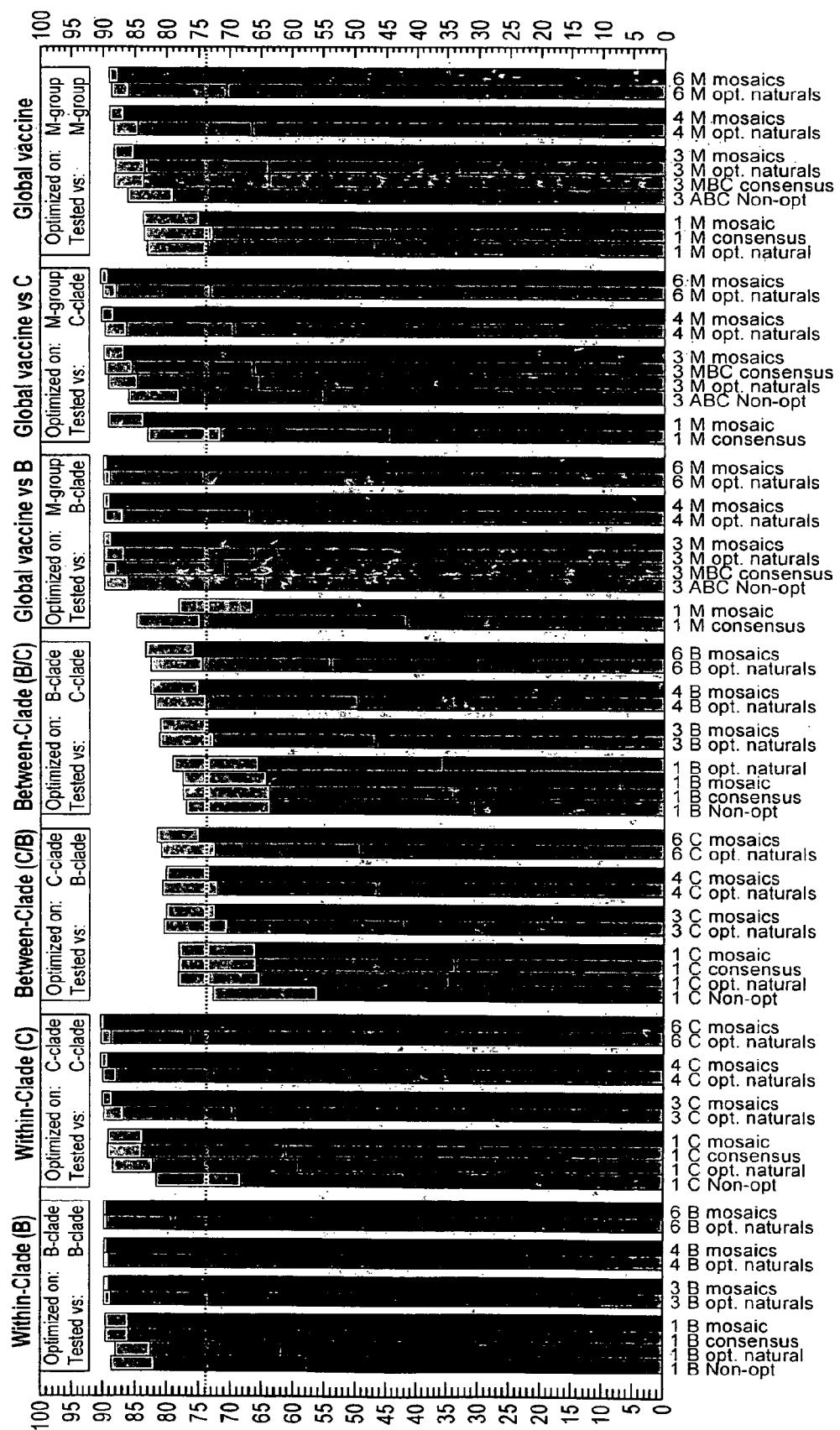
FIGS. 6A and 6B. Overall coverage of vaccine candidates: coverage of 9-mers in B-clade, C-clade, and M-group sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 6A) and Nef (core) (FIG. 6B) for seven test situations: within-clade (B- or C-clade-optimized candidates scored against the same clade), between-clade (B- or C-clade-optimized candidates scored against the other clade), global vaccine against single subtype (M-group-optimized candidates scored against B- or C-clade), global vaccine against global viruses (M-group-optimized candidates scored against all M-group sequences). Within each set of results, vaccine candidates are grouped by number of sequences in the cocktail (1-6); mosaic sequences are plotted with darker colors. "Non-opt" refers to a particular set of natural sequences previously proposed for a vaccine (Kong, W. P. et al. J Virol 77, 12764-72 (2003)); "mosaic" denotes sequences generated by the genetic algorithm; "opt. natural" denotes intact natural sequences selected for maximum 9-mer coverage; "MBC consensus" denotes a cocktail of 3 consensus sequences, for M-group, B-subtype, and C-subtype. A dashed line is shown at the level of exact-match M-group coverage for a 4-valent mosaic set optimized on the M-group.
Figure 6B:
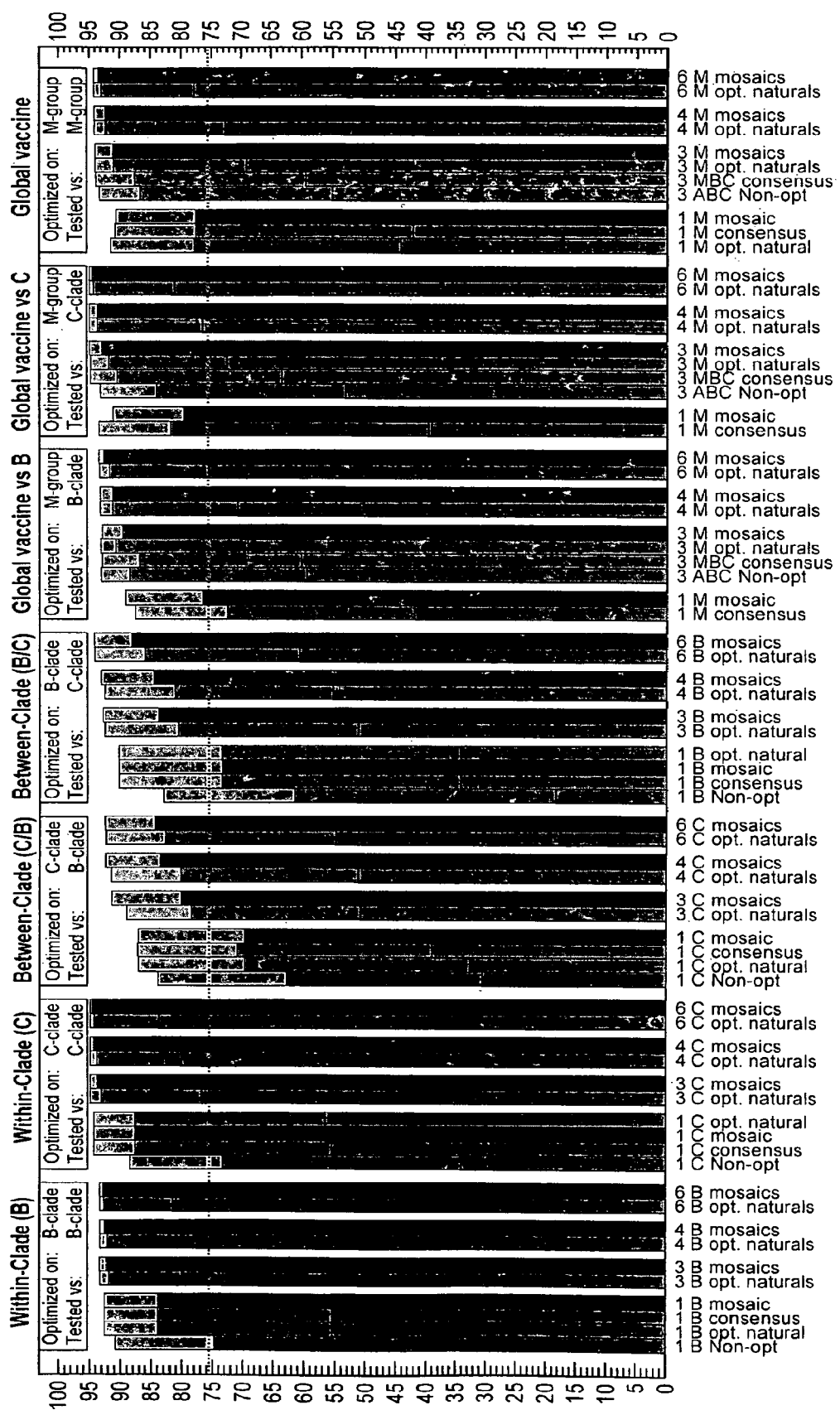

FIG. 5 summarizes total coverage for the different vaccine design strategies, from single proteins through combinations of mosaic proteins, and compares within-subtype optimization to M group optimization. The performance of a single mosaic is comparable to the best single natural strain or a consensus sequence. Although a single consensus sequence out-performs a single best natural strain, the optimized natural-sequence cocktail does better than the consensus cocktail: the consensus sequences are more similar to each other than are natural strains, and are therefore somewhat redundant. Including even just two mosaic variants, however, markedly increases coverage, and four and six mosaic proteins give progressively better coverage than polyvalent cocktails of natural or consensus strains. Within-subtype optimized mosaics perform best—with four mosaic antigens 80-85% of the 9-mers are perfectly matched—but between-subtype coverage of these sets falls off dramatically, to 50-60%. In contrast, mosaic proteins optimized using the full M group give coverage of approximately 75-80% for individual subtypes, comparable to the coverage of the M group as a whole (FIGS. 5 and 6). If imperfect 8/9 matches are allowed, both M group optimized and within-subtype optimized mosaics approach 90% coverage.

Figure 7A:
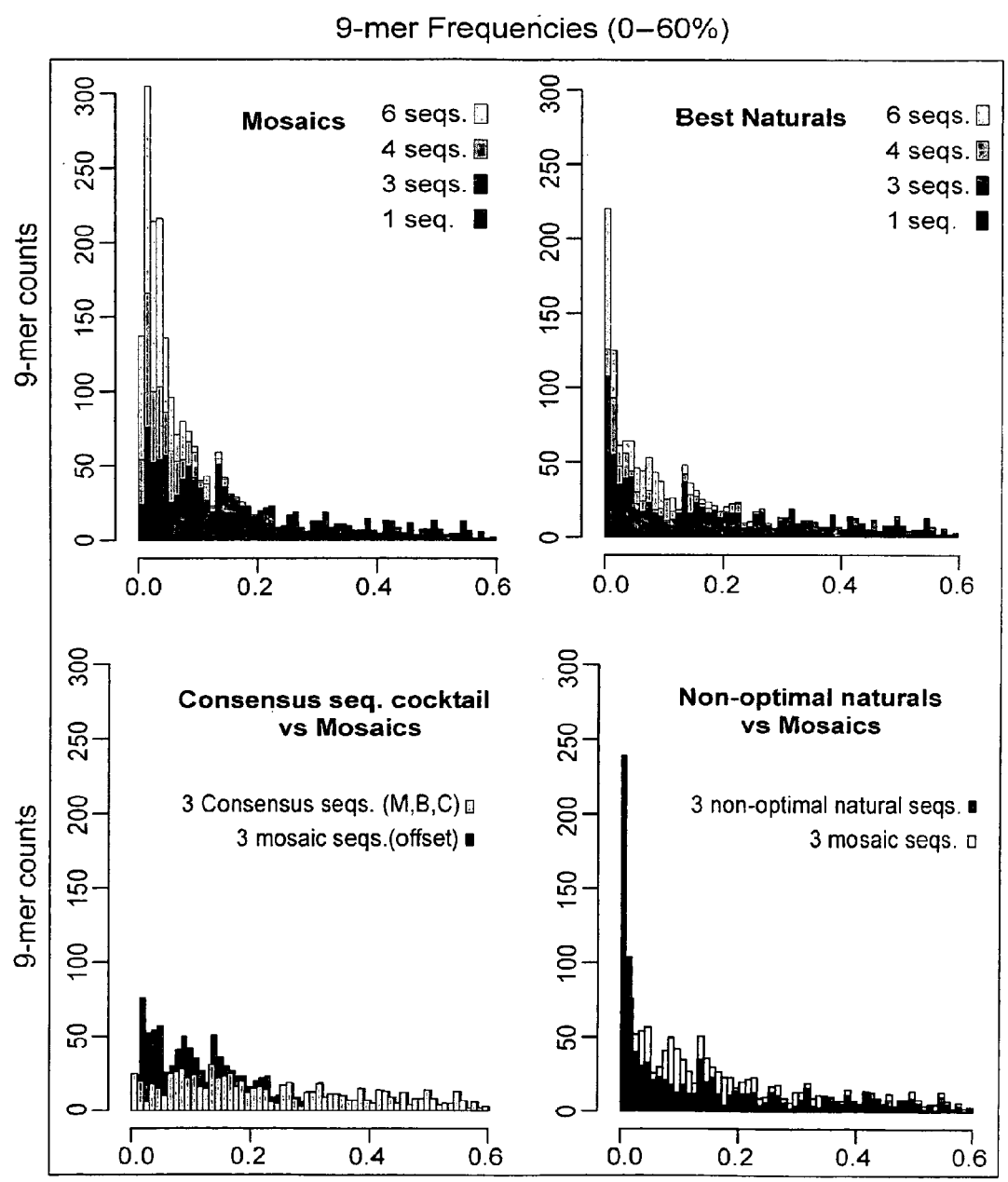
Figure 8A:
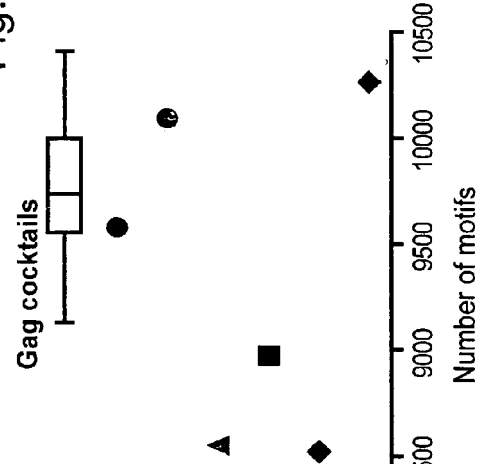
FIGS. 8A-8D. HLA binding potential of vaccine candidates.
Figure 8B:
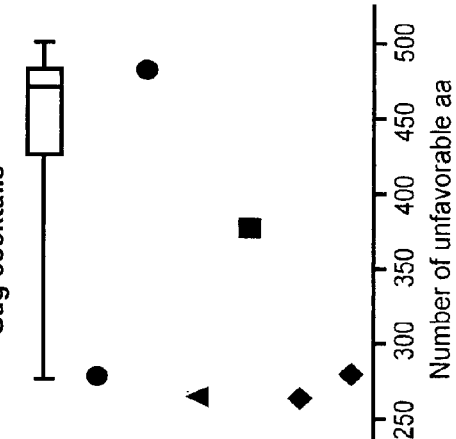
Figure 8C:
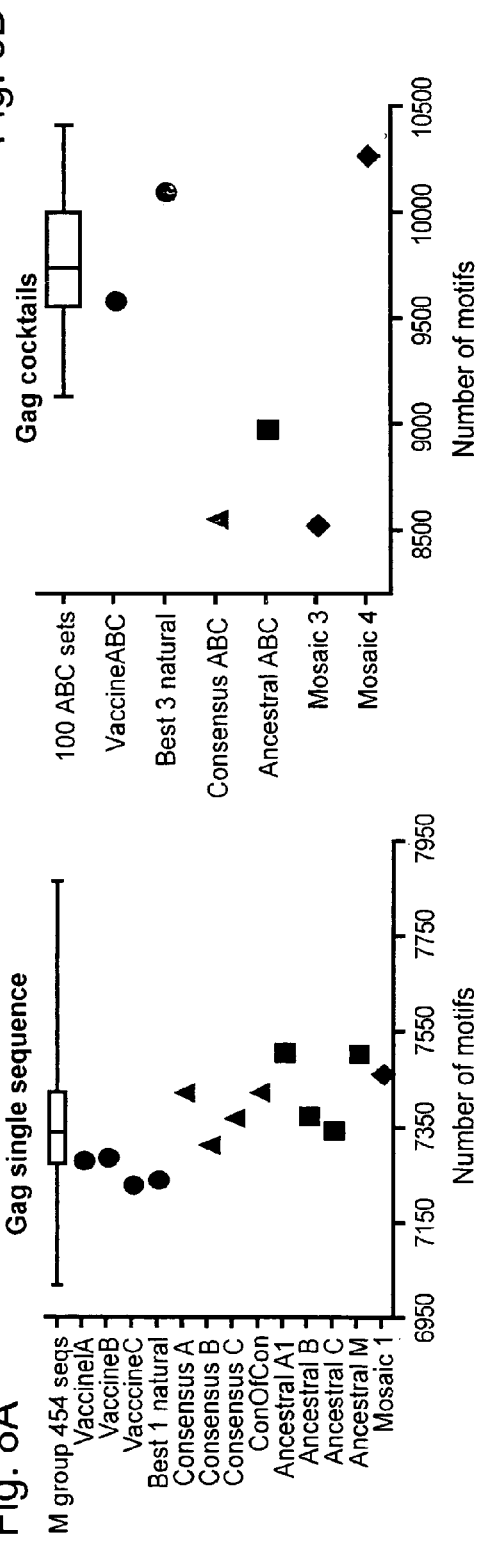
Figure 8D:
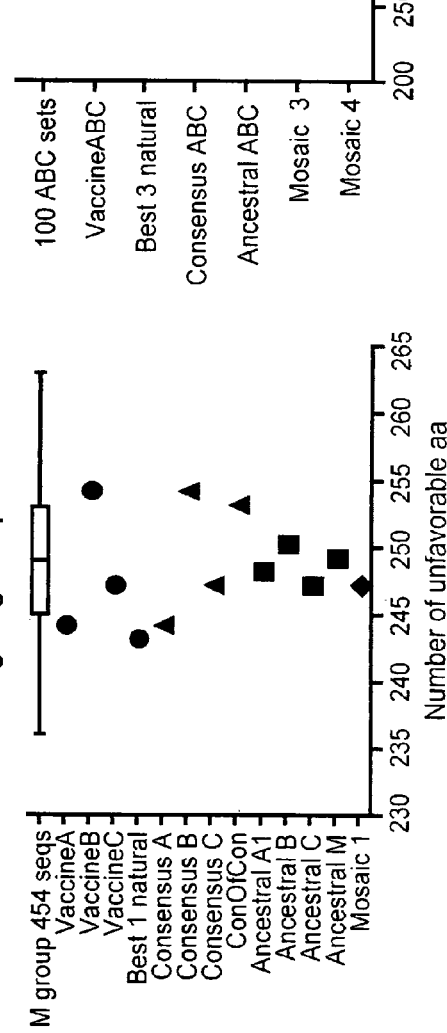

Since coverage is increased by adding progressively rarer 9-mers, and rare epitopes may be problematic (e.g., by inducing vaccine-specific immunodominant responses), an investigation was made of the frequency distribution of 9-mers in the vaccine constructs relative to the natural sequences from which they were generated. Most additional epitopes in a k=6 cocktail compared to a k=4 cocktail are low-frequency (<0.1, FIG. 7). Despite enhancing coverage, these epitopes are relatively rare, and thus responses they induce might draw away from vaccine responses to more common, thus more useful, epitopes. Natural-sequence cocktails actually have fewer occurrences of moderately low-frequency epitopes than mosaics, which accrue some lower frequency 9-mers as coverage is optimized. On the other hand, the mosaics exclude unique or very rare 9-mers, while natural strains generally contain 9-mers present in no other sequence. For example, natural M group Gag sequences had a median of 35 (range 0-148) unique 9-mers per sequence. Retention of HLA-anchor motifs was also explored, and anchor motif frequencies were found to be comparable between four mosaics and three natural strains. Natural antigens did exhibit an increase in number of motifs per antigen, possibly due to inclusion of strain-specific motifs (FIG. 8).

The increase in ever-rarer epitopes with increasing k, coupled with concerns about vaccination-point dilution and reagent development costs, resulted in the initial production of mosaic protein sets limited to 4 sequences (k=4), spanning Gag and the central region of Nef, optimized for subtype B, subtype C, and the M group (these sequences are included in FIG. 9; mosaic sets for Env and Pol are set forth in FIG. 10). Synthesis of various four-sequence Gag-Nef mosaics and initial antigenicity studies are underway. In the initial mosaic vaccine, targeted are just Gag and the center of the Nef protein, which are conserved enough to provide excellent global population coverage, and have the desirable properties described above in terms of natural responses (Bansal et al, Aids 19:241-50 (2005)). Additionally, including B subtype p24 variants in Elispot peptide mixtures to detect natural CTL responses to infection significantly enhanced both the number and the magnitude of responses detected supporting the idea that including variants of even the most conserved proteins will be useful. Finally, cocktails of proteins in a polyvalent HIV-1 vaccine given to rhesus macaques did not interfere with the development of robust responses to each antigen (Seaman et al, J. Virol. 79:2956-63 (2005)), and antigen cocktails did not produce antagonistic responses in murine models (Singh et al, J. Immunol. 169:6779-86 (2002)), indicating that antigenic mixtures are appropriate for T-cell vaccines.

Even with mosaics, variable proteins like Env have limited coverage of 9-mers, although mosaics improve coverage relative to natural strains. For example three M group natural proteins, one each selected from the A, B, and C clades, and currently under study for vaccine design (Seaman et al, J. Virol. 79:2956-63 (2005)) perfectly match only 39% of the 9-mers in M group proteins, and 65% have at least 8/9 matches. In contrast, three M group Env mosaics match 47% of 9-mers perfectly, and 70% have at least an 8/9 match. The code written to design polyvalent mosaic antigens is available, and could readily be applied to any input set of variable proteins, optimized for any desired number of antigens. The code also allows selection of optimal combinations of k natural strains, enabling rational selection of natural antigens for polyvalent vaccines. Included in Table 1 are the best natural strains for Gag and Nef population coverage of current database alignments.

TABLE 1

Natural sequence cocktails having the best available 9-mer coverage for different genes, subtype sets, and numbers of sequences Gag, B-subtype, 1 natural sequence B.US.86.AD87__AF004394
Gag, B-subtype, 3 natural sequences B.US.86.AD87__AF004394
B.US.97.Ac__06__AY247251
B.US.88.WR27__AF286365
Gag, B-subtype, 4 natural sequences B.US.86.AD87__AF004394
B.US.97.Ac__06__AY247251
B.US.__.R3__PDC1__AY206652
B.US.88.WR27__AF286365
Gag, B-subtype, 6 natural sequences B.CN.__.CNHN24__AY180905
B.US.86.AD87__AF004394
B.US.97.Ac__06__AY247251
B.US.__.P2__AY206654
B.US.__.R3__PDC1__AY206652
B.US.88.WR27__AF286365
Gag, C-subtype, 1 natural sequence C.IN.__.70177__AF533131
Gag, C-subtype, 3 natural sequences C.ZA.97.97ZA012
C.ZA.x.04ZASK161B1
C.IN.-.70177__AF533131
Gag, C-subtype, 4 natural sequences C.ZA.97.97ZA012
C.ZA.x.04ZASK142B1
C.ZA.x.04ZASK161B1
C.IN.__.70177__AF533131
Gag, C-subtype, 6 natural sequences C.ZA.97.97ZA012
C.ZA.x.04ZASK142B1
C.ZA.x.04ZASK161B1
C.BW.99.99BWMC168__AF443087
C.IN.__.70177__AF533131
C.IN.__.MYA1__AF533139
Gag, M-group, 1 natural sequence C.IN.__70177__AF533131
Gag, M-group, 3 natural sequences B.US.90.US2__AY173953
C.IN.-.70177__AF533131
15__01B.TH.99.99TH__R2399__AF530576
Gag, M-group, 4 natural sequences B.US.90.US2__AY173953
C.IN.__.70177__AF533131
C.IN.93.93IN999__AF067154
15__01B.TH.99.99TH__R2399__AF530576
Gag, M-group, 6 natural sequences C.ZA.x.04ZASK138B1
B.US.90.US2__AY173953
B.US.__.WT1__PDC1__AY206656

TABLE 1-continued

Natural sequence cocktails having the best available 9-mer coverage for different genes, subtype sets, and numbers of sequences C.IN._.70177_AF533131
C.IN.93.93IN999_AF067154
15_01B.TH.99.99TH_R2399_AF530576
Nef (central region), B-subtype, 1 natural sequence B.GB.94.028jh_94_1_NP_AF129346
Nef (central region), B-subtype, 3 natural sequences B.GB.94.028jh_94_1_NP_AF129346
B.KR.96.96KCS4_AY121471
B.FR.83.HXB2_K03455
Nef (central region), B-subtype, 4 natural sequences B.GB.94.028jh_94_1_NP_AF129346
B.KR.96.96KCS4_AY121471
B.US.90.E90NEF_U43108
B.FR.83.HXB2_K03455
Nef (central region), B-subtype, 6 natural sequences B.GB.94.028jh_94_1_NP_AF129346
B.KR.02.02HYJ3_AY121454
B.KR.96.96KCS4_AY121471
B.CN._.RL42_U71182
B.US.90.E90NEF_U43108
B.FR.83.HXB2_K03455
Nef (central region), C-subtype, 1 natural sequence C.ZA.04.04ZASK139B1
Nef (central region), C-subtype, 3 natural sequences C.ZA.04.04ZASK180B1
C.ZA.04.04ZASK139B1
C.ZA._.ZASW15_AF397568
Nef (central region), C-subtype, 4 natural sequences C.ZA.97.ZA97004_AF529682
C.ZA.04.04ZASK180B1
C.ZA.04.04ZASK139B1
C.ZA._.ZASW15_AF397568
Nef (central region), C-subtype, 6 natural sequences C.ZA.97.ZA97004_AF529682
C.ZA.00.1192M3M
C.ZA.04.04ZASK180B1
C.ZA.04.04ZASK139B1
C.04ZASK184B1
C.ZA._.ZASW15_AF397568
Nef (central region), M-group, 1 natural sequence B.GB.94.028jh_94_1_NP_AF129346
Nef (central region), M-group, 3 natural sequences 02_AG.CM._.98CM1390_AY265107
C.ZA.03.03ZASK020B2
B.GB.94.028jh_94_1_NP_AF129346
Nef (central region), M-group, 4 natural sequences 02_AG.CM._.98CM1390_AY265107
01A1.MM.99.mCSW105_AB097872
C.ZA.03.03ZASK020B2
B.GB.94.028jh_94_1_NP_AF129346
Nef (central region), M-group, 6 natural sequences 02_AG.CM._.98CM1390_AY265107
01A1.MM.99.mCSW105_AB097872
C.ZA.03.03ZASK020B2
C.03ZASK111B1
B.GB.94.028jh_94_1_NP_AF129346
B.KR.01.01CWS2_AF462757

Summarizing, the above-described study focuses on the design of T-cell vaccine components to counter HIV diversity at the moment of infection, and to block viral escape routes and thereby minimize disease progression in infected individuals. The polyvalent mosaic protein strategy developed here for HIV-1 vaccine design could be applied to any variable protein, to other pathogens, and to other immunological problems. For example, incorporating a minimal number of variant peptides into T-cell response assays could markedly increase sensitivity without excessive cost: a set of k mosaic proteins provides the maximum coverage possible for k antigens.

A centralized (consensus or ancestral) gene and protein strategy has been proposed previously to address HIV diversity (Gaschen et al, Science 296:2354-2360 (2002)). Proof-of-concept for the use of artificial genes as immunogens has been demonstrated by the induction of both T and B cell responses to wild-type HIV-1 strains by group M consensus immunogens (Gaschen et al, Science 296:2354-2360 (2002), Gao et al, J. Virol. 79:1154-63 (2005), Doria-Rose et al, J. Virol. 79:11214-24 (2005), Weaver et al, J. Virol., in press)). The mosaic protein design improves on consensus or natural immunogen design by co-optimizing reagents for a polyclonal vaccine, excluding rare CD8+ T-cell epitopes, and incorporating variants that, by virtue of their frequency at the population level, are likely to be involved in escape pathways.

The mosaic antigens maximize the number of epitope-length variants that are present in a small, practical number of vaccine antigens. The decision was made to use multiple antigens that resemble native proteins, rather than linking sets of concatenated epitopes in a poly-epitope pseudo-protein (Hanke et al, Vaccine 16:426-35 (1998)), reasoning that in vivo processing of native-like vaccine antigens will more closely resemble processing in natural infection, and will also allow expanded coverage of overlapping epitopes. T-cell mosaic antigens would be best employed in the context of a strong polyvalent immune response; improvements in other areas of vaccine design and a combination of the best strategies, incorporating mosaic antigens to cover diversity, may ultimately enable an effective cross-reactive vaccine-induced immune response against HIV-1.

EXAMPLE 2

Group M consensus envelope and trivalent mosaic envelopes (both of which were designed by in silico modeling and are predicted to be superior than wildtype envelopes) will be compared to a monovalent wild-type envelope and trivalent wild-type transmitted envelopes in a 4 arm immunogenicity clinical trial. The mosaic antigens have been designed based on the current Los Alamos database, a set that includes more full length envelopes sampled globally from more than 2000 individuals with a large set of sequences of transmitted viruses primarily from the CHAVI database.

The selection of the natural strains to be used for the comparison is based on the following criteria: For the monovalent natural antigen, use will be made of the single transmitted virus that is the best choice in terms of providing coverage of potential T cell epitopes in the global database. The database is biased towards B clade envelopes, so the single best acute Env is a B clade representative. One A, one B and one C subtype transmitted virus sequence is proposed for inclusion in the trivalent set, to compensate for the biases in sampling inherent in the global sequence collection, and to better reflect the circulating pandemic strains. The A and C natural sequences are those that optimally complement the best B clade sequence to provide potential epitope coverage of the database. Vaccine antigens have been selected from among available SGA sequenced acute samples, each representing a transmitted virus. Therefore, this study, although primarily a T cell study, will also provide important additional data regarding the ability of transmitted envelope vaccines to elicit neutralizing antibodies.

For a mosaic/consensus human trial, the following 4 arm trial is proposed, 20 people per group, with a negative control:
1) Con S (a well studied consensus of the consensus of each clade, based on the 2002 database; Con S has been extensively tested in animal models, and has theoretical coverage roughly comparable to a single mosaic.)
2) A 3 mosaic M group antigen set designed to, in combination, provide optimal global coverage of 9 amino acid long stretches in the database. Such 9-mers represent potential epitope coverage of the database. Unnatural 9-mers are excluded in mosaics, and rare variants minimized
3) The optimal single best natural protein selected from sequences sampled from acutely infected patients with SGA sequences available; these sequences should correspond to viable, transmitted sequences. As in (2), this sequence will be selected to be the one that provides optimal 9-mer coverage of the database. The B clade currently dominates sampling for the sequence database, so the sequence with the best database coverage will be a B clade sequence.
4) The best natural strains from acute infection SGA sequences that in combination provide the best global coverage. (Note: the B and C dominate the M group sampling hence the code naturally selects one of each as the two best. Thus, the third complementary sequence was forced to be selected from an acute SGA A clade set, to counter this bias and better reflect the global epidemic).
5) Negative control buffer/saline The current M group alignment in the HIV database was combined with all of the newer CHAVI sequences—this includes a total of 2020 sequences:
728 B clade
599 C clade
693 that are all other clades, circulating recombinant forms, and unique recombinants. This was used for the M group vaccine design.

This sampling is obviously skewed toward the B and C clade. As will be shown subsequently, the coverage of "potential epitopes" (9-mers) in other clades is still excellent.

The Sequences

M consensus
>ConS
(SEQ ID NO: 219)
MRVRGIQRNCQHLWRWGTLILGMLMICSAAENLWVTVYYGVPVWK
EANTTLFCASDAKAYDTEVHNVWATHACVPTDPNPQEIVLENVTENF
NMWKNNMVEQMHEDIISLWDQSLKPCVKLTPLCVTLNCTNVNVTNT
TNNTEEKGEIKNCSFNITTEIRDKKQKVYALFYRLDVVPIDDNNNNSSN
YRLINCNTSAITQACPKVSFEPIPIHYCAPAGFAILKCNDKKFNGTGPC
KNVSTVQCTHGIKPVVSTQLLLNGSLAEEEIIRSENITNNAKTIIVQL
NESVEINCTRPNNNTRKSIRIGPGQAFYATGDIIGDIRQAHCNISGTKW
NKTLQQVAKKLREHFNNKTIIFKPSSGGDLEITTHSFNCRGEFFYCNTS
GLFNSTWIGNGTKNNNNTNDTITLPCRIKQIINMWQGVGQAMYAPPIEG
KITCKSNITGLLLTRDGGNNNTNETEIFRPGGGDMRDNWRSELYKYKVV -continued
KIEPLGVAPTKAKRRVVEREKRAVGIGAVFLGELGAAGSTMGAASITL
TVQARQLLSGIVQQQSNLLRAIEAQQHLLQLTVWGIKQLQARVLAVE
RYLKDQQLLGIWGCSGKLICTTTVPWNSSWSNKSQDEIWDNMTWME
WEREINNYTDIIYSLIEESQNQQEKNEQELLALDKWASLWNWFDITNW
LWYIKIFIMIVGGLIGLRIVFAVLSIVNRVRQGYSPLSFQTLIPNPRGP
DRPEGIEEEGGEQDRDRSIRLVNGFLALAWDDLRSLCLFSYHRLRDFIL
IAARTVELLGRKGLRRGWEALKYLWNLLQYWGQELKNSAISLLDTTAIA
VAEGTDRVIEVVQRACRAILNIPRRIRQGLERALL 3 mosaics
>M_mos_3_1
(SEQ ID NO: 177)
MRVKGIRKNYQHLWRWGTMLLGMLMICSAAEQLWVTVYYGVPVW
RDAETTLFCASDAKAYEREVHNVWATHACVPTDPNPQEIVLENVTEE
FNMWKNNMVDQMHEDIISLWDESLKPCVKLTPLCVTLNCTDVNVTK
TNSTSWGMMEKGEIKNCSFNMTTELRDKKQKVYALFYKLDIVPLEEN
DTISNSTYRLINCNTSAITQACPKVTEEPIPIHYCTPAGFAILKCNDKK
FNGTGPCKNVSTVQCTHGIRPVVTTQLLLNGSLAEEEIIRSENLTNNA
KTIIVQLNESVVINCTRPNNNTRKSIRIGPGQTFYATGDIIGNIRQAHC
NISREKWINTTRDVRKKLQEHFNKTIIFNSSSGGDLEITTHSFNCRGEF
FYCNTSKLENSVWGNSSNVTKVNGTKVKETITLPCKIKQIINMWQEVGR
AMYAPPIAGNITCKSNITGLLLVRDGGNVTNNTEIFRPGGGNMKDNWR
SELYKYKVVEIKPLGIAPTKAKRRVVEREKRAVGLGAVFLGELGAAGST
MGAASMTLTVQARQLLSGIVQQQSNLLRAIEAQQHMLQLTVWGIKQLQA
RILAVERYLRDQQLLGIWGCSGKLICTTNVPWNSSWSNKSLDEIWNN
MTWMQWEKEIDNYTSLIYTLIEESQNQQEKNEQDLLALDKWANLWN
WFDISNWLWYIRIFIMIVGGLIGLRIVFAVLSIVNRVRKGYSPLSFQTL
TPNPRGPDRLGRIEEEGGEQDKDRSIRLVNGFLALAWDDLRNLCLFSYH
RLRDLLLIVTRIVELLGRRGWEALKYLWNLLQYWIQELKNSAVSLLN
ATAIAVAEGTDRVIEVVQRACRAILHIPRRIRQGLERALL >M_mos_3_2
(SEQ ID NO: 220)
MRVKETQMNWPNLWKWGTLILGLVIICSASDNLWVTVYYGVPVWKE
ATTTLFCASDAKAYDTEVHNVWATYACVPTDPNPQEVVLGNVTENF
NMWKNNMVEQMHEDIISLWDQSLKPCVRLTPLCVTLNCSNANTTNT
NSTEEIKNCSFNITTSIRDKVQKEYALFYKLDVVPIDNDNTSYRLISCN
TSVITQACPKVSFEPIPIHYCAPAGFAILKCKDKKENGTGPCTNVSTVQ
CTHGIRPVVSTQLLLNGSLAEEEVVIRSENFTNNAKTIIVHLNKSVEIN
CTRPNNNTRKSIHIGPGRAFYATGEIIGDIRQAHCNISRAKWNNTLKQI
VKKLKEQFNKTHENQSSGGDPEITTHSFNCGGEFFYCNTSGLENSTWNS
TATQESNNTELNGNITLPCRIKQIVNMWQEVGKAMYAPPIRGQIRCSSN
ITGLILTRDGGNNNSTNETFRPGGGDMRDNWRSELYKYKVVKIEPLGV
APTKAKRRVVQREKRAVGTIGAMFLGFLGAAGSTMGAASLTLTVQA
RLLLSGIVQQQNNLLRAIEAQQHLLQLTVWGIKQLQARVLAVERYLK

DQQLLGIWGCSGKLICTTTVPWNTSWSNKSLNEIWDNMTWMEWEREI

DNYTGLIYTLLEESQNQQEKNEQELLELDKWASLWNWFDITKWLWYI

KIFIMIVGGLVGLRIVETVLSIVNRVRQGYSPLSFQTHLPAPRGPDRP

EGIEEEGGERDRDRSGRLVDGFLAIIWVDLRSLCLFSYHQLRDFILIA

ARTVELLGHSSLKGLRRGWEALKYWWNLLQYWSQELKNSAISLLNTTAI

VVAEGTDRIIEVLQRAGRAILHIPTRIRQGLERLLL

>M_mos_3_3 (SEQ ID NO: 179)
MRVRGIQRNWPQWWIWGILGFWMLMICNVVGNLWVTVYYGVPVW

KEAKTTLFCASDAKAYEKEVHNVWATHACVPTDPSPQEVVLENVTEN

FNMWKNDMVDQMHEDVISLWDQSLKPCVKLTHLCVTLNCTNATNT

NYNNSTNVTSSMIGEMKNCSFNITTEIRDKSRKEYALFYRLDIVPLNEQ

NSSEYRLINCNTSTITQACPKVSFDPIPIHYCAPAGYAILKCNNKTFNG

TGPCNNVSTVQCTHGIKPVVSTQLLLNGSLAEGEIIIRSENLTDNAKTI

IVHLNESVEIVCTRPNNNTRKSVRIGPGQAFYATGDIIGDIRQAHCNLS

RTQWNNTLKQIVTKLREQFGNKTIVFNQSSGGDPEIVMHSFNCGGEFFYC

NTTQLFNSTWENSNITQPLTLNRTKGPNDTITLPCRIKQIINMWQGVGR

AMYAPPIEGLIKCSSNITGLLLTRDGGNNSETKTTETFRPGGGNMRDN

WRNELYKYKVVQIEPLGVAPTRAKRRVVEREKRAVGIGAVFLGELGT

AGSTMGAASITLTVQARQVLSGIVQQQSNLLKAIEAQQHLLKLTVWGI

KQLQTRVLAIERYLKDQQLLGLWGCSGKLICTTAVPWNSSWSNKSQT

DIWDNMTWMQWDREISNYTDTIYRLLEDSQNQQEKNEKDLLALDSW

KNLWNWFDITNWLWYIKIFIHVGGLIGLRIIFAVLSIVNRCRQGYSPLS

LQTLIPNPRGPDRLGGIEEEGGEQDRDRSIRLVSGFLALAWDDLRSLCL

FSYHRLRDFILIVARAVELLGRSSLRGLQRGWEALKYLGSLVQYWGLEL

KKSAISLLDTIAIAVAEGTDRIIEVIQRICRAIRNIPRRIRQGPEAALL

Single optimal natural sequence selected from available acute SGA sequences:

>B.acute.Con.1059 (SEQ ID NO: 221)
MRVTEIRKNYLWRWGIMLLGMLMICSAAEQLWVTVYYGVPVWKEA

TTTLFCASDAKAYTAEAHNVWATHACVPTDPNPQEVVLENVTENFN

MWKNNMVEQMHEDIISLWDQSLKPCVKLTPLCVTLNCTDLANNTNL

ANNTNSSISSWEKMEKGEIKNCSFNITTVIKDKIQKNYALFNRLDIVPI

DDDDTNVTNNASYRLISCNTSVITQACPKISFEPIPIHYCAPAGFAILK

CNDKKFNGTPCTNVSTVQCTHGIKPVVSTQLLLNGSLAEEEVVIRSE

NFTDNVKTIIVQLNESVIINCTRPNNNTRKSITFGPGRAFYTTGDIIGD

IRKAYCNISSTQWNNTLRQIARRLREQFKDKTIVFNSSSGGDPEIVMHS

FNCGGEFFYCNTTQLFNSTWNGNDTGEFNNTGKNITYITLPCRIKQIIN

MWQEVGKAMYAPPIAGQIRCSSNITGILLTRDGGNSSEDKEIFRPEGGN

MRDNWRSELYKYKVVKIEPLGVAPTKAKRRVVQREKRAVGIGAVFLGFL

GAAGSTMGAASMTLTVQARLLLSGIVQQQNNLLRAIEAQQHLLQLTVWG

IKQLQARVLAVERYLKDQQLLGIWGCSGKLICTTAVPWNASWSNRSLD

NIWNNMTWMEWDREINNYTNLIYNLIEESQNQQEKNEQELLELDKW

ASLWNWFDITKWLWYIKIFIMIVGGLVGLRIVFVILSIVNRVRQGYSPL

SFQTHLPTPRGLDRHEGTEEEGGERDRDRSGRLVDGFLTLIWIDLRSLC

LFSYHRLRDLLLIVTRIVELLGRRGWEILKYWWNLLQYWSQELKNSA

VSLLNATAIAVAEGTDRIIEIVQRIFRAILHIPTRIRQGLERALL 3 optimal natural selected from available acute, SGA sequences:

>B.acute.Con.1059 (SEQ ID NO: 221)
MRVTEIRKNYLWRWGIMLLGMLMICSAAEQLWVTVYYGVPVWKEA

TTTLFCASDAKAYTAEAHNVWATHACVPTDPNPQEVVLENVTENFN

MWKNNMVEQMHEDIISLWDQSLKPCVKLTPLCVTLNCTDLANNTNL

ANNTNSSISSWEKMEKGEIKNCSFNITTVIKDKIQKNYALFNRLDIVP

IDDDDTNVTNNASYRLISCNTSVITQACPKISFEPIPIHYCAPAGFAIL

KCNDKKFNGTPCTNVSTVQCTHGIKPVVSTQLLLNGSLAEEEVVIRS

ENFTDNVKTIIVQLNESVIINCTRPNNNTRKSITFGPGRAFYTTGDIIG

DIRKAYCNISSTQWNNTLRQIARRLREQFKDKTIVFNSSSGGDPEIVMH

SFNCGGEFFYCNTTQLFNSTWNGNDTGEFNNTGKNITYITLPCRIKQII

NMWQEVGKAMYAPPIAGQIRCSSNITGILLTRDGGNSSEDKEIFRPEGG

NMRDNWRSELYKYKVVKIEPLGVAPTKAKRRVVQREKRAVGIGAVFLGF

LGAAGSTMGAASMTLTVQARLLLSGIVQQQNNLLRAIEAQQHLLQLTVW

GIKQLQARVLAVERYLKDQQLLGIWGCSGKLICTTAVPWNASWSNRSLD

NIWNNMTWMEWDREINNYTNLIYNLIEESQNQQEKNEQELLELDKW

ASLWNWFDITKWLWYIKIFIMIVGGLVGLRIVFVILSIVNRVRQGYSPL

SFQTHLPTPRGLDRHEGTEEEGGERDRDRSGRLVDGFLTLIWIDLRSLC

LFSYHRLRDLLLIVTRIVELLGRRGWEILKYWWNLLQYWSQELKNSA

VSLLNATAIAVAEGTDRIIEIVQRIFRAILHIPTRIRQGLERALL

>C.acute.Con.0393 (SEQ ID NO: 222)
MRVRGILRNYQQWWIWGILGFWMLMICSVGGNLWVTVYYGVPVWR

EAKTTLFCASDAKAYERVEHNVWATHACVPTDPNPQELFLENVTENF

NMWKNDMVDQMHEDIISLWDQSLKPCVKLTPLCVTLNCSNANITRNS

TDGNTTRNSTATPSDTINGEIKNCSFNITTELKDKKKKEYALFYRLDIV

PLNEENSNFNEYRLINCNTSAVTQACPKVSFDPIPIHYCAPAGYAILKC

NNKTFNGTPCNNVSTVQCTHGIKPVVSTQLLLNGSLAEEEIIIRSENL

TNNAKTIIVHLKEPVEIVCTRPNNNTRKSMRIGPGQTFYATDIIGDIRQ

ASCNIDEKTWNNTLNKVGEKLQEHFPNKTLNFAPSSGGDLEITTHSFNC

RGEFFYCNTSKLFYKTEFNSTTNSTITLQCRIKQIINMWQGVGRAMYA

PPIEGNITCKSNITGLLLTRDGGTNDSMTETFRPGGGDMRDNWRSELYK

YKVVEIKPLGVAPTEAKRRVVEREKRALTLGALFLGFLGTAGSTMGAA

SITLTVQARQLLSGIVQQQSNLLKAIEAQQHLLQLTVWGIKQLQTRVL

-continued

AIERYLQDQQLLGLWGCSGKLICTTAVPWNSSWSNKSQGEIWGNMT

WMQWDREISNYTNTIYRLLEDSQIQQEKNEKDLLALDSWKNLWSWFS

ITNWLWYIKIFIMIVGGLIGLRIIFAVLSIVNRVRQGYSPLPFQTLIPN

PRGPDRLGRIEEEGGEQDRDRSIRLVNGFLAIAWDDLRSLCLFSYHRLR

DFILIAARAAELLGRSSLRGLQRGWEALKYLGSLVQYWGLELKKSAISL

LDTVAITVAEGTDRIIEVVQRICRAICNIPRRIRQGFEAALQ

Coverage Comparison of the Four Vaccine Antigens.

Mosaics and naturals are optimized for the first red bar on the left for each vaccine (the total). The "total" represents all sequences, database+CHAVI. The "B" is the subset that are B clade, "C" the subset that are C clade, and "N" the remaining M group sequences that are not B or C (all other clades and recombinants). As B is most common, the single best natural is of course a B, and B thus has the best coverage for Nat.1. Con S, as expected, provides much more even coverage for all clades, and provides better coverage for all the groups except B clade. (Note: in a Con S Macaque study, the natural B was not selected to be optimal, and Con S had better coverage even within B clade than the B vaccine strain that had been used; this was reflected in the number of detected responses to heterogeneous B's. A difference here is that the natural B was selected to be the natural B clade sequence from acute infection that provides optimal coverage). Nat.3 gives good broad coverage, Mos.3 better. (See FIG. 11.)

The mosaics will minimize rare 9-mers but in Env they cannot be excluded or it is not possible to span certain really variable regions to make intact proteins. For all other HIV proteins tested, it was possible to exclude 9-mers that were found at 3 times or less. Still, the 3 best natural Envs contain more than twice the number of rare 9-mer variants relative to the 3 Env mosaics.

Figure 12:
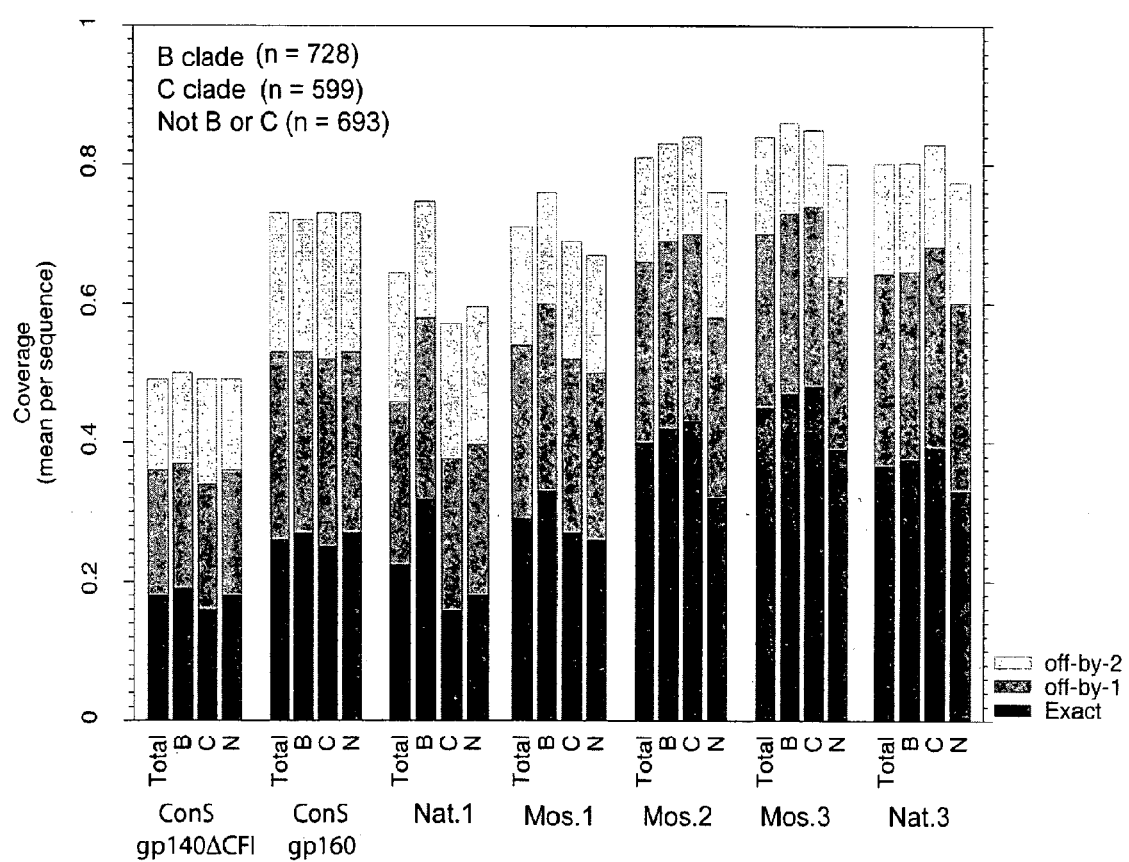
FIG. 12. Additional summaries of coverage.

FIG. 12 includes additional summaries of coverage; ConS gp 160 contains quite a few conserved 9-mers that are missed in gp140DCFI, as one would expect. ConS provides slightly less coverage than a single mosaic, but it is already known that ConS works very well in macaques so serves as a good positive control. 1, 2, and 3 mosaics give increasingly better coverage, and Nat.3 is not as good as Mos.3.

Figure 13:
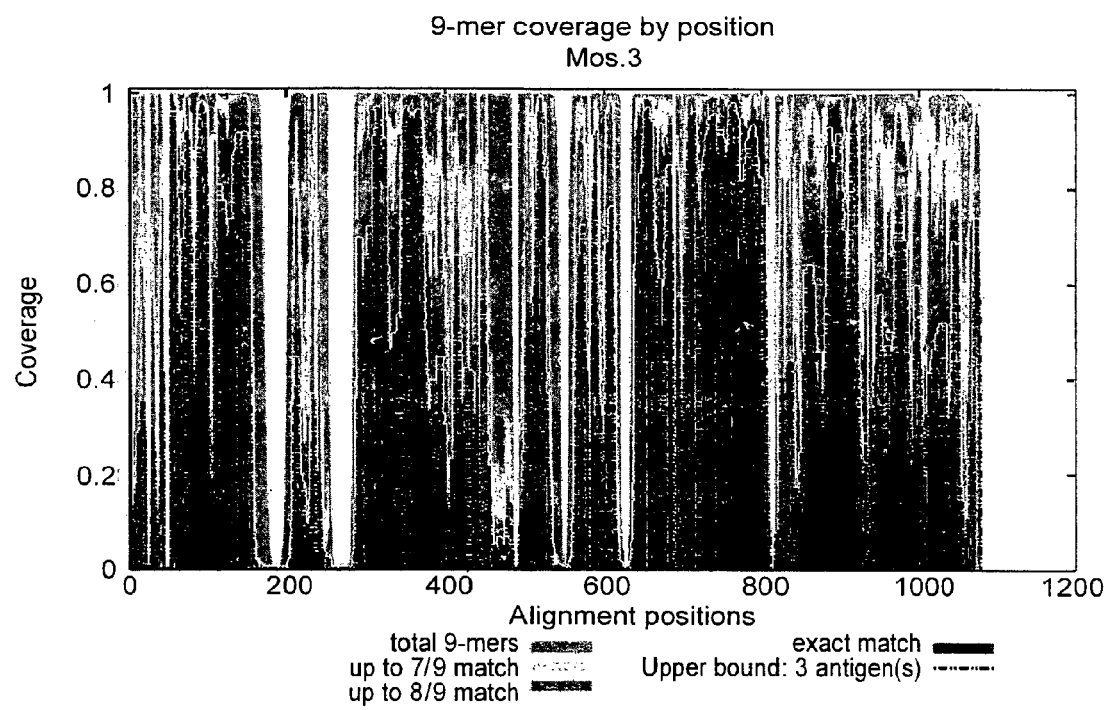
FIG. 13. 9-mer coverage by position (Mos.3 vaccine cocktail).

FIG. 13 is alignment dependent, and based on the database alignment (the tow plots above this are alignment independent). Each position represents the 9-mer it initiates as one moves across the protein. The upper bound (black dashed lined) is the sum of the frequencies of the three most common 9-mers starting from each position; it represents the maximal limit that could be achieved for coverage with 3 proteins, and this is not quite achievable in practice because there can be conflicts in a given position for overlapping 9-mers, although the 3 mosaic combination very nearly achieves it. The reason the "total 9-mers" shown in grey varies is because of insertions and deletions in the alignment.

Only the Mos.3 vaccine cocktail is shown in FIG. 13. However, all four vaccines resorted by coverage is shown in FIG. 14, where those positions that start the 9-mers that are best covered by the vaccine are moved to the left. The exact match line is left in all four plots for a reference point. Not only does Mos.3 (red) approach the maximum, but the orange and yellow near-matches that have potential for cross-reactivity are also improved in this vaccine cocktail as compared to the others.

The plots shown in FIG. 15 map every amino acid in every sequence in the full database alignment. A row of pixels is a sequence, a column is an alignment position. White patches are insertions to maintain the alignment. All 9-mers that encompass an amino acid are considered. If every 9-mer that spans the amino acid has a perfect match in the vaccine cocktail, the pixel is yellow, so yellow is good. If one is off, light orange, two off, darker orange . . . through no spanning 9-mer matches represented by black. Note: lots of yellow for 3 mosaics, relative to the other vaccines. There is a big patch of the most yellow for the B clade in Nat.1 as the single best natural is a B clade. Note, all those dark bits: in these regions the sequences in the database are different than any 9-mer in the vaccine, so cross-reactivity would be several limited.

Optimization Using 9-Mers.

Figure 16:
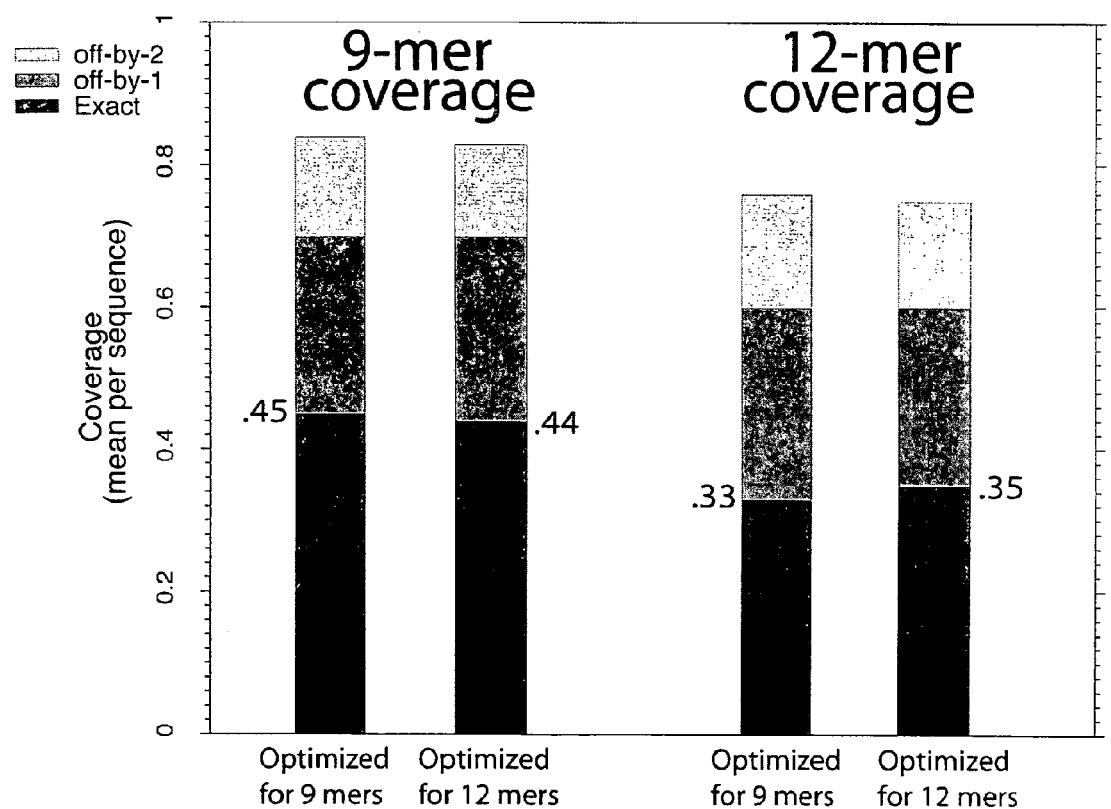
FIG. 16. 3 Mosaic, M group Optimizations.

9-mers were selected because that is the most common size of an optimal CD8+ T cell epitope. They range from 8-12, and optimal CD4+ T cell epitopes can be even be larger or smaller. As it turns out, coverage of 9-mers is best when optimized for 9-mer coverage, but if optimization on a different size yields very little decrease in coverage for 9-mers. The same goes for all lengths, 8-12, the peak coverage is for the size selected but the coverage is excellent for other lengths, as the solutions are related. 9-versus 12-mers are shown in FIG. 16, 12 being the most extreme value one might reasonably consider. The coverage is nearly identical for 9-mers optimized for 9 or 12, or for 12-mers optimized for 9 or 12; it is 1-2% higher for the length selected for optimization. Naturally, 12-mers have fewer identities than 9-mers in general, because they are longer so it is harder to find a prefect match. A more comprehensive study was made of this for HIV proteins showing that the loss was consistently larger for 12-mers when optimized on 9 rather than vice versa, and that, in other proteins, this difference could be up to 4-5%. Thus, for Env the selection of 9-mers is less of a problem. Given all of the above, 9-mers were selected since this is the most common optimal CTL epitope length, and since optimal coverage of 9-mers provides approaching optimal coverage of other lengths.

Options for the 3 Best Natural Strains: Acute Transmission Cases, SGA Sequences.

Use of all database sequences as a source for natural strains for vaccine cocktails was first explored, and then a comparison was made of that with selecting from a restricted group of just acute SGA sequences, essentially transmitted viruses. Essentially comparable coverage of the full database could be achieved by restricting to acute infection sequences. As these have other obvious advantages, they will be used for the natural sequences.

First, the exploration of coverage using the full database as a source for a natural cocktail. As noted above, the current M group Env one-seq-per-person data set is dominated by B clade infections, closely followed by C clade. Thus, the single best optimal natural selected by the vaccine design program to cover 9-mers in the (database+CHAVI) data set is a B. If one picks from among any sequence in the database, YU-2 comes up as the best single sequence. To get better representation of other clades, the best B was fixed, and then the next best sequence was added to complement YU-2, which is (logically) a C clade sequence, DU467. Those two were then fixed, and the third complement of the antigen was selected. (If the first two are not fixed, and the program is allowed to choose the third, it logically found a B/C recombinant, it has to be forced to select an A. It is believed that forcing the ABC set would improve global coverage, and partly counteract the B & C clade sampling bias among sequences.)

The optimal naturals from the database tend to harken back to older sequences; this is not surprising, as the older sequences tend to be more central in phylogenetic trees, and thus more similar other circulating strains. For this study, however, it is preferred to use more contemporary Envelope proteins sampled during acute infection and sequenced using SGA, as these sequences accurately reflect the transmitted virus. Given that constraint, it is still desired to optimize for 9-mer coverage, so that the cocktail of natural sequences is given the best chance for success in the comparison with mosaics. It turns out when this was done there was an extremely minor loss of coverage when comparing the trivalent cocktail selected from among acute SGA sequences to the trivalent antigen selected from the entire database, (in both cases optimizing for coverage the full database). Thus, by restricting the antigen cocktails to transmitted virus, coverage is not compromised. This alternative has several advantages. Most importantly, it enables a determination of the cross-reactive potential of antibodies generated from acute infection viruses used for the natural cocktail relative to consensus or mosaics as a secondary endpoint of interest, without compromising the primary endpoint focusing on a comparison of T-cell response breadth of coverage. A large set of B (113) and C (40) clade acute samples sequenced from CHAVI study is available, giving a large dataset from which to select an optimum combination. For the selection of the complementary sequence from the A clade, to complete the B and C in the trivalent vaccine. Several acute sequences were available.

Analysis of gp160 was undertaken that included the 8 subtype A gp160s, and also a subregion analysis was done with all 15 in V1-V4, to get an indication of whether or not more sequencing was required. Fortunately, one of the available full length sequences made an excellent complement to the B and C acutes, essentially as good as any of the others. This comparison indicated there was no particular need to do more sequencing at this time. It is believed that this is appropriate since with such a limited A baseline to select from, because the A sequence only needs to complement the choice of B and C clade strains, and many Bs and Cs were available from which to choose. Two of the patients from which the Nat.3 cocktail is derived are below. Nat.1 is just the first one.

Figure 18:
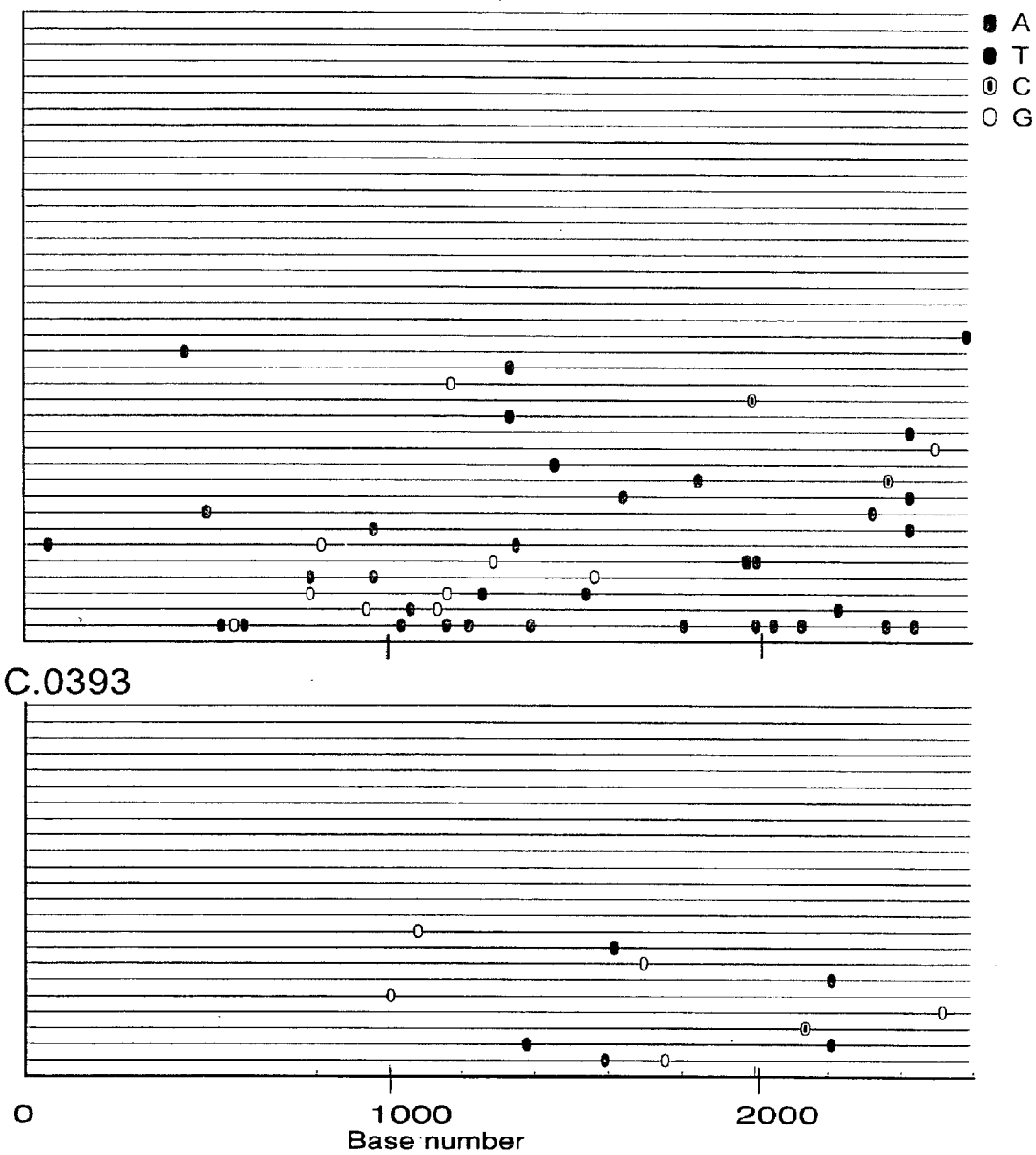
FIG. 18. Differences in acute infection patient sequences compared to patient consensus.

B Patient 1059
Patient Sex=M
RiskFactor=PPD
Sample country=USA
Sample city=Long Beach, Calif.
Patient cohort=CA-UCSF
Patient health status=Acute
Viral Load=2,800,000
Infection country=USA
Sample date=Mar. 26, 1998
C Patient 0393
Fiebig Stage=4
Infection country=Malawi
Sample date=17 Jul. 2003
Viral Load=12,048,485
Patient sex=F
CD4count=618 (measured 13 days after sequenced sample)
Patient age=23
STD=GUD, PID FIGS. 17 and 18 illustrate the minimal loss of coverage in selecting from acute SGA sequences, and a highlighter plot of each of the 3 patients env sequences, that shows that the consensus of each patient is equivalent to the most common strains, and thus an excellent estimate of the actual transmitted virus.

Why M Group and not Clade Specific Coverage?

Figure 19:
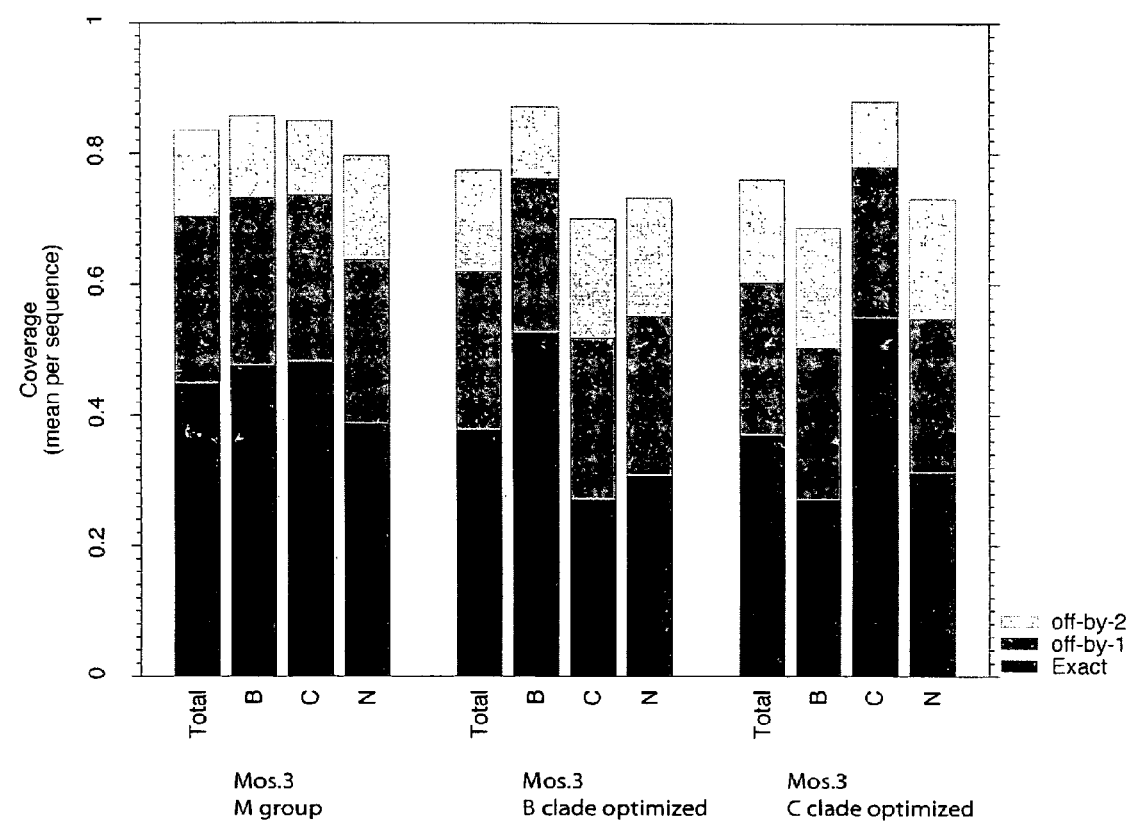

It is believed that it is important to strive for a global HIV vaccine, if at all possible, with exploratory methods such as these since many nations have multiclade epidemics, and people travel. While intra-clade coverage can definitely be gained by a within-clade optimized vaccine, the result of such a strategy would be dramatic loss of inter-clade coverage. The hope is that a multivalent mosaic could provide enough breadth to counter viruses of virtually any clades or recombinants. The compromise and benefit in terms of coverage for Env M group versus subtype-specific design is shown in FIG. 19.

Why Env?

Figure 20:
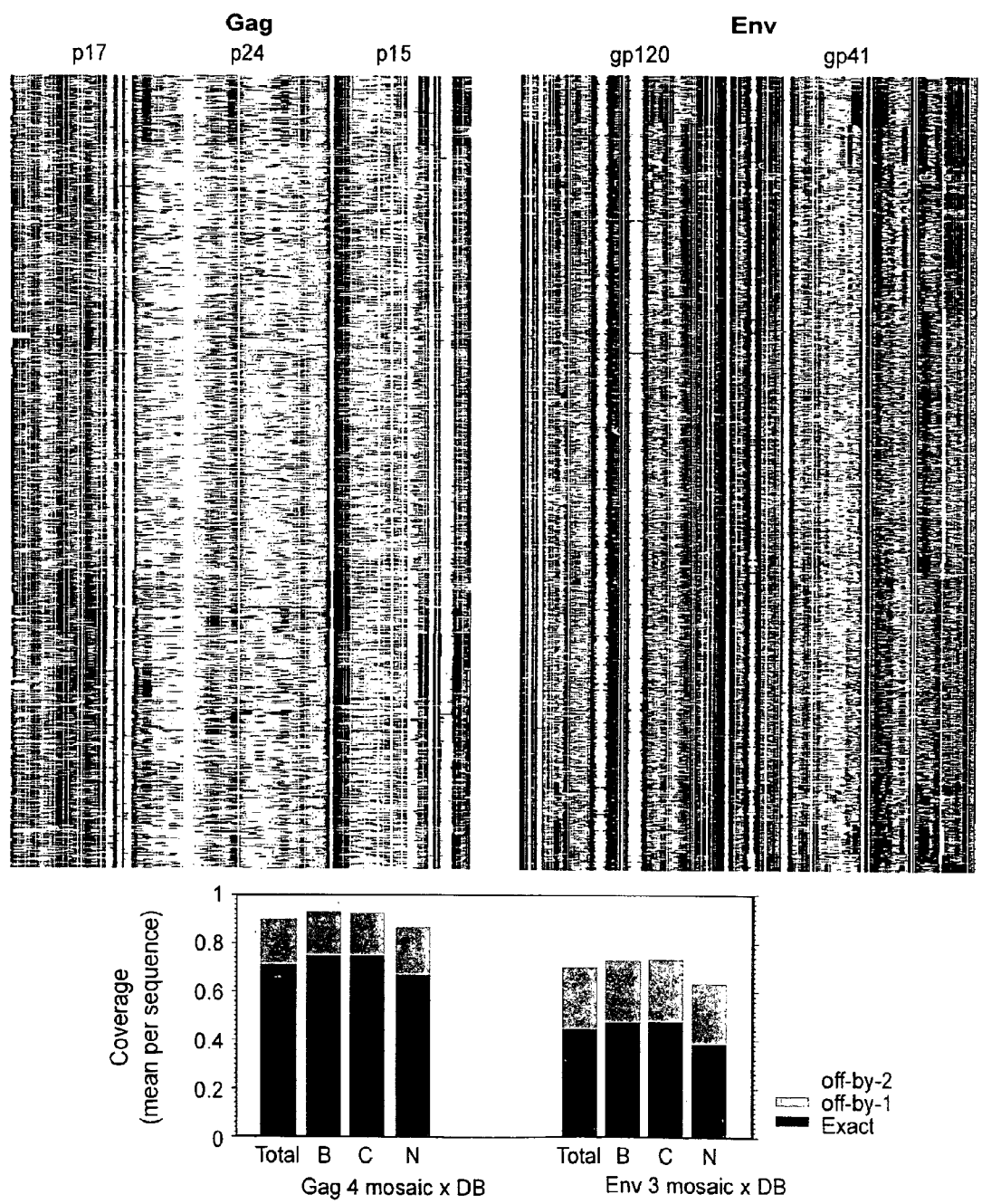
FIG. 20. Proposed vaccine mosaic coverage of Gag and Env.

This proof of concept study is well positioned to see differences in breadth of responses using Env as the test antigen. This is partly because of the theoretical considerations described herein (ENV has twice many conserved 9 mers in the mosaics relative to the best natural strain, and only half as many rare variants) and partly because of the prior animal studies. Env studies with a consensus versus natural in macaques showed a highly significant increase in breadth of responses: 3-4 fold more epitopes per Env protein were recognized (Santra et al, in press, PNAS). Env mosaics have shown an even more profound advantage in a mouse study (up to 10-fold over comparable numbers of natural antigens, manuscript in preparation in collaboration with the VRC). Based on this prior work, it makes sense to start with a small human trial testing the breadth of responses to Env. Ultimately, the hope is to apply the proof of concept gained with Env to a more conserved protein like a Gag where it may be possible to confer broadest protection. Gag gives outstanding coverage of the full M group. Tests of Gag and Nef are ongoing in macaque, using a 4 mosaic vaccine cocktail approach (see Example 3). A coverage comparison of macaque 4 mosaic Gag vaccine and proposed human Env 3 mosaic vaccine against the current database is in FIG. 20. There is more theoretical potential for cross-reactivity with the Gag vaccine, but more progress has been made with Env in the animal models to date, so Env has the best foundation to justify moving forward. The three mosaic Env sequences described above and the sequences used in Example 3 are shown in FIG. 21.

DNA

The DNAs to be used will be in the form of the full gp160 Env. The gp160 would be in the PCMVR plasmid (Gary Nabel) and will be the identical plasmid used in all VRC DNA immunization trials. Dose is anticipated to be 4 mg. The following DNA constructs will be used:
    DNA optimal Wildtype Env transmitted/founder env (WT Env)
    DNA group M consensus Env (ConS Env)
    DNA Trivalent optimal wildtype transmitted/founder Env (WT Tri Env)
    DNA Trivalent Mosaic Env

NYVAC

NYVAC (vP866) is a recombinant poxvirus vector which has an 18 gene deletion versus wild-type virus. The NYVAC vector will be licensed from Sanofi-Pasteur and manufactured by a third party contractor and will be propagated on a CEF cell substrate. The Env construct expressed in NYVAC will be gp140C (entire Env with transmembrane and cytoplasmic domain deleted and gp41/gp120 cleavage site mutated) or will be a full gp160. The choice of construct design will depend on the ability to make the NYVAC with gp160 forms vs gp140. The dose of NYVAC is anticipated to be ~1×10^7 TCID50. The following NYVAC constructs will be used:
    NYVAC WT Env
    NYVAC ConS Env
    NYVAC Trivalent Native Env
    NYVAC Trivalent Mosaic Env Vaccinations will be given by intramuscular injection.

TABLE

Protocol Schema

| Group | Number | Injection schedule in weeks / Dose | | | |
|---|---|---|---|---|---|
| | | 0 | 4 | 20 | 24 |
| | | DNA WT | DNA WT | NYVAC WT | NYVAC WT |
| 1 | 20 | Env | Env | EnvA | EnvA |
| | 4 | Placebo | Placebo | Placebo | Placebo |
| | | DNA ConS | DNA ConS | NYVAC ConS | NYVAC ConS |
| 2 | 20 | Env | Env | | |
| | 4 | Placebo | Placebo | Placebo | Placebo |
| | | DNA Trivalent | DNA Trivalent | NYVAC Trivalent | NYVAC Trivalent |
| 3 | 20 | Native Env | Native Env | Native Env | Native Env |
| | 4 | Placebo | Placebo | Placebo | Placebo |
| | | DNA Trivalent | DNA Trivalent | NYVAC Trivalent | NYVAC Trivalent |
| 4 | 20 | Mosaic Env | Mosaic Env | Mosaic Env | Mosaic Env |
| | 4 | Placebo | Placebo | Placebo | Placebo |
| Total | 96 (80/16) | | | | |

Participants:
Healthy, HIV-1-uninfected volunteers aged 18 to 50 years:
 80 vaccinees
 16 control recipients
 96 total participants
Design:
Randomized, placebo-controlled, double-blind trial
Duration Per Participant:
Approximately 12 months
Estimated Total Study Duration:
Approximately 18 months

EXAMPLE 3

Construction of the Plasmid DNA Vaccines and Recombinant Vaccinia (rVV). Mosaic gag and nef genes, group M consensus gag and nef genes were generated by converting amino acid sequences of said Gag and Nef, group M consensus Gag and Nef CON-S to nucleotide sequences using a strategy for optimal gene expression. For use as a DNA vaccine, mosaic gag and nef genes, group M consensus gag and nef genes were subcloned into WLV0001-AM DNA vaccine vector. Endotoxin-free plasmid DNA preparation were produced by Puresyn, Inc. (Malvern, Pa.) for the immunization of rhesus monkeys. For boosting recombinant vaccinia viruses expressing the individual mosaic gag and nef genes, group M consensus gag and nef genes were generated. The methods used were as previously described (Liao et al, Virology 353:268-282 (2006); Earl, BioTechniques 23:1094-1097 (1997)).

Experimental Groups and Vaccination Schedule. Three groups of rhesus monkeys were immunized with either 10 mg of the empty DNA vector plasmid (group 1, 6 monkeys), or 5 mg each of group M gag and nef plasmid DNA (group 2, 12 monkeys) or 1.25 mg each of 4 mosaic gag and 4 nef plasmid DNA (group 3, 12 monkeys) intramuscularly at Day 0 and Day 30. The monkeys will be boosted with the corresponding rVV expressing the initial immunizing immunogen ($10^9$ pfu/monkey) 5 month post-immunization with the $2^{nd}$ DNA immunization.

Myristoylation of Gag and Nef has a potential down regulation effect on immune responses and thus the myristoylation of Gag and Nef has been mutated in the sequences used in this study.

All documents and other information sources cited above are hereby incorporated in their entirety by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09821053B2). An electronic copy of the "Sequence Listing" will also be available from the USPTO upon request and payment of the fee set forth in 37 CFR 1.19(b)(3).

What is claimed is:

1. An immunogenic composition comprising a recombinant polypeptide comprising the amino acid sequences of SEQ ID NO:221 (B.acute.con1059).

2. The immunogenic composition of claim 1, further comprising an adjuvant.

3. An immunogenic composition comprising the recombinant polypeptide of SEQ ID NO:221 (B.acute.con1059).

4. The immunogenic composition of claim 3, further comprising an adjuvant.

5. A method of inducing an immune response against HIV-1 in a host comprising administering to the host the composition of claim 2 in an amount sufficient to effect the induction.

6. A method of inducing an immune response against HIV-1 in a host comprising administering to the host the composition of claim 4 in an amount sufficient to effect the induction.

7. An immunogenic composition comprising a nucleic acid comprising nucleotides encoding the recombinant polypeptide of SEQ ID NO:221 (B.acute.con1059).

8. The immunogenic composition of claim 7, comprising a nucleic acid encoding the recombinant of SEQ ID NO:221 (B.acute.con1059).

9. The immunogenic composition of claim 7, further comprising an adjuvant.

10. The immunogenic composition of claim 8, further comprising an adjuvant.

11. The immunogenic composition of claim 5, wherein the nucleic acid is operably linked to a promoter in a vector.

12. The immunogenic composition of claim 10, wherein the nucleic acid is operably linked to a promoter in a vector.

13. The immunogenic composition of claim 11, wherein the vector is viral vector.

14. The immunogenic composition of claim 12, wherein the vector is viral vector.

15. A method of inducing an immune response against HIV-1 in a host comprising administering to the host the composition of claim 9 in an amount sufficient to effect the induction.

16. A method of inducing an immune response against HIV-1 in a host comprising administering to the host the composition of claim 10 in an amount sufficient to effect the induction.

17. A method of inducing an immune response against HIV-1 in a host comprising administering to the host the composition of claim 11 in an amount sufficient to effect the induction.

18. A method of inducing an immune response against HIV-1 in a host comprising administering to the host the composition of claim 12 in an amount sufficient to effect the induction.

* * * * *